(12) United States Patent
Banks et al.

(10) Patent No.: US 6,573,270 B1
(45) Date of Patent: Jun. 3, 2003

(54) PYRAZOLES

(75) Inventors: Bernard Joseph Banks, Sandwich (GB); Nathan Anthony Logan Chubb, Sandwich (GB); James John Eshelby, Sandwich (GB); Darren John Schulz, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/934,119

(22) Filed: Aug. 21, 2001

Related U.S. Application Data

(63) Continuation of application No. 09/628,493, filed on Jul. 28, 2000, now abandoned.

(30) Foreign Application Priority Data

Jul. 29, 1999 (GB) ................................................ 9917858
May 31, 2000 (GB) ................................................ 0013368

(51) Int. Cl.[7] .................... A61K 31/506; C07D 237/24
(52) U.S. Cl. ...................... 514/274; 514/407; 544/316; 548/368.1
(58) Field of Search ................................ 514/274, 407; 544/316; 548/368.1

(56) References Cited

FOREIGN PATENT DOCUMENTS

| EP | 0627423 | * | 7/1994 |
| WO | 93/15060 | * | 8/1993 |

* cited by examiner

*Primary Examiner*—Deborah C. Lambkin
*Assistant Examiner*—Sonya Wright
(74) *Attorney, Agent, or Firm*—Peter C. Richardson; Gregg C. Benson; Lisa A. Samuels

(57) ABSTRACT

Compounds of formulae (IA) and (IB):

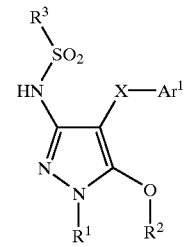

(IA)

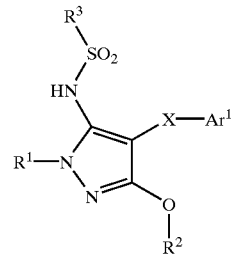

(IB)

wherein $R^1$, $R^2$, $R^3$, $Ar^1$ and X are as defined above, are endothelin antagonists. The compounds are therefore useful in the treatment of a variety of conditions mediated by endothelin, such as restenosis, renal failure and systemic and pulmonary hypertension.

8 Claims, No Drawings

PYRAZOLES

CROSS REFERENCE TO RELATED APPLICATIONS

This application is a continuation of and claims the benefit of priority from U.S. application Ser. No. 09/628,493, filed Jul. 28, 2000 now abandoned, and from United Kingdom application 9917858.4, filed Jul. 29, 1999 and from United Kingdom application 0013368.6, filed May 31, 2000.

This invention relates to pyrazole derivatives useful in the treatment of a variety of conditions mediated by endothelin and to pharmaceutical formulations containing such compounds useful for the treatment of humans and non-human mammals.

Endothelin (ET) is a potent vasoconstrictor synthesised and released by endothelial cells. There are three distinct isoforms of ET:ET-1, ET-2 and ET-3, all being 21-amino acid peptides and herein the term 'endothelin' refers to any or all of the isoforms. Two receptor subtypes, $ET_A$ and $ET_B$ have been pharmacologically defined (see for example H. Arai et al., Nature, 348, 730, 1990) and further subtypes have recently been reported. Stimulation of $ET_A$ promotes vasoconstriction and stimulation of $ET_B$ receptors causes either vasodilation or vasoconstriction. The main effects of ET are observed in the cardiovascular system, particularly in the coronary, renal, cerebral and mesenteric circulation, and the effects of endothelin are often long-lasting. Stimulation of ET receptors also mediate further biological responses in cardiovascular and non-cardiovascular tissues such as cell proliferation and matrix formation.

Increased circulating levels of endothelin have been observed in patients who have undergone percutaneous transluminal coronary angioplasty (PTCA) (A. Tahara et al., Metab. Clin. Exp. 40, 1235, 1991) and ET-1 has been found to induce neointimal formation in rats after balloon angioplasty (S. Douglas et al., J. Cardiovasc. Pharm., 22 (Suppl 8), 371, 1993). The same workers have found that an endothelin antagonist, SB-209670, causes a 50% reduction in neointimal formation relative to control animals (S. Douglas et al., Circ Res, 75, 1994). Antagonists of the endothelin receptor may thus be useful in preventing restenosis post PTCA. The $ET_{A/B}$ receptor antagonist Bosentan reportedly decreased blood pressure in hypertensive patients (H. Krum et al., New Eng. J. Med. (1998) 338, 784–790). Antagonists of $ET_B$ receptors such as BQ-788 have been demonstrated to increase peripheral resistance in man (Hypertension (1999) 33, 581–585). Thus $ET_A$-selective receptor antagonists are most likely to be of benefit in hypertension.

Endothelin-1 is produced in the human prostate gland and endothelin receptors have been identified in this tissue (Y. Saita et al., Eur. J. Pharmacol. (1988) 349, 123–128). Since endothelin is a contractile and proliferative agent, endothelin antagonists could be useful in the treatment of benign prostate hypertrophy.

There is widespread localisation of endothelin and its receptors in the central nervous system and cerebrovascular system (R. K. Nikolov et al., Drugs of Today, 28(5), 303, 1992) with ET being implicated in cerebral vasospasm, cerebral infarcts, septic shock, myocardial infarction and neuronal death.

Elevated levels of endothelin have also been observed in patients with:

recurrent airway obstruction (Pulm. Pharm. Ther. (1998) 11:231–235);

asthma (Am. J. Resp. Crit. Care Med., (1995) 151:1034–1039);
acute renal failure (K. Tomita, et al., Med. Philos. (1994) 13(1), 64–66);
chronic renal failure (F. Stockenhuber et al., Clin Sci (Lond.), 82, 255, 1992);
ischaemic Heart Disease (M. Yasuda, Am. Heart J., 119, 801, 1990);
stable or unstable angina (J. T. Stewart, Br. Heart J., 66, 7 1991);
pulmonary hypertension (D. J. Stewart et al., Ann. Internal Medicine, 114, 464, 1991);
congestive heart failure (R. J. Rodeheffer et al., Am. J. Hypertension, 4, 9A, 1991);
preeclampsia (B. A. Clark et al., Am. J. Obstet. Gynecol., 166, 962, 1992);
diabetes (A. Collier et al., Diabetes Care, 15 (8), 1038, 1992);
Crohn's disease (S. H. Murch et al., Lancet, 339, 381, 1992); and
atherosclerosis (A. Lerman et al., New Eng. J. Med., 325, 997, 1991).

In every case the disease state associated with the physiologically elevated levels of endothelin is potentially treatable with a substance which decreases the effect of endothelin, such as an endothelin receptor antagonist, or a compound which binds endothelin such that it reduces the effective concentration thereof at the endothelin recepotors.

Compounds that antagonise the $ET_A$ receptor to a greater extent than the $ET_B$ receptor are preferred as $ET_A$ receptors are predominantly present in vascular smooth muscles. Blockade of $ET_B$ receptor activation may reverse endothelial dependent vasodilation which is beneficial in hypertension. ET may also mediate regeneration of damaged tissue via the $ET_B$ receptor, such as proximal tubule cells in the kidney. Thus blockade of $ET_B$ receptors, e.g. with a non-selective ET antagonist could inhibit tissue repair. $ET_B$ receptors are also involved in the clearance of ET from the systemic circulation. Increased levels of ET are generally considered detrimental. Rises in circulating levels have been observed with non-selective ET antagonists. Treatment with selective $ET_A$ receptor antagonists are not likely to induce such rises in circulating levels.

There are a number of publications relating to N-(pyrimidin-4-yl)sulphonamide derivatives having endothelin binding/antagonist activity, for example EP-A-0743307, EP-A-0658548, EP-A-0633259, EP-A-0882719, WO-A-96/20177, EP-A-0801062, WO-A-97/09318, EP-A-0852226, EP-A-0768304, WO-A-96/19459, WO-A-98/03488 and EP-A-0713875.

International Patent Application publication number WO-A-96/19455 discloses phenyl and pyridin-4-yl sulphonamides as endothelin antagonists.

International Patent Application publication number WO-A-97/11942 discloses various (4-arylthioisoxazol-3-yl) sulphonamides, with an aldehyde moiety linked to the 5-position of the isoxazole ring, as selective $ET_B$ receptor selective antagonists.

We have unexpectedly found that pyrazoles of formulae IA and IB below have good affinity for endothelin receptors, and are selective for $ET_A$ over $ET_B$.

According to the present invention, there are provided compounds of formulae IA and IB:

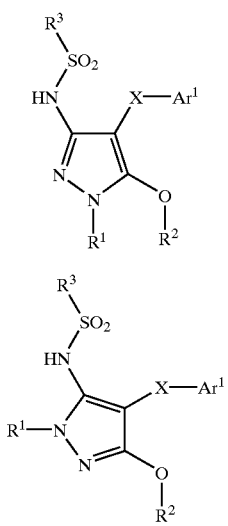

Wherein

R$^1$ is H, C$_{1-6}$ alkyl (optionally substituted by one or more halo, OR$^4$ or NR$^4$R$^5$ groups), C$_{2-6}$ alkenyl (optionally substituted by one or more halo groups), C$_{2-6}$ alkynyl (optionally substituted by one or more halo groups), C(O)R$^4$, CO$_2$R$^4$, CH$_2$aryl$^4$, CONR$^4$R$^5$, aryl$^4$ or het$^1$, R$^2$ is C$_{1-6}$ alkyl, cyclopropylmethyl, or CH$_2$CH$_2$OG where G is H, C$_{1-6}$ alkyl (optionally substituted by a C$_{3-6}$ cycloalkyl group), C(O)R$^4$, CONHAr$^2$ or Ar$^2$, R$^4$ and R$^5$ are each independently H or C$_{1-6}$ alkyl (optionally substituted by one or more halo groups), X is a direct link O, S, SO, SO$_2$, CO or CH$_2$, R$^3$ is
  a) a C$_{6-14}$ aromatic hydrocarbon group; or
  b) an optionally benzo-fused 5- or 6-membered heterocyclic group with one to three hetero-atoms atoms in the heterocyclic ring, which hetero-atoms are independently selected from N, O and S; or
  c) CH$_2$CH$_2$Ph, CH:CHPh; or
  d) C$_{1-6}$ alkyl, optionally substituted by 1–4 substituents selected from: halo, C$_{1-6}$ alkoxy, CO$_2$R$^4$, OC(O)R$^4$ and NR$^4$R$^5$,
  each of which groups (a), (b) and (c) is optionally substituted by up to four substituents independently selected from:
    i) C$_{1-6}$ alkyl, optionally substituted by 1–4 substituents selected from: halo, OR$^4$, CO$_2$R$^4$, OC(O)R$^4$ and NR$^4$R$^5$;
    ii) C$_{1-6}$ alkoxy;
    iii) CO$_2$R$^4$ and OC(O)R$^4$;
    Halo;
    NO$_2$;
    vi) CN;
    NR$^4$R$^5$;
    C$_{1-3}$ alkylenedioxy;
    OH;
    Alkoxy carbonyl;

Ar$^1$ and Ar$^2$ are each independently aryl$^5$ or het$^1$
  aryl$^4$ is a phenyl or naphthyl group optionally substituted by up to three substituents independently selected from C$_{1-3}$ alkyl, CF$_3$, halogen, C$_{1-3}$ alkoxy, CF$_{1-3}$O, OH, NO$_2$, CN, NR$^4$R$^5$, COR$^4$, CO$_2$R$^4$, CONR$^4$R$^5$, S(O)$_p$(C$_{1-3}$ alkyl), CH$_2$NR$^4$R$^5$, NR$^4$COR$^5$, COCF$_3$, CH$_2$OH, S(O)$_p$CF$_3$, C(=NH)NH$_2$, aryl$^5$ is a phenyl, 1,3-benzodioxyl or naphthyl group optionally substituted by up to three substituents independently selected from C$_{1-3}$ alkyl, CF$_3$, halogen, C$_{1-3}$ alkoxy, OCF$_3$, OH, NO$_2$, CN, NR$^4$R$^5$, C(O)R$^4$, CO$_2$R$^4$, CONR$^4$R$^5$, S(O)$_p$(C$_{1-3}$ alkyl), CH$_2$NR$^4$R$^5$, NR$^4$COR$^5$,COCF$_3$, CH$_2$OH S(O)$_p$CF$_3$, C(=NH)NH$_2$, C$_{2-3}$ alkynyl, C$_{2-3}$ alkenyl, phenyl and het$^2$, het$^1$ is a 5- to 7-membered heterocyclic group with one to three hetero-atoms in the heterocyclic ring,
  which hetero-atoms are independently selected from N, O and S,
  which heterocyclic ring is optionally benzo-fused, which group may be fully saturated or partially or fully unsaturated, and which is optionally substituted by up to three substituents independently selected from C$_{1-3}$ alkyl, CF$_3$, halogen, C$_{1-3}$ alkoxy, CF$_3$O, OH, NO$_2$, CN, NR$^4$R$^5$, COR$^4$, CO$_2$R$^4$, CONR$^4$R$^5$, S(O)$_p$(C$_{1-3}$ alkyl), CH$_2$NR$^4$R$^5$, NR$^4$COR$^5$, COCF$_3$, CH$_2$OH, S(O)$_p$CF$_3$, C(=NH)NH$_2$, C$_{2-3}$ alkynyl, C$_{2-3}$ alkenyl, phenyl and het$^2$, and, when present in the G moiety, is linked to the O atom to which it is joined to the remainder of the compound of formula (IA) or (IB) via a carbon atom in said het$^1$ group, het$^2$ is a 5- to 7-membered heterocyclic group with one to three hetero-atoms in the heterocyclic ring,
  which hetero-atoms are independently selected from N, O and S,
  which group may be fully saturated or partially or fully unsaturated,
  and p is 0, 1 or 2,
  and pharmaceutically acceptable derivatives thereof, hereinafter referred to as the "substances of the invention".

Pharmaceutically acceptable derivatives include those compounds in which the functional groups explicitly recited above have been derivatised to provide prodrugs which can be converted to the parent compound in vivo. Such prodrugs are discussed in Drugs of Today, Vol 19, 499–538 (1983) and Annual Reports in Medicinal Chemistry, Vol 10, Ch 31 p306–326. In addition, pharmaceutically acceptable derivatives include pharmaceutically acceptable salts, such as alkali metal salts (for example sodium salts) of any acidic groups that may be present. Also included are zwitterionic species which may exist.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 66, 1–19, 1977.

Halo includes fluoro, chloro, bromo and iodo groups.

Alkyl, alkenyl and alkynyl groups may be straight chain, branched or cyclic where the number of carbon atoms allows.

A C$_{6-14}$ aromatic hydrocarbon group may include such groups as phenyl, naphthyl, indenyl, anthryl and phenanthryl.

In one embodiment of the invention, $R^1$ is H, $C_{1-6}$ alkyl (optionally substituted by one or more halo, $OR^4$ or $NR^4R^5$ groups), $C_{2-6}$ alkenyl (optionally substituted by one or more halo groups), $C_{2-6}$ alkynyl (optionally substituted by one or more halo groups), $CO(C_{1-6}$ alkyl optionally substituted by one or more halo groups), $CO_2(C_{1-6}$ alkyl optionally substituted by one or more halo groups), $CONR^4R^5$, aryl$^4$ or het$^1$, Preferably $R^1$ is H, $CH_3$, $CH_2Ph$, $CH_2CH_2OH$.
More preferably $R^1$ is H, $CH_3$.
Most preferably $R^1$ is $CH_3$.

In one embodiment of the invention, $R^2$ is $CH_2CH_2OG$ where G is H or $Ar^2$, Preferably $R^2$ is $CH_3$, cyclopropylmethyl, $CH_2CH_2OG$, wherein G is H, Ph, $C(O)CH_3$, $C_{1-2}$ alkyl, N-(2-pyridyl) aminocarbonyl, 4-fluorophenyl or pyrimidin-2-yl, said pyrimidin-2-yl optionally substituted at the 5 position by F, Cl, Br, $CH_3$, $CH_2OH$, $C(O)H$, $SO_2CH_3$, $NO_2$, $NH_2$, $SCH_3$, $S(O)CH_3$, furan-2-yl or thien-2-yl.

More preferably $R^2$ is $CH_2CH_2OG$, wherein G is Et or pyrimidin-2-yl, said pyrimidin-2-yl optionally substituted at the 5 position by Cl, Br, $CH_2OH$, $SO_2CH_3$, $SCH_3$, $S(O)CH_3$ or thien-2-yl. Most preferably $R^2$ is $CH_2CH_2OG$, wherein G is pyrimidin-2-yl, said pyrimidin-2-yl optionally substituted at the 5 position by Cl, Br.

In one embodiment, $R^3$ is a phenyl group or an optionally benzo-fused 5- or 6-membered heterocyclic group with one to three hetero-atoms in the heterocyclic ring, which heteroatoms are independently selected from N, O and S, each of which groups is optionally substituted by up to three substituents independently selected from halogen, $C_{1-6}$ alkyl (optionally substituted by OH, halo, $NR^4R^5$ or $CO_2R^4$), CN, $OC_{1-6}$ alkyl (optionally substituted by one or more halogen) and $CO_2R^4$.

Preferably $R^3$ is
a) phenyl; or
b) an optionally benzo-fused 5- or 6-membered heterocyclic group with one to three hetero-atoms in the heterocyclic ring, which hetero-atoms are independently selected from N, O and S; or
c) $CH_2CH_2Ph$, CH:CHPh each of which groups (a) and (b) is optionally substituted by up to three substituents independently selected from:
i) halo,
ii) $C_{1-6}$ alkyl optionally substituted by OH, halo, $NR^4R^5$ or $CO_2R^4$,
iii) CN,
iv) $O(C_{1-6}$ alkyl optionally substituted by one or more halogen) and
v) $OC(O)R^4$ and $CO_2R^4$, and group (c) is optionally substituted by 1–3 substituents selected from H, halo and $C_{1-6}$ alkyl.

More preferably $R^3$ is
a) Phenyl, optionally substituted at the 4 position by: $CH(CH_3)_2$, $C(CH_3)_3$, $C(CH_3)_2CO_2Et$, $C(CH_3)_2CO_2H$, $C(CH_3)_2CH_2OH$, $C(CH_3)_2CH_2OC(O)CH_3$, Cl, Br, I $CH_3O$, $CF_3$, $C(CH_3)_2CH_2CH_3$;
b) Pyrid-2-yl, optionally substituted at the 5 position by $CH(CH_3)_2$, $CH_3$ or $CH(CH_3)$ $CH_2OH$;
c) $CH_2CH_2Ph$, CH:CHPh, said Ph groups optionally substituted by H, halo or $C_{1-3}$ alkyl.

Yet more preferably $R^3$ is
a) Phenyl, optionally substituted at the 4-position by: $C(CH_3)_3$, $C(CH_3)_2CO_2H$, $C(CH_3)_2CH_2OH$, $C(CH_3)_2CH_2OC(O)CH_3C(CH_3)_2CH_2CH_3$;
b) Pyrid-2-yl, substituted at the 5 position by $CH(CH_3)$ $CH_2OH$;

c) $CH_2CH_2Ph$, CH:CHPh, said Ph groups optionally substituted by H, Cl or $C_{1-2}$ alkyl.

Most preferably $R^3$ is
a) Phenyl, substituted at the 4 position by: $C(CH_3)_3$, $C(CH_3)_2CO_2H$, $C(CH_3)_2CH_2OH$, $C(CH_3)_2CH_2OC(O)CH_3$;
b) Pyrid-2-yl, substituted at the 5 position by $CH(CH_3)$ $CH_2OH$;
c) $CH_2CH_2Ph$, CH:CHPh.

Preferably X is a direct link or O.
More preferably X is a direct link.

Preferably $Ar^1$ is
a) Phenyl, optionally substituted at the 4 position by: $CF_3$, CN, vinyl, $C(O)CH_3$, $OCF_3$, COOH, F, Cl, $OCH_3$, $CH_2OH$, $CH_3$;
b) 3,4-dihydroxyphenyl, 3,4-dimethoxyphenyl, 3-methylphenyl, 3-methoxyphenyl, 3-chlorophenyl, benzo[b]thien-2-yl, 1,3-benzodiox-5-yl.

More preferably $Ar^1$ is
a) Phenyl, optionally substituted at the 4 position by F, Cl, $OCH_3$, $CH_2OH$ or $CH_3$;
b) 3,4-dimethoxyphenyl, 3-methylphenyl, 3-methoxyphenyl, 1,3-benzodiox-5-yl.

Most preferably $Ar^1$ is
a) Phenyl, substituted at the 4 position by $CH_2OH$ or $CH_3$;
b) 1,3-benzodiox-5-yl.

Preferably $R^4$ and $R^5$ are H and $C_{1-3}$ alkyl (optionally substituted by one or more halo groups).
More preferably $R^4$ and $R^5$ are $C_{1-3}$ alkyl.
Most preferably $R^4$ and $R^5$ are $CH_3$.

Preferably $Ar^2$ is a phenyl or pyrimidyl group optionally substituted by up to three substituents independently selected from $C_{1-3}$ alkyl, $CF_3$, halogen, $C_{1-3}$ alkoxy, $CF_3O$, OH, $NO_2$, CN, $NH_2$, CHO, $CO_2H$, $CONH_2$, $S(O)_p(C_{1-3}$ alkyl), thienyl and furyl.

More preferably $Ar^2$ is phenyl, 5-bromopyrimid-2-yl, 5-nitroopyrimid-2-yl, 5-aminopyrimid-2-yl, 5-formylpyrimid-2-yl, 5-methoxypyrimid-2-yl, 5-chloropyrimid-2-yl, 5-(thien-2-yl)pyrimid-2yl, 5-(furan-2-yl)pyrimid-2-yl, pyrimid-2-yl, 5-fluoropyrimid-2-yl, 5-methylthiopyrimid-2-yl, 5-methylsulphonylpyrimid-2-yl or 5-methylsulphoxypyrimid-2-yl.

Most preferably $Ar^2$ is 5-bromopyrimid-2-yl.

A preferred group of compounds are selected from the Examples and pharmaceutical derivatives thereof.

A more preferred group of compounds are:

N-(4-(1,3-benzodioxol-5-yl)-3-{2-[(5-bromo-2-pyrimidinyl)oxy]ethoxy}-1-methyl-1H-pyrazol-5-yl)-4-(tert-butyl)benzenesulfonamide N-(4-(1,3-benzodioxol-5-yl)-3-{2-[5-chloro-2-pyrimidinyl)oxy]ethoxy}-1-methyl-1H-pyrazol-5-yl)-4-(tert-butyl)benzenesulphonamide N-[4-(1,3-benzodioxol-5-yl)-1-methyl-3-(2-{[5-(methylsulfonyl)-2-pyrimidinyl]oxy}ethoxy)-1H-pyrazol-5-yl]-4-(tert-butyl)benzenesulfonamide N-(4-(1,3-benzodioxol-5-yl)-3-{2-[(5-chloro-2-pyrimidinyl)oxy]ethoxy-1-methyl-1H-pyrazol-5-yl)-1-methyl-1H-imidazole-4-sulfonamide N-(4-(1,3-benzodioxol-5-yl)-3-{2-[(5-chloro-2-pyrimidinyl)oxy]ethoxy}-1-methyl-1H-pyrazol-5-yl)-4-(2-hydroxy-1,1-dimethylethyl)benzenesulfonamide N-(4-(1,3-benzodioxol-5-yl)-3-{2-[(5-chloro-2-pyrimidinyl)oxy]ethoxy}-1-methyl-1H-pyrazol-5-yl)benzenesulfonamide N-(4-(1,3-benzodioxol-5-yl)-3-{2-[(5-chloro-2-pyrimidinyl)oxy]ethoxy}-1-methyl-1H-pyrazol-5-yl)-1-methyl-1H-imidazole-4-sulfonamide N-[4-(1,3-benzodioxol-5-yl)-3-(2-{[5-(methylsulfonyl)-2-pyrimidinyl]oxy}ethoxy)-1H-pyrazol-5-yl]-4-(tert-butyl)benzenesulfonamide N-[3-{2-[(5-bromo-2-pyrimidinyl)oxy]ethoxy}-1-methyl-4-(4-methylphenyl)-1H-pyrazol-5-yl]-4-(tert-pentyl)benzenesulfonamide 2-[4-({[3-{2-[(5-bromo-2-pyrimidinyl)oxy]ethoxy}-1-methyl-4-(4-methylphenyl)-1H-pyrazol-5-yl]amino}sulfonyl)phenyl]-2-methylpropanoic acid N-[3-{2-[(5-bromo-2-pyrimidinyl)oxy]ethoxy}-1-methyl-4-(4-methylphenyl)-1H-pyrazol-5-yl]-4-(2-hydroxy-1,1-dimethylethyl)benzenesulfonamide N-[3-(2-ethoxyethoxy)-1-methyl-4-(4-methylphenyl)-1H-pyrazol-5-yl]-4-(2-hydroxy-1,1-dimethylethyl)benzenesulfonamide N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide 4-(tert-butyl)-N-[3-{2-[(5-chloro-2-pyrimidinyl)oxy]ethoxy}-1-methyl-4-(4-methylphenyl)-1H-pyrazol-5-yl]benzenesulfonamide 4-(tert-butyl)-N-[3-{2-[(5-methylthio-2-pyrimidinyl)oxy]ethoxy}-1-methyl-4-(4-methylphenyl)-1H-pyrazol-5-yl]benzenesulfonamide 4-(tert-butyl)-N-[1-methyl-4-(4-methylphenyl)-3-{2-[(5-methylsulfinyl-2-pyrimidinyl)oxy]ethoxy}-1H-pyrazol-5-yl]benzenesulfonamide 4-(tert-butyl)-N-[1-methyl-4-(4-methylphenyl)-3-{2-[(5-methylsulfonyl-2-pyrimidinyl)oxy]ethoxy}-1H-pyrazol-5-yl]benzenesulfonamide 4-tert-butyl-N-[3-(2-{[2-(hydroxymethyl)-5-pyrimidinyl]oxy}ethoxy)-1-methyl-4-(4-methylphenyl)-1H-pyrazol-5-yl]benzenesulfonamide N-[3-{2-[(5-bromo-2-pyrimidinyl)oxy]ethoxy}-4-(4chlorophenyl)-1-methyl-1H-pyrazol-5-yl]-4-(tert-butyl)benzenesulfonamide N-[3-{2-[(5-bromo-2-pyrimidinyl)oxy]ethoxy}-4-(4-methoxyphenyl)-1-methyl-1H-pyrazol-5yl]-4-(tert-butyl)benzenesulfonamide 4-(tert-butyl)-N-[3-{2-[(5-bromo-2-pyrimidinyl)oxy}ethoxy}-4-(3-methoxyphenyl)-1-methyl-1H-pyrazol-5-yl-benzenesulphonamide 4-(tert-butyl)-N-[3-{2-[(5-bromo-2-pyrimidinyl)oxy]ethoxy}-4-(3,4-dimethoxyphenyl)-1-methyl-1H-pyrazol-5-yl]-4-benzenesulphonamide N-[3-{2-[(5-bromo-2-pyrimidinyl)oxy]ethoxy}-4-(4-fluorophenyl)-1-methyl-1H-pyrazol-5-yl]-4-(tert-butyl)benzenesulfonamide N-{3-{2-[(5-bromo-2-pyrimidinyl)oxy]ethoxy}-4-[4-(hydroxymethyl)phenyl]-1-methyl-1H-pyrazol-5-yl}-4-(tert-butyl)benzenesulfonamide N-{3-{2-[(5-bromo-2-pyrimidinyl)oxy]ethoxy}-4-[4-(hydroxymethyl)phenyl]-1-methyl-1H-pyrazol-5-yl}4-(2-hydroxy-1,1-dimethylethyl)benzenesulfonamide N-[3-{2-[(5-bromo-2-pyrimidinyl)oxy]ethoxy}-1-methyl-4-(4-carboxymethylphenyl)-1H-pyrazol-5-yl]-4-(tert-butyl hydroxy)benzenesulfonamide 2-[4-({[3-{2-[(5-bromo-2-pyrimidinyl)oxy]ethoxy}-1-methyl-4-(4-methylphenyl)-1H-pyrazol-5-yl]amino}sulfonyl)phenyl]-2-methylpropyl acetate N-[3-{2-[(5-bromo-2-pyrimidinyl)oxy]ethoxy}-1-methyl-4-(4-methylphenyl)-1H-pyrazol-5-yl]-5-isopropyl-2-pyridinesulfonamide 5-isopropyl-N-[1-methyl-4-(4-methylphenyl)-3-(2-{[5-(methylsulfonyl)-2-pyrimidinyl]oxy}ethoxy)-1H-pyrazol-5-yl]-2-pyridinesulfonamide N-[3-(2-{[5-(hydroxymethyl)-2-pyrimidinyl]oxy}ethoxy)-1-methyl-4-(4-methylphenyl)-1H-pyrazol-5-yl]-5-isopropyl-2-pyridinesulfonamide N-(4-(1,3-benzodioxol-5-yl)-3-{2-[(5-chloro-2-pyrimidinyl)oxy]ethoxy}-1-methyl-1H-pyrazol-5-yl)-5-isopropyl-2-pyridinesulfonamide N-(4-(1,3-benzodioxol-5-yl)-3-{2-[(5-chloro-2-pyrimidinyl)oxy]ethoxy}-1-methyl-1H-pyrazol-5-yl)-5-(2-hydroxy-1-methylethyl)-2-pyridinesulfonamide N-(4-(1,3-benzodioxol-5-yl)-3-{2-[(5-bromo-2-pyrimidinyl)oxy]ethoxy}-1-methyl-1H-pyrazol-5-yl)-5-isopropyl-2-pyridinesulfonamide N-[4-(1,3-benzodioxol-5-yl)-1-methyl-3-(2-{[5-(methylsulfonyl)-2-pyrimidinyl]oxy}ethoxy)-1H-pyrazol-5-yl]-5-isopropyl-2-pyridinesulfonamide N-[4-1,3-benzodioxol-5-yl)-3-{2-[(5-brompyrimidin-2-yl)oxy]ethoxy}-1-methyl-1H-pyrazol-5-yl]-2-pyridine sulphonamide N-[4-1,3-benzodioxol-5-yl)-3-{2-[(5-chloropyrimidin-2-yl)oxy]ethoxy}-1-methyl-1H-pyrazol-5-yl]-2-pyridine sulphonamide.

Most preferred are the compounds:

N-[4-(1,3-benzodioxol-5-yl)-1-methyl-3-(2-{[5-(methylsulfonyl)-2-pyrimidinyl]oxy}ethoxy)-1H-pyrazol-5-yl]-5-isopropyl-2-pyridinesulfonamide N-(4-(1,3-benzodioxol-5-yl)-3-{2-[(5-chloro-2-pyrimidinyl)oxy]ethoxy}-1-methyl-1H-pyrazol-5-yl)-5-(2-hydroxy-1-methylethyl)-2-pyridinesulfonamide N-(4-(1,3-benzodioxol-5-yl)-3-{2-[(5-bromo-2-pyrimidinyl)oxy]ethoxy}-1-methyl-1H-pyrazol-5-yl)-4-(tert-butyl)benzenesulfonamide N-(4-(1,3-benzodioxol-5-yl)-3-{2-[(5-chloro-2-pyrimidinyl)oxy]ethoxy}-1-methyl-1H-pyrazol-5-yl)-4-(2-hydroxy-1,1-dimethylethyl)benzenesulfonamide N-[4-(1,3-benzodioxol-5-yl)-3-(2-{[5-(methylsulfonyl)-2-pyrimidinyl]oxy}ethoxy)-1H-pyrazol-5-yl]-4-(tert-butyl)benzenesulfonamide 2-[4-({[3-{2-[(5-bromo-2-pyrimidinyl)oxy]ethoxy}-1-methyl-4-(4-methylphenyl)-1H-pyrazol-5-yl]amino}sulfonyl)phenyl]-2-methylpropanoic acid N-[3-{2-[(5-bromo-2-pyrimidinyl)oxy]ethoxy}-1-methyl-4-(4-methylphenyl)-1H-pyrazol-5-yl]-4-(2-hydroxy-1,1-dimethylethyl)benzenesulfonamide N-[3-(2-ethoxyethoxy)-1-methyl-4-(4-methylphenyl)-1H-pyrazol-5-yl]-4-(2-hydroxy-1,1-dimethylethyl)benzenesulfonamide 4-(tert-butyl)-N-[3-{2-[(5-chloro-2-pyrimidinyl)oxy]ethoxy}-1-methyl-4-(4-methylphenyl)-1H-pyrazol-5-yl]benzenesulfonamide 4-(tert-butyl)-N-[1-methyl-4-(4-methylphenyl)-3-{2-[(5-methylsulfonyl-2-pyrimidinyl)oxy]ethoxy}-1H-pyrazol-5-yl]benzenesulfonamide N-{3-{2-[(5-bromo-2-pyrimidinyl)oxy]ethoxy}-4-[4-(hydroxymethyl)phenyl]-1-methyl-1H-pyrazol-5-yl}-4-(tert-butyl)benzenesulfonamide N-{3-{2-[(5-bromo-2-pyrimidinyl)oxy]ethoxy}-4-[4-(hydroxymethyl)phenyl]-1-methyl-1H-pyrazol-5-yl}-4-(2-hydroxy-1,1-dimethylethyl)benzenesulfonamide.

The substances of the invention may possess one or more chiral centres and so exist in a number of stereoisomeric forms. All stereoisomers and mixtures thereof are included in the scope of the present invention. Racemic substances may either be separated using preparative HPLC and a column with a chiral stationary phase or resolved to yield individual enantiomers utilising methods known to those skilled in the art. In addition, chiral intermediates may be resolved and used to prepare chiral compounds of formulae IA and IB.

The substances of the invention are useful because they blockade ET receptors and are thus useful in the treatment or prevention of any diseases for which such a blockade is beneficial. More particularly, they are useful in the treatment and prevention of restenosis, acute/chronic renal failure, hypertension including pulmonary and systemic hypertension; benign prostatic hypertrophy, male erectile dysfunction, prostate cancer, metastatic bone cancer, congestive heart failure, stroke, subarachnoid haemorrhage, angina, atherosclerosis, cerebral and cardiac ischaemia, prevention of ischaemia/reperfusion injury (e.g. allografts), cyclosporin induced nephrotoxicity, glaucoma, radiocontrast nephropathy, diabetic neuropathy, allergy, restoration of organ perfusion in haemorrhagic shock, lipoprotein lipase related disorders, chronic obstructive pulmonary disease and hyaline membrane disease in newborn. The treatment of restenosis, renal failure and systemic and pulmonary hypertension are of particular interest. The substances of the invention may be administered alone or as part of a combination therapy.

The invention further provides Methods for the production of substances of the invention, which are described below and in the Examples and Preparations section. The skilled man will appreciate that the substances of the invention could be made by methods other than those herein described, by adaptation of the methods herein described and/or adaptation of a plethora of methods known in the art. It is to be understood that the synthetic transformation methods specifically mentioned herein may be carried out in various different sequences in order that the desired substances can be efficiently assembled. The skilled chemist will exercise his judgement and skill as to the most efficient sequence of reactions for synthesis of a given target substance.

It will be apparent to those skilled in the art that sensitive functional groups may need to be protected and deprotected during synthesis of a substance of the invention. This may be achieved by conventional techniques, for example as described in 'Protective Groups in Organic Synthesis' by T W Greene and P G M Wuts, John Wiley and Sons Inc, 1991.

In the Methods below, unless otherwise specified, the substituents are as defined above with reference to the compounds of formula (I) above.

Method 1

Compounds of formulae IA and IB can be made via reaction of the corresponding compounds of formula IIA or IIB as appropriate

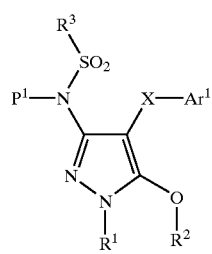

(IIA)

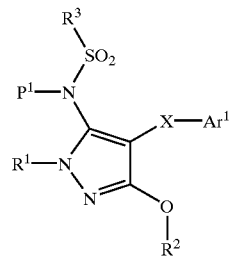

(IIB)

where $P^1$ is a nitrogen protecting group, by deprotection of said nitrogen-protecting group with a suitable reagent and under suitable conditions. A suitable example of such a protecting group is the 2-methoxyethoxymethyl group, which can be removed by treatment with acidic ethanol at elevated temperature, as exemplified in Example 12 below.

Compounds of formulae IIA and IIB may be made via conventional methods as exemplified in the Preparations section below, see for instance Preparation 1.

Method 2

Compounds of formulae IA and IB where $R^2$ is $CH_2CH_2OH$ may be made via hydrolysis of the corresponding ester of formula IIIA or IIIB:

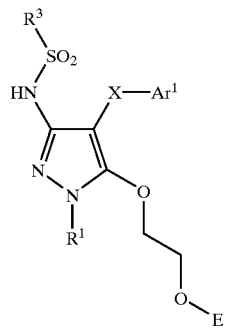

(IIIA)

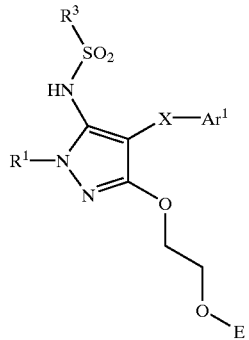

(IIIB)

wherein E is $(C_{1-4}$ alkyl)CO, for example by treatment with aqueous base such as aqueous sodium hydroxide or aqueous potassium carbonate, in a suitable solvent such as methanol or ethanol. This type of reaction is exemplified in Examples 2, 52 and 78 below.

Compounds of formulae IIIA and IIIB may be made via conventional methods as exemplified in the Preparations section below (see for instance Preparation 4).

Method 3

Compounds of formulae IA and IB where $R^2$ is $CH_2CH_2OG$ and where G is $Ar^2$ can be made from the corresponding compound of formulae IA or IB where G is H, for instance via reaction of the compound of formula IA or IB where G is H with a reagent of formula "Ar²—L", where "L" is a suitable leaving group such as a halo, arenesulphonate, $C_{1-4}$ alkanesulphonate or perfluoro($C_{1-4}$ alkane)sulphonate ion, suitably a chloride, phenylsulphonate, p-toluenesulphonate or mesylate ion, suitably in the presence of a base such as sodium hydride or potassium carbonate, in a suitable inert organic solvent such as N,N-dimethylformamide (DMF) or tetrahydrofuran (THF).

Preferably, Ar² is 5-chloro-pyrimidin-2-yl or 5-bromo-pyrimidin-2-yl.

This type of reaction is mentioned in for example U.S. Pat. No. 5,728,706 and Tetrahedron (1984) 40, 1433, and is exemplified below in Examples 3, 4, 5, 9, 11, 13, 14, 16, 18, 20, 22, 24, 26, 28, 31, 33, 34, 36, 41, 42, 44, 45, 48, 49, 51, 53, 68, 69, 80, 91, 92, 93, 94, 95, 97, 103 and 109 and the same type of transformation is disclosed in Preparation 27.

Method 4

Compounds of formulae IA and IB can be made via reaction of the corresponding compound of formula IVA or IVB as appropriate,

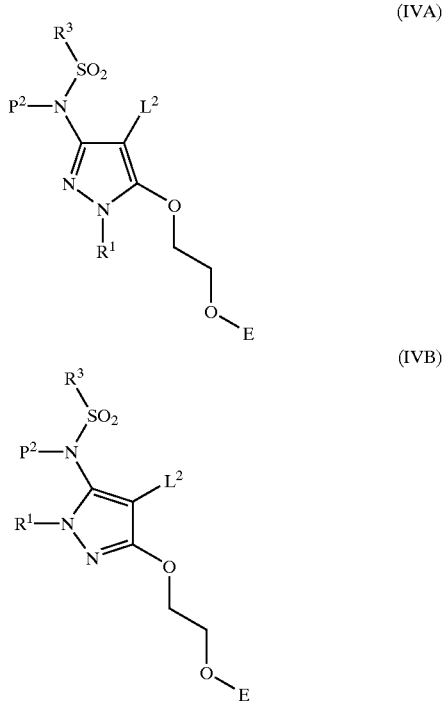

where L² is a leaving group such as Cl, Br, I or triflate, P² is H, R³SO₂ or a nitrogen-protecting group such as methoxymethyl, iso-butoxycarbonyl, etc., and E is G as defined with reference to compounds of formulae IA and IB above, or E is a suitable oxygen-protecting group such as ($C_{1-4}$ alkyl)CO (which protecting groups may be removed during the reaction or subsequent to it), with a reagent which is equivalent to a "Ar¹—X³¹ " synthon.

For instance where X is a direct link, the reagent which acts as the "Ar¹—X⁻" synthon can be an organometallic species such as an arylboronic acid Ar¹—B(OH)₂, and aryltin species Ar¹—SnBu₃, an arylzinc species Ar¹—ZnCl. Such reagent types are well known in the art as are the reaction conditions, catalysts, co-reagents, solvents, etc.

This type of reaction is exemplified in Examples 10, 30, 32 and 96 below, and the same reaction-site transformation is described in Preparations 13, 16, 18, 20 and 22.

Compounds of formulae IVA and IVB may be made via conventional methods as exemplified in the Preparations section below.

Method 5

Compounds of formulae IA and IB can be made via reaction of the corresponding compound of formula VA or VB as appropriate

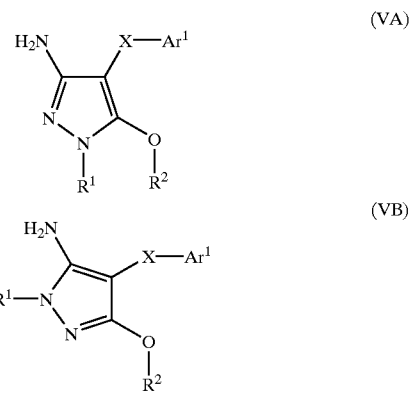

with a reagent R³—SO₂—L³ where (L³)⁻ is a suitable leaving group such as a halogen, particularly chloride, under standard N-sulphonylation conditions, such as those exemplified in Examples 8, 40, 43, 47, 50, 59, 60, 61, 63, 64, 65, 66, 67, 75, 105 and 107. The same type of reaction is also used in Preparations 1, 4, 9, 23, 25 and 29.

Compounds of formulae VA and VB may be made via conventional methods as exemplified in the Preparations section below, e.g. Preparation 5.

Method 6

Compounds of formulae IA and IB where R² is CH₂CH₂OG, where G is CONHaryl⁵ can be made from the corresponding compound of formulae IA or IB where G is H (Method 2), via reaction of the compound of formula IA or IB where G is H, with a reagent of formula "aryl⁵—CO₂H", in the presence of an aryl substituted phosphoryl azide, suitable base such as triethylamine, 4-dimethylaminopyridine and a suitable inert organic solvent such as toluene at a temperature of 0–100° C., preferably a temperature of 35–40° C.

This type of reaction is mentioned below in Example 57.

Method 7

Compounds of formulae IA and IB where R₁ is CH₂CH₂OH can be made via reaction of the corresponding compounds of formula VIA or VIB as appropriate

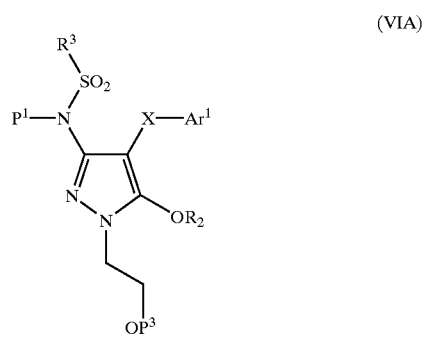

-continued

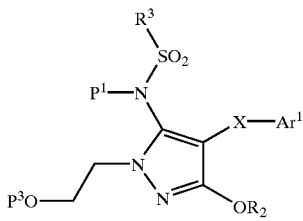
(VIB)

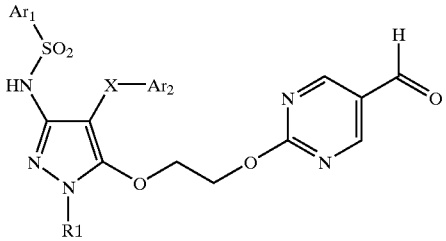
(VIIIA)

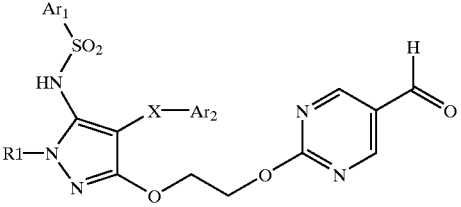
(VIIIB)

where P¹ is H, or a suitable N protecting group such as methoxy methyl group and P³ is a suitable hydroxy protecting group such as CO(C$_{1-4}$ alkyl) or a silyl optionally substituted with C$_{1-4}$ alkyl and/or phenyl groups and treated with a suitable acid such as oxalic acid, as exemplified in Example 81 or a suitable fluoride source such as tetrabutyl ammonium fluoride as exemplified in Example 39. Compounds of formulae VIA and VIB may be made via conventional methods as exemplified in the Preparations section below, see for instance Preparations 27 and 54.

Method 8

Compounds of formulae IA and IB where R¹ is H can be made via reaction of the corresponding compounds of formula VIIA or VIIB as appropriate

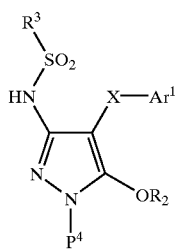
(VIIA)

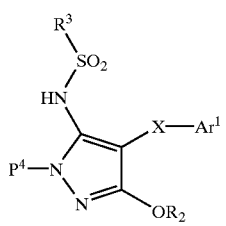
(VIIB)

where P⁴ a suitable protecting group such as a benzyl group and is treated under suitable hydrogenolysis conditions in a suitable solvent such as acetic acid and treated with a suitable catalyst such as Pearlman's catalyst under a positive pressure of hydrogen, as exemplified in Example 79. Compounds of formulae VIIA and VIIB may be made via conventional methods as exemplified in the Preparations section below, see for instance Preparation 52.

Method 9

Compounds of formulae IA and IB where R² is CH$_2$CH$_2$OG, where G is 2-(hydroxymethyl)-5-pyrimidinyl can be made via reaction of the corresponding compounds of formula VIIIA or VIIIB with a suitable reducing agent such as sodium borohydride in a suitable solvent such as ethanol, as exemplified in Example 90. Compounds of formulae VIIIA and VIIIB may be made via conventional methods as exemplified in the synthetic sequence of the derivatives Examples 2, 3, 38 and Preparation 4 respectively.

It is to be understood that certain substances of the invention can be interconverted into certain other substances of the invention by standard methodology.

Where desired or necessary the compound of formula IA or IB is converted into a pharmaceutically or veterinarily acceptable salt thereof. A pharmaceutically or veterinarily acceptable salt of a compound of formula (I) may be conveniently be prepared by mixing together solutions of a compound of formula (I) and the desired acid or base, as appropriate. The salt may be precipitated from solution and collected by filtration, or may be collected by other means such as by evaporation of the solvent.

The compounds of the invention may be separated and purified by conventional methods.

The invention provides for a compound of the invention as defined above, for use as a medicament.

The invention also provides for the use of a substance of the invention as defined above, in the manufacture of a medicament for the treatment of restenosis, acute/chronic renal failure, pulmonary hypertension, systemic hypertension; benign prostatic hyperplasia, male erectile dysfunction, prostate cancer, metastatic bone cancer, congestive heart failure, stroke, subarachnoid haemorrhage, angina, atherosclerosis, cerebral and cardiac ischaemia, prevention of ischaemia/reperfusion injury (e.g. allografts), cyclosporin induced nephrotoxicity, glaucoma, radiocontrast nephropathy, diabetic neuropathy, allergy, restoration of organ perfusion in haemorrhagic shock, lipoprotein lipase related disorders, chronic obstructive pulmonary disease and hyaline membrane disease in newborn.

The invention also provides the use of a compound of the invention in the preparation of a medicament for the treatment of conditions mediated by endothelin, particularly endothelin-A. Also provided is a method of treatment of conditions mediated by endothelin, particularly endothelin-A, which comprises administering a therapeutically effective amount of a substance of the invention, to a patient in need of such treatment.

Reference to treatment herein includes prevention of undesirable conditions as well as alleviation or cure of said conditions.

The biological activity of the substances of the invention may be demonstrated as follows:

Dog Binding Assay

Competition between test substances and ligands binding to canine endothelin receptors is determined as follows:

Dog ET-A Binding Assay

50 µl of a 500 pM solution of $^{125}$I-PD-151242 (Specific activity 2,000 Ci/mM) is mixed with 50 µl samples of test substances (final concentrations in the range from 0.01–10,000 nM). 100 µg of purified dog kidney homogenate is added in 150 µl of the following buffer: 50 mM Tris, 10 mM MgCl$_2$ and 0.05% Bovine Serum Albumen at pH 7.4. The solution is incubated at room temperature for 2 hours. After the incubation, the unbound ligand is separated from receptor bound ligand by filtration with a Brandel cell harvester, followed by 5 washes with buffer (Tris 50 mM, MgCl$_2$ 10 mM). Filter papers are counted for radioactivity and the K$_i$ (an IC$_{50}$ corrected for the dissociation constant and concentration of the ligand added) is determined for the concentration range tested.

Dog ET-B Binding Assay

50 µl of a 100 pM solution of $^{125}$I-IRL-1620 (Specific activity 2,200 Ci/mM) is mixed with 50 µl samples of test substances (final concentrations in the range from 0.01–10,000 nM). 50 µg of purified Dog cerebellum homogenate is added in 150 µl of the following buffer; 50 mM Tris, 10 mM MgCl$_2$ and 0.05% Bovine Serum Albumen at pH 7.4. The solution is incubated at 30° C. for 90 minutes. After the incubation, the unbound ligand is separated from receptor bound ligand by filtration with a Brandel cell harvester, followed by 5 washes with buffer (Tris 50 mM, MgCl$_2$ 10 mM). Filter papers are counted for radioactivity and the K$_i$ (an IC$_{50}$ corrected for the dissociation constant and concentration of the ligand added) is determined for the concentration range tested.

Human Binding Assay

Competition between test substances and $^{125}$I-ET-1 binding to human endothelin receptors is determined as follows.

Binding to ET$_A$ Receptors

25 µl of a 30 pM solution of [$^{125}$I]Tyr$^{13}$ ET-1 (specific activity 2,200 Ci/mM) is mixed with 25 µl samples of test substance (final concentrations in the range 0.1 nM–50,000 nM). 200 µl of a solution containing cloned human ET$_A$ receptor (0.75 pmoles receptor protein/ml), 50 mM Tris, 0.5 mM CaCl$_2$, 0.1% human serum albumen, 0.1% bacitracin, 0.05% Tween 20, pH 7.4 is added. The solution is mixed at 37° C. for 2 hours. After the incubation, the unbound ligand is separated from receptor bound ligand by filtration with a Brandel cell harvester, followed by three washes of buffer. Filter papers are counted for radioactivity, and the IC$_{50}$ (the concentration of test compound at which 50% of the radio-labelled compound is unbound) determined for the concentration range tested.

Binding to ET$_B$ Receptors

25 µl of a 30 pM solution of [$^{125}$I]Tyr$^{13}$ ET-1 (specific activity 2,200 Ci/mM) is mixed with 25 µl samples of test substance (final concentration 0.1 nM–50,000 nM). 200 µl of a solution containing cloned human ET$_B$ receptor (0.25 pmoles receptor protein/ml), 50 mM Tris, 0.5 mM CaCl$_2$, 0.1% human serum albumen, 0.1% bacitracin, 0.05% Tween 20, pH 7.4 is added. The solution is mixed at 37° C. for 2 hours. After the incubation, the unbound ligand is separated from receptor bound ligand by filtration with a Brandel cell harvester, followed by three washes of buffer. Filter papers are counted for radio-activity, and the IC$_{50}$ (the concentration of test compound at which 50% of the radio-labelled compound is unbound) determined for the concentration range tested.

The compounds of the present invention wee tested and found to have good affinity for endothelin receptors and to be selective for ET$_A$ over ET$_B$.

The substances of the invention can be administered alone but will generally be administered in admixture with a pharmaceutical carrier selected with regard to the intended route of administration and standard pharmaceutical or veterinary practice. For example they can be administered orally in the form of tablets containing such excipients as starch or lactose or in capsules or ovules either alone or in admixture with excipients or in the form of elixirs, solutions or suspensions containing the substance in a liquid carrier, for example a vegetable oil, glycerine or water with a flavouring or colouring agent. They can be injected parenterally, for example intravenously, intramuscularly or subcutaneously. For parental administration, they are best used as sterile aqueous solutions which may contain other substances, for example, enough glucose or salts to make the solution isotonic with blood. For parenteral administration the substance may also be administered as a solution or suspension in a suitable oil, for example polyethylene glycol, lecithin or sesame oil.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Substances of the invention may also be administered through inhalation of a solution, suspension or emulsion that may be administered as a dry powder or in the form of an aerosol using a conventional propellant such as dichlorodifluoromethane.

For oral or parenteral administration to human patients the daily dosage levels of substances of the invention will be from 0.01 to 30 mg/kg (in single or divided doses) and preferably will be in the range 0.01 to 5 mg/kg. Thus tablets will contain 1 mg to 0.4 g of substance for administration singly or two or more at a time, as appropriate. The above dosages are, of course only exemplary of the average case and there may be instances where higher or lower doses are merited, and such are within the scope of the invention.

Alternatively the substances of the invention can be administered in the form of a suppository or pessary, or they may be applied topically in the form of a lotion, solution, cream, ointment or dusting powder or in the form of a medicated plaster, patch or membrane. For example they may be incorporated in a cream containing an aqueous emulsion of polyethylene glycols or liquid paraffin. The compounds may also be administered intranasally.

For veterinary use although it is possible to administer a substance of the invention directly without any formulation, the substances are preferably employed in the form of a pharmaceutical or veterinary formulation comprising a pharmaceutically or veterinarily acceptable carrier, diluent or excipient and a substance of the invention. Such compositions will contain from 0.1 percent by weight to 90.0 percent by weight of the active ingredient.

The methods by which the compounds may be administered include oral administration by capsule, bolus, tablet or drench, topical administration as an ointment, a pour-on, spot-on, dip, spray, mousse, shampoo or powder formulation or, alternatively, they can be administered by injection (e.g. subcutaneously, intramuscularly or intravenously), or as an implant.

Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc or magnesium stearate, etc. Oral drenches are prepared by dissolving or suspending the active ingredient in a suitable medium. Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol.

Alternatively, pour-on, spot-on or spray formulations can be prepared by encapsulation, to leave a residue of active agent on the surface of the animal. Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristrate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.1 to 10% by weight of the active ingredient.

These formulations will vary with regard to the weight of active substance contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

As an alternative for veterinary use the substances may be administered with animal feedstuff and for this purpose a concentrated feed additive or premix may be prepared for mixing with the normal animal feed.

Thus, according to a further aspect of the invention, there are provided pharmaceutical formulations comprising a substance of the invention, as defined above, and a pharmaceutically-acceptable adjuvant, diluent or carrier.

EXAMPLES AND PREPARATIONS

The present invention is illustrated by the following examples. However, it should be noted that the invention is not limited to the specific detail of these examples. HPLC retention times and UV spectra were recorded using a Hewlett-Packard 1090 LUSI diode-array spectrophotometer method A). All NMR spectra were measured in $CDCl_3$ or MeOD by an Inova 300 MHz or 500 MHz spectrometer unless otherwise indicated and peak positions are expressed in parts per million (ppm) downfield from tetramethylsilane.

The peak shapes are denoted as follows:s, singlet; d, doublet; t, triplet; q, quartet; m, multiplet; br broad.

High resolution MS data was acquired on a AutoSpecQ with electrospray ionisation using a PEG reference (or on a Bruker Apex II FTMS with ESI where indicated).

Low resolution MS data was acquired on a Finnigan Mat. TSQ 7000 or a Fisons Instruments Trio 1000.

HPLC-MS data was acquired using a Hewlett-Packard 1090M liquid chromatograph interfaced to a VG platform II mass spectrometer equipped with an ES source (method B). The calculated and observed ions quoted refer to the isotopic composition of the lowest mass. Reference to common solvents may be abbreviated; tetrahydrofuran (THF), dichloromethane (DCM), diethyl ether (ether), N,N-dimethylacetamide (DMF), n-hexane (hexane), trifluoroacetic acid (TFA).

| HPLC method A: | |
|---|---|
| Column | Beckman Ultrasphere 5 micron ODS 4 mm × 25cm |
| Mobile Phase | Linear gradient: methanol:water (65:35) to methanol:water (95:5) over 40 minutes |
| Flow rate | 0.85 ml/min |
| HPLC-MS method B: | |
| Column | Magellan 5 micron ODS 4.6 mm × 15 cm |
| Mobile Phase | Gradient: 0.1% v/v trifluoroacetic acid (TFA) in water:acetonitrile (90:10) 0.1% TFA : acetonitrile (2:98) over 5 minutes, maintain 0.1% TFA : acetonitrile (2:98) 5 to 11.5 minutes; return to initial conditions 11.5 to 12.5 minutes. |
| Flow rate | 0.85 ml/min |

Use is made of the following fermentation media.

| AS-7H inoculum medium | |
|---|---|
| Cornstarch (Hidex ™) | 20 g |
| Cotton Seed Meal (Pharmamedia ™) | 15 g |
| Ardamine pH ™ | 5 g |
| Calcium carbonate | 2 g |
| Tap water | 1 l |
| NaOH | To pH 7.2 |
| AP-5H Production Medium | |
| Cornststarch | 80 g |
| Yeast extract (Oxoid ™) | 5 g |
| $K_2HPO_4$ | 1 g |
| $MgSO4.7H2O$ | 1 g |
| Glutamic acid | 1 g |
| $FeSO_4.7H_2O$ | 0.01 g |
| $ZnSO_4.2H2O$ | 0.001 g |
| $MnSO_4.2H2O$ | 0.001 g |
| $CaCO_3$ | 7 g |
| Tap water | 1 l |
| NaOH | To pH 7.0 |
| MY Inoculum and Production Medium | |
| Glucose | 10 g |
| Peptone (Difco ™) | 5 g |
| Yeast extract (Oxoid ™) | 3 g |
| Malt extract (Oxoid ™) | 5 g |
| Tap water | 1 l |
| NaOH | To pH 6.3–6.5 |

-continued

| Tomato Inoculum and Production Medium | |
|---|---|
| Tomato Paste | 40 g |
| Corn Steep Liquor | 2.5 g |
| Oats | 10 g |
| Cerelose | 10 g |
| $FeSO_4 \cdot 7H_2O$ | 0.001 g |
| $ZnSO_4 \cdot 2H2O$ | 0.001 g |
| $MnSO_4 \cdot 2H2O$ | 0.001 g |
| Demineralised Water | 1 l |
| NaOH | To pH 6.8 |

Example 1

4-(tert-butyl)-N-[1-methyl-4-(4-methylphenyl)-3-(2-phenoxyethoxy)-1H-pyrazol-5-yl]benzenesulfonamide

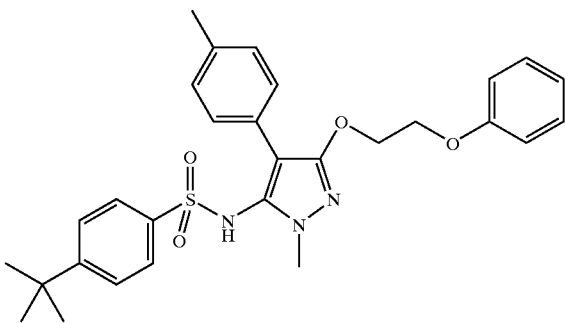

To 4-(tert-butyl)-N-{[4-(tert-butyl)phenyl]sulfonyl}-N-[1-methyl-4-(4-methylphenyl)-3-(2-phenoxyethoxy)-1H-pyrazol-5-yl]benzenesulfonamide (Preparation 1) (80 mg) in ethanol (20 ml) at room temperature was added sodium hydroxide (2N, 2 ml) and the mixture was stirred for 16 hrs. The mixture was reduced in volume to 10 ml under reduced pressure, diluted with water (50 ml) and extracted with ethyl acetate (30 ml). The organic fraction was dried over magnesium sulfate, filtered and concentrated under reduced pressure. The residue was purified by column chromatography on silica (10 g) eluted with dichloromethane:ether (7:1) to yield the title compound as a colourless glass-like solid (7 mg).

$\delta_H$ (300 MHz, $CDCl_3$) 7.40 (2H, d), 7.25 (2H, t), 7.10 (2H, d), 6.90–7.00 (3H, m), 6.80 (4H, dd), 6.55 (1H, s), 4.35 (2H, t), 4.25 (2H, t), 3.80 (3H, s), 2.10 (3H, s), 1.15 (9H, s). m/z (thermospray) [$MH^+$]=520.5; $C_{29}H_{34}N_3O_4S$ requires 520.2.

Example 2

4-(tert-butyl)-N-[3-(2-hydroxyethoxy)-1-methyl-4-(4-methylphenyl)-1H-pyrazol-5-yl]benzenesulfonamide

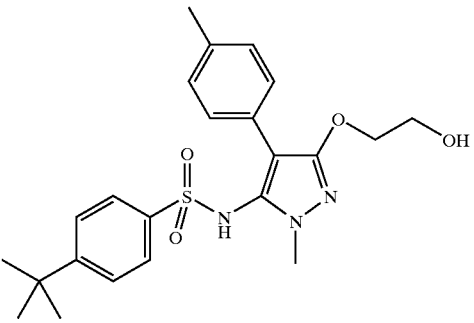

To 2-{[5-(bis {[4-(tert-butyl)phenyl]sulfonyl}amino)-1-methyl-4-(4-methylphenyl)-1H-pyrazol-3-yl]oxy}ethyl acetate (Preparation 4) (80 mg) in ethanol (20 ml) at room temperature was added 2M sodium hydroxide (2 ml) and the mixture was stirred for 16 hrs. The mixture was reduced in volume to 10 ml by rotary evaporation, diluted with water (50 ml) and extracted with ethyl acetate (2×50 ml). The organic fraction was dried over magnesium sulfate, filtered and concentrated under reduced pressure. The residue was purified by column chromatography on silica (10 g) eluted with dichloromethane to yield the title compound as a white solid (25 mg).

$\delta_H$ (300 MHz, $CDCl_3$) 7.40 (2H, d), 7.15 (2H, d), 6.90 (2H, d), 6.80 (2H, d), 4.35 (2H, t), 3.85 (2H, t), 3.80 (3H, s), 2.75 (2H, br. s), 2.10 (3H, s), 1.20 (9H, s).

Example 3

N-[3-{2[(5-bromo-2-pyrimidinyl)oxy]ethoxy}-1-methyl-4-(4-methylphenyl)-1H-pyrazol-5-yl]-4-(tert-butyl)benzenesulfonamide

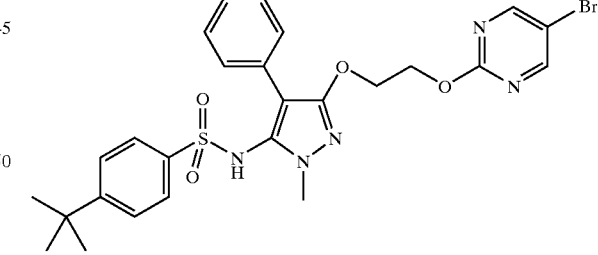

To 4-(tert-butyl)-N-[3-(2-hydroxyethoxy)-1-methyl-4-(4-methylphenyl)-1H-pyrazol-5-yl]benzenesulfonamide (Example 2) (25 mg) in tetrahydrofuran (2 ml) at room temperature under an atmosphere of nitrogen was added sodium hydride (60% dispersion in oil, 4.5 mg) and the mixture was stirred for 5 minutes. To the mixture was added 5-bromo-2-chloropyrimidine (*Liquid Crystals*, 1993, 14(3), 741) (12 mg) and the reaction was stirred for 30 minutes after which dimethyl acetamide (0.5 ml) was added to give a homogenous mixture. After further stirring for 3 hrs the reaction was diluted with water (20 ml) and extracted with ethyl acetate (20 ml). The organic fraction was dried over magnesium sulfate, filtered concentrated under reduced pressure. The residue was purified by column chromatography on silica (10 Og) eluted with dichloromethane ether (1:1) to yield the title compound as a white solid (12 mg).

$\delta_H$ (300 MHz, CDCl$_3$) 8.25 (2H, s), 7.35 (2H, d), 7.15 (2H, d), 6.80 (4H, dd), 6.60 (1H, s), 4.65 (2H, t), 4.50 (2H, t), 3.80 (3H, s), 2.10 (3H, s), 1.15 (9H, s). m/z (thermospray) [MH$^+$]=600.3; C$_{27}$H$_{31}$BrN$_5$O$_4$S requires 600.1

Example 4

4-(tert-butyl)-N-[3-{2-[(5-methoxy-2-pyrimidinyl)oxy]ethoxy}-1-methyl-4-(4-methylphenyl)-1H-pyrazol-5-yl]benzenesulfonamide

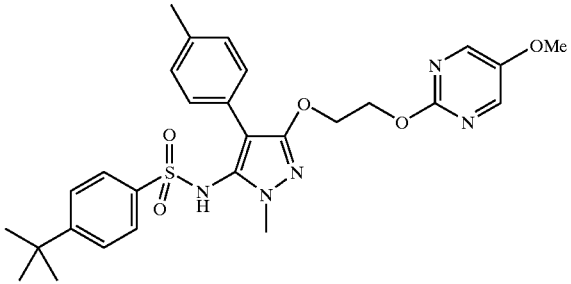

To 4-(tert-butyl)-N-[3-(2-hydroxyethoxy)-1-methyl-4-(4-methylphenyl)-1H-pyrazol-5-yl]benzenesulfonamide (Example 2) (250 mg) in tetrahydrofuran (20 ml) at room temperature under an atmosphere of nitrogen was added sodium hydride (60% dispersion in oil, 47 mg) and the mixture was stirred for 5 minutes. To the mixture was added a solution of 5-methoxy-2-methylsulphonylpyrimidine (Aktual. Probl. Razvit. Nauchn. Issled. Molodykh Uch. Spets. Vil'nyus. Gosuniv. im. V. Kapsukasa, Mater. Konf. Molodykh Uch. Spets. Estestv. Khim. Fak. (1980), 87–90. Editor(s): Grigonis, I. Publisher: Vil'nyus. Gos. Univ. im. V. Kapsukasa, Vilnius, USSR.) (160 mg) in dimethylacetamide (2 ml) and the reaction was stirred for a further 16 hrs. The reaction was diluted with water (100 ml) and extracted with ethyl acetate (100 ml). The organic fraction was dried over magnesium sulfate, filtered and concentrated under reduced pressure. The residue was purified by column chromatography on silica (10 g) eluted with dichloromethane: ether:hexane (10:2.5:1) to yield the title compound as a white solid (190 mg).

$\delta_H$ (300 MHz, CDCl$_3$) 8.15 (2H, s), 7.20 (2H, d), 7.10 (2H, d), 6.80 (1H, s), 6.75 (4H, s), 4.65 (2H, t), 4.55 (2H, t), 3.85 (3H, s), 3.80 (3H, s), 2.10 (3H, s), 1.15 (9H, s). m/z (thermospray) [MH$^+$]=552.2; C$_{28}$H$_{34}$N$_5$O$_5$S requires 552.2

Example 5

4-(tert-butyl)-N-[3-{2-[(5-chloro-2-pyrimidinyl)oxy]ethoxy}-1-methyl-4-(4-methylphenyl)-1H-pyrazol-5-yl]benzenesulfonamide

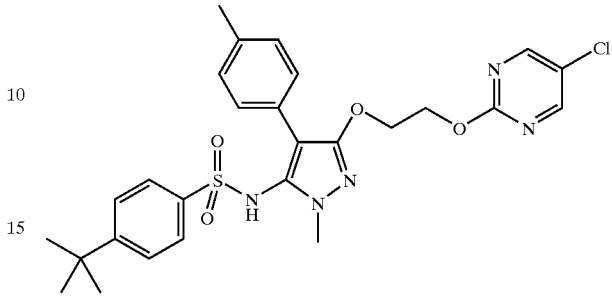

To 4-(tert-butyl)-N-[3-(2-hydroxyethoxy)-1-methyl-4-(4-methylphenyl)-1H-pyrazol-5-yl]benzenesulfonamide (Example 2) (196 mg) in tetrahydrofuran (2.5 ml) at room temperature under an atmosphere of nitrogen was added sodium hydride (60% dispersion in oil, 37 mg) and the mixture was stirred for 5 minutes. To the mixture was added a solution of 5-chloro-2-methylsulphonylpyrimidine (94 mg) in tetrahydrofuran (5 ml) and dimethylacetamide (0.5 ml) the mixture was stirred for a further 48 hrs. The reaction was diluted with water (200 ml) and extracted with dichloromethane (3×50 ml). The organic fractions were combined, washed with brine (10 ml), dried over magnesium sulfate, filtered and concentrated under reduced pressure. The residue was purified by column chromatography on silica (20 g) eluted with ether:hexane (4:1) to yield the title compound as a white solid (170 mg).

$\delta_H$ (300 MHz, CDCl$_3$) 8.20 (2H, s), 7.20 (2H, d), 7.15 (2H, d), 6.80 (4H, dd), 6.80 (1H, s), 4.65 (2H, t), 4.55 (2H, t), 3.80 (3H, s), 2.10 (3H, s), 1.15 (9H, s). m/z (negative ion electrospray) [MH$^+$]=554.0; C$_{27}$H$_{31}$ClN$_5$O$_4$S requires 554.2

Example 6

4-(tert-butyl)-N-[1-methyl-4-(4-methylphenyl)-3-(2-{[5-(2-thienyl)-2-pyrimidinyl]oxy}ethoxy)-1H-pyrazol-5-yl]benzenesulfonamide

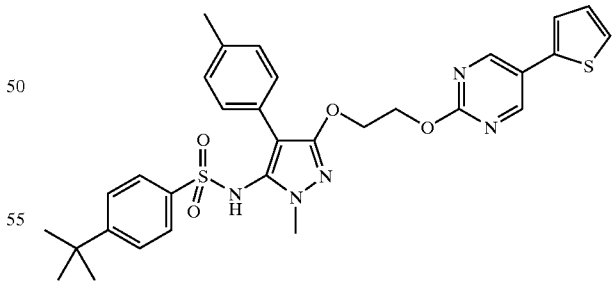

To N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (Example 3) (111 mg) in 1,4-dioxane (5 ml) at room temperature was added 2-(tributylstannyl)thiophene (103 mg) and bis(triphenylphosphine)palladium (II) chloride (6.5 mg) the mixture was stirred and heated to reflux for 3 hrs followed by 16 hrs. at room temperature. To the mixture was added bis(triphenylphosphine)palladium (II) chloride (6.5 mg) and the mixture was heated to reflux for a further 4 hrs. The reaction was diluted with ethyl acetate (100 ml), washed with a 10% solution of potassium fluoride in water (100 ml) and brine (100 ml), dried over magnesium sulfate, filtered and concentrated under reduced pressure. The residue was purified by column chromatography on silica (10 g) eluted with ethyl acetate:hexane (1:1) to yield the title compound as a white solid (75 mg).

$\delta_H$ (300 MHz, CDCl$_3$) 8.65 (2H, s), 7.00–7.20 (8H, m), 6.80 (4H, dd), 4.75 (2H, t), 4.55 (2H, t), 3.80 (3H, s), 2.10 (3H, s), 1.15 (9H, s). m/z (positive ion electrospray) [MH$^+$]= 604.0; $C_{31}H_{34}N_5O_4S_2$ requires 604.2

Example 7

4-(tert-butyl)-N-[3-(2-{[5-(2-furyl)-2-pyrimidinyl]oxy}ethoxy)-1-methyl-4-(4-methylphenyl)-1H-pyrazol-5-yl]benzenesulfonamide

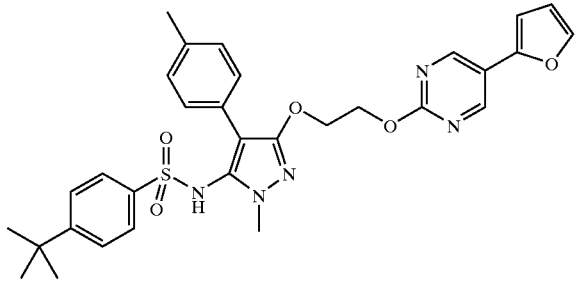

To N-[3-{2-[(5-bromo-2-pyrimidinyl)oxy]ethoxy}-1-methyl-4-(4-methylphenyl)-1H-pyrazol-5-yl)]4-(tert-butyl)benzenesulfonamide (Example 3) (277 mg) in 1,4-dioxane (7.5 ml) at room temperature was added 2-(tributylstannyl) furan (329 mg) and bis(triphenylphosphine)palladium (II) chloride (32 mg) the mixture was stirred and heated to reflux for 16 hrs. The reaction was diluted with ethyl acetate (100 ml) and washed with a 10% solution of potassium fluoride in water (100 ml), the aqueous portion was then extracted with ethyl acetate (100 ml). The organic fractions were separated and combined, washed with brine (100 ml), dried over magnesium sulfate, filtered and concentrated under reduced pressure. The residue was purified by column chromatography on silica (10 g) eluted with ethyl acetate-:hexane (3:2) to yield an oil which was dissolved in acetonitrile (20 ml) and washed with hexane (6×10 ml). Evaporation of the acetonitrile under reduced pressure yielded the title compound as a white solid (235 mg).

$\delta_H$ (300 MHz, CDCl$_3$) 8.65 (2H, s), 7.50 (1H, d), 7.20 (2H, d), 7.10 (2H, d), 6.75 (4H, dd), 6.60 (1H, d), 6.50 (1H, t), 4.75 (2H, t), 4.55 (2H, t), 3.80 (3H, s), 2.15 (3H, s), 1.20 (9H, s). m/z (thermospray) [MH$^+$]=588.2; $C_{31}H_{34}N_5O_5S$ requires 588.2

Example 8

N-3-(2-hydroxyethoxy)-1-methyl-4-(4-methylphenyl)-1H-pyrazol-5-yl]4-(tert-pentyl)benzenesulfonamide

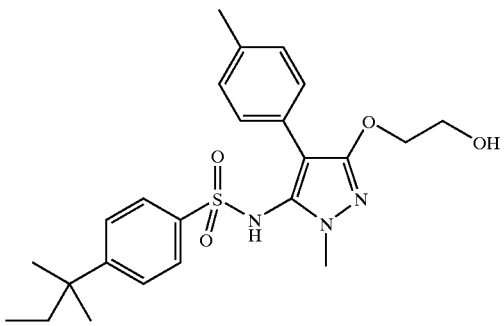

To 2-{[5-amino-1-methyl-4-(4-methylphenyl)-1H-pyrazol-3-yl]oxy}ethyl acetate (Preparation 5) (1.0 g) in dimethylacetamide (10 ml) at 0° C. under an atmosphere of nitrogen was added sodium hydride (60% dispersion in oil, 415 mg) followed by 4-tert-amylbenzenesulphonyl chloride and (938 mg), the mixture was stirred for 2 hrs. The reaction was diluted with water (50 ml) and extracted with dichloromethane (5×30 ml). The crude mixture was dissolved in ethanol (50 ml) and sodium hydroxide (2N, 5 ml) was added, the mixture was stirred at room temperature for 48 hrs and then neutralised to pH 7 by addition of hydrochloric acid (2N) and extracted with dichloromethane (2×50 ml). The organic fractions were combined, dried over magnesium sulfate, filtered and concentrated under reduced pressure. The residue was purified by column chromatography (silica, 10 g) eluted with ethyl acetate:hexane (1:1) to yield the title compound as a white solid (290 mg).

$\delta_H$ (300 MHz, CDCl$_3$) 7.45 (2H, d), 7.15 (2H, d), 6.90 (2H, d), 6.85 (2H, d), 6.75 (1H, br. s), 4.30 (2H, t), 3.90 (2H, t), 3.80 (3H, s), 2.25 (3H, s), 1.60 (2H, q), 1.20 (6H, s), 0.65 (3H,t). m/z (positive ion electrospray) [MH$^+$]=458.0; $C_{24}H_{32}N_3O_4S$ requires 458.2

Example 9

N-[3-{2-[(5bromo-2-pyrimidinyl)oxy]ethoxy}-1-methyl-4-(4-methylphenyl)-1H-pyrazol-5-yl]-4-(tert-pentyl)benzenesulfonamide

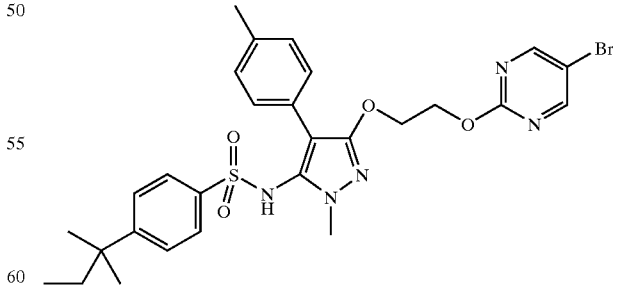

To N-[3-(2-hydroxyethoxy)-1-methyl-4-(4-methylphenyl)-1H-pyrazol-5-yl]-4-(tert-pentyl)benzenesulfonamide (Example 8) (270 mg) in tetrahydrofuran (4 ml) at room temperature under an atmosphere of nitrogen was added sodium hydride (60% dispersion in oil, 50 mg) and the mixture was stirred for 1 minute. To the mixture was added dimethyl acetamide (0.5 ml) followed by 5-bromo-2-chloropyrimidine (171 mg). The mixture was stirred for 2 hours at room temperature and then diluted with water (20 ml) and extracted with ether (2×20 ml). The organic fractions were combined, dried over magnesium sulfate, filtered and concentrated under reduced pressure. The residue was purified by column chromatography on silica (35 g) eluted with hexane:ethyl acetate (2:1 to 1:2) to yield the title compound as an orange oil (292 mg).

$\delta_H$ (300 MHz, CDCl$_3$) 8.45 (2H, s), 7.40 (2H, d), 7.10 (2H, d), 6.80 (4H, dd), 4.65 (2H, t), 4.55 (2H, t), 3.80 (3H, s), 2.10 (3H, s), 1.35 (2H, q), 1.10 (6H, s), 0.65 (3H, t). m/z (thermospray) [MH$^+$]=614.1; C$_{28}$H$_{33}$N$_5$O$_4$S requires 614.1

Example 10

N-[4-(1-benzo[b]thiophen-2-yl)-3-(2-hydroxyethoxy)-1-methyl-1H-pyrazol-5-yl]-4-(tert-butyl)benzenesulfonamide

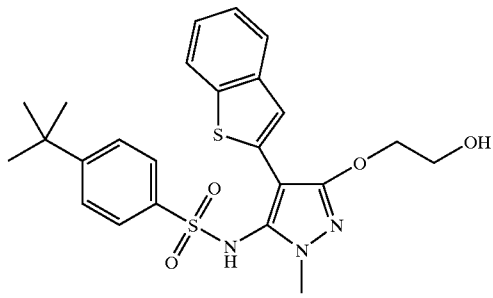

Isobutyl 2-{3-[2-(acetyloxy)ethoxy]-4-iodo-1-methyl-1H-pyrazol-5-yl}-2-{[4-(tert-butyl)phenyl]sulfonyl}acetate (Preparation 6) (312 mg), benzo[b]thiophene-2-boronic acid (98 mg) and cesium carbonate (0.66 g) were suspended in 1,4-dioxane (10 ml) and water (1 ml). The mixture was degassed (vacuum and nitrogen atmosphere) and then tetrakis(triphenylphosphine)-palladium(0) (15 mg) was added and the mixture degassed again. The mixture was heated at reflux for 3 hours and cooled to room temperature. Ethanol (10 ml) and 2M NaOH (10 ml) were then added to the reaction and the mixture stirred for a further 1 hour at room temperature. The reaction was quenched with saturated aqueous ammonium chloride and extracted with ethyl acetate (3×10 ml). The combined organics were washed with brine, dried with magnesium sulfate, filtered and concentrated under reduced pressure. The crude product was purified by chromatography on silica eluted with ethyl acetate-:hexane (3:1) yielded the desired product as a beige solid (121 mg).

$\delta_H$(300 MHz, CDCl$_3$) 7.62–7.46 (4H, m), 7.30–7.17 (2H, m), 7.15 (2H, d), 6.88 (1H,s), 1H, s), 4.50–4.40 (2H, m), 4.03–3.97 (2H, m), 3.82 (3H, s), 0.98 (9H, s). m/z (positive ion electrospray) [MH$^+$]=486.1; C$_{24}$H$_{28}$N$_3$O$_4$S$_2$ requires 486.1

Example 11

N-(4-(1-benzothiophen-2-yl)-3-{2-[(5-bromo-2-pyrimidinyl)oxy]ethoxy}-1-methyl-1H-pyrazol-5-yl)-4-(tert-butyl)benzenesulfonamide

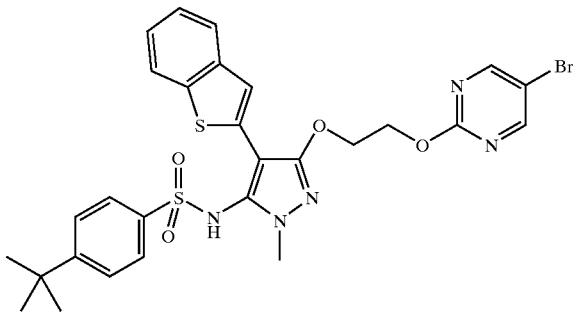

To N-[4-(1-benzo[b]thiophen-2-yl)-3-(2-hydroxyethoxy)-1-methyl-1H-pyrazol-5-yl]-4-(tert-butyl)benzenesulfonamide (Example 10) (60 mg) in THF (6 ml) at room temperature was added sodium hydride (11 mg of a 60% dispersion in oil) and the mixture was stirred for five minutes. A solution of 5-bromo-2-chloropyrimidine (*Liquid Crystals* 1993, 14(3), 741–761) (35.9 mg) in dimethylacetamide (2.5 ml) was then added dropwise to the reaction, which was then allowed to stir for one hour at room temperature and then a further portion of 5-bromo-2-chloropyrimidine (10 mg) was added and the reaction stirred overnight. The reaction was poured onto water (50 ml) and extracted with ethyl acetate (3×20 mls.). The organics were then back-washed with brine, dried over magnesium sulfate, filtered and concentrated under reduced pressure to yield the crude material (97 mg). The crude material was purified by HPLC on a 5 μODS Phenomenex Primesphere™ column with a gradient elution of acetonitrile (5% to 95%) and 0.1M NH$_4$OAc (95% to 5%) to yield the desired product as an off white solid (4 mg).

$\delta_H$ (300 MHz, CDCl$_3$) 8.49 (2H, s), 7.58–7.42 (4H, m), 7.30–7.11 (2H, m), 7.08 (2H, d), 6.87 (1H, s), 4.79–4.71 (2H, m), 4.69–4.60 (2H, m), 3.82 (3H, s), 0.94 (9H, s). m/z (thermospray) [MH$^+$]=641.7; C$_{28}$H$_{29}$BrN$_5$O$_4$S$_2$ requires 642.1

Example 12

4-(tert-butyl)-N-{3-(2-hydroxyethoxy)-1-methyl-4-[4-(trifluoromethyl)phenyl]-1H-pyrazol-5-yl)benzenesulfonamide

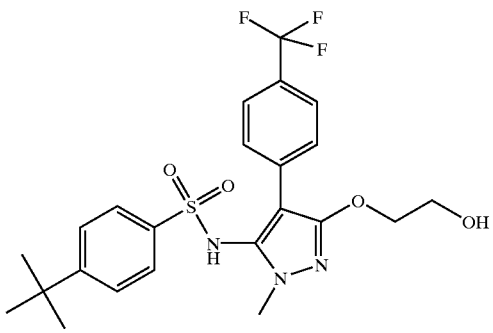

To 4-(tert-butyl)-N-{3-(2-hydroxyethoxy)-1-methyl-4-[4-(trifluoromethyl)phenyl]-1H-pyrazol-5-yl}-N-[(2- methoxyethoxy)methyl]benzenesulfonamide (Preparation 12) in ethanol (1.5 ml) was added hydrochloric acid (6M, 1.5 ml). The reaction mixture was refluxed for 5 hours and then left at room temperature overnight. The reaction was concentrated under reduced pressure and the residue was partitioned between water (10 ml) and ethyl acetate (10 ml). The aqueous was extracted with ethyl acetate (2×20 ml). The organics were combined, dried over magnesium sulfate, filtered and concentrated under reduced pressure to yield the desired product (120 mg) as a white solid. Taken on crude to the next step.

$\delta_H$ (300 MHz, CDCl$_3$) 7.39 (2H, d), 7.29 (2H, d), 7.22–7.09 (4H, m), 4.40–4.32 (2H, m), 3.98–3.89 (2H, m), 3.80 (3H, s), 1.22 (9H, s). m/z (thermospray) [MH$^+$]=498.2; C$_{23}$H$_{27}$F$_3$N$_3$O$_4$S requires 498.2

Example 13

N-{3-{2-[(5-bromo-2-pyrimidinyl)oxy]ethoxy}-1-methyl-4-[4-(trifluoromethyl)phenyl]-1H-pyrazol-5-yl)}-4-(tert-butyl)benzenesulfonamide

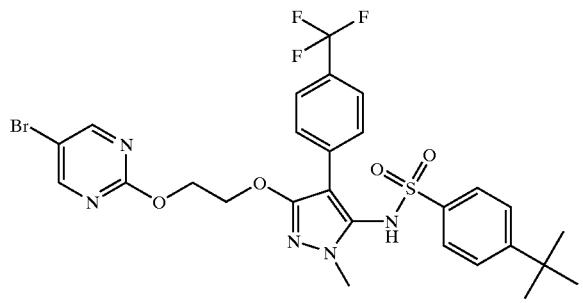

To 4-(tert-butyl)-N-{3-(2-hydroxyethoxy)-1-methyl-4-[4-(trifluoromethyl)phenyl]-1H-pyrazol-5-yl}benzenesulfonamide (Example 12) (60 mg) in THF (6 ml) at 0° C. was added sodium hydride (12 mg of a 60% dispersion in oil) followed by the 5-bromo-2-chloropyrimidine (39 mg). The reaction was stirred for one hour at 0° C. and then at room temperature overnight. Water (5 ml) was then added to the reaction followed by saturated aqueous ammonium chloride (5 ml) and the mixture was extracted with ethyl acetate (3×10 ml). The combined organics were washed with saturated aqueous ammonium chloride (20 ml), dried over magnesium sulfate, filtered and concentrated under reduced pressure to yield the crude material (61 mg). The crude material was purified by HPLC on a 5μ ODS Phenomenex Magellen™ column with a gradient elution of acetonitrile (5% to 95%) and 0.1M NH$_4$OAc (95% to 5%) to yield the desired product as an off white solid (15.5 mg).

$\delta_H$ (300 MHz, CDCl$_3$) 8.49 (2H, s), 7.40 (2H, d), 7.30–7.22 (3H, m), 7.18 (2H, d), 7.10 (2H, d), 4.77–4.66 (2H, m), 4.62–4.55 (2H, m), 3.82 (3H, s), 0.94 (9H, s). m/z (negative ion electrospray) [MH$^+$]=652; C$_{27}$H$_{23}$BrF$_3$N$_3$O$_4$S requires 652.1

Example 14

4-(tert-butyl)-N-{3-{2-[(5-methoxy-2-pyrimidinyl)oxy]ethoxy}-1-methyl-4-[4-(trifluoromethyl)phenyl]-1H-pyrazol-5-yl}benzenesulfonamide

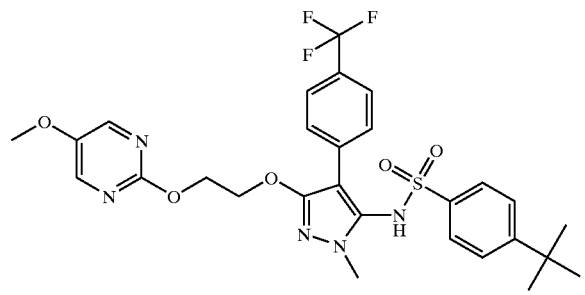

The title compound was made according to the procedure used for Example 13 except that 5-methoxy-2-methylsulphonylpyrimidine (34 mg) was used in place of the 5-bromo-2-chloropyrimidine. The reaction yielded the crude material (61 mg) which was purified by HPLC on a 5μ ODS Phenomenex Magellen™ column with a gradient elution of acetonitrile (5% to 95%) and 0.1M NH$_4$OAc (95% to 5%) to yield the desired product as an off white solid (13 mg).

$\delta_H$ (300 MHz, CDCl$_3$) 8.19 (2H, s), 7.40 (2H, d), 7.22 (2H, d), 7.20 (1H, s), 7.19–7.08 (4H, m), 4.69–4.60 (2H, m), 4.60–4.50 (2H, m), 3.85 (3H, s), 3.82 (3H, s), 1.22 (9H, s). m/z (thermospray) [MH$^+$]=606.1; C$_{28}$H$_{31}$F$_3$N$_5$O$_5$S requires 606.2

Example 15

4-(tert-butyl)-N-{3-(2-hydroxyethoxy)-1-methyl-4-phenyl-1H-pyrazol-5-yl)benzenesulfonamide

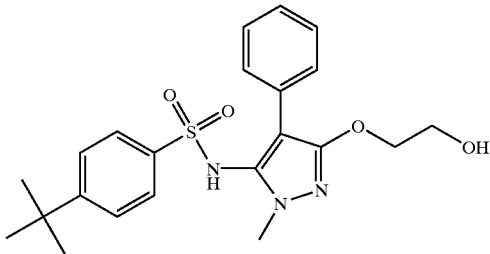

To 4-(tert-butyl)-N-[3-(2-hydroxyethoxy)-1-methyl-4-phenyl-1H-pyrazol-5-yl]-N-[(2-methoxyethoxy)methyl]benzenesulfonamide (528 mg)

(Preparation 15) in ethanol (10 ml) was added hydrochloric acid (6M, 10 ml). The reaction mixture was refluxed for 2 hours and then left at room temperature overnight. The reaction was concentrated under reduced pressure and the residue was partitioned between water (50 ml) and ethyl acetate (50 ml). The aqueous layer was extracted with ethyl acetate (3×20 ml). The organics were combined, dried over magnesium sulfate, filtered and concentrated under reduced pressure. The crude material was purified by chromatography on a suction column packed with silica eluted with ethyl acetate:hexane (1:3 to 3:1) to yield the desired product as an off white solid (165 mg).

$\delta_H$ (300 MHz, CDCl$_3$) 7.40 (2H, d), 7.16 (2H, d), 7.09–7.00 (3H, m), 7.00–6.90 (2H, m), 6.85 (2H, d), 4.38–4.30(2H, m), 3.92–3.88 (2H, m), 3.82 (3H, s), 1.22 (9H, s). m/z (negative ion electrospray) [MH$^+$]=428.1; C$_{22}$H$_{28}$N$_3$O$_4$S requires 428.2

Example 16

N-(3-{2-[(5-bromo-2-pyrimidinyl)oxy]ethoxy}-1-methyl-4-phenyl-1H-pyrazol-5-yl)-4-(tert-butyl)benzenesulfonamide

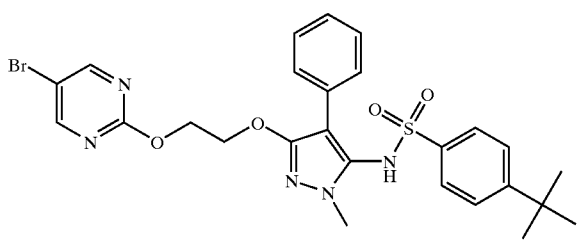

The title compound was made according to the procedure used for Example 13 except that (63 mg) of 5-bromo-2-chloropyrimidine was used and that 4-(tert-butyl)-N-{3-(2-hydroxyethoxy)-1-methyl-4-phenyl-1H-pyrazol-5-yl}benzenesulfonamide (Example 15) (80 mg) was used in place of 4-(tert-butyl)-N-{3-(2-hydroxyethoxy)-1-methyl-4-[4-(trifluoromethyl)phenyl]-1H-pyrazol-5-yl}benzenesulfonamide (Example 12). The crude material was purified by HPLC on a 5µ ODS Phenomenex Magellen™ column with a gradient elution of acetonitrile (5% to 95%) and 0.1M NH$_4$OAc (95% to 5%) to yield the desired product as an off white solid (52 mg).

$\delta_H$ (300 MHz, CDCl$_3$) 8.49 (2H, s), 7.38 (2H,d), 7.16 (2H, d), 7.02–6.96 (4H, m), 6.91–6.83 (2H, m), 4.71–4.68 (2H, m), 4.60–4.52 (2H, m), 3.82 (3H, s), 1.22 (9H, s). m/z (positive ion electrospray) [MH$^+$]=586; C$_{26}$H$_{29}$BrN$_5$O$_4$S requires 586.1

Example 17

N-[4-(1,3-benzodioxol-5-yl)-3-(2-hydroxyethoxy)-1-methyl-1H-pyrazol-5-yl]-4-(tert-butyl)benzenesulfonamide

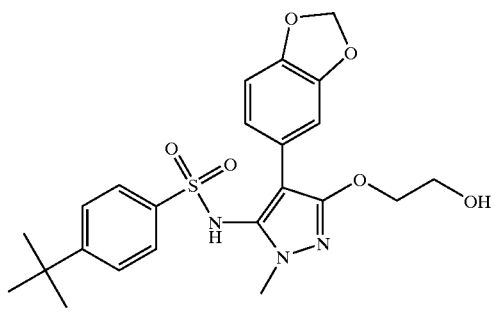

To N-[4-(1,3-benzodioxol-5-yl)-3-(2-hydroxyethoxy)-1-methyl-1H-pyrazol-5-yl]4-(tert-butyl)-N-[(2-methoxyethoxy)methyl]benzenesulfonamide (Preparation 17) (380 mg) in ethanol (8 ml) was added hydrochloric acid 6M (8 ml). The reaction mixture was refluxed for 2 hours and then left at room temperature overnight. The reaction was concentrated under reduced pressure and the residue was partitioned between water (50 ml) and ethyl acetate (50 ml). The aqueous layer was extracted with ethyl acetate (3×20 ml). The organics were combined, dried over magnesium sulfate, filtered and concentrated under reduced pressure. The crude material was purified by chromatography on a suction column packed with silica eluted with ethyl acetate:hexane (1:3 to 3:1) to yield the desired product as an off white solid (131 mg).

$\delta_H$ (300 MHz, CDCl$_3$) 7.40 (2H, d), 7.16 (2H, d), 7.09–7.00 (3H, m), 7.00–6.90 (2H, m), 6.85 (2H, d), 4.38–4.30(2H, m), 3.92–3.88 (2H, m), 3.82 (3H, s), 1.22 (9H, s). m/z (negative ion electrospray) [MH$^+$]=472.1; C$_{23}$H$_{28}$N$_3$O$_6$S requires 472.2

Example 18

N-(4-(1,3-benzodioxol-5-yl)-3-{2-[(5-bromo-2-pyrimidinyl)oxy]ethoxy}-1-methyl-1H-pyrazol-5-yl)-4-(tert-butyl)benzenesulfonamide

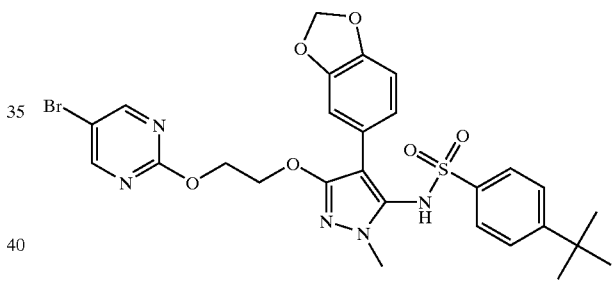

The title compound was made according to the procedure used for Example 13 except that (45 mg) of 5-bromo-2-chloropyrimidine was used and that N-[4-(1,3-benzodioxol-5-yl)-3-(2-hydroxyethoxy)-1-methyl-1H-pyrazol-5-yl]-4-(tert-butyl)benzenesulfonamide (Example 17) (70 mg) was used in place of 4-(tert-butyl)-N-{3-(2-hydroxyethoxy)-1-methyl-4-[4-(trifluoromethyl)phenyl]-1H-pyrazol-5-yl}benzenesulfonamide (Example 12). The crude was purified by HPLC on a 5µ ODS Phenomenex Magellen™ column with a gradient elution of acetonitrile (5% to 95%) and 0.1M NH$_4$OAc (95% to 5%) to yield the desired product as an off white solid (19.6 mg).

$\delta_H$ (300 MHz, CDCl$_3$) 8.49 (2H, s), 7.42 (2H, d), 7.21 (2H, d), 7.25 (1H, s), 6.60–6.57 (1H, m), 6.48 (1H, d), 6.40–6.32 (2H, m), 5.83 (2H, s), 4.75–4.68 (2H, m), 4.59–4.52 (2H, m), 3.82 (3H, s), 3.76 (3H, s), 1.22 (9H, s). m/z (positive ion electrospray) [MH$^+$]=630; C$_{27}$H$_{30}$BrN$_5$O$_6$S requires 630.1

Example 19

4-(tert-butyl)-N-[4-(4-chlorophenyl)-3-(2-hydroxyethoxy)-1-methyl-1H-pyrazol-5-yl]benzenesulfonamide

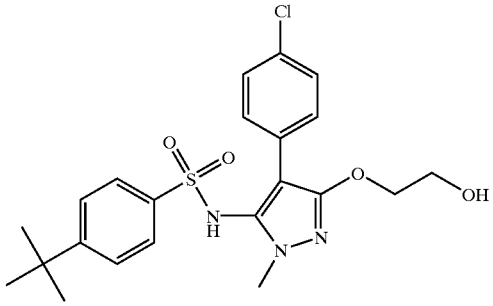

To 4-(tert-butyl)-N-[4-(4-chlorophenyl)-3-(2-hydroxyethoxy)-1-methyl-1H-pyrazol-5-yl]-N-[(2-methoxyethoxy)methyl]benzenesulfonamide (610 mg) (Preparation 19) in ethanol (12 ml) was added hydrochloric acid 6M (12 ml). The reaction mixture was refluxed for 2 hours and then left at room temperature overnight. The reaction was concentrated under reduced pressure and the residue was partitioned between water (50 ml) and ethyl acetate (50 ml). The aqueous layer was extracted with ethyl acetate (3×20 ml). The organics were combined, dried over magnesium sulfate, filtered and concentrated under reduced pressure. The crude material was purified by chromatography on a suction column packed with silica (20 g) eluted with ethyl acetate:hexane (1:3 to 3:1) to yield the desired product as an off white solid (30 mg).

$\delta_H$ (300 MHz, CDCl$_3$) 7.51–7.35 (2H, m), 7.20 (2H, d), 7.05–6.95 (4H, m), 6.88 (2H, d), 4.35–4.40 (2H, m), 3.87–3.90 (2H, m), 3.82 (3H, s), 1.22 (9H, s).

Example 20

N-[3-{2-[(5-bromo-2-pyrimidinyl)oxy]ethoxy}-4-(4-chlorophenyl)-1-methyl-1H-pyrazol-5-yl]-4-(tert-butyl)benzenesulfonamide

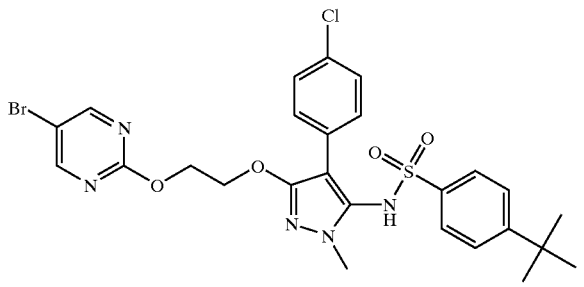

The title compound was made according to the procedure used for Example 13 except that (21 mg) of 5-bromo-2-chloropyrimidine was used and 4-(tert-butyl)-N-[4-(4-chlorophenyl)-3-(2-hydroxyethoxy)-1-methyl-1H-pyrazol-5-yl]benzenesulfonamide (Example 19) (30 mg) was used in place of 4-(tert-butyl)-N-(3-(2-hydroxyethoxy)-1-methyl-4-[4-(trifluoromethyl)phenyl]-1H-pyrazol-5-yl}benzenesulfonamide (Example 12). The crude material was purified by HPLC on a 5μ ODS Phenomenex Magellen column with a gradient elution of acetonitrile (5% to 95%) and 0.1M NH$_4$OAc (95% to 5%) to yield the desired product as an off white solid (3 mg).

$\delta_H$ (300 MHz, CDCl$_3$) 8.49 (2H, s), 7.40 (2H, d), 7.18 (2H, d), 6.98 (2H, d), 6.88 (2H, d), 4.71–4.65 (2H, m), 4.60–4.54 (2H, m), 3.82 (3H, s), 3.76 (3H, s), 1.22 (9H, s).

Example 21

4-(tert-butyl)-N-[3-(2-hydroxyethoxy)-4-(4-methoxyphenyl)-1-methyl-1H-pyrazol-5-yl]benzenesulfonamide

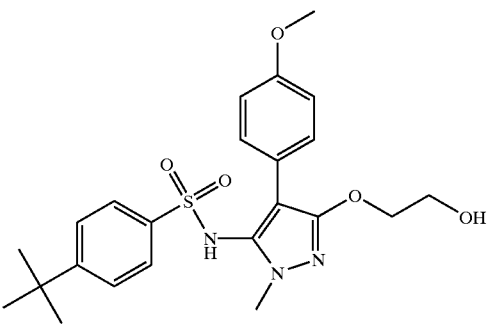

The title compound was made according to the procedure of Example 15 except that 4tert-butyl)-N-[4-(4-methoxyphenyl)-3-(2-hydroxyethoxy)-1-methyl-1H-pyrazol-5-yl]-N-[(2-methoxyethoxy)methyl]benzenesulfonamide (Preparation 21) (507 mg) was used in place of 4-(tert-butyl)-N-[3-(2-hydroxyethoxy)-1-methyl-4-phenyl-1H-pyrazol-5-yl]-N-[(2-methoxyethoxy)methyl]benzenesulfonamide (528 mg) (Preparation 15). The desired product was obtained as an off white solid (169 mg).

$\delta_H$ (300 MHz, CDCl$_3$) 7.40 (2H, d), 7.12 (2H, d), 6.90 (2H, d), 6.55 (2H, d), 4.32–4.28 (2H, m), 3.90–3.83 (2H, m), 3.75 (3H, s), 3.69 (3H, s), 1.22 (9H, s). m/z (positive ion electrospray) [MH$^+$]=460.1; C$_{23}$H$_{31}$N$_3$O$_3$S requires 460.2

Example 22

N-[3-{2-[(5-bromo-2-pyrimidinyl)oxy]ethoxy}-4-(4-methoxyphenyl)-1-methyl-1H-pyrazol-5-yl]-4-(tert-butyl)benzenesulfonamide

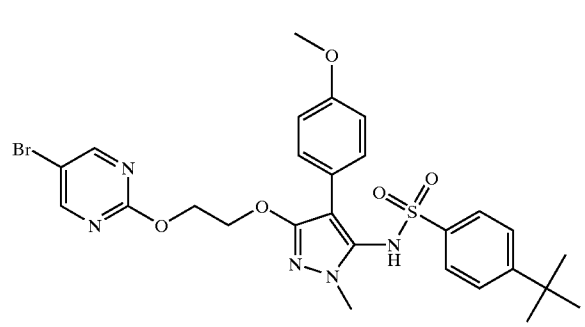

The title compound was made according to the procedure used for Example 13 except that (60 mg) of 5-bromo-2-chloropyrimidine was used and 4-(tert-butyl)-N-[3-(2-hydroxyethoxy)-4-(4-methoxyphenyl)-1-methyl-1H-pyrazol-5-yl]benzenesulfonamide (Example 21) (85 mg) was used in place of 4-(tert-butyl)-N-{3-(2-hydroxyethoxy)-1-methyl-4-[4-(trifluoromethyl)phenyl]-1H-pyrazol-5-yl}benzenesulfonamide (Example 12). The crude material was purified by HPLC on a 5μ ODS Phenomenex Magellen column with a gradient elution of acetonitrile (5% to 95%) and 0.1M NH₄OAc (95% to 5%) to yield the desired product as an off white solid (30.2 mg).

$\delta_H$ (300 MHz, CDCl$_3$) 8.49 (2H, s), 7.40 (2H, d), 7.19 (2H, d), 6.85 (2H, d), 6.82 (2H, d), 6.80 (1H, s), 6.60 (1H, s), 4.72–4.68 (2H, m), 4.59–4.51 (2H, m), 3.82 (3H, s), 3.76 (3H, s), 1.22 (9s). m/z (thermospray) [MH$^+$]=616.3; C$_{27}$H$_{31}$BrN$_5$O$_5$S requires 616.1

Example 23

4-(tert-butyl)-N-[5-(2-hydroxyethoxy)-1-methyl-4-(4-methylphenyl)-1H-pyrazol-5-yl]benzenesulfonamide

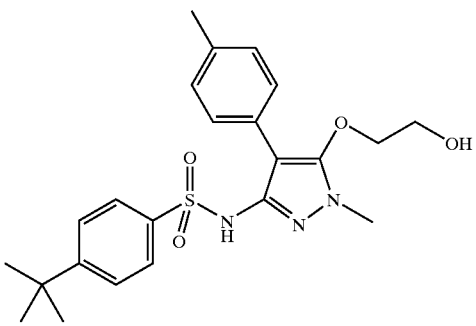

To 2-{[3-(bis{[4-(tert-butyl)phenyl]sulfonyl}amino)-1-methyl-4-(4-methylphenyl)-1H-pyrazol-5-yl]oxy}ethyl acetate (Preparation 23) (38 mg) in ethanol (10 ml) at room temperature was added 2M sodium hydroxide (0.5 ml) and the mixture was stirred for 16 hrs. The mixture was reduced in volume to 10 ml by rotary evaporation, diluted with water (10 ml) and extracted with dichloromethane (3×10 ml). The organic fractions were combined, dried over magnesium sulfate, filtered and concentrated under reduced pressure. The residue was purified by column chromatography (silica, 5 g) eluting with ether:dichloromethane (1:1) to yield the title compound as a white solid (16 mg).

$\delta_H$ (300 MHz, CDCl$_3$) 7.65 (2H, d), 7.40 (2H, d), 7.10 (4H, dd), 3.85 (2H, t), 3.60–3.75 (5H, m), 2.35 (3H, s), 1.30 (9H, s). m/z (thermospray)[MH$^+$]=444; C$_{23}$H$_{31}$N$_3$O$_4$S requires 444.2

Example 24

N-[5-{2-[(5-bromo-2-pyrimidinyl)oxy]ethoxy}-1-methyl-4-(4-methylphenyl)-1H-pyrazol-3-yl]-4-(tert-butyl)benzenesulfonamide

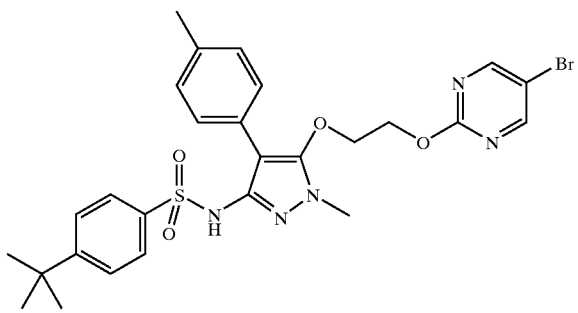

To 4-(tert-butyl)-N-[5-(2-hydroxyethoxy)-1-methyl-4-(4-methylphenyl)-1H-pyrazol-3-yl]benzenesulfonamide (Example 23) (16 mg) in tetrahydrofuran (1.5 ml) at room temperature under an atmosphere of nitrogen was added sodium hydride (60% dispersion in oil, 3 mg) and the mixture was stirred for 5 minutes. To the mixture was added a solution of 5-chloro-2-methylsulphonylpyrimidine (10.5 mg) in tetrahydrofuran (0.5 ml) and dimethyl acetamide (0.5 ml). The mixture was stirred for a further 1 hr. The reaction was diluted with water (10 ml) and extracted with dichloromethane (3×10 ml). The organic fractions were combined, washed with brine (10 ml), dried over magnesium sulfate, filtered and concentrated under reduced pressure. The residue was purified by column chromatography on silica (20 g) eluted with ether dichloromethane (1:1) to yield the title compound as a white solid (15 mg).

$\delta_H$ (300 MHz, CDCl$_3$) 8.45 (2H, s), 7.75 (2H, d), 7.40 (2H, d), 7.05 (4H, s), 6.35 (1H, br, s), 4.40 (2H, t), 4.10 (2H, t), 3.65 (3H, s), 2.30 (3H, s), 1.30 (9H, s). m/z (positive ion electrospray) [MH$^+$]=599.9; C$_{27}$H$_{31}$BrN$_5$O$_4$S requires 600.1

Example 25

N-[1-methyl-4-(4-methylphenyl)-3-{2-[(2-pyrimidinyl)oxy]ethoxy}-1H-pyrazol-5yl]-4-(tert-butyl)benzenesulfonamide

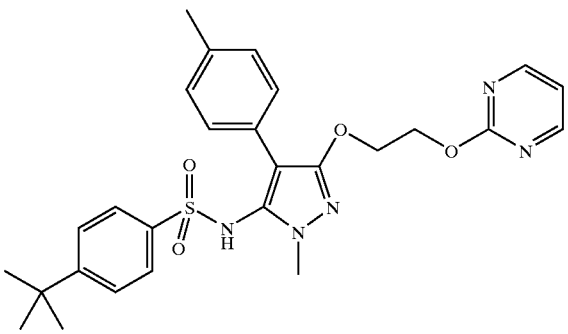

To N-[3-{2-[(5-bromo-2-pyrimidinyl)oxy]ethoxy}-1-methyl-4-(4-methylphenyl)-1H-pyrazol-5-yl]4-(tert-butyl)benzenesulfonamide (Example 3, 100 mg) in anhydrous tetrahydrofuran (2 ml) at 0° C. under an atmosphere of nitrogen was added sodium hydride (60% dispersion in oil, 18 mg), followed by dimethyl acetamide (0.5 ml). The mixture was cooled to −78° C. and n-butyl lithium (1.6M in hexanes, 0.1 ml) was added dropwise under an atmosphere of nitrogen. The yellow solution was allowed to stir at −78° C. for 20 minutes. 1.25 ml of this solution was withdrawn by syringe and added dropwise to a mixture of ether (10 m) and water (10 ml). The aqueous layer was extracted with ether (3×10 ml). The organic fractions were combined, dried over magnesium sulphate, filtered and concentrated under reduced pressure. The residue was purified by column chromatography on silica (10 g) eluted with ethyl acetate-:hexane (2:1) to yield the title compound as a white solid (5 mg).

$\delta_H$ (300 MHz, CDCl$_3$) 8.45 (2H, d), 7.35 (2H, d), 7.15 (2H, d), 6.90 (1H, t), 6.75 (4H, dd), 6.45 (1H, s), 4.65 (2H, t), 4.55 (2H, t), 3.85 (3H, s), 2.10 (3H, s), 1.10 (9H, s). m/z (thermospray) [MH$^+$]=522.2; C$_{27}$H$_{32}$N$_5$O$_4$S requires 522.2

Example 26

4-(tert-butyl)-N-[3-{2-[(5-methylthio-2-pyrimidinyl)oxy]ethoxy}-1-methyl-4-(4-methylphenyl)-1H-pyrazol-5-yl]benzenesulfonamide

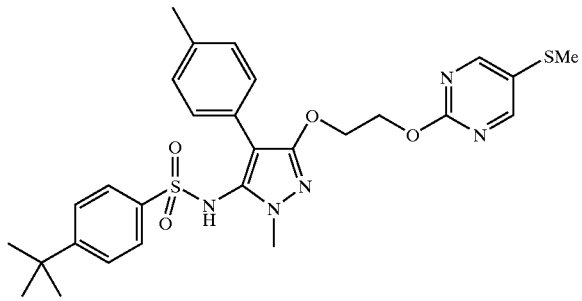

To 4-(tert-butyl)-N-[3-(2-hydroxyethoxy)-1-methyl-4-(4-methylphenyl)-1H-pyrazol-5-yl]benzenesulfonamide (Example 2, 743 mg) in tetrahydrofuran (25 ml) at 0° C. under an atmosphere of nitrogen was added sodium hydride (60% dispersion in oil, 141 mg), the reaction mixture was stirred for 5 minutes. A solution of 2-chloro-5-(methylthio)pyrimidine (269 mg) in dimethyl acetamide (5 ml) was added and the reaction mixture allowed to warm up to room temperature. The reaction mixture was stirred for a further 2 hours. The reaction mixture was poured cautiously into a stirred bi-phasic solution of saturated aqueous ammonium chloride solution (100 ml) and ethyl acetate (100 ml). The organic fraction was separated, dried over magnesium sulphate, filtered and concentrated under reduced pressure. The residue was purified by column chromatography on silica (140 g) eluted with ethyl acetate:hexane (1:1) to yield the title compound as a yellow oil (921 mg).

$\delta_H$ (300 MHz, CDCl$_3$) 8.45 (2H, s), 7.35 (2H, d), 7.10 (2H, d), 6.85 (1H, s), 6.75 (4H, s), 4.65 (2H, t), 4.55 (2H, t), 3.80 (3H, s), 2.45 (3H, s), 2.10 (3H, s), 1.15 (9H, s). m/z (thermospray) [MH$^+$]=568.1; C$_{28}$H$_{34}$N$_5$O$_4$S$_2$ requires 568.2

Examples 27 and 29

4-(tert-butyl)-N-[1-methyl-4-(4-methylphenyl)-3-{2-[(5-methylsulfinyl-2-pyrimidinyl)oxy]ethoxy}-1H-pyrazol-5-yl]benzenesulfonamide 27

4-(tert-butyl)-N-[1-methyl-4-(4-methylphenyl)-3-{2-[(5-methylsulfonyl-2-pyrimidinyl)oxy]ethoxy}-1H-pyrazol-5-yl]benzenesulfonamide 29

27

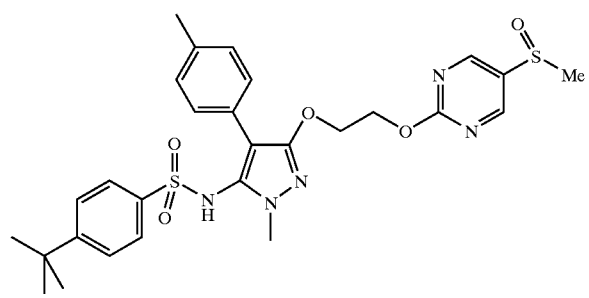

29

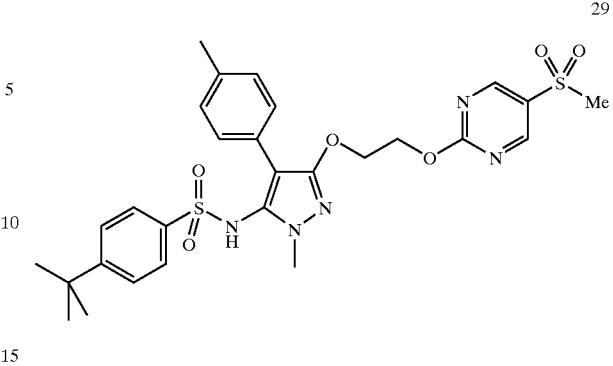

To a solution of 4-(tert-butyl)-N-[1-methyl-4-(4-methylphenyl)-3-{2-[(5-methylthio-2-pyrimidinyl)oxy]ethoxy}-1H-pyrazol-5-yl]benzenesulfonamide (Example 26, 200 mg) in dichloromethane (4 ml) was added dropwise a solution of 3-chloroperoxybenzoic acid (moist 50–55%, 182 mg). The reaction was left to stir for 105 minutes at room temperature. The mixture was diluted with dichloromethane (20 ml) and washed with saturated aqueous ammonium chloride solution (20 ml). The organic fraction was separated, dried over magnesium sulphate, filtered and concentrated under reduced pressure. The residue was purified by column chromatography on silica (25 g) eluted with ethyl acetate:hexane (2:1) to yield a further elution of the column with ethyl acetate:methanol (20:1) gave on evaporation the title compound (Example 27) as a white solid. (70 mg). The crude form of the title compound (Example 29) was further purified by preparative HPLC on a 5μ ODS Phenomenex Magellen™ column with gradient elution of acetonitrile (5% to 95%) and 0.1M NH$_4$OAc (95% to 5%) to give the title compound (Example 29) as a white solid (77 mg).

Example 27

$\delta_H$ (300 MHz, CDCl3) 8.70 (2H, s), 7.35 (2H, d), 7.10 (2H, d), 6.95 (1H, s), 6.80 (4H, s), 4.75 (2H, t), 4.55 (2H, t), 3.80 (3H, s), 2.80 (3H, s), 2.10 (3H, s), 1.15 (9H, s). m/z (thermospray) [MH$^+$]=584.5; C$_{28}$H$_{34}$N$_5$O$_5$S$_2$ requires 584.2

Example 29

$\delta_H$ (300 MHz, CDCl$_3$) 8.90 (2H, s), 7.35 (2H, d), 7.10 (2H, d), 7.00 (1H, s, br), 6.80 (4H, s), 4.80 (2H, t), 4.55 (2H, t), 3.80 (3H, s), 3.10 (3H, s), 2.10 (3H, s), 1.15 (9H, s). m/z (thermospray) [MH$^+$]=600.2; C$_{28}$H$_{34}$N$_5$O$_6$S$_2$ requires 600.2

Example 28

4-(tert-butyl)-N-[3-{2-[(5-fluoro-2-pyrimidinyl)oxy]
ethoxy}-1-methyl-4-(4-methylphenyl)-1H-pyrazol-
5-yl]benzenesulfonamide

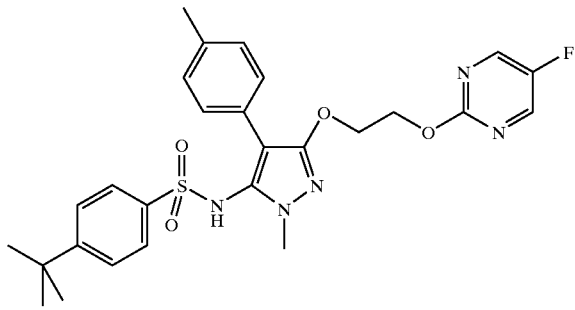

To 4-(tert-butyl)-N-[3-(2-hydroxyethoxy)-1-methyl-4-(4-methylphenyl)-1H-pyrazol-5-yl]benzenesulfonamide (Example 2, 126 mg) in tetrahydrofuran (5 ml) at room temperature under an atmosphere of nitrogen was added sodium hydride (60% dispersion in oil, 34 mg) and the reaction mixture was stirred for 5 minutes. To the reaction mixture was added a solution of 2-chloro-5-fluoropyrimidine (50 mg) in dimethyl acetamide (1 ml) and the reaction was stirred for a further 16 hours. The reaction was poured cautiously into a stirred mixture of saturated aqueous ammonium chloride solution (10 ml) and ethyl acetate (10 ml). The organic fraction was separated, dried over magnesium sulphate, filtered and concentrated under reduced pressure. The residue was purified by preparative HPLC on a 5μ ODS Phenomenex Magellen™ column with gradient elution of acetonitrile (5% to 95%) and 0.1M NH$_4$OAc (95% to 5%) to yield the title compound as a white solid (19 mg).

$\delta_H$ (300 MHz, CDCl$_3$) 8.30 (2H, s), 7.35 (2H, d), 7.10 (2H, d), 6.85 (1H, s), 6.80 (4H, s), 4.65 (2H, t), 4.50 (2H, t), 3.80 (3H, s), 2.05 (3H, s), 1.15 (9H, s). m/z (thermospray) [MH$^+$]=540.2; C$_{27}$H$_{31}$FN$_5$O$_4$S requires 540.2

Example 30

4-(tert-butyl)-N-[3-(2-hydroxyethoxy)-4-(3-methoxyphenyl)-1-methyl-1H-pyrazol-5-yl]
benzenesulphonamide

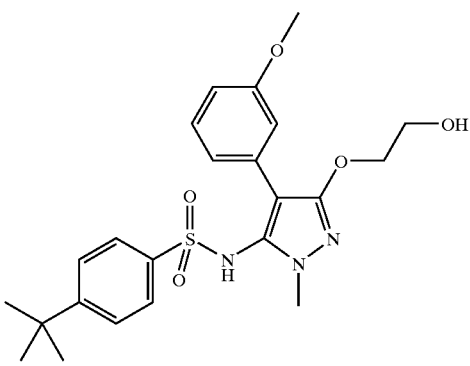

To a solution of isobutyl 2-{3-[2-(acetyloxy)ethoxy]-4-iodo-1-methyl-1H-pyrazol-5-yl}-2-{[4-(tert-butyl)phenyl] sulfonyl}acetate (Preparation 6) (400 mg, 0.6 mmol) in dioxane (12 ml) 2-methoxybenzeneboronic acid (200 mg, 1.2 mmol), cesium carbonate (780 mg, 2.4 mmol) and water (1.2 ml) were added. The resulting solution was de-oxygenated by placing it under vacuum and subsequently re-pressurising with nitrogen gas. This process was repeated a further three times. Tetrakis(triphenylphosphine)palladium (0) (20 mg) was added and the mixture was degassed following the same process as above. The reaction mixture was then heated to reflux for 3 hours. To the reaction mixture ethanol (20 ml) and aqueous sodium hydroxide (2N, 20 ml) were added; the reaction mixture was stirred at room temperature overnight. The reaction mixture was partitioned between saturated aqueous ammonium chloride (100 ml) and ethyl acetate (50 ml). The aqueous layer was extracted with ethyl acetate (2×50 ml). The organics were combined, dried on magnesium sulphate, filtered and concentrated under reduced pressure to yield the crude product. The crude was purified by flash chromatography on a 7 cm diameter suction column packed to a depth of 3.5 cm with silica eluted with ethyl acetate:hexane (1:1 to 4:1) to yield the desired product as an off white solid (98 mg).

$\delta_H$ (300 MHz, CDCl$_3$) 7.43 (2H, d), 7.17 (2H, d), 6.99 (1H, t), 6.63–6.54 (3H, m), 6.50 (1H, d), 4.38–4.30 (2H, m), 3.94–3.88 (2H, m), 3.84 (3H, s), 3.50 (3H, s), 1.26 (9H, s). m/z (positive ion electrospray) [MH$^+$]=460; C$_{23}$H$_{30}$N$_3$O$_5$S requires 460.2

Example 31

4-(tert-butyl)-N-[3-{2-[(5-bromo-2-pyrimidinyl) oxy}ethoxy}-4-(3-methoxyphenyl)-1-methyl-1H-pyrazol-5-yl-benzenesulphonamide

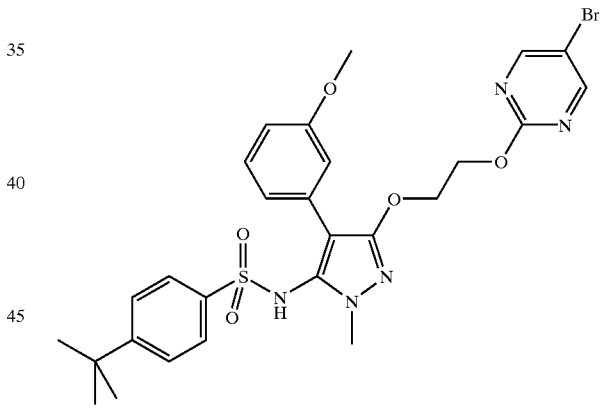

To a solution of 4-(tert-butyl)-N-[3-(2-hydroxyethoxy)-4-(3-methoxyphenyl)-1-methyl-1H-pyrazol-5-yl] benzenesulphonamide (Example 30) (45 mg, 0.09 mmol) in anhydrous tetrahydrofuran (6 ml), sodium hydride 60% dispersion in oil (9 mg, 0.22 mmol) was added under an atmosphere of nitrogen. The resulting mixture was allowed to stir at room temperature, under an atmosphere of nitrogen, for 5 minutes. A solution of 2-chloro-5-bromopyrimidine (29 mg, 0.15 mmol) in dimethylacetamide (2.5 ml) was then added dropwise and the reaction mixture was left to stir at room temperature over the weekend.

The reaction mixture was partitioned between water (50 ml) and ethyl acetate (20 ml). The aqueous phase was extracted with ethyl acetate. The organics were washed with brine, dried on a magnesium sulphate, filtered and concentrated under reduced pressure to yield 90 mg of crude product. The residue was purified by preparative HPLC on a 5μ ODS Phenomenex Primesphere™ column with gradient elution of acetonitrile (5% to 95%) and 0.1M NH₄OAc (95% to 5%) to yield the title compound as a off-white solid (7 mg).

$\delta_H$ (300 MHz, CDCl₃), 8.49 (2H, s), 7.41 (2H, d), 7.14 (2H, d), 6.91 (1H, t), 6.60 (2H, s), 6.52 (1H, d), 6.48 (1H, d), 4.74–4.66 (2H, m), 4.60–4.54 (2H, m), 3.84 (3H, s), 3.66 (3H, s), 1.22 (9H, s). m/z (negative ion electrospray) [MH⁻]=614; $C_{27}H_{31}N_5O_5S$ requires 614.1

Example 32

4-(tert-butyl)-N-[4-(3,4dimethoxyphenyl)-3-(2-hydroxyethoxy)-1-methyl-1H-pyrazol-5-yl]benzenesulphonamide

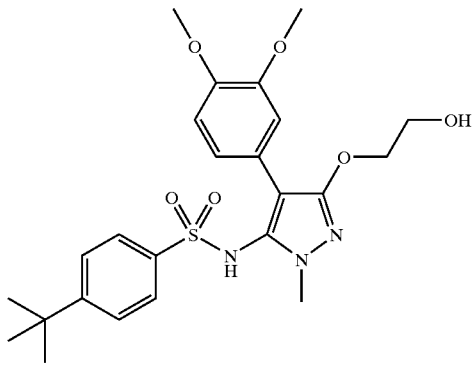

The title compound was made according to the procedure described for example (Example 30) with isobutyl 2-{3-[2-(acetyloxy)ethoxy]-4-iodo-1-methyl-1H-pyrazol-5-yl}-2-{[4-(tert-butyl)phenyl]sulfonyl}acetate (Preparation 6) (400 mg, 0.6 mmol) and 3,4-dimethoxybenzeneboronic acid (218 mg, 1.2 mmol). The crude material was purified by chromatography on a 7 cm suction column packed with silica to a depth of 3 cm eluted with ethyl acetate:hexane (1:1 to 4:1) to yield the title compound (180 mg, 90% pure product). 30 mg of this compound was then further purified by preparative HPLC on a 5μ ODS, Phenomenex Primesphere™ column with gradient of NH₄OAc 0.1M (95% to 5%), acetonitrile (5% to 95%). This yielded 3 mg of the desired product as an off-white solid.

$\delta_H$ (300 MHz, CDCl₃), 7.44 (2H, d), 7.23 (2H, d), 6.70 (1H, s), 6.61 (1H, d), 6.51 (1H, d), 6.42 (1H, s), 4.38–4.32 (2H, m), 3.97–3.83 (2H, m), 4.81 (3H, s), 4.78 (3H, s), 4.73 (3H, s), 1.24 (9H, s). m/z (negative ion electrospray) [M⁻]= 488; $C_{24}H_{32}N_3O_6S$ requires 488.2

Example 33

4-(tert-butyl)-N-[3-{2-(5-bromo-2-pyrimidinyl)oxy]ethoxy}-4-3,4-dimethoxyphenyl)-1-methyl-1H-pyrazol-5-yl]-4-benzenesulphonamide

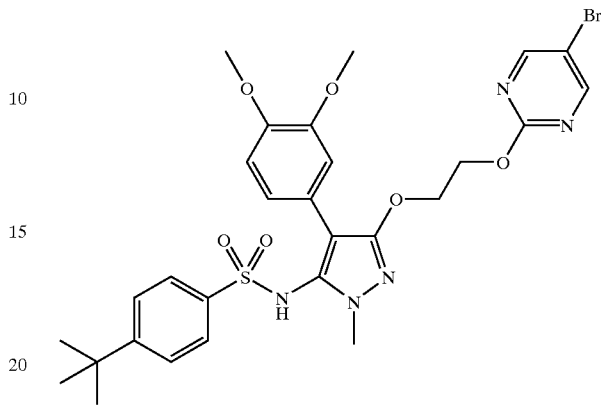

The title compound was made according to the procedure used for Example 31 with 4-(tert-butyl)-N-[4-(3,4-dimethoxyphenyl)-3-(2-hydroxyethoxy)-1-methyl-1H-pyrazol-5-yl]benzenesulphonamide (Example 32) (90 mg, 0.18 mmol), 2-chloro-5-bromopyrimidine (53 mg, 0.28 mmol), sodium hydride 60% dispersion in oil (15 mg, 0.36 mmol), anhydrous tetrahydrofuran (10 ml) and dimethyl acetamide (3 ml).

The reaction mixture was separated between water and ethyl acetate. The aqueous phase was extracted with ethyl acetate (3×20 ml). The organics were washed with brine, dried over magnesium sulphate, filtered and concentrated under reduced pressure to yield 78 mg of crude product. The residue was purified by preparative HPLC on a 5μ ODS Phenomenex Primesphere™ column with gradient elution of acetonitrile (5% to 95%) and 0.1M NH₄OAc (95% to 5%) to yield the title compound as an off-white solid (11 mg).

$\delta_H$ (300 MHz, CDCl₃), 8.49 (2H, s), 7.49 (2H, d), 7.20 (2H, d), 6.74 (1H, s), 6.53 (1H, d), 6.50–6.44 (1H, m), 6.41 (1H, s), 4.71–4.64 (2H, m), 4.6–4.54 (2H, m), 3.78 (6H, s), 3.70 (3H, s), 1.24 (9H, s). m/z (thermospray) [MH⁺]=646.4; $C_{28}H_{33}BrN_5O_6S$ requires 646.6

Example 34

N-(4-(1,3-benzodioxol-5-yl)3-{2-[5-chloro-2-pyrimidinyl)oxy]ethoxy}-1-methyl-1H-pyrazol-5-yl)-4-(tert-butyl)benzenesulphonamide

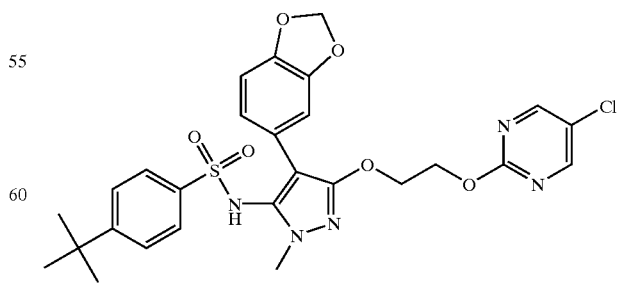

To a solution of N-[4-(1,3-benzodioxol-5-yl)-3-(2-hydroxyethoxy)-1-methyl-1H-pyrazol-5-yl]-4-(tert-butyl)

benzenesulfonamide (Example 17) (300 mg, 0.63 mmol) in anhydrous tetrahydrofuran (12 ml) and dimethyl acetamide, sodium hydride 60% dispersion in oil (55 mg, 1.39 mmol) was added under an atmosphere of nitrogen. The reaction mixture was stirred at room temperature for 20 minutes. 2-Methylsulphonyl-5-chloropyrimidine (133 mg, 0.69 mmol) was added, in one portion, to the reaction mixture which was then stirred at room temperature for 2 hours. The reaction mixture was concentrated and the residue poured onto water (150 ml). The aqueous was extracted with ethyl acetate (4×50 ml). The organic fractions were washed with brine, dried over magnesium sulphate, filtered and concentrated under reduced pressure to yield an off white foam. The foam was crystallised from ether (5 ml) to yield 100 mg of the title compound.

$\delta_H$ (300 MHz, CDCl$_3$), 8.41 (2H, s), 7.42 (2H, d), 7.20 (2H, d), 6.52–6.42 (2H, m), 6.40–6.28 (2H, m), 5.84 (2H, s), 4.76–4.66 (2H, m), 4.60–4.52 (2H, m), 3.82 (3H, s), 1.24 (9H, s). m/z, (thermospray) [MH$^+$]=586.1; C$_{27}$H$_{29}$ClN$_5$O$_6$S requires 586.1

Example 35

4-(tert-butyl)-N-[3-[2-(4-fluorophenoxy)ethoxy]-1-methyl-4-(4-methylphenyl)-1H-pyrazol-5-yl]benzenesulfonamide

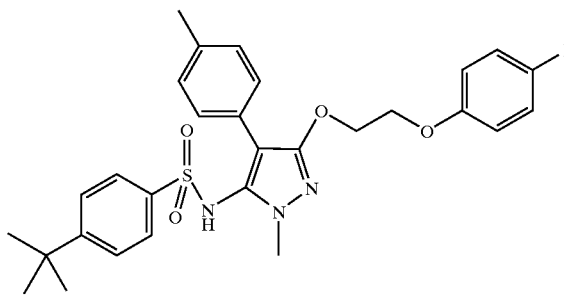

To 4-(tert-butyl)-N-{[4-(tert-butyl)phenyl]sulfonyl}-N-[3-[2-(4-fluorophenoxy)ethoxy]-1-methyl-4-(4-methylphenyl)-1H-pyrazol-5-yl]benzenesulfonamide (Preparation 25) (180 mg) in dioxan (5 ml) at room temperature was added 1N aqueous sodium hydroxide (5 ml) and the mixture was stirred and heated to 100° C. for 1.5 hrs. The reaction was partitioned between 2N aqueous hydrochloric acid (25 ml) and ethyl acetate (25 ml). The organic layer was separated, washed with water, then brine, dried over magnesium sulfate, filtered and concentrated under reduced pressure. The residue was purified by column chromatography using silica gel (20 g), eluting with a solvent gradient of pentane:ethylacetate (19:1 changing to 7:3), to yield the title compound as a glass (106 mg).

$\delta_H$ (300 MHz, CDCl$_3$) 7.35 (2H, d), 7.10 (2H, d), 6.70–7.00 (8H, m), 6.45 (1H, s), 4.50 (2H, t), 4.25 (2H, t), 3.85 (3H, s), 2.10 (3H, s), 1.15 (9H, s). m/z (thermospray) [MH$^+$]=538.5; C$_{29}$H$_{33}$FN$_3$O$_4$S requires 538.2

Example 36

4-(tert-butyl)-N-(1-methyl-4-(4-methylphenyl)-3-{2-[(5-nitro-2-pyrimidinyl)oxy]ethoxy}-1H-pyrazol-5-yl)benzenesulphonamide

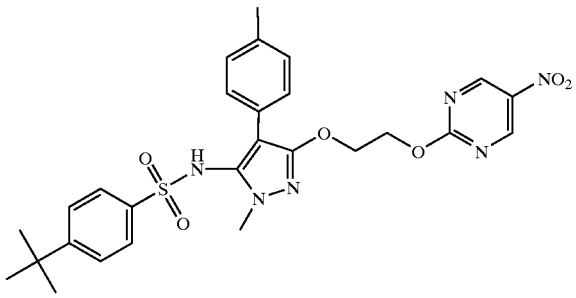

To a solution of 4-(tert-butyl)-N-[3-(2-hydroxyethoxy)-1-methyl-4-(4-methylphenyl)-1H-pyrazol-5-yl]-benzenesulphonamide (Example 2) (1838 mg) in anhydrous THF (18 ml) at 0° C. stirred under an atmosphere of nitrogen was added sodium hydride (60% dispersion in oil, 348 mg) A precipitate began to form which was stirred at 0° C. for 15 min. 2-Chloro-5-nitropyrimidine (Wempen, I.; Blank, H. U.; Fox, J. J. *J. Heterocyclic Chem.* 1969, 6, 593. Hurst, D. T.; *Heterocycles* 1984, 22, 79; *Heterocycles*, 1977, 6, 1999–2004.) (661 mg) in anhydrous DMA (3 ml) was added dropwise and the solution was allowed to warm to room temperature. The reaction was quenched after 130 min by cautiously pouring the mixture onto a vigorously stirred mixture of ethyl acetate (300 ml) and saturated ammonium chloride solution (300 ml). The ethyl acetate layer was separated off, dried (MgSO$_4$) and evaporated to dryness. This afforded a yellow residue (3.44 g) which was purified by column chromatography on silica gel (256 g), eluting with a gradient of ethyl acetate:hexane (4:5 to 5:4).

$\delta_H$ (300 MHz, CDCl$_3$) 9.35 (2H, s), 7.60 (2H, d), 7.20 (2H, d), 6.85 (4H, s), 4.50 (2H, t), 3.95 (2H, t), 3.75 (3H, s), 3.00 (1H, br s), 2.25 (3H, s), 1.25 (9H, s). m/z (thermospray) [MH+]=567.2; C$_{27}$H$_{31}$N$_6$O$_6$S requires 567.2

Example 37

N-[3-{2-[(5-amino-2-pyrimidinyl)oxy]ethoxy}-1-methyl-4-(4-methylphenyl)-1H-pyrazol-5-yl]-4-(tert-butyl)benzenesulfonamide

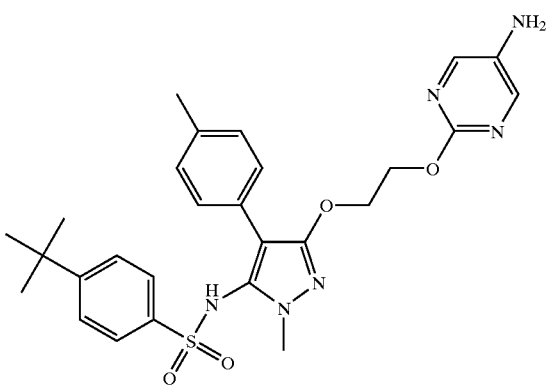

A solution of 4-(tert-butyl)-N-(1-methyl-4-(4-methylphenyl)-3-{2-[(5-nitro-2-pyrimidinyl)oxy]ethoxy}-

1H-pyrazol-5-yl)benzenesulfonamide (Example 36) (1276 mg) in ethanol (20 ml) was placed under an atmosphere of hydrogen at 50 psi for 12 hrs using palladium on carbon (5%) as catalyst. The catalyst was filtered through Celite (30 g), and washed with ethanol (3×10 ml). Concentration of the filtrate under reduced pressure afforded a yellow residue. The crude material was purified by column chromatography on silica gel (150 g), eluting with ethyl acetate:hexane (1:1), to yield the title compound as a yellow solid (569 mg).

$\delta_H$ (300 MHz, CDCl$_3$) 8.25 (2H, s), 7.65 (2H, d), 7.15 (2H, d), 6.85 (2H, d), 6.75 (2H, d), 4.45 (2H, t), 3.95 (2H, t), 3.75 (3H, s), 3.40 (1H, s), 2.20 (3H, s), 1.30 (9H, s). m/z (thermospray) [MH$^+$]=537.4; C$_{27}$H$_{32}$N$_6$O$_4$S requires 537.2

Example 38

4-(tert-butyl)-N-[3-{2-[(5-formyl-2-pyrimidinyl)oxy]ethoxy}-1-methyl(4-methylphenyl)-1H-pyrazol-5yl]benzenesulfonamide

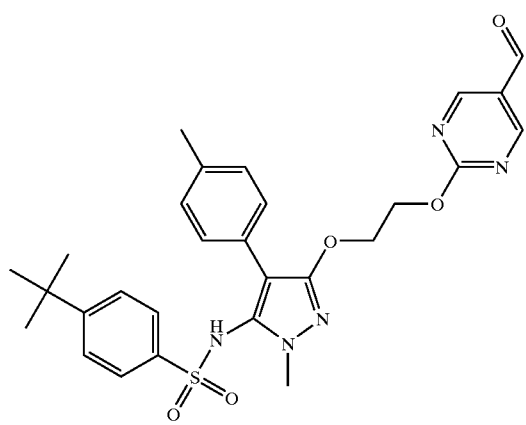

To N-[3-{2-[(5-bromo-2-pyrimidinyl)oxy]ethoxy}-1-methyl-4-(4-methylphenyl)-1H-pyrazol-5-1H-pyrazol-5-yl]-4-(tert-butyl)benzenesulfonamide (Example 3) (332 mg) in tetrahydrofuran (10 ml) at −78° C. under an atmosphere of nitrogen was added n-butyllithium in hexanes (0.69 ml of 1.6M). Dimethylformamide (86 μl) was added dropwise to the solution after 20 minutes of stirring at −78° C. After a further 20 minutes of stirring at −78° C., the mixture was quenched with saturated ammonium chloride solution (2 ml). The mixture was diluted with ammonium chloride (50 ml), extracted with ethyl acetate (50 ml), dried over magnesium sulphate, filtered and the filtrate was evaporated to dryness. Purification of the residue by column chromatography on silica gel (32 g), eluting with an ethyl acetate:hexane gradient (1:1 to 3:1) yielded the title compound as a cream solid (52 mg).

$\delta_H$ (300 MHz, CDCl$_3$) 9.95 (1H, s), 8.90 (2H, s), 7.40 (2H, d), 7.10 (2H, d), 6.75 (4H, d), 4.85 (2H, t), 4.60 (2H, t), 3.85 (3H, s), 2.20 (3H, s), 1.25 (9H, s). m/z (thermospray) [MH$^+$]=550.2; C$_{28}$H$_{32}$N$_5$O$_5$S requires 550.2

Example 39

4-(tert-butyl)-N-[3-(2-[{5-chloro-2-pyrimidinyl}oxy]ethoxy)-1-(2-hydroxyethyl)-4-(4-methylphenyl)-1H-pyrazol-5-yl]benzenesulfonamide

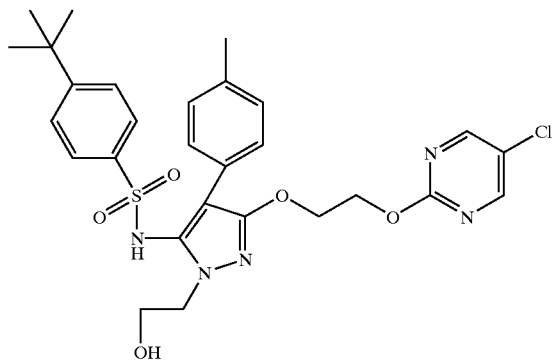

A solution of 4-(tert-butyl)-N-[1-(2-{[tert-butyl(dimethyl)silyl]oxy}ethyl)-3-2-[{5-chloro-2-pyrimidinyl}oxy]ethoxy)-4-(4-methylphenyl)-1H-pyrazol-5-yl]benzenesulfonamide (Preparation 27) (90 mg) and tetrabutylammonium fluoride (1.0M in THF, 0.1 3 ml) in anhydrous THF (2 ml) was stirred for 3 hours at room temperature. After this period, tlc analysis (2:1 ethyl acetate:hexane) showed that little reaction had occurred. A second aliquot of 1.0M tetrabutylammonium fluoride in THF (0.13 ml) was added to the reaction solution and the resulting mixture was stirred at room temperature overnight. The reaction mixture was diluted with ether (30 ml) and then extracted with 1.0M citric acid (20 ml) and water (20 ml). The organic phase was dried over magnesium sulfate, filtered and concentrated under reduced pressure. The residue was purified by chromatography on a Biotage Flash 12i cartridge at 10 psi using 60% ethyl acetate/hexane as eluent to give the title compound as a colourless oil (56 mg).

$\delta_H$ (300 MHz, CDCl$_3$) 8.39 (2H, s), 7.58 (1H, broad s), 7.38 (2H, d), 7.10 (2H, d), 6.88 (2H, d), 6.79 (2H, d), 4.67 (2H, t), 4.53 (2H, t), 4.25 (2H, t), 3.97 (2H, t), 3.70 (1H, broad s), 2.20 (3H, s), 1.24 (9H, s). m/z (electrospray) [MH$^+$]=586.1; C$_{28}$H$_{33}$ClN$_5$O$_5$S requires 586.2

Example 40

N-[3-(2-hydroxyethoxy)-1-methyl-4-(4-methylphenyl)-1H-pyrazol-5-yl]-5-isopropyl-2-pyridinesulfonamide

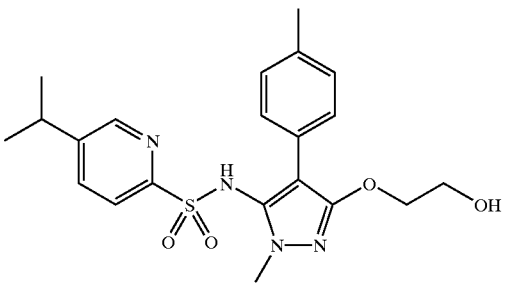

To a solution of 2-{[5-amino-1-methyl-4-(4-methylphenyl)-1H-pyrazol-3-yl]oxy}ethyl acetate (Preparation 5) (3.80 g) in anhydrous pyridine (25 ml) at room temperature and under an atmosphere of nitrogen was added 4-dimethylaminopyridine (0.85 g) and 5-isopropyl-2-pyridinesulfonyl chloride (2.00 g). After being left to stir overnight, the reaction mixture was poured onto saturated citric acid solution (300 ml) and extracted with ethyl acetate (2×200 ml). The organic fractions were washed with brine (200 ml), dried over magnesium sulfate, filtered and concentrated under reduced pressure. To a solution of the residue (4.45 g) in ethanol (100 ml) was added sodium hydroxide solution (2.76 g in 10 ml water). The red solution which formed was stirred for 1 hour before being concentrated to approximately 20 ml under reduced pressure and partitioned between ethyl acetate (2×100 ml) and saturated citric acid solution (100 ml). Washing of the organic fractions with brine (100 ml), drying over magnesium sulfate, filtering and concentration under reduced pressure afforded a brown residue. Purification by column chromatography on silica gel (200 g), eluting in an isocratic fashion with dichloromethane:methanol (20:1) afforded the title compound as a brown foam (1.85 g).

$\delta_H$ (300 MHz, CDCl$_3$) 8.75 (1H, br), 8.00 (1H, s), 7.55 (1H, d), 7.35 (1H, d), 7.00 (2H, d), 6.90 (2H, d), 4.25 (2H, t), 3.85 (2H, t), 3.75 (3H, s), 2.75 (1H, sept), 2.20 (3H, s), 1.15 (6H, d). m/z (thermospray) [MH$^+$]=431.3; $C_{21}H_{27}N_4O_4S$ requires 431.18

Example 41

N-[3-{2-[(5-bromo-2-pyrimidinyl)oxy]ethoxy}-1-methyl-4-(4-methylphenyl)-1H-pyrazol-5-yl]-5-isopropyl-2-pyridinesulfonamide

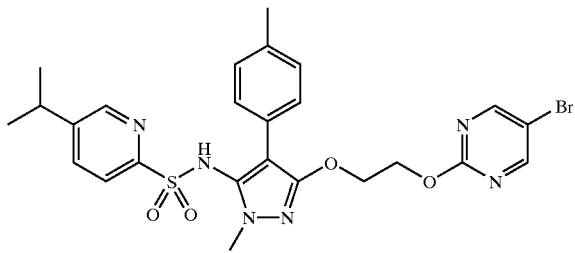

To a solution of N-[3-(2-hydroxyethoxy)-1-methyl-4-(4-methylphenyl)-1H-pyrazol-5-yl]-5-isopropyl-2-pyridinesulfonamide (Example 40) (1.00 g) in anhydrous THF (10 ml) at 0° C. and under an atmosphere of nitrogen was added sodium hydride (60% dispersion in oil, 195 mg) and the mixture was stirred for 5 minutes. To the mixture was added 5-bromo-2-chloropyrimidine (Liquid Crystals, 1993, 14(3), 741) (1.12 g) in dimethylacetamide (3 ml). After stirring for 1 hr, the reaction mixture was partitioned between ethyl acetate (100 ml) and saturated ammonium chloride solution (100 ml). The organic fraction was washed with brine (100 ml), followed by drying over magnesium sulfate, filtering and concentration under reduced pressure. Purification of the residue by preparative HPLC on a Phenomenex Magellen column using a 0.1M ammonium acetate:acetonitrile gradient (95:5 to 50:50 over 5 minutes) afforded the title compound as a white solid (625 mg).

$\delta_H$ (300 MHz, CDCl$_3$) 8.50 (2H, s), 8.00 (1H, s), 7.55 (1H, d), 7.35 (1H, d), 6.85 (4H, dd), 4.65 (2H, t), 4.55 (2H, t), 3.80 (3H, s), 2.80 (1H, sept), 2.25 (3H, s), 1.20 (6H, d). m/z (electrospray) [MH$^+$]=587.0; $C_{25}H_{29}BrN_6O_4S$ requires 587.10

Example 42

5-isopropyl-N-[1-methyl-4-(4-methylphenyl)-3-(2-{[-(methylsulfonyl)-2-pyrimidinyl]oxy}ethoxy)-1H-pyrazol-5-yl]-2-pyridinesulfonamide

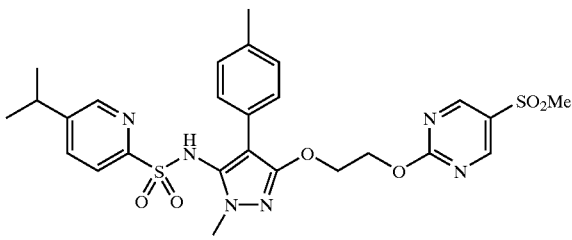

To a solution of N-[3-(2-hydroxyethoxy)-1-methyl-4-(4-methylphenyl)-1H-pyrazol-5-yl]-5-isopropyl-2-pyridinesulfonamide (Example 40) (112 mg) in anhydrous THF (5 ml) at 0° C. and under an atmosphere of nitrogen was added sodium hydride (60% dispersion in oil, 21.8 mg) and the mixture was stirred for 5 minutes. To the mixture was added 2-chloro-5-(methylsulfonyl)pyrimidine (50 mg) in dimethylacetamide (1 ml). After stirring for 150 min. the reaction mixture was partitioned between ethyl acetate (50 ml) and saturated ammonium chloride solution (50 ml). The ethyl acetate layer was washed with brine (50 ml), dried (MgSO$_4$), filtered and evaporated to dryness. Purification of the residue on a Phenomenex Magellen™ column using a 0.1M NH$_4$OAc:MeCN gradient (95:5 to 60:40) over 5min. and then an isocratic flow (60:40) for 15 minutes gave the title compound as a white solid (31 mg).

$\delta_H$ (300 MHz, CDCl$_3$) 8.95 (2H, s), 8.00 (1H, s), 7.55 (1H, d), 7.40 (1H, d), 6.85 (4H, s), 4.80 (2H, t), 4.55 (2H, t), 3.80 (3H, s), 3.10 (3H, s), 2.80 (1H, sept), 2.25 (3H, s), 1.20 (6H, d). m/z (electrospray) [MH$^+$]=587.1; $C_{26}H_{31}N_6O_6S_2$ requires 587.17

Example 43

N-[4-(1,3-benzodioxol-5-yl)-3-(2-hydroxyethoxy)-1-methyl-1H-pyrazol-5-yl]-5-isopropyl-2-pyridinesulfonamide

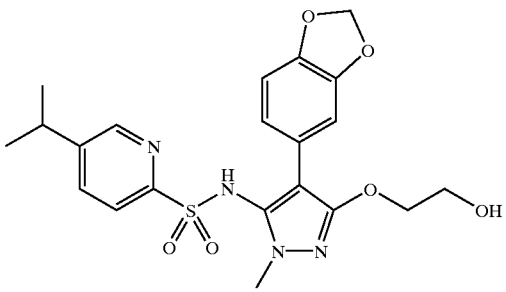

To a solution of 2-{[5-amino-4-(1,3-benzodioxol-5-yl)-1-methyl-1H-pyrazol-3-yl]oxy}ethyl acetate (Preparation 33) (500 mg) in anhydrous pyridine (5 ml) at room temperature and under an atmosphere of nitrogen was added 4-dimethylaminopyridine (191 mg) and 5-isopropyl-2-pyridinesulfonyl chloride (1.72 g). After being left to reflux overnight, the reaction mixture was poured onto saturated citric acid solution (50 ml) and extracted with ethyl acetate (2×50 ml). The organic fractions were washed with brine (50 ml), followed by drying over magnesium sulfate, filtering

47 and concentration under reduced pressure. To a solution of the residue in ethanol (50 ml) was added sodium hydroxide solution (5 ml of 2M). The mixture was stirred overnight before being concentrated to approximately 5 ml under reduced pressure and partitioned between ethyl acetate (2×100 ml) and saturated citric acid solution (100 ml). Washing of the organic fractions with brine (100 ml), drying over magnesium sulfate, filtering and concentration under reduced pressure afforded a brown residue. Purification by column chromatography on silica gel (5 g), eluting in an isocratic fashion with ethyl acetate:hexane (2:1) afforded the title compound as a gum (18 mg).

$\delta_H$ (300 MHz, CDCl$_3$) 8.20 (1H, s), 7.95 (1H, br), 7.60 (1H, d), 7.45 (1H, d), 6.50 (3H, s), 5.85 (2H, s), 4.30 (2H, t), 3.90 (2H, t), 3.80 (3H, s), 2.90 (1H, sept), 1.25 (6H, d). m/z (thermospray) [MH$^+$]=461.3; C$_{21}$H$_{25}$N$_4$O$_6$S requires 461.15

Example 44

N-(4-(1,3-benzodioxol-5-yl)-3-{2-[(5-bromo-2-pyrimidinyl)oxy]ethoxy}-1-methyl-1H-pyrazol-5-yl)-5-isopropyl-2-pyridinesulfonamide

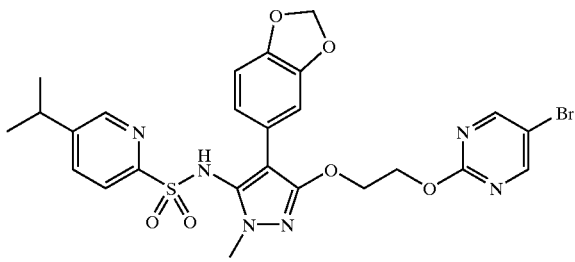

To a solution of N-[4-(1,3-benzodioxol-5-yl)-3-(2-hydroxyethoxy)-1-methyl-1H-pyrazol-5-yl]-5-isopropyl-2-pyridinesulfonamide (Example 43) (18 mg) in anhydrous THF (0.5 ml) at 0° C. and under an atmosphere of nitrogen was added sodium hydride (60% dispersion in oil, 3.3 mg) and the mixture was stirred for 5 minutes. To the mixture was added 5-bromo-2-chloropyrimidine (*Liquid Crystals*, 1993, 14(3), 741) (11.3 mg) in dimethylacetamide (0.1 ml). After stirring for 90 min, the reaction mixture was partitioned between ethyl acetate (3 ml) and saturated ammonium chloride solution (5 ml). The ethyl acetate layer was dried (MgSO$_4$) and blown down under nitrogen to, afford a gummy residue. Purification of the residue by column chromatography on silica gel (5 g), eluting in an isocratic fashion with ethyl acetate:hexane (7:4) afforded the title compound as a white solid (6 mg) after freeze drying from t-butanol.

$\delta_H$ (400 MHz, CDCl$_3$) 8.50 (2H, s), 8.20 (1H, s), 7.55 (1H, d), 7.45 (1H, d), 6.50 (3H, d), 5.85 (2H, s), 4.70 (2H, t), 4.50 (2H, t), 3.80 (3H, s), 2.90 (1H, sept), 1.20 (6H, d). m/z (electrospray) [MH$^+$]=617.3; C$_{25}$H$_{27}$BrN$_6$O$_6$S requires 617.07

48

Example 45

N-[4-(1,3-benzodioxol-5-yl)-1-methyl-3-(2-{[5-(methylsulfonyl)-2-pyrimidinyl]oxy}ethoxy)-1H-pyrazol-5-yl]-5-isopropyl-2-pyridinesulfonamide

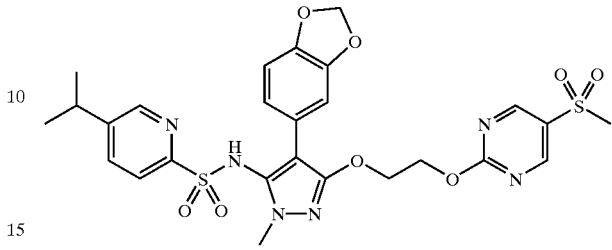

To a solution of N-[4-(1,3-benzodioxol-5-yl)-3-(2-hydroxyethoxy)-1-methyl-1H-pyrazol-5-yl]-5-isopropyl-2-pyridinesulfonamide (Example 43) (124 mg) in anhydrous THF (5 ml) at 0° C. and under an atmosphere of nitrogen was added sodium hydride (60% dispersion in oil, 33.9 mg) and the mixture was stirred for 5 minutes. To the mixture was added 2-chloro-5-(methylsulfonyl)pyrimidine (93 mg) in dimethylacetamide (1 ml). After being left to stir overnight, the reaction mixture was partitioned between ethyl acetate (100 ml) and saturated ammonium chloride solution (100 ml). The ethyl acetate layer was washed with brine (100 ml), dried over magnesium sulfate, filtered and concentrated to dryness. Purification of the residue on a Phenomenex Magellen™ column eluting in an isocratic fashion with acetonitrile:ammonium acetate solution (0.1M) (3:7) afforded the title compound as a white solid (11 mg).

$\delta_H$ (300 MHz, CDCl$_3$) 8.95 (2H, s), 8.20 (1H, s), 7.55 (1H, d), 7.45 (1H, d), 6.45 (3H, s), 5.85 (2H, s), 4.85 (2H, t), 4.55 (2H, t), 3.80 (3H, s), 3.10 (3H, t) 2.90 (1H, sept), 1.25 (6H, d). m/z (electrospray) [MH$^+$]=617.2; C$_{26}$H$_{29}$N$_6$O$_8$S$_2$ requires 617.15

Example 46

N-[3-(2-{[5-hydroxymethyl)-2-pyrimidinyl]oxy}ethoxy)-1-methyl-4-(4-methylphenyl)-1H-pyrazol-5yl]-5-isopropyl-2-pyridinesulfonamide

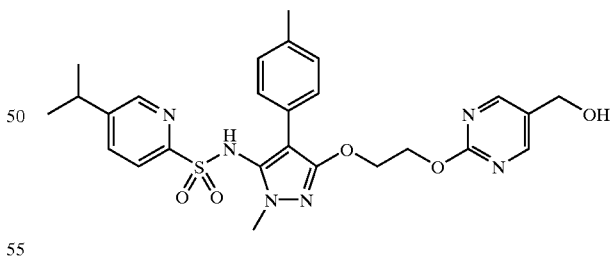

Carbon monoxide gas was bubbled through a solution of N-[3-{2-[(5-bromo-2-pyrimidinyl)oxy]ethoxy}-1-methyl-4-(4-methylphenyl)-1H-pyrazol-5-yl]-5-isopropyl-2-pyridinesulfonamide (Example 41) (100 mg), sodium formate (17.4 mg) and dichlorobis(triphenylphosphine) palladium (II) (4.8 mg) in anhydrous dimethylformamide (2 ml), the mixture was heated at 100° C. for two hours. On cooling to room temperature the reaction mixture was diluted with ethyl acetate and filtered through a Celite plug (5 g). The filtrate and Celite washings (total volume 100 ml) were washed with water (2×100 ml) and brine (100 ml)

before being dried (Na₂SO₄) and concentrated to dryness. The residue was taken up in absolute ethanol (1.5 ml) and cooled to 0° C. before sodium borohydride powder (4 mg) was added in one flush. The reaction mixture was stirred at room temperature for 30 minutes, followed by the partitioning of the reaction mixture between ethyl acetate (20 ml) and saturated ammonium chloride solution (20 ml). Washing of the organic phase with brine (20 ml), drying (Na₂SO₄), filtering and concentration to dryness afforded an off-white foam. Purification by flash chromatography on silica gel (5 g), eluting isocratically with ethyl acetate gave the title compound as a white solid (13 mg). $\delta_H$ (300 MHz, d₆-DMSO) 8.50 (2H, s), 8.20 (1H, s), 7.55 (1H, d), 7.45 (1H, d), 7.05 (2H, d), 6.75 (2H, d), 5.25 (1H, t), 4.60 (2H, t), 4.40 (4H, d), 3.60 (3H, s), 2.85 (1H, sept), 2.15 (3H, s), 1.15 (6H, d). m/z (electrospray) [MH⁺]=539.1; $C_{26}H_{31}N_6O_5S$ requires 539.21

Example 47

N-[4-1,3-benzodioxol-5-yl)-3-2-hydroxyethoxy)-1-methyl-1H-pyrazol-5-yl]pyridine-2-sulphonamide

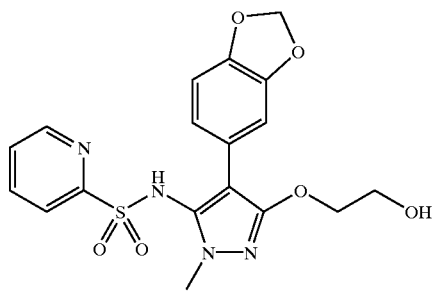

To 2-{[5-amino-4-(1,3-benzodioxol-5-yl)-1-methyl-1H-pyrazol-3-yl]oxy}ethylacetate (Preparation 33) (640 mg) in dry pyridine (3 ml) at room temperature was added pyridine-2-sulfonyl chloride (J. Org. Chem., 1989, 54(2), 389–393) (712 mg), and the mixture was stirred for 16 hours. The mixture was concentrated under reduced pressure, then dissolved in dioxan (2 ml) and 1N NaOH (aq.) (4 ml) was added. The mixture was stirred at 60° C. for 1.5 hours. The reaction was then treated with ammonium chloride (sat. aq., 50 ml) and extracted with ethyl acetate (2×50 ml). The combined organic fractions were combined, washed with ammonium chloride (sat. aq., 50 ml), brine (50 ml), dried over magnesium sulfate, filtered and concentrated under reduced pressure. The residue was purified by column chromatography on silica gel (50 g) eluting with a solvent gradient of pentane:ethyl acetate (8:2 to 2:8 by volume). The material thus obtained was dissolved in dioxan (4 ml) and 1N NaOH (15 ml) was added. The mixture was stirred at 60° C. for 1.5 hours. The reaction was treated with ammonium chloride (sat. aq., 50 ml), and extracted with ethyl acetate (50 ml), dried over magnesium sulfate, filtered and concentrated under reduced pressure to yield the title compound as a colourless gum (286 mg).

$\delta_H$ (300 MHz, CDCl₃) 8.35 (1H, s), 7.65 (2H, d), 7.30 (1H, m), 6.60 (1H, d), 6.45 (1H, d), 6.35 (1H, s), 5.90 (2H, s), 4.30 (2H, t), 3.85 (2H, t), 3.80 (3H, s), 1.25 (1H, m). m/z (electrospray) [MH⁺]=419.0; $C_{18}H_{19}N_4O_6S$ requires 419.10

Example 48

N-[4-1,3-benzodioxol-5-yl)-3-{2-[(5-brompyrimidin-2-yl)oxy]ethoxy}-1-methyl-1H-pyrazol-5-yl]-2-pyridine sulphonamide

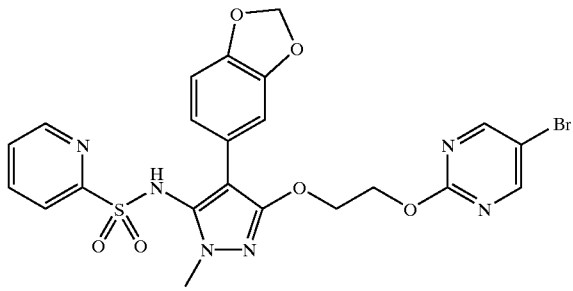

To N-[4-1,3-benzodioxol-5-yl)-3-(2-hydroxyethoxy)-1-methyl-1H-pyrazol-5-yl]-2-pyridine sulphonamide (Example 47) (100 mg) in dry tetrahydrofuran (10 ml) at room temperature was added sodium hydride (80% dispersion in oil, 16 mg) the mixture was stirred for 10 minutes. A solution of 5-bromo-2-chloropyrimidine (Liquid Crystals, 1993, 14(3), 741) (69 mg) in dry dimethyl acetamide (4 ml) was then added dropwise and the mixture was stirred for a further 16 hours. The mixture was then treated with further sodium hydride (80% dispersion in oil, 16 mg) and 5-bromo-2-chloropyrimidine (69 mg) was added. The mixture was stirred for 24 hours. The reaction was treated with saturated aqueous ammonium chloride (50 ml) and extracted with ethyl acetate (3×50 ml). The combined organics were washed with brine (50 ml), dried over magnesium sulfate, filtered and concentrated under reduced pressure. The residue was purified by column chromatography on silica (10 g) eluted with a solvent gradient of pentane:ethyl acetate (8:2 to 0:1) to yield the tile compound as a yellow solid (29 mg).

$\delta_H$ (300 MHz, CDCl₃) 8.50 (2H, s), 8.35 (1H, d), 7.60 (2H, m), 7.30 (1H, m), 6.85 (1H, s), 6.55 (1H, d), 6.40 (1H, d), 5.80 (2H, s), 4.65 (2H, t), 4.50 (2H, t), 4.35 (1H, s), 3.85 (2H, s). m/z (electrospray) [MH⁺]=575.0; $C_{22}H_{20}BrN_6O_6S$ requires 575.03

Example 49

N-[4-1,3-benzodioxol-5-yl)-3-{2-[(5-chloropyrimidin-2-yl)oxy]ethoxy}-1-methyl-1H-pyrazol-5-yl]-2-pyridine sulphonamide

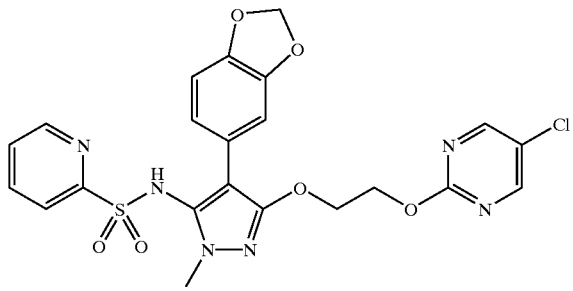

To N-[4-1,3-benzodioxol-5-yl)-3-(2-hydroxyethoxy)-1-methyl-1H-pyrazol-5-yl]-2-pyridine sulphonamide (Example 47) (100 mg) in dry tetrahydrofuran (5 ml) at room temperature was added sodium hydride (80% dispersion in oil, 16 mg) the mixture was stirred for 15 minutes.

A solution of 5-chloro-2-methylsulphonylpyrimidine (84 mg) in dry tetrahydrofuran (2.5 ml) was then added dropwise and the mixture was stirred for a further 16 hours. The mixture was then treated with 5-chloro-2-methylsulphonylpyrimidine (84 mg) and stirred for 4 hours. The reaction was treated with citric acid (10% aq.) and extracted with ethyl acetate (50 ml). The organic fraction was washed with brine (50 ml), dried over magnesium sulfate, filtered and concentrated under reduced pressure. The residue was purified by column chromatography on silica (10 g) eluted with a solvent gradient of pentane:ethyl acetate (7:3 to 0:1) to yield the tile compound as a yellow solid (97 mg).

$\delta_H$ (300 MHz, CDCl$_3$) 8.40 (2H, s), 8.30 (1H, d), 7.60 (1H, m), 7.30 (1H, m), 7.00 (1H, s), 6.50 (1H, d), 6.45 (1H, d), 6.30 (1H, s), 5.85 (2H, s), 4.65 (2H, t), 4.50 (2H, t), 4.35 (1H, s), 3.80 (3H, s). m/z (electrospray) [MH$^+$]=529.1; C$_{22}$H$_{20}$ClN$_6$O$_6$S requires 529.07

Example 50

N-[3-(2-hydroxyethoxy)-1-methyl-4-(4-methylphenyl)-1H-pyrazol-5-yl]-5-methylpyridine-2-sulphonamide

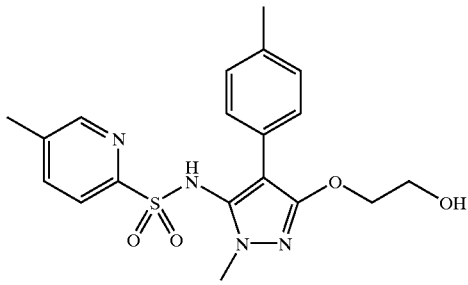

To 2-{[5-amino-1-methyl-4-methylphenyl)-1H-pyrazol-3-yl]oxy}ethylacetate (Preparation 5) (400 mg) in dry pyridine (1 ml) at room temperature was added 5-methylpyridine-2-sulfonyl chloride (*Biorg. Med. Chem. Lett.*, 1997, 7(17), 2223–2228) (1.2 g), and the mixture was stirred for 16 hours. The reaction was partitioned between 10% aqueous citric acid (50 ml) and ethyl acetate (50 ml). The organic fraction was washed with water (50 ml), brine (50 ml), dried over magnesium sulfate, filtered and concentrated under reduced pressure. The residue was purified by column chromatography on silica gel (50 g) eluting with a solvent gradient of pentane: ethyl acetate (8:2 to 0:1 by volume). The material thus obtained was dissolved in dioxan (6 ml) and 1N NaOH (6 ml) was added. The mixture was stirred at 60° C. for 1.5 hours. The reaction was traeted with 10% aqueous citric acid (50 ml), and extracted with ethyl acetate (50 ml), dried over magnesium sulfate, filtered and concentrated under reduced pressure to yield the title compound as a yellow solid (176 mg).

$\delta_H$ (300 MHz, d$_6$DMSO) 10.5 (1H, s), 8.10 (1H, s), 7.35–7.45 (1H, m), 7.05 (2H, d) 6.85 (2H, d), 4.70 (1H, t), 4.10 (1H, t), 3.60 (2H, m), 3.60 (2H, m), 3.55 (3H, s), 2.20 (3H, s), 2.20 (3H, s). m/z (electrospray) [MH$^+$]=403.0; C$_{19}$H$_{23}$N$_4$O$_4$S requires 403.14

Example 51

N-[3-{2-[(5-chloropyrimidin-2-yl)oxy]ethoxy}-1-methyl-4-(4-methylphenyl)-1H-pyrazol-5-yl]-5-methylpyridine-2-sulphonamide

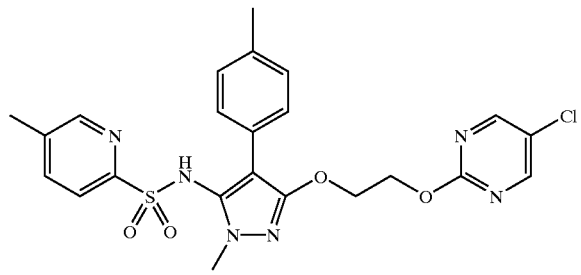

To N-[3-(2-hydroxyethoxy)-1-methyl-4-(4-methylphenyl)-1H-pyrazol-5-yl]-2-pyridine sulphonamide (Example 50) (100 mg) in dry tetrahydrofuran (5 ml) at room temperature was added sodium hydride (80% dispersion in oil, 20 mg) the mixture was stirred for 20 minutes. A solution of 5-chloro-2-methylsulphonylpyrimidine (72 mg) in dry tetrahydrofuran (2.5 ml) was then added and the mixture was stirred for a further 16 hours. The mixture was then treated with further sodium hydride (80% dispersion in oil, 20 mg) and after 15 minutes stirring further 5-chloro-2-methylsulphonylpyrimidine (84 mg) was also added. The mixture was stirred for 4 hours. The reaction was treated with citric acid (10% aq.) and extracted with ethyl acetate (50 ml). The organic fraction was washed with brine (50 ml), dried over magnesium sulfate, filtered and concentrated under reduced pressure. The residue was purified by column chromatography on silica (10 g) eluted with a solvent gradient of pentane:ethyl acetate (8:2 to 0:1) to yield the tile compound as a yellow solid (101 mg).

$\delta_H$ (300 MHz, CDCl$_3$) 8.40 (2H, s), 7.90 (1H, s), 7.45 (1H, d), 7.30 (1H, d), 6.85 (2H, d), 6.75 (2H, d), 4.65 (2H, t), 4.50 (2H, t), 3.85 (3H, s), 2.30 (3H, s), 2.20 (3H, s). m/z (electrospray) [MH$^+$]=515.0; C$_{23}$H$_{24}$ClN$_6$O$_4$S requires 515.13

Example 52

N-[3-(2-hydroxyethoxy)-1-methyl-4-(4-methylphenyl)-1H-pyrazol-5-yl]-pyridine-2-sulphonamide To N-[3-(2-acetoxyethoxy)-1-methyl-4-(4-methylphenyl)-1H-pyrazole-5-yl]-2-pyridine

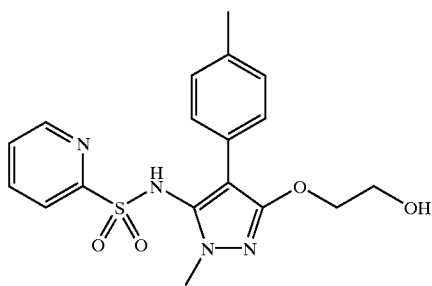

sulfonamide (Preparation 35) (1.05 g) in dioxan (10 ml) was added 1N NaOH (aq.) (5.34 ml). The mixture was stirred at 50° C. for 1 hour. The reaction was concentrated under reduced pressure to low volume and then partitioned between ethyl acetate (20 ml) and water (15 ml). The aqueous layer was separated and acidified to pH 6 with 2N hydrochloric acid (aq.). the product was extracted with ethyl acetate (2×20 ml), washed with water, dried over magnesium sulfate, filtered and concentrated under reduced pressure. The residue was purified by column chromatography on silica gel eluting with solvent gradient, pentane:ethyl acetate (4:6 to 0:1, by volume) to yield the title compound as a colourless foam (560 mg).

$\delta_H$ (400 MHz, CDCl$_3$) 8.20 (1H, m), 7.65–7.50 (2H, m), 7.15 (1H, m), 7.10 (1H, bs), 6.90 (2H, d), 6.80 (2H, d), 4.30 (2H, m), 3.85 (5H, m), 2.90 (1H, bs), 2.25 (3H, s). m/z (electrospray) [MH$^+$]=389.3; C$_{18}$H$_{21}$N$_4$O$_4$S requires 389.4

Example 53

N-[3-{2-[(5-chloropyrimidin-2-yl)oxy]ethoxy}-1-methyl-4-(4methylphenyl)-1H-pyrazol-5-yl] pyridine-2-sulphonamide

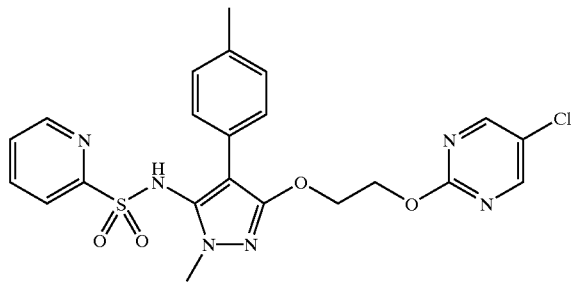

To N-[3-(2-hydroxyethoxy)-1-methyl-4-(4-methylphenyl)-1H-pyrazol-5-yl]-2-pyridine sulphonamide (Example 52) (200 mg) in dry tetrahydrofuran (2 ml) at room temperature was added sodium hydride (80% dispersion in oil, 35 mg) the mixture was stirred for 10 minutes. A solution of 5-chloro-2-methylsulphonylpyrimidine (134 mg) in dry tetrahydrofuran (2.5 ml) was then added and the mixture was stirred for a further 4 hours. The mixture was stirred for 4 hours. The reaction was treated with water (50 ml) and extracted with ethyl acetate (50 ml). The aqueous phase was neutralised to pH7 with 2N hydrochloric acid (aq.). The organic fraction was washed with brine (50 ml), dried over magnesium sulfate, filtered and concentrated under reduced pressure. The residue was purified by column chromatography on silica (10 g) eluted with a solvent gradient of pentane:ethyl acetate (1:1 to 0:1) to yield the tile compound as a colourless foam (120 mg).

$\delta_H$ (400 MHz, CDCl$_3$) 8.40 (2H, s), 8.20 (1H, m), 7.60–7.50 (2H, m), 7.15 (1H, m), 7.05 (1H, bs), 6.80 (4H, m), 4.65 (2H, m), 4.55 (2H, m), 3.85 (3H, s), 2.25 (3H, s).

Example 54

5-Isopropyl-N-{1-methyl-4-(4-methylphenyl)-3[(2-pyrimidinyloxy)ethoxy]-1H-pyrazol-5-yl}-pyridine-2-sulfonamide

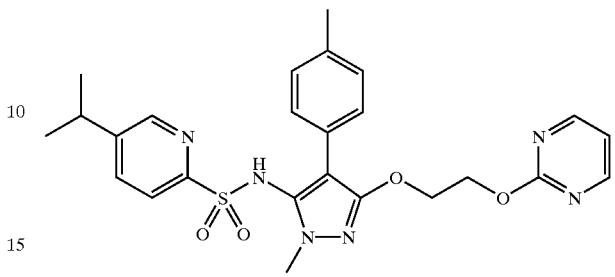

N-[3-{2-[(5-bromo-2-pyrimidinyl)oxy]ethoxy}-1-methyl-4-(4-methylphenyl)-1H-pyrazol-5-yl]-5-isopropylpyridine-2-sulfonamide (Example 41) (393 mg), powdered sodium formate (68 mg) and dichlorobis (triphenylphosphine)palladium (II) (9.4 mg) were placed in a Wheaton® vial (2.5 ml) volume containing a stirring vane. Dimethylformamide (2.0 ml) which had been saturated with carbon monoxide gas at room temperature, was added to the vial so as to produce a yellow solution. The sealed vial was magnetically stirred at 100° C. (oil bath temperature) for 3 hours before being left to cool to room temperature. A TLC check showed the presence of a significant amount of starting material. Addition of dichlorobis (triphenylphosphine)palladium (II) (9.4 mg) and resaturation of the dimethylformamide with carbon monoxide was followed by heating of the vial's contents for a further hour. On cooling to room temperature, the solution was degassed by bubbling nitrogen gas through it. The mixture was treated with ethyl acetate and filtered through a bed of Celite™ (5 g), followed by washing the Celite with ethyl acetate so as to take the solution volume to 100 ml. Washing of this phase with water (3×100 ml) and brine (100 ml), was followed by drying (Na$_2$SO$_4$), filtering and concentration in vacuo. This afforded the title compound as white crystals (157 mg).

$\delta_H$ (300 MHz, CDCl$_3$) 8.70 (2H, d), 8.05 (1H, t), 7.50–7.55 (1H, m), 7.30–7.40 (2H, m), 6.80–6.95 (4H, m), 4.65 (2H, t), 4.55 (2H, t), 3.85 (3H, s), 2.80 (1H, septet), 2.25 (3H, s), 1.20 (6H, d). m/z (electrospray) [MH$^+$]=509.3; C$_{25}$H$_{29}$N$_6$O$_4$S requires 509.1

Example 55

4-(tert-Butyl)-N-[3-(2-methoxyethoxy)-1-methyl-4-(4-methylphenyl)-1H-pyrazol-5-yl) benzenesulfonamide

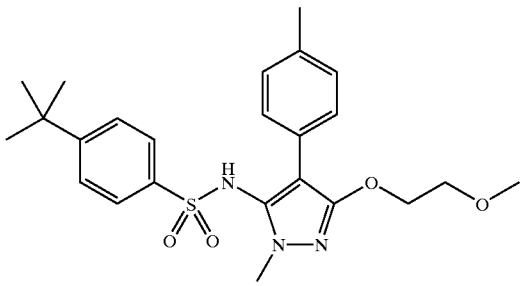

4-(tert-butyl)-N-{[4-(tert-butyl)phenyl]sulfonyl}-N-[3-(2-methoxyethoxy)-1-methyl-4-methylphenyl)-1H-pyrazol- 5-yl]benzenesulfonamide (278 mg) (Preparation 36) was dissolved in dioxane, 1M sodium hydroxide solution (4 ml) was added and the reaction was stirred at reflux for 0.5 hours. The solvent was removed under reduced pressure. The residue was partitioned between ethyl acetate (25 ml) and 1M hydrochloric acid (25 ml). The organic phase was separated, dried over magnesium sulphate and the solvent removed under reduced pressure. The product was purified on silica (10 g) eluting with a solvent gradient of pentane-:ethyl acecate (1:0 to 6.4) to yield the title compound as a white solid (160 mg).

$\delta_H$ (400 MHz, CDCl$_3$) 7.36 (2H, d), 7.12 (2H, d), 6.85 (2H, d), 6.80 (2H, d), 6.55 (1H, s), 4.32 (2H, m), 3.85 (3H, s), 3.66 (2H, m), 3.35 (3H, s), 2.23 (3H, s), 1.24 (9H, s). m/z (electrospray) [MH$^+$]=458.0; C$_{24}$H$_{32}$N$_3$O$_4$S requires 457.1

Example 56

4-(tert-butyl)-N-[3-(2-ethoxyethoxy)-1-methyl-4-(4-methylphenyl)-1H-pyrazol-5-yl)benzenesulfonamide

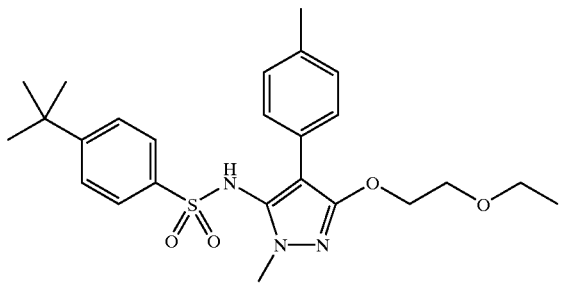

The method employed for Example 55 was used to prepare the title compound from 4-(tert-butyl)-N-{[4-(tert-butyl)phenyl]sulfonyl}-N-[3-(2-ethoxyethoxy)-1-methyl-4-(4-methylphenyl)-1H-pyrazol-5-yl]benzenesulfonamide (Preparation 38)

$\delta_H$ (400 MHz, CDCl$_3$) 7.36 (2H, d), 7.12 (2H, d), 6.85 (2H, d), 6.80 (2H, d), 6.85 (1H, s), 4.32 (2H, m), 3.83 (3H, s), 3.72 (2H, m), 3.52 (2H, q), 2.23 (3H, s), 1.24 (9H, s), 1.89 (3H). m/z (electrospray) [MH$^+$]=472.0; C$_{25}$H$_{34}$N$_3$O$_4$S requires 472.1

Example 57

2-{[5-({[4-tert-butyl)phenyl]sulfonyl}amino)-1-methyl-4-(4-methylphenyl)-1H-pyrazol-3-yl]oxy}ethyl-2-pyridinylcarbamate

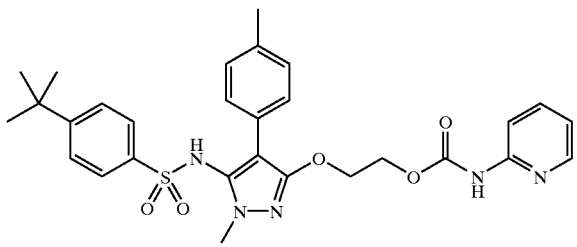

2-Pyridine carboxylic acid (278 mg) and triethylamine (0.321 ml) in toluene (10 ml) was stirred under nitrogen at room temperature for 10 mins. Diphenyl phosphoryl azide (621 mg) was added to the reaction and warmed to 35–40° C. for 1 hour and then at 100° C. until the effervescence had ceased. 4-(tert-butyl)-N-[3-(2-hydroxyethoxy)-1-methyl-4-(4-methylphenyl)-1H-pyrazol-5-yl]benzenesulfonamide (200 mg) (Example 2) and 4-dimethylaminopyridine (8 mg) in toluene (5 ml) was added to the reaction and stirred at 100° C. for a further 45 minutes. The reaction was quenched with water (2 ml) and left to cool. The crude product was loaded onto silica (25 g) and eluted with a solvent gradient of pentane:ethyl acetate (1:0 to 0:1) to yield the title compound as a white solid (106 mg).

$\delta_H$ (400 MHz, CDCl$_3$) 8.34 (1H, d), 7.90 (1H, d), 7.65 (1H, m), 7.43 (1H, s), 7.13 (2H, d), 6.95 (1H, m), 6.83 (1H, d), 6.77 (2H, d), 4.47 (4H, m), 3.83 (3H, s), 2.23 (3H, s), 1.24 (9H, s). m/z (electrospray) [MH$^+$]=563.0; C$_{29}$H$_{34}$N$_5$O$_5$S requires 563.1

Example 58

N-[1-benzyl-3-(2-hydroxyethoxy)-4-(4-methylphenyl)-1H-pyrazol-5-yl]-4-(tert-butyl)benzenesulfonamide

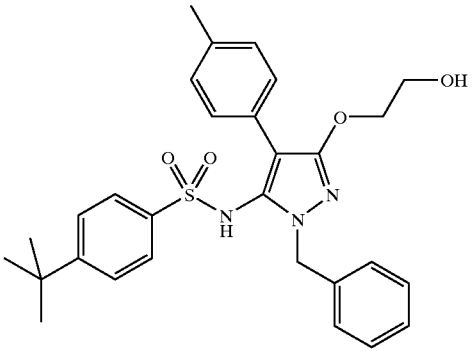

To a stirring solution of 2-{[1-benzyl-5-(bis{[4-(tert-butyl)phenyl]sulfonyl}amino)4-(4-methylphenyl)-1H-pyrazol-3-yl]oxy}ethyl acetate (Preparation 40) (1.01 g) in ethanol (20 ml) was slowly added sodium hydroxide solution (2M, 2 ml). The reaction mixture was left stirring at room temperature overnight. The solvent was removed in vacuo and the residue was taken up in ethyl acetate (30 ml) and washed with water (15 ml) followed by brine (15 ml). It was then dried (MgSO$_4$) and the solvent removed in vacuo to yield the crude material as a yellow oil (ca.1 g). Purification was achieved using the Biotage™ Flash 40 system (silica, 90 g) with a gradient elution of hexane (75% to 65%) and ethyl acetate (25% to 35%) to yield the title product as a yellow solid (250 mg).

$\delta_H$ (400 MHz, CDCl$_3$) 7.40(2H, d), 7.30–7.40(3H, m), 7.25(2H, d), 7.15(2H, d), 6.80–6.95(4H, m), 6.55(1H, br), 5.40(2H, s), 4.30–4.35(2H, m), 3.80–3.90(2H, m), 3.05(1H, t), 2.25(3H, s), 1.25(9H, s). m/z (thermospray) [MH$^+$]= 520.6; C$_{29}$H$_{34}$N$_3$O$_4$S requires 520.7.

Example 59

N-[4-(1,3-benzodioxol-5-yl)-3-methoxy-1-methyl-1H-pyrazol-5-yl]-4-(tert-butyl)benzenesulfonamide

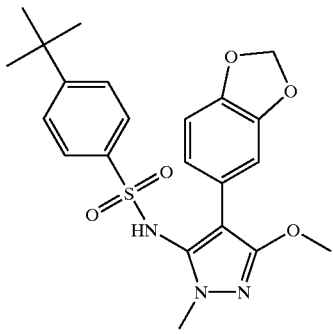

4-(tert-butyl)benzenesulfonyl chloride (190 mg) was added at room temperature under an atmosphere of nitrogen to a solution of 5-amino-4-(1,3-benzodioxol-5-yl)-3-methoxy-1-methyl-1H-pyrazol-3-ol (Preparation 43) (100 mg) and dimethylaminopyridine (50 mg) in anhydrous pyridine (4 ml). The reaction was stirred overnight. The mixture was concentrated under reduced pressure, then a saturated solution of ammonium chloride (6 ml), ethyl acetate (6 ml), and brine (6 ml) were sequentially added. The aqueous phase was extracted with ethyl acetate (2×8 ml) and the combined organic fractions were washed with brine (10 ml), dried over sodium sulfate and concentrated under reduced pressure. The residue was purified to yield the title compound (10 mg).

column:Phenomenex Magellen™, type 5u ODS, size 150×21.2 mm, eluent:water95% to 30% over 2.5 mins then 5% over 15 mins Acetonitrile 5% to 70% over 2.5 mins then 95% over 15 mins Flow rat 20 ml/min Detection UV at 230 nm Column temp 40 degC.

$\delta_H$ (300 MHz, CDCl$_3$) 1.25 (9H, s), 3.85 (3H, s), 3.9 (3H, s), 5.85 (2H, s), 6.35–6.45 (2H, m), 6.55 (1H, d), 6.6 (1H, bs), 7.35 (4H, dd). m/z (electrospray) [MH$^+$]444.1592; C$_{22}$H$_{26}$N$_3$O$_5$S requires 444.1593.

Example 60

N-[4-(1,3-benzodioxol-5-yl)-3-methoxy-1-methyl-1H-pyrazol-5-yl]-4-bromobenzenesulfonamide

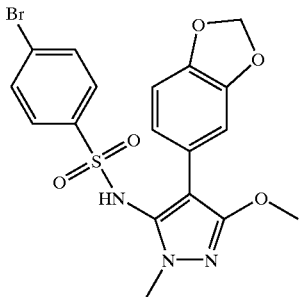

4-Bromobenzenesulfonyl chloride (210 mg) was added at room temperature under an atmosphere of nitrogen to a solution of 5-amino-4-(1,3-benzodioxol-5-yl)-3-methoxy-1-methyl-1H-pyrazole (Preparation 43) (100 mg) and dimethylaminopyridine (50 mg) in anhydrous pyridine (4 ml). The reaction was stirred overnight. The mixture was concentrated under reduced pressure, then a saturated solution of ammonium chloride (6 ml), ethyl acetate (6 ml), and brine (6 ml) were sequentially added. The aqueous phase was extracted with ethyl acetate (2*8 ml) and the combined organic fractions were washed with brine (10 ml), dried over sodium sulfate and concentrated under reduced pressure. The residue was purified to yield the title compound (4 mg).

column:Phenomenex Magellen™, type 5u ODS, size 150×21.2 mm, eluent:water95% to 30% over 2.5 mins then 5% over 15 mins Acetonitrile 5% to 70% over 2.5 mins then 95% over 15 mins Flow rat 20 ml/min Detection UV at 230 nm Column temp 40 degC.

$\delta_H$ (300 MHz, CDCl$_3$) 3.85 (3H, s), 3.9 (3H, s), 5.95 (2H, s), 6.35 (1H, s), 6.4 (1H, m), 6.55 (1H, bs), 6.6 (1H, d), 7.30 (4H, m). m/z (electrospray) [MH$^+$]466.0076; C$_{18}$H$_{17}$BrN$_3$O$_5$S requires 466.0072.

Example 61

N-[4-(1,3-benzodioxol-5-yl)-3-methoxy-1-methyl-1H-pyrazol-5-yl]-4-isopropylbenzenesulfonamiide

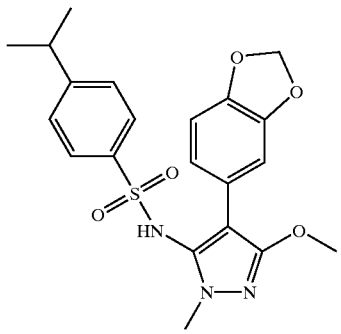

4-Isopropylbenzenesulfonyl chloride (176 mg) was added at room temperature under an atmosphere of nitrogen to a solution of 5-amino-4-(1,3-benzodioxol-5-yl)-3-methoxy-1-methyl-1H-pyrazole (Preparation 43) (100 mg) and dimethylaminopyridine (50 mg) in anhydrous pyridine (4 ml). The reaction was stirred overnight. The mixture was concentrated under reduced pressure, then a saturated solution of ammonium chloride (6 ml), ethyl acetate (6 ml), and brine (6 ml) were sequentially added. The aqueous phase was extracted with ethyl acetate (2*8 ml) and the combined organic fractions were washed with brine (10 ml), dried over sodium sulfate and concentrated under reduced pressure. The residue was purified to yield the title compound (11.9 mg).

column:phenomenex Magellen, type 5u ODS, size 150× 21.2 mm, eluent:water 95% to 30% over 2.5 mins then 5% over 15 mins Acetonitrile 5% to 70% over 2.5 mins then 95% over 15 mins Flow rat 20 ml/min Detection UV at 230 nm Column temp 40 degC.

$\delta_H$ (300 MHz, CDCl$_3$) 1.2 (6H, d), 2.85 (1H, m), 3.85 (3H, s), 3.90 (3H, s), 5.85 (2H, s), 6.4 (2H, m), 6.55 (1H, d), 6.65 (1H, br.s), 7.25 (4H, dd). m/z (electrospray) [MH$^+$] 430.1446; $C_{21}H_{24}N_3O_5S$ requires 430.1436.

Example 62

N-[4-(1,3-benzodioxol-5-yl)-3-methoxy-1-methyl-1H-pyrazol-5-yl]-4-chlorobenzenesulfonamide

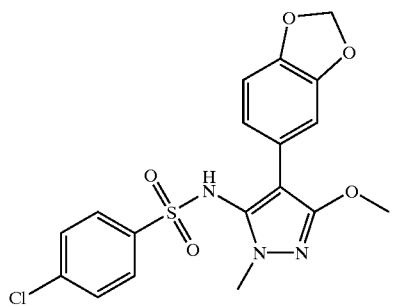

An aqueous solution of sodium hydroxyde (2M, 270 □l), was added at room temperature to a solution of N-[4-(1,3-benzodioxol-5-yl)-3-methoxy-1-methyl-1H-pyrazol-5-yl]-4-chloro-N-[(4-chlorophenyl)sulfonyl]benzenesulfonamide (Preparation 43) (32 mg) in a mixture of methanol (1 ml) and dichloromethane (1 ml). After 1 h, an aqueous saturated solution of ammonium chloride (4 ml) and water (4 ml) were added and the mixture was extracted with dichloromethane (3×5 ml). The combined organic fractions were dried over sodium sulfate and concentrated under reduced pressure. The residue was purified by preparative TLC (silica) eluted with dichloromethane:methanol (95:5) to yield the title compound as colourless oil (15.1 mg).

$\delta_H$ (300 MHz, CDCl$_3$) 3.85 (3H, s), 3.9 (3H, s), 5.95 (2H, s), 6.35 (1H, s), 6.4 (1H, d), 6.6 (1H, d), 6.75 (1H, br.s) 7.27 (4H, dd). m/z (electrospray) [MH$^+$]422.0584; $C_{18}H_{17}ClN_3O_5S$ requires 422.0577

Example 63

N-[4-(1,3-benzodioxol-5-yl)-3-methoxy-1-methyl-1H-pyrazol-5-yl]-4-iodobenzenesulfonamide

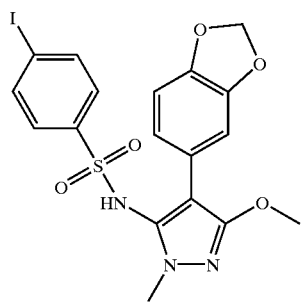

4-Iodobenzenesulfonyl chloride (245 mg) was added at room temperature under an atmosphere of nitrogen to a solution of 5-amino-4-(1,3-benzodioxol-5-yl)-3-methoxy-1-methyl-1H-pyrazole (Preparation 43) (100 mg) and dimethylaminopyridine (50 mg) in anhydrous pyridine (4 ml).

The reaction was stirred overnight. The mixture was concentrated under reduced pressure, then a saturated solution of ammonium chloride (6 ml), ethyl acetate (6 ml), and brine (6 ml) were sequentially added. The aqueous phase was extracted with ethyl acetate (2*8 ml) and the combined organic fractions were washed with brine (10 ml), dried over sodium sulfate and concentrated under reduced pressure. The residue was purified by physical sciences. (15.9 mg)

column:Phenomenex Magellen™, type 5u ODS, size 150×21.2 mm, eluent:water 95% isocratic over 2.5 min then 5% over 12.5 mins Acetonitrile 5% isocratic over 2.5 mins then 95% over 15 mins Flow rat 20 ml/min Detection UV at 230 nm Column temp 40 degC.

$\delta_H$ (300 MHz, CDCl$_3$) 3.85 (3H, s), 3.9 (3H, s), 6.0 (2H, s), 6.35 (1H, s), 6.4 (1H, m), 6.6 (1H, d), 6.7 (1H, bs), 7.35 (4H, dd). m/z (electrospray) [MH$^+$]513.9949; $C_{18}H_{17}IN_3O_5S$ requires 513.9934.

Example 64

N-[4-(1,3-benzodioxol-5-yl)-3-methoxy-1-methyl-1H-pyrazol-5-yl]-4-methoxybenzenesulfonamide.

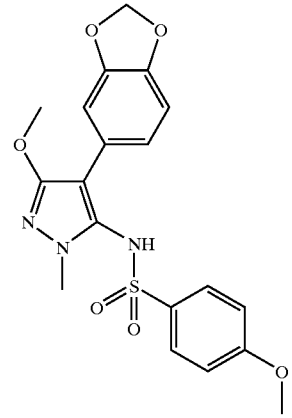

To a solution of 5-amino-4-(1,3-benzodioxol-5-yl)-3-methoxy-1-methyl-1H-pyrazole (Preparation 43) (100 mg) and 4-dimethylaminopyridine (50 mg) in pyridine (4 ml) at room temperature was added 4-methoxybenzenesulfonyl chloride (145 mg), the resulting mixture was stirred at room temperature for 16 hours. The reaction mixture was concentrated under reduced pressure and the residue quenched with citric acid (10%, 10 ml) and then extracted with ethyl acetate (2×10 ml). The organic fractions were combined and washed with saturated aqueous sodium chloride solution (50 ml) the organic fraction was then dried over anhydrous magnesium sulfate, filtered and concentrated under reduced pressure. The residue (259 mg) was purified by preparative HPLC on a 5μ ODS Phenomenex Magellen™ column with a gradient elution of acetonitrile (5% to 95%) and 0.1M NH$_4$OAc (95% to 5%) to yield the desired product as an amorphous white solid (10 mg).

$\delta_H$ (300 MHz, CDCl$_3$) 7.38 (2H, d), 6.62 (2H, d), 6.56 (1H, d), 6.50 (1H, d), 6.42–6.38 (1H, m). 6.32 (1H, d), 5.88 (2H, s), 3.88 (3H, s), 3.84 (3H, s), 3.82 (3H, s). m/z (electrospray) [MH$^+$]=418.1; $C_{19}H_{20}N_3O_6S$ requires 418.1.

Example 65

N-[4-(1,3-benzodioxol-5-yl)-3-methoxy-1-methyl-1H-pyrazol-5-yl]-3,4-dimethoxybenzenesulfonamide.

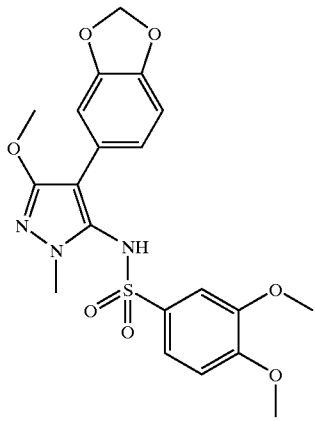

The title compound was prepared in the same manner as Example 64 except that 3,4-dimethoxybenzenesulfonyl chloride (166 mg) was substituted for 4-methoxybenzenesulfonyl chloride. The desired product was recovered as an amorphous white solid (8 mg).

$\delta_H$ (300 MHz, CDCl$_3$) 7.10–7.06 (1H, m), 6.82–6.84 (1H, m), 6.58 (1H, d), 6.54 (1H, d) 6.40 (1H, d), 5.90 (2H, s), 3.92–3.84 (9H, m), 3.74 (3H, s). m/z (electrospray) [MH$^+$]= 448; C$_{20}$H$_{22}$N$_3$O$_7$S requires 448.1.

Example 66

N-[4-(1,3-benzodioxol-5-yl)-3-methoxy-1-methyl-1H-pyrazol-5-yl]-2,1,3-benzothiadiazole-4-sulfonamide

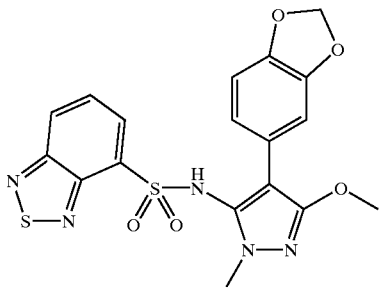

To a solution of 4-dimethylaminopyridine in anhydrous pyridine at 0° C. under an atmosphere of nitrogen was added 2,1,3-benzothiadiazole-4-sulfonyl chloride (142 mg) in pyridine (1.5 ml). After 10 min the reaction was treated with 5-amino-4-(1,3-benzodioxol-5-yl)-3-methoxy-1-methyl-1H-pyrazole (Preparation 43) (100 mg) and the reaction was allowed to warm to room temperature and stirred for 12 h. The reaction was concentrated under reduced pressure, the residue diluted with brine (100 ml) and extracted with dichloromethane (3×50 ml). The combined organic fractions were dried over sodium sulfate, filtered and concentrated under reduced pressure. The residue was purified by HPLC (eluent of 55% water in acetonitrile to 30% water in acetonitrile over 8 mins, then 30% water in acetonitrile for 13 mins. Phenomenex Magellen™ 150 mm×21.5 mm column, 40° C.) to yield the title compound as an off-white solid (7 mg).

$\delta_H$ (300 MHz, CDCl$_3$) 3.80 (s, 3H), 3.90 (s, 3H), 5.85 (s, 2H), 5.90 (s, 1H), 6.05 (d, 1H), 6.15 (d, 1H), 7.50 (m, 1H), 7.90 (d, 1H), 8.05 (d, 1H) m/z (thermospray) [MH$^+$]=446.1; C$_{18}$H$_{16}$N$_5$O$_5$S$_2$ requires 446.1

Example 67

N-[4-(1,3-benzodioxol-5-yl)-3-methoxy-1-methyl-1H-pyrazol-5-yl]-4-(trifluoromethyl)benzenesulfonamide

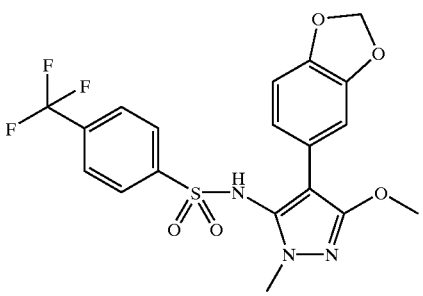

To a solution of 4-dimethylaminopyridine in anhydrous pyridine at 0° C. under an atmosphere of nitrogen was added 4-(trifluoromethyl)benzenesulfonyl chloride (148 mg) in pyridine (1.5 ml). After 10 min the reaction was treated with 5-amino-4-(1,3-benzodioxol-5-yl)-3-methoxy-1-methyl-1H-pyrazole (Preparation 43) (100 mg) and the reaction was allowed to warm to room temperature and stirred for 12 h. The reaction was concentrated under reduced pressure, the residue treated with 1.0M aqueous citric acid (100 ml) and extracted with dichloromethane (3×50 ml). The combined organic fractions were dried over sodium sulfate, filtered and concentrated under reduced pressure. The residue was purified by HPLC (eluent of 55% water in acetonitrile to 30% water in acetonitrile over 8 mins, then 30% water in acetonitrile for 13 mins. Phenomenex Magellen™ 150 mm×21.5 mm column, 40° C.) to yield the title compound as an off-white solid (1 mg).

$\delta_H$ (300 MHz, CDCl$_3$) 3.85 (3H, s), 3.90 (3H, s), 5.80 (2H, s), 6.30–6.40 (2H, m), 7.45 (2H, d), 7.60 (2H, d) m/z (thermospray) [MH$^+$]=456; C$_{19}$H$_{17}$F$_3$N$_3$O$_5$S requires 456.4

Example 68

N-[4-(1,3-benzodioxol-5-yl)-1-methyl-3-(2-{[5-(methylsulfonyl)-2-pyrimidinyl]oxy}ethoxy)-1H-pyrazol-5-yl]-4-(tert-butyl)benzenesulfonamide

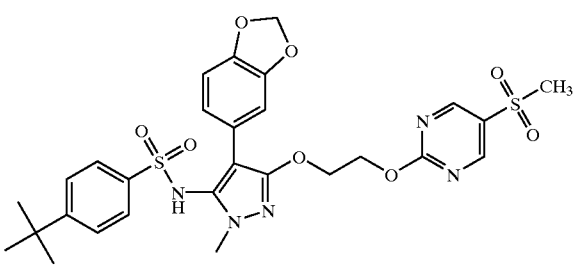

To a solution of N-[4-(1,3-benzodioxol-5-yl)-3-(2-hydroxyethoxy)-1-methyl-1H-pyrazol-5-yl]-4-(tert-butyl)benzenesulfonamide (Example 17) (300 mg, 0.63 mmol) in anhydrous tetrahydrofuran (12 ml) and dimethyl acetamide, sodium hydride 60% dispersion in oil (55 mg, 1.39 mmol)

was added under an atmosphere of nitrogen. The reaction mixture was stirred at room temperature for 20 minutes. 2-chloro-5-(methylsulfonyl)pyrimidine (0.69 mmol) was added, in one portion, to the reaction mixture which was then stirred at room temperature for 2 hours. The reaction mixture was concentrated and the residue poured onto water (150 ml). The aqueous was extracted with ethyl acetate (4×50 ml). The organic fractions were washed with brine (4×100 ml), dried over magnesium sulphate, filtered and concentrated under reduced pressure to yield the title compound (65 mg) as a yellow crystalline solid.

$\delta_H$ (300 MHz, CDCl$_3$) 8.98 (2H, s), 7.42 (2H, d), 7.22 (2H, d), 6.52–6.32 (4H, m), 5.86 (2H, s), 4.88–4.82 (2H, m), 4.62–4.56 (2H, m), 3.82 (3H, s), 3.10 (3H, s). m/z (thermospray) [MH$^+$]=630.1; $C_{28}H_{32}N_5O_8S_2$ requires 630.2.

Example 69

N-(4-(1,3-benzodioxol-5-yl)-3-{2-[(5-chloro-2-pyrimidinyl)oxy]ethoxy}-1-methyl-1H-pyrazol-5-yl)-1-methyl-1H-imidazole-4-sulfonamide

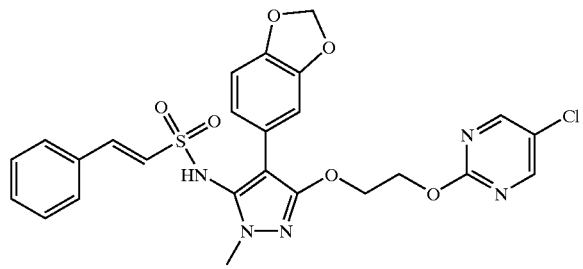

Sodium hydride (60% dispersion in oil, 20 mg) was carefully added to a solution of (E)-N-[-4-(1,3-benzodioxol-5-yl)-3-(2-hydroxyethoxy)-1-methyl-1H-pyrazol-5-yl]-2-phenyl-1-ethenesulfonamide (Preparation 44) (100 mg) in anhydrous dimethylformamide (4.4 ml) at room temperature under an atmosphere of nitrogen. After 10 minutes the 5-chloro-2-(methylsulfonyl)pyrimidine (104 mg) was added and the mixture was stirred overnight. To the reaction mixture was then sequentially added an aqueous solution of ammonium chloride (4 ml) and water (30 ml) before being extracted with ether (3×8 ml). Combined organic phases were sequentially washed with water (20 ml), brine (20 ml), dried over magnesium sulfate and concentrated under reduced pressure. A purification by column chromatography (silica, 10 g) eluted with dichloromethane:methanol (95:5) yielded the title compound as a colourless oil (85 mg).

$\delta_H$ (300 MHz, CDCl$_3$) 3.8 (s, 3H), 4.55 (2H, m), 4.72 (2H, m), 5.65 (2H, s), 6.25 (1H, d), 6.55 (1H, d), 6.65–6.75 (3H, m), 7.05 (1H, d), 7.15 (1H, d), 7.25–7.4 (3H, m), 8.4 (2H, s). m/z (electrospray) [MH$^+$]556.1056; $C_{25}H_{23}ClN_5O_6S$ requires 556.1052.

Example 70

N-(4-(1,3-benzodioxol-5-yl)-3-{2-[(5-chloro-2-pyrimidinyl)oxy]ethoxy}-1-methyl-1H-pyrazol-5-yl)-4-(2-hydroxy-1,1-dimethylethyl)benzenesulfonamide

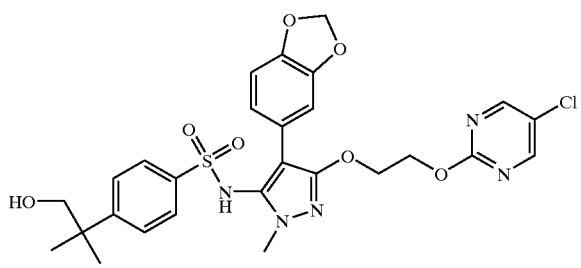

*Amycolata autotrophica* ATCC35203 maintained on a ¼ strength ATCC172 agar slope was inoculated as a loopful of spores into a 300 ml Erlenmeyer flasks each containing 50 ml of of MY inoculum medium. This was allowed to incubate for 2 days at 28° C., 200 rpm on an Infors Multitron Shaker with 1" throw. 2 mls of this inoculum was then transferred to each of nine 300 ml Erlenmeyer flask containing 50 ml of MY production medium and incubated under the same conditions for a further 24 hours. At this point 5 mg of N-(4-(1,3-benzodioxol-5-yl)-3-{2-[(5-chloro-2-pyrimidinyl)oxy]ethoxy}-1-methyl-1H-pyrazol-5-yl)4-(tert-butyl)benzenesulfonamide (Example 34) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm) in seven injections. Using a gradient mobile phase of 35:65 to 20:80 water/methanol from 1.5 to 20 minutes at a flow rate of 20 ml/min, the product was eluted at 8.4 minutes. The product fractions were concentrated under reduced pressure to yield the title compound as a colourless amorphous solid (10.0 mg).

HPLC retention time—Method A; 8 minutes.

$\delta_H$ (300 MHz, CDCl$_3$) 8.40 (2H, s); 7.40 (2H, d); 7.20 (2H, d); 6.45 (2H, s); 6.40 (1H, s); 5.85 (2H, s); 4.70 (2H, m); 4.50 (2H, m); 3.85 (3H, s); 3.55 (2H, s); 1.25 (6H, s) m/z (ESI) [M+H$^+$]=602.1474; $C_{27}H_{28}ClN_5O_7S$ requires 602.1476 m/z (ESI) [M+Na$^+$]=624.1273; $C_{27}H_{28}ClN_5O_7SNa$ requires 624.1296

$\nu_{max}$ (NaCl, film) 3384, 2964, 1580, 1551, 1486, 1428, 1325, 1231, 1163, 1107, 1041, 936 cm$^{-1}$

Example 71

Preparation of N-[4-(1,3-benzodioxol-5-yl)-3-(2-hydroxyethoxy)-1-methyl-1H-pyrazol-5-yl]-4-(2-hydroxy-1,1-dimethylethyl)benzenesulfonamide

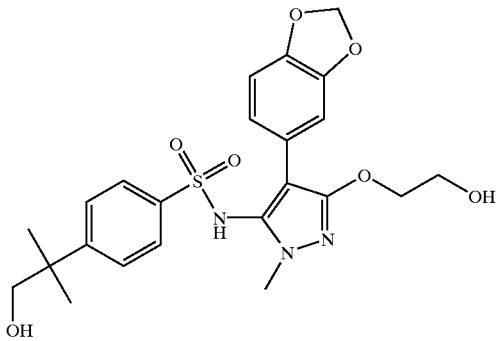

*Amycolata autotrophica* ATCC35203 maintained on a ¼ strength ATCC172 agar slope was inoculated as a loopful of spores into a 300 ml Erlenmeyer flasks each containing 50 ml of of MY inoculum medium. This was allowed to incubate for 2 days at 28° C., 200 rpm on an Infors Multitron Shaker with 1" throw. Two mls of this inoculum was then transferred to each of twenty 300 ml Erlenmeyer flask containing 50 ml of MY production medium and incubated under the same conditions for a further 24 hours. At this point 5 mg of N-[4-(1,3-benzodioxol-5-yl)-3-(2-hydroxyethoxy)-1-methyl-1H-pyrazol-5-yl]-4-(tert-butyl)benzenesulfonamide (Example 17) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm) in two injections. Using a gradient mobile phase of 85:15 to 15:85 water/methanol from 0 to 25 minutes at a flow rate of 20 ml/min, the product was eluted at 14.4 minutes. The product fractions were concentrated under reduced pressure to yield the title compound as a colourless amorphous solid (19.8 mg).

HPLC retention time—Method A; 3.8 minutes.

$\delta$H (300 MHz, CD$_3$OD) 7.45 (2H, d); 7.20 (2H, d); 6.80 (1H, s); 6.75 (1H, d); 6.45 (1H, d); 5.85 (2H, s); 4.20 (2H, m); 3.80 (2H, m); 3.70 (3H, s); 3.45 (2H, s); 1.25 (6H, s) m/z (ESI) [MH$^+$]=490.1669; C$_{23}$H$_{28}$N$_3$O$_7$S requires 490.1648 m/z (ESI) [MNa$^+$]=512,1467; C$_{23}$H$_{27}$N$_3$O$_7$SNa requires 512.1467

$u_{max}$ (PE) 3310, 2923, 1596, 1502, 1336, 1231, 1164, 1106, 1040, 934

Example 72

N-(4-(1,3-benzodioxol-5-yl)-3-{2-[(5-chloro-2-pyrimidinyl)oxy]ethoxy}-1-methyl-1H-pyrazol-5-yl)benzenesulfonamide

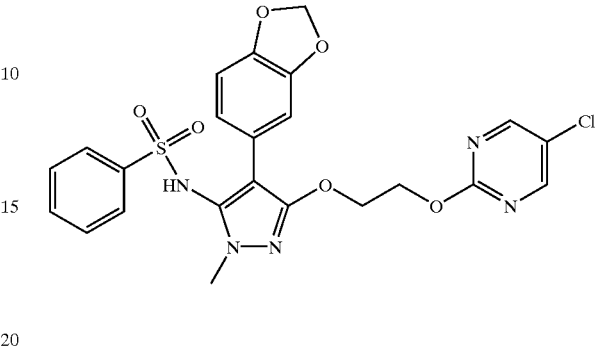

To a solution of N-(4-(1,3-benzodioxol-5-yl)-3-{2-[(5-chloro-2-pyrimidinyl)oxy]ethoxy}-1-methyl-1H-pyrazol-5-yl)-N-(phenylsulfonyl)benzene sulfonamide (Example 47) (60 mg) in methanol (4 ml), at room temperature, was added an aqueous solution of sodium hydroxyde (1M, 510 μl). After three hours the reaction was quenched by the addition of an aqueous saturated solution of ammonium chloride (5 ml) and extracted with ethyl acetate (3×5 ml). The combined organic fractions were washed with brine (10 ml), dried over sodium sulfate and concentrated under reduced pressure. The yellow residue was purified by preparative TLC (silica) eluted with dichloromethane:methanol (95:5) yielding the title compound as a colourless oil (26 mg).

$\delta_H$ (300 MHz, CDCl$_3$) 3.8 (s, 3H), 4.5 (2H, m), 4.7 (2H, m), 5.85 (2H, s), 6.3 (1H, s) 6.35 (1H, d), 6.45 (1H, d), 7.05 (1H, bs), 7.2 (2H, t), 7.35 (1H, t), 7.45 (2H, d), 8.4 (2H, s). m/z (electrospray) [MH$^+$]530.09104; C$_{23}$H$_{21}$ClN$_5$O$_6$S requires 530.0901.

Example 73

N-(4-(1,3-benzodioxol-5-yl)-3-{2-[(5-chloro-2-pyrimidinyl)oxy]ethoxy}-1-methyl-1H-pyrazol-5-yl)methanesulfonamide

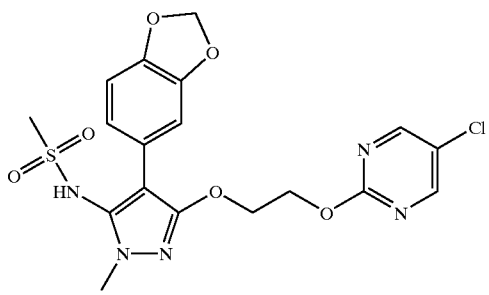

An aqueous solution of sodium hydroxyde (1M, 0.91 ml) was added at room temperature to a solution of N-(4-(1,3-benzodioxol-5-yl)-3-{2-[(5-chloro-2-pyrimidinyl)oxy]ethoxy}-1-methyl-1H-pyrazol-5-yl)-N-(methylsulfonyl)methane sulfonamide (Preparation 49) (50 mg) in a mixture of methanol (1 ml) and dichloromethane (0.3 ml). After 1 h the reaction was diluted with an aqueous saturated solution of ammonium chloride (4 ml) and the mixture was extracted with dichloromethane (3*5 ml). The combined organic fractions were dried over sodium sulfate and concentrated under reduced pressure. The pale yellow oil was purified by preparative TLC (silica) eluted with dichloromethane:methanol (95:5) to yield the title compound as a colourless oil (33 mg)

$\delta_H$ (300 MHz, CDCl$_3$) 2.4 (s, 3H), 3.6 (3H, s), 4.0 (1H, bs), 4.45 (2H, m), 4.6 (2H, m), 5.8 (2H, s), 6.6 (1H, d), 6.95 (1H, d), 7.0 (1H, s), 8.35 (2H, s). m/z (electrospray) [MH$^+$] 468.0744; C$_{18}$H$_{19}$ClN$_5$O$_6$S requires 468.0744.

Example 74

N-(4-(1,3-benzodioxol-5-yl)-3-{2-[(5-chloro-2-pyrimidinyl)oxy]ethoxy}-1-methyl-1H-pyrazol-5-yl)-1-methyl-1H-imidazole-4-sulfonamide

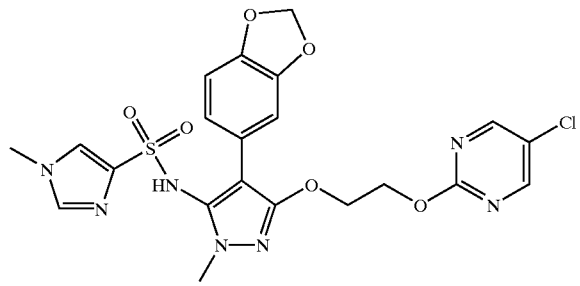

1-Methyl-1H-imidazole-4-sulfonyl chloride (45 mg) was carefully added at room temperature under an atmosphere of nitrogen to a solution of 4-(1,3-benzodioxol-5-yl)-3-{2-[(5-chloro-2-pyrimidinyl)oxy]ethoxy}-1-methyl-1H-pyrazol-5-ylamine (Preparation 48) (50 mg) and dimethylaminopyridine (16 mg) in anhydrous pyridine (2.4 ml). The reaction was stirred for two days, then the mixture was concentrated under reduced pressure and a saturated solution of ammonium chloride (6 ml), ethyl acetate (6 ml) and brine (6 ml) were sequentially added. The aqueous phase was extracted with ethyl acetate (2×8 ml) and the combined organic phases were washed with brine (10 ml), dried over sodium sulfate and concentrated under reduced pressure. The black residue was purified by preparative TLC (silica) eluted with dichloromethane:methanol (95:5) yielding a mixture of title compound and N-(4-(1,3-benzodioxol-5-yl)-3-{2-[(5-chloro-2-pyrimidinyl)oxy]ethoxy}-1-methyl-1H-pyrazol-5-yl)-1-methyl-N-[(1-methyl-1H-imidazol-4-yl)sulfonyl]-1H-imidazole-4-sulfonamide. The title compound was purified by HPLC (5.4 mg).

column:Phenomenex Magellen™, type C18 5μ ODS, size 150×21.2 mm, eluent:gradient:water:acetonitrile (60:40) to 55:45 to 1 to 12 min then at 55:45 to 14 min Flow rat 20 ml/min Detection UV at 230 nm Column temp 40 degC.

$\delta_H$ (300 MHz, CDCl$_3$) 3.7 (3H, s), 3.8 (s, 3H), 4.55 (2H, m), 4.7 (2H, m), 5.9 (2H, s), 6.6–6.7 (3H, m), 7.0 (1H, s), 7.1 (1H, s), 8.4 (2H, s). m/z (electrospray) [MH$^+$]534.0963; C$_{21}$H$_{21}$ClN$_7$O$_6$S requires 534.0962.

Example 75 ethyl 2-{4-[([4-(1,3-benzodioxol-5-yl)-3-(cyclopropylmethoxy)-1-methyl-1H-pyrazol-5-yl]amino)sulfonyl]phenyl}-2-methylpropanoate

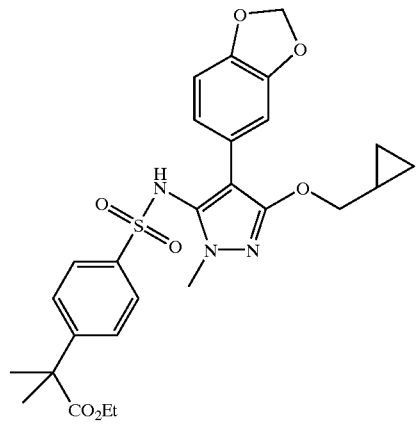

To 4-(1,3-benzodioxol-5-yl)-3-(cyclopropylmethoxy)-1-methyl-1H-pyrazol-5-ylamine (Preparation 50) (230 mg) in anhydrous pyridine (8 ml) at room temperature under an atmosphere of nitrogen was added dimethylaminopyridine (108 mg) and ethyl 2-[4-(chlorosulfonyl)phenyl]-2-methylpropanoate (512 mg). The mixture was stirred overnight and then concentrated under reduced pressure. HCl 0.01N (100 ml) was poured on the resulting yellow syrup and the resulting mixture was extracted with dichloromethane (3×50 ml). The organic fraction was concentrated under reduced pressure and the residue was dissolved in methanol (8 ml). An aqueous solution of sodium hydroxyde (2M, 2 ml) was added and the reaction was stirred overnight. Water (10 ml) was then added, the mixture was acidified with an aqueous solution of HCl (1N) and extracted with dichloromethane (3×10 ml). The combined organic fractions were dried on sodium sulfate and concentrated under reduced pressure. The residue was purified by column chromatography (silica, 35 g) eluted with hexane:ethyl acetate (2:1) to yield the title as a pale yellow oil (281 mg).

$\delta_H$ (300 MHz, CDCl$_3$) 0.3 (2H, m), 0.55 (2H, m), 1.2 (3H, t), 1.55 (6H, s), 3.8 (3H, s), 4.0 (2H, d), 4.1 (2H, q), 5.9 (2H, s), 6.4 (1H, m), 6.5–6.6 (2H, m), 7.32 (4H, AB syst). m/z (electrospray) [M+H$^+$]542.1947; C$_{27}$H$_{32}$N$_3$O$_7$S requires 542.1961.

Example 76

2-[4-({[4-(1,3-benzodioxol-5-yl)-3-(cyclopropylmethoxy)-1-methyl-1H-pyrazol-5-yl]amino}sulfonyl)phenyl]-2-methylpropanoic acid

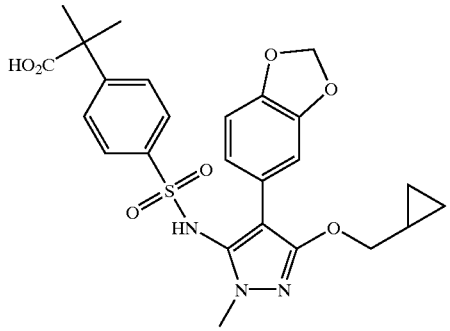

An aqueous solution of sodium hydroxyde (2N, 1 ml) was slowly added to a solution of ethyl 2-{4-[({4-(1,3-benzodioxol-5-yl)-3-(cyclopropylmethoxy)-1-methyl-1H-pyrazol-5-yl]amino)sulfonyl]phenyl}-2-methylpropanoate (Example 75) (83 mg) in a mixture of methanol:water:tetrahydrofuran (1:1:1) (6 ml) and the reaction was heated to 50 C. for 24 h. The reaction was quenched by the addition of a saturated aqueous solution of ammonium chloride (8 ml) and extracted with dichloromethane (3×8 ml). The organic fraction was dried over sodium sulfate and concentrated under reduced pressure. The residue was purified by preparative TLC eluted with dichloromethane:methanol (9:1) yielding the title compound as a white solid (28.8 mg).

$\delta_H$ (300 MHz, CDCl$_3$) 0.3 (2H, m), 0.55 (2H, m), 1.25 (1H, m), 1.6 (6H, s), 3.8 (3H, s), 4.0 (2H, d), 5.8 (2H, s), 6.5 (2H, s), 6.6 (1H, s), 7.32 (4H, AB syst). m/z (electrospray) [M+H$^+$]514.1629; C$_{25}$H$_{28}$N$_3$O$_7$S requires 514.1647.

Example 77 ethyl 2-[4-({[4-(1,3-benzodioxol-5-yl)-3-(2-hydroxyethoxy)-1-methyl-1H-pyrazol-5-yl]amino}sulfonyl)phenyl]-2-methylpropanoate

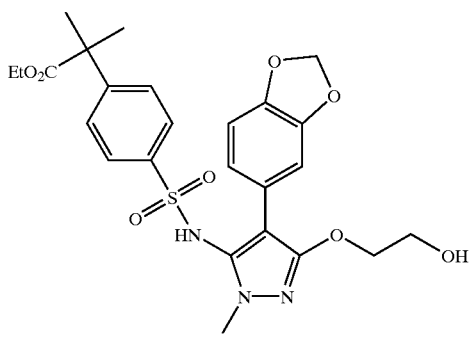

Solid potassium carbonate (290 mg) was added at room temperature to a solution of impure ethyl 2-{4-[({3-[2-(acetyloxy)ethoxy]-4-(1,3-benzodioxol-5-yl)-1-methyl-1H-pyrazol-5-yl}{[4-(2-ethoxy-1,1-dimethyl-2-oxoethyl)phenyl]sulfonyl}amino)sulfonyl]phenyl}-2-methylpropanoate (Preparation 51) in a mixture of methanol (3 ml) and dichloromethane (3 ml). The reaction was left overnight, then an aqueous saturated solution of ammonium chloride (10 ml) was added. The aqueous phase was acidified by the addition of an aqueous solution of HCl (1N, few drops), the phases were separated and the aqueous phase was extracted with dichloromethane (2×10 ml). The organic fraction was dried over sodium sulfate, concentrated under reduced pressure, and the residue was purified by column chromatography (silica, 3.5 g) eluted with hexane:ethyl acetate (1:1) yielding the title compound as a colourless oil (240 mg).

$\delta_H$ (300 MHz, CDCl$_3$) 1.15 (3H, t), 1.55 (6H, s), 3.8 (3H, s), 3.9 (2H, m), 4.1 (2H, q), 4.35 (2H, m), 5.9 (2H, s), 6.4 (1H, d), 6.45 (1H, s), 6.55 (1H, d), 6.6 (1H, bs), 7.35 (4H, dd). m/z (electrospray) [MH$^+$]532.1750; C$_{25}$H$_{30}$N$_3$O$_8$S requires 532.1754.

Example 78

N-[4-(1,3-benzodioxol-5-yl)-1-benzyl-3-(2-hydroxyethoxy)-1H-pyrazol-5-yl]-4-(tert-butyl)benzenesulfonamide

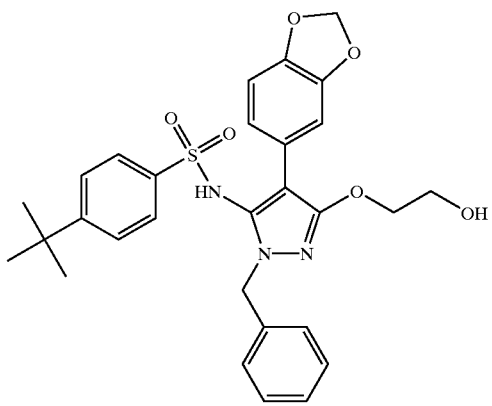

An aqueous solution of sodium hydroxyde (2N, 75 ml) was added at room temperature to a solution of 2-{[4-(1,3-benzodioxol-5-yl)-1-benzyl-5-(bis{[4-(tert-butyl)phenyl]sulfonyl}amino)-1H-pyrazol-3-yl]oxy}ethyl acetate (Preparation 52) (24 g) in ethanol (300 ml) and left overnight. The reaction mixture was then diluted with water (1000 ml), acidified with an aqueous solution of HCl (1N) and extracted with ethyl acetate (3×500 ml). The combined organic phases were washed with brine (500 ml) and concentrated under reduced pressure. The yellow oil was purified by column chromatography (silica, 500 g) eluted with hexane:ethyl acetate (1:1) yielding the title compound as a pale beige solid (16 g).

$\delta_H$ (300 MHz, CDCl$_3$) 1.25 (9H, s), 3.1 (1H, bs), 3.85 (2H, m), 4.35 (2H, m), 5.35 (2H, s), 5.85 (2H, s), 6.40–6.60 (3H, m), 6.65 (1H, bs), 7.20–7.45 (9H, m). m/z (electrospray) [MH$^+$]550.2014; C$_{29}$H$_{32}$N$_3$O$_6$S requires 550.2011.

Example 79

N-[4-(1,3-benzodioxol-5-yl)-3-(2-hydroxyethoxy)-1H-pyrazol-5-yl]-4-(tert-butyl)benzenesulfonamide

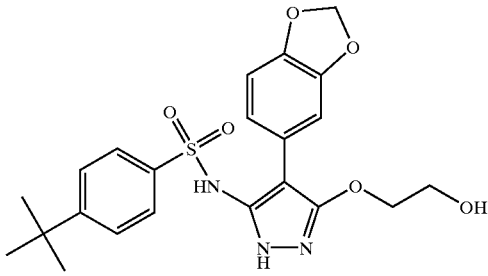

N-[4-(1,3-benzodioxol-5-yl)-1-benzyl-3-(2-hydroxyethoxy)-1H-pyrazol-5-yl]-4-(tert-butyl)benzenesulfonamide (Example 78) (15.8 g) was dissolved in acetic acid (500 ml). Under an atmosphere of nitrogen, Pearlmann's catalyst (JM type 91, 1.6 g) was added and the reaction was stirred for 48 h under 4 bars of hydrogen at 50° C. The reaction mixture was filtered on a short pad of Celite® and concentrated under reduced pressure. To the oily residue was added water (300 ml) and dichloromethane (300 ml). The phases were separated, the organic phase washed with a 5% aqueous solution of sodium bicarbonate (2×150 ml), dried over sodium sulfate and concentrated under reduced pressure. The residue was dissolved in methanol (300 ml), solid potassium carbonate (8 g) was added in one portion and the reaction mixture was stirred overnight and then concentrated under reduced pressure. Water (500 ml) was added to the resulting solid and the mixture as extracted with dichloromethane (3×500 ml). The organic fraction was dried on sodium sulfate and concentrated under reduced pressure. The red-yellow solid was re-crystallised in ethyl acetate yielding the title compound as a white solid (7.2 g)

$\delta_H$ (300 MHz, CDCl$_3$) 1.25 (9H, s), 3.65 (2H, m), 4.15 (2H, m), 4.75 (1H, bs), 5.85 (2H, s), 6.55 (1H, d), 6.62 (1H, d), 6.75 (1H, s), 7.25 (4H, AB syst), 10.2 (1H, s), 12.2 (1H, s). m/z (electrospray) [MH$^+$]460.1534; $C_{22}H_{26}N_3O_6S$ requires 460.1542.

Example 80

N-[4-(1,3-benzodioxol-5-yl)-3-(2-{[5-(methylsulfonyl)-2-pyrimidinyl]oxy}ethoxy)-1H-pyrazol-5-yl]-4-(tert-butyl)benzenesulfonamide

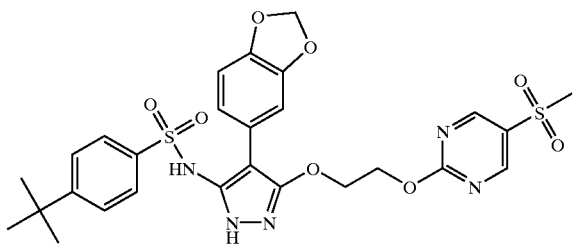

Sodium hydride (60% dispersion in oil, 20 mg) was added at 0° C. under an atmosphere of nitrogen, to a solution of N-[4-(1,3-benzodioxol-5-yl)-3-(2-hydroxyethoxy)-1H-pyrazol-5-yl]-4-(tert-butyl)benzenesulfonamide (Example 79) (50 mg) in a mixture of anhydrous tetrahydrofuran (3 ml) and anhydrous dimethylacetamide (0.8 ml). The reaction mixture was stirred for 10 minutes at 0° C. before a solution of 2-chloro-5-(methylsulfonyl)pyrimidine (42 mg) in anhydrous tetrahydrofuran (1 ml) was added. The reaction mixture was slowly allowed to room temperature and after 4 h, a solution of 2-chloro-5-(methylsulfonyl)pyrimidine (22 mg) in anhydrous tetrahydrofurane (0.5 ml) was added. The reaction was stirred overnight and then was poured into ether (10 ml) and an aqueous solution of HCl (1N, 10 ml). The remaining insoluble material was dissolved by the addition of ethyl acetate. The organic fraction was washed with water (twice 30 ml), brine (50 ml), dried on sodium sulfate and concentrated under reduced pressure. The yellow oil was purified by

HPLC:

column:phenomenex Magellen, type 5$\mu$ODS, size 150× 21.2 mm eluent gradient over 5 min: 0.1M NH$_4$OAc 95% to 50% acetonitrile 5% to 50% then isocratic for 20 min).

$\delta_H$ (300 MHz, CDCl$_3$) 1.3 (9H, s), 3.1 (3H, s), 4.6 (2H, m), 4.85 (2H, m), 5.85 (2H, s), 6.2 (1H, d), 6.25 (1H, s), 6.5(1H, d), 7.55 (4H, AB syst), 8.95 (2H, s). m/z (electrospray) [MH$^+$]616.1539; $C_{27}H_{30}N_5O_8S_2$ requires 616.1536.

Example 81

N-[4-(1,3-benzodioxol-5-yl)-1-(2-hydroxyethyl)-5-methoxy-1H-pyrazol-3-yl]-2-phenyl-1-ethanesulfonamide

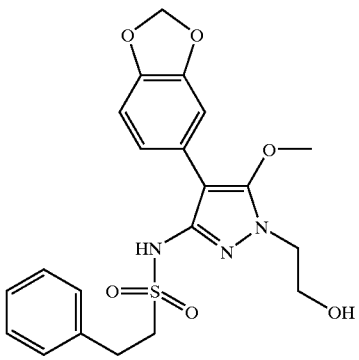

2-{4-(1,3-Benzodioxol-5-yl)-5-methoxy-3-[(methoxymethyl)(phenethylsulfonyl)amino]-1H-pyrazol-1-yl}ethyl acetate (Preparation 54) (70 mg), oxalic acid (200 mg) were dissolved in a mixture of water (2 ml) and methanol (2 ml) and refluxed for two days. The reaction was diluted with water (10 ml) and the mixture was then extracted with dichloromethane (3×8 ml). The combined organic fractions were dried over sodium sulfate, concentrated under reduced pressure to yield a pale yellow oil which was purified by column chromatography (Sep-Pak™, 10 g) eluted with dichloromethane:methanol (97:3) to yield the title compound as a colourless oil (32 mg).

$\delta_H$ (300 MHz, CDCl$_3$) 2.70 (1H, br. s), 3.15 (2H, m), 3.60 (2H, m), 3.70 (3H, s), 3.95 (2H, m), 4.10 (2H, m), 6.00 (2H, s), 6.10 (1H, br. s), 6.80 (1H, m), 6.90 (2H, m), 7.00 (2H, m), 7.15–7.35 (5H, m). m/z (electrospray) [MH$^+$]446.1398; $C_{21}H_{24}N_3O_6S$ requires 446.1385

Example 82

2-{[5-{[(4-tert-butylphenyl)sulfonyl]amino}-1-methyl-4-(4-methylphenyl)-1H-pyrazol-3-yl]oxy}ethyl acetate

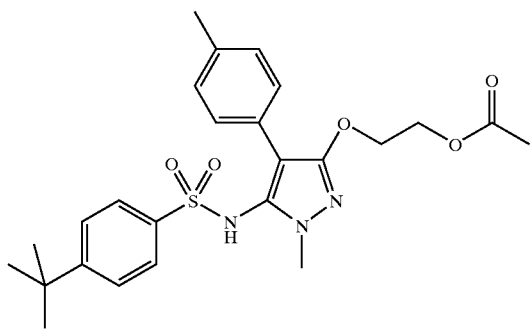

To 2-{[5-amino-1-methyl-4-(4-methylphenyl)-1H-pyrazol-3-yl]oxy}ethyl acetate (Preparation 5) (250 mg) in dimethyl acetamide (2 ml) at room temperature was added sodium hydride (41 mg, 60% dispersion in oil), the mixture was stirred for 5 minutes. To the mixture was added 4-tert-butylbenzenesulphonyl chloride (79 mg), the mixture was stirred for a further 1 hour. The reaction was diluted with water (20 ml) and extracted with diethyl ether (20 ml). The organic fraction was dried over magnesium sulfate, filtered and concentrated under reduced pressure. The residue was purified by column chromatography (silica, 10 g) eluted with dichloromethane:ether (1:1) to yield the title compound as a pale orange solid (40 mg).

$\delta_H$ (300 MHz, CDCl$_3$) 7.35 (2H, d), 7.15 (2H, d), 6.70–6.80 (4H, m), 4.05 (4H, s), 3.55 (3H, s), 2.35 (3H, s), 2.05 (3H, s), 1.10 (9H, s) m/z (thermospray) [MH$^+$]=486.1; C$_{25}$H$_{32}$N$_3$O$_5$S requires 486.2

Example 83

2-[4-({[3-{2-[(5-bromo-2-pyrimidinyl)oxy]ethoxy}-1-methyl-4-(4-methylphenyl)-1H-pyrazol-5-yl]amino}sulfonyl)phenyl]-2-methylpropanoic acid

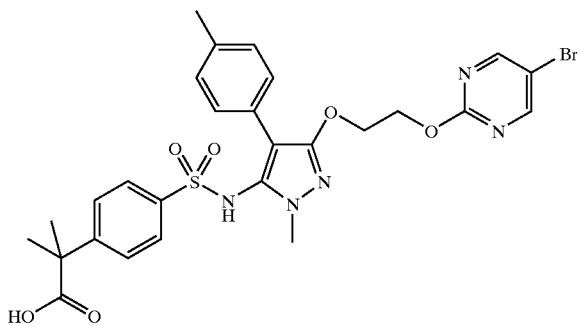

*Amycolata autotrophica* ATCC35203 maintained on a ¼ strength ATCC172 agar slope was inoculated as a loopful of spores into five 300 ml Erlenmeyer flasks each containing 50 ml of MY inoculum medium. This was allowed to incubate for 2 days at 28° C., 200 rpm on an Infors Multitron Shaker with 1" throw. 2 mls of this inoculum was then transferred to each of sixty 300 ml Erlenmeyer flask containing 50 ml of MY production medium and incubated under the same conditions for a further 24 hours. At this point 20 mg of N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (Example 3) dissolved in 0.5 ml of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid, 2.0 g.

The crude extract (281 mg) was purified by preparative reversed phase HPLC with a Phenomenex Magellen™ 5μ C18 column (150 mm×21.2 mm). Using a gradient mobile phase of 35% to 20% (0.1% trifluoroacetic acid in water)/methanol from 1.5 to 20 mins at a flow rate of 20 ml/min, the product was eluted at 11.5 min. The product fractions were concentrated under reduced pressure to yield the tide compound as a colourless amorphous solid (10.6 mg).

HPLC retention time—Method A; 11.5 minutes.

δH (300 MHz, CDCl$_3$) 8.65 (2H, s), 7.15 (4H, m), 6.95 (2H, d), 6.90 (s,1H), 6.70 (2H, d), 4.65 (2H, m), 4.45 (2H, m), 3.90 (3H, s), 2.30 (3H, s), 1.55 (6H, s) m/z (ESI) [M+H]$^+$=630.1005; C$_{27}$H$_{29}$BrN$_5$O$_6$S requires 630.1022 m/z (ESI) [M+Na]$^+$=652.0842; C$_{27}$H$_{28}$BrN$_5$O$_6$SNa requires 652.0841

$v_{max}$ (NaCl, film) 3241, 2976, 1710, 1572, 1551, 1427, 1327, 1167, 1085

Example 84

N-[3-{2-[(5-bromo-2-pyrimidinyl)oxy]ethoxy}-1-methyl-4-(4-methylphenyl)-1H-pyrazol-5-yl]-4-(2-hydroxy-1,1-dimethylethyl)benzenesulfonamide

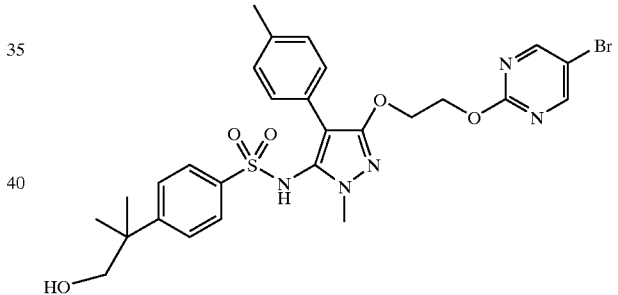

*Streptomyces rimosus* subsp. *rimosus* ATCC10970 maintained on a ¼ strength ATCC172 agar slope was inoculated as a loopful of spores into a 300 ml Erlenmeyer flask containing 50 ml of AS7-H inoculum medium. This was allowed to incubate for 2 days at 28° C., 200 rpm on an Infors Multitron™ Shaker with 1" throw. 2 mls of this inoculum medium was then transferred to each of sixteen 300 ml Erlenmeyer flask containing 50 ml of AP-5H production medium and incubated under the same conditions for a further 24 hours. At this point 20 mg of N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (Example 3) dissolved in 0.5 ml of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid, 1.4 g.

The crude extract was purified by preparative reversed phase HPLC with a Phenomenex Magellen™ 5μ C18 column (150 mm×21.2 mm). Using a gradient mobile phase of 35% to 20% (0.1% trifluoroacetic acid in water)/methanol from 1.5 to 20 mins at a flow rate of 20 ml/min, the product was eluted at 11.4 min in three injections. The fractionation was repeated with another 3 injections using a gradient mobile phase of 35% to 20% water/methanol at a flow rate of 20 ml/min. The compound of interest eluted again at 11.4 min and the product fractions were concentrated under reduced pressure to yield the title compound as a colourless amorphous solid (53.5 mg).

HPLC retention time—Method A; 11.5 minutes.

$\delta_H$ (300 MHz, CDCl$_3$) 8.45 (2H, s), 7.40 (2H, d), 7.15 (1H, s), 7.10 (2H, d), 6.80 (4H, s), 4.65 (2H, m), 4.55 (2H, m), 3.80 (3H, s), 3.50 (2H,s ), 2.20 (3H, s), 1.15 (6H, s) m/z (ESI) [M+H$^+$]=616.1216; C$_{27}$H$_{31}$BrN$_5$O$_5$S requires 616.1229 m/z (ESI) [M+Na$^+$]=638.1060; C$_{27}$H$_{30}$BrN$_5$O$_5$SNa requires 638.1049

Example 85

4-(2-hydroxy-1,1-dimethylethyl)-N-[3-(2-hydroxyethoxy)-1-methyl-4-(4-methylphenyl)-1H-pyrazol-5-yl]benzenesulfonamide

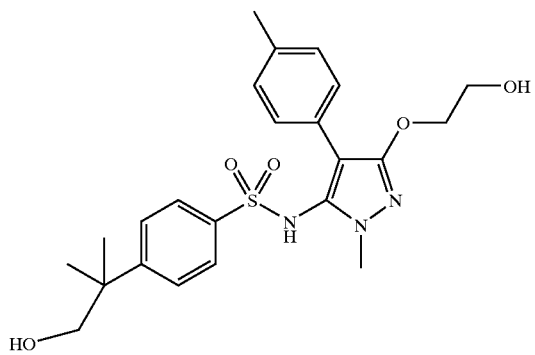

*Streptomyces rimosus* subsp. *rimosus* ATCC10970 maintained on a ¼ strength ATCC172 agar slope was inoculated as a loopful of spores into five 300 ml Erlenmeyer flask containing 50 ml of AS7-H inoculum medium. This was allowed to incubate for 2 days at 28° C., 200 rpm on an Infors Multitron™ Shaker with 1" throw. 2 mls of this inoculum medium was then transferred to each of sixty 300 ml Erlenmeyer flask containing 50 ml of AP-5H production medium and incubated under the same conditions for a further 24 hours. At this point 10 mg of N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (Example 3) dissolved in 0.5 ml of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm) in seven injections. Using a gradient mobile phase of 35% to 20% water/methanol from 1.5 to 20 minutes at a flow rate of 20 ml/min, the product was eluted at 5.3 minutes. The product fractions were concentrated under reduced pressure to yield the title compound as a colourless amorphous solid (15.4 mg).

$\delta_H$ (300 MHz, CD$_3$OD) 7.40 (2H, d), 7.20 (2H, d), 7.10 (2H, d), 6.85 (2H, d), 4.20 (2H, m 3.80 (2H, m), 3.70 (3H, s), 3.45 (2H, s), 2.25 (3H, s), 1.25 (6H, s) m/z (ESI) [MH$^+$]=460.1899; C$_{23}$H$_{30}$N$_3$O$_5$S requires 460.1906 m/z (ESI) [MNa$^+$]=482.1728; C$_{23}$H$_{29}$N$_3$O$_5$SNa requires 482.1726

$v_{max}$ (PE) 3287, 2920, 1582, 1518, 1493, 1330, 1086, 1056 cm$^{-1}$

Example 86

N-[3-(2-ethoxyethoxy)-1-methyl-4-(4-methylphenyl)-1H-pyrazol-5-yl]-4-(2-hydroxy-1,1-dimethylethyl)benzenesulfonamide

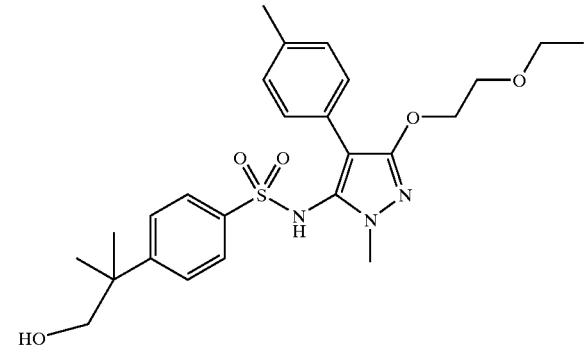

*Amycolata autotrophica* ATCC35203 maintained on a ¼ strength ATCC172 agar slope was inoculated as a loopful of spores into five 300 ml Erlenmeyer flasks each containing 50 ml of of MY inoculum medium. This was allowed to incubate for 2 days at 28° C., 200 rpm on an Infors Multitron Shaker with 1" throw. 2 mls of this inoculum was then transferred to each of sixty 300 ml Erlenmeyer flask containing 50 ml of MY production medium and incubated under the same conditions for a further 24 hours. At this point 20 mg of N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (Example 3) dissolved in 0.5 ml of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid, 2.0 g.

The crude extract was purified by preparative reversed phase HPLC with a Phenomenex Magellen™ 5μ C18 column (150 mm×21.2 mm) in five injections. Using a gradient mobile phase of 35:65 to 20:80 water/methanol from 1.5 to 20 minutes at a flow rate of 20 ml/min, the product was eluted at 9.1 minutes. The product fractions were concentrated under reduced pressure to yield the title compound as a colourless amorphous solid (3.0 mg).

HPLC retention time—Method A; 10 minutes.

$\delta_H$ (300 MHz, CDCl$_3$) 7.40 (2H, d), 7.15 (2H, d), 6.90 (4H, m), 4.35 (2H, m), 3.85 (3H, s), 3.85 (2H, m), 3.55 (2H, q), 3.50 (2H, s), 2.25 (3H, s), 1.25 (6H, s), 1.20 (3H, t) m/z (ESI) [MH$^+$]=488.2218; C$_{25}$H$_{34}$N$_3$O$_5$S requires 488.2219 m/z (ESI) [MNa$^+$]=510.2026; C$_{25}$H$_{33}$N$_3$O$_5$SNa requires 510.2039

$v_{max}$ (PE) 3352, 2920, 1572, 1519, 1428, 1328, 1167 cm$^{-1}$

Example 87

Preparation of 2-[4-({[3-(2-ethoxyethoxy)-1-methyl-4-(4-methylphenyl)-1H-pyrazol-5-yl]amino}sulfonyl)phenyl]-2-methylpropanoic acid

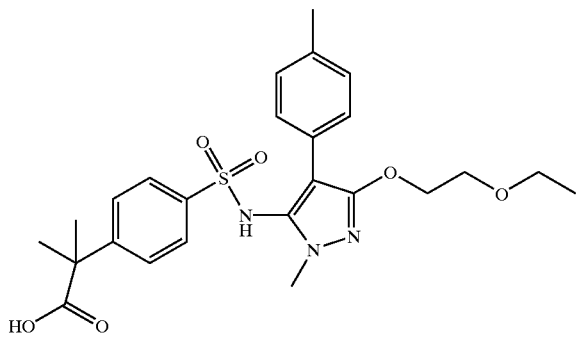

*Amycolata autotrophica* ATCC35203 maintained on a ¼ strength ATCC172 agar slope was inoculated as a loopful of spores into a 300 ml Erlenmeyer flasks each containing 50 ml of MY inoculum medium. This was allowed to incubate for 2 days at 28° C., 200 rpm on an Infors Multitron Shaker with 1" throw. 2 mls of this inoculum was then transferred to each of six 300 ml Erlenmeyer flask containing 50 ml of MY production medium and incubated under the same conditions for a further 24 hours. At this point 5 mg of 4-(tert-butyl)-N-[3-(2-ethoxyethoxy)-1-methyl-4-(4-methylphenyl)-1H-pyrazol-5-yl]benzenesulfonamide (Example 56) disolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5µ C18 column (150 mm×21.2 mm) in one injection. Using a gradient mobile phase of 85:15 to 15:85 water/methanol from 0 to 25 minutes at a flow rate of 20 ml/min, the product was eluted at 16.5 minutes. The product fractions were concentrated under reduced pressure to yield the title compound as a colourless amorphous solid (1.5 mg).

HPLC retention time—Method A; 9.3 minutes.

$\delta_H$ (300 MHz, $CDCl_3$:$CD_3OD$ 3:1) 7.30 (4H, m), 7.05 (2H, d), 6.75 (2H, d), 4.10 (2H, m), 3.60 (2H, m), 3.45 (2H, q), 3.35 (3H, s), 2.10 (3H, s), 1.30 (6H, s), 1.05 (3H, t) m/z (ESI, FTMS) [MH$^+$]=502.1995; $C_{25}H_{32}N_3O_6S$ requires 502.2006 m/z (ESI, FTMS) [MNa$^+$]=524.1811; $C_{25}H_{31}N_3O_6SNa$ requires 524.1825

Example 88

Preparation of 2-[4-({[3-(2-ethoxyethoxy)-1-methyl-4-(4-methylphenyl)-1H-pyrazol-5-yl]amino}sulfonyl)phenyl]-2-methylpropanoic acid

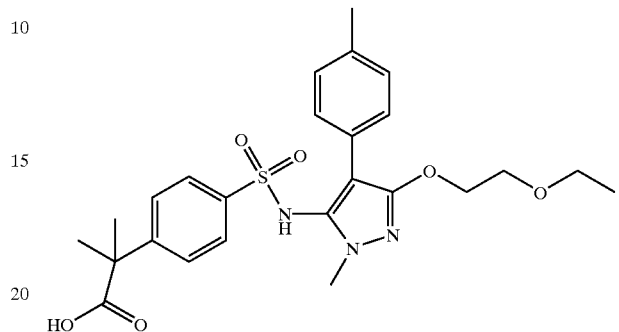

*Amycolata autotrophica* ATCC35203 maintained on a ¼ strength ATCC172 agar slope was inoculated as a loopful of spores into a 300 ml Erlenmeyer flasks each containing 50 ml of of MY inoculum medium. This was allowed to incubate for 2 days at 28° C., 200 rpm on an Infors Multitron™ Shaker with 1" throw. 2 mls of this inoculum was then transferred to each of six 300 ml Erlenmeyer flask containing 50 ml of MY production medium and incubated under the same conditions for a further 24 hours. At this point 5 mg of 4-(tert-butyl)-N-[3-(2-ethoxyethoxy)-1-methyl-4-(4-methylphenyl)-1H-pyrazol-5-yl]benzenesulfonamide (Example 56) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5µ C18 column (150 mm×21.2 mm) in one injection. Using a gradient mobile phase of 85:15 to 15:85 water/methanol from 0 to 25 minutes at a flow rate of 20 ml/min, the product was eluted at 16.5 minutes. The product fractions were concentrated under reduced pressure to yield the title compound as a colourless amorphous solid (1.5 mg).

HPLC retention time—Method A; 9.3 minutes.

$\delta_H$ (300 MHz, $CDCl_3$:$CD_3OD$ 3:1) 7.30 (4H, m), 7.05 (2H, d), 6.75 (2H, d), 4.10 (2H, m), 3.60 (2H, m), 3.45 (2H, q), 3.35 (3H, s), 2.10 (3H, s), 1.30 (6H, s), 1.05 (3H, t) m/z (ESI, FTMS) [MH$^+$]=502.1995; $C_{25}H_{32}N_3O_6S$ requires 502.2006 m/z (ESI, FTMS) [MNa$^+$]=524.181 1; $C_{25}H_{32}N_3O_6SNa$ requires 524.1825

Example 89

Preparation of 2-[4-({[3-(2-hydroxyethoxy)-1-methyl-4-(4-methylphenyl)-1H-pyrazol-5-yl]amino}sulfonyl)phenyl]-2-methylpropanoic acid

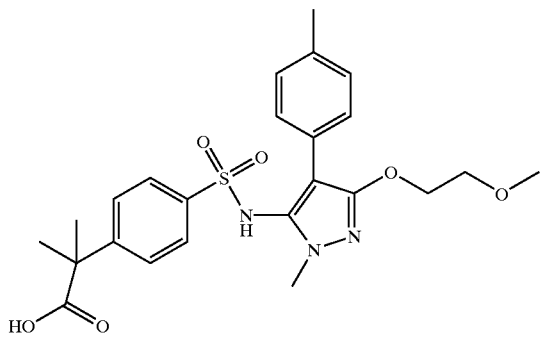

*Amycolata autotrophica* ATCC35203 maintained on a ¼ strength ATCC172 agar slope was inoculated as a loopful of spores into a 300 ml Erlenmeyer flasks each containing 50 ml of of MY inoculum medium. This was allowed to incubate for 2 days at 28° C., 200 rpm on an Infors Multitron™ Shaker with 1" throw. 2 mls of this inoculum was then transferred to each of six 300 ml Erlenmeyer flask containing 50 ml of MY production medium and incubated under the same conditions for a further 24 hours. At this point 5 mg of 4-(tert-butyl)-N-[3-(2-methoxyethoxy)-1-methyl-4-(4-methylphenyl)-1H-pyrazol-5-yl]benzenesulfonamide (Example 55) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm) in one injection. Using a gradient mobile phase of 85:15 to 15:85 water/methanol from 0 to 25 minutes at a flow rate of 20 ml/min, the product was eluted at 17.0 minutes. The product fractions were concentrated under reduced pressure to yield the title compound as a colourless amorphous solid (4.0 mg).

HPLC retention time—Method A; 7.4 minutes.

$\delta_H$ (300 MHz, CDCl$_3$:CD$_3$OD 3:1) 7.30 (4H, m), 7.05 (2H, d), 6.80 (2H, d), 4.15 (2H, m), 3.60 (2H, m), 3.35 (3H, s), 3.30 (3H, s), 2.15 (3H, s), 1.35 (6H, s) m/z (ESI, FTMS) [MH$^+$]=488.1833; C$_{24}$H$_{30}$N$_3$O$_6$S requires 488.1850

$\nu_{max}$ (PE) 3373, 2968, 1564, 1483, 1399, 1358, 1171, 1134, 1099

Example 90

4-tert-butyl-N-[3-(2-{[2-(hydroxymethyl)-5-pyrimidinyl]oxy}ethoxy)-1-methyl-4-(4-methylphenyl)-1H-pyrazol-5-yl]benzenesulfonamide

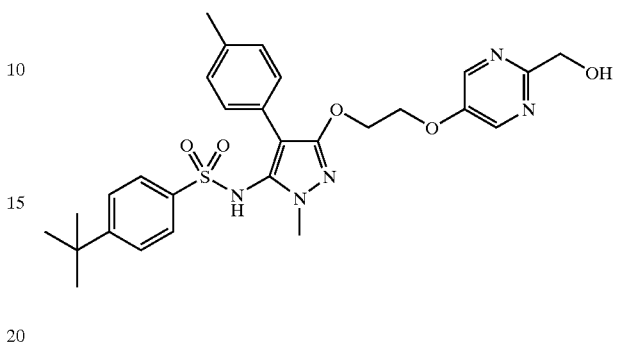

To 4-(tert-butyl)-N-[3-{2-[(5-formyl-2-pyrimidinyl)oxy]ethoxy}-1-methyl-4-(4-methylphenyl)-1H-pyrazol-5-yl]benzenesulfonamide (Example 38) (25 mg) in ethanol (0.5 ml) at room temperature was added sodium borohydride (2 mg) the mixture was stirred for 1 hr. The reaction was treated with ammonium chloride (aq. sat. 5 ml) and extracted with diethyl ether (1×5 ml, 1×2 ml). The organic fraction was dried over magnesium sulfate, filtered and concentrated under reduced pressure to yield the title compound as a white solid (20 mg).

$\delta_H$ (300 MHz, CDCl$_3$) 8.35 (2H, s), 7.40 (2H, d), 7.05 (2H, d), 6.70–6.80 (4H, m), 4.65 (2H, t), 4.55 (2H, t), 3.80 (3H, s), 3.70 (2H, s), 2.10 (3H, s), 1.10 (9H, s) m/z (thermospray) [MH$^+$]=552.1; C$_{28}$H$_{34}$N$_5$O$_5$S requires 552.2

Example 91

N-[3-{2-[(2-bromo-5-pyrimidinyl)oxy]ethoxy}-4-(4-cyanophenyl)-1-methyl-1H-pyrazol-5-yl]-4-tert-butylbenzenesulfonamide

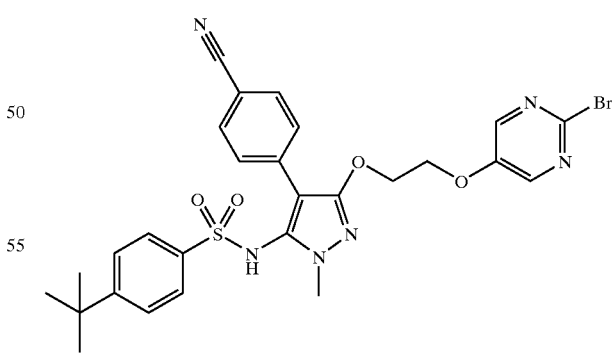

To 4-tert-butyl-N-[4-(4-cyanophenyl)-3-(2-hydroxyethoxy)-1-methyl-1H-pyrazol-5-yl]benzenesulfonamide (Preparation 60) (2700 mg) in tetrahydrofuran (20 ml) at room temperature was added sodium hydride (476 mg, 60% dispersion in oil), the mixture was stirred for 10 minutes. To the mixture was added dimethylacetamide (5 ml) followed by 5-chloro-5-bromopyrimidine (1700 mg), the mixture was stirred for a further 16 hours. The reaction was treated with ammonium chloride (aq. sat. 50 ml) and extracted with ethyl acetate (50 ml). The organic fraction was dried over magnesium sulfate, filtered and concentrated under reduced pressure. The residue was purified by column chromatography (silica, 100 g) eluted with ethylacetate:hexane (1:1) to yield the title compound as a white solid (900 mg).

$\delta_H$ (300 MHz, CDCl$_3$) 8.50 (2H, s), 7.40 (2H, d), 7.25 (2H, d), 7.05–7.10 (4H, m), 6.75 (1H, br. s), 4.70 (2H, t), 4.60 (2H, t), 3.80 (3H, s), 1.10 (9H, s) m/z (thermospray) [MH$^+$]=612.1; C$_{27}$H$_{28}$BrN$_6$O$_4$S requires 612.2

Example 92

N-[3-{2-[(5-bromo-2-pyrimidinyl)oxy]ethoxy}-1-methyl-4-(3-methylphenyl)-1H-pyrazol-5-yl]-4-(tert-butyl)benzenesulfonamide

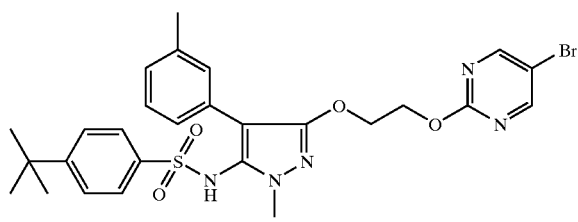

To 4-(tert-butyl)-N-[3-(2-hydroxyethoxy)-1-methyl-4-(3-methylphenyl)-1H-pyrazol-5-yl]benzenesulfonamide (Preparation 61) (101 mg) in tetrahydrofuran (2 ml) and N,N-dimethylacetamide (0.5 ml) at 0° C. was added sodium hydride (20 mg of a 60% dispersion in oil) followed by the 5-bromo-2-chloropyrimidine (66 mg) The reaction was stirred for one hour at 0° C. and then at room temperature overnight. Water (3 ml) was then added to the reaction followed by saturated aqueous ammonium chloride (3 ml) and the mixture was extracted with ethyl acetate (3×5 mls). The combined organics were then washed with 1:1 saturated ammonium chloride and water (4×15 ml) and dried over magnesium sulfate, filtered and concentrated under reduced pressure to yield the crude material (130 mg). The crude material was purified by HPLC on a 5μ ODS Phenomenex Magellen™ column with a gradient elution of acetonitrile (5% to 95%) and 0.1M NH$_4$OAc (95% to 5%) to yield the desired product as an off white solid (12 mg).

$\delta_H$ (300 MHz, CDCl$_3$) 8.48 (2H, s), 7.40 (2H, d), 7.14(2H, d), 6.82–6.72 (4H, m), 6.64(1H, s), 4.72–4.64 (2H, m), 4.58–4.52 (2H, m), 3.82 (3H, s), 2.14 (3H, s), 1.22 (9H, s). m/z (electrospray) [MH]$^+$=600; C$_{27}$H$_{31}$BrN$_5$O$_4$S requires 600.1

Example 93

N-[3-{2-[(5-bromo-2-pyrimidinyl)oxy]ethoxy}-4-(4-fluorophenyl)-1-methyl-1H-pyrazol-5-yl]-4-(tert-butyl)benzenesulfonamide.

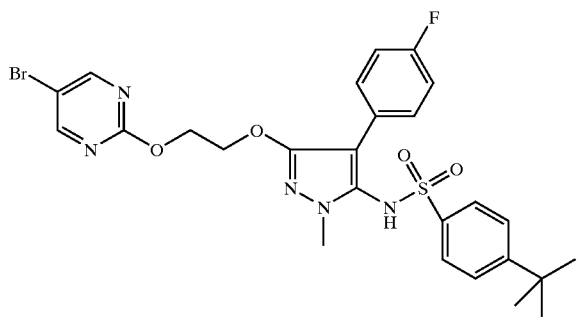

The title compound was prepared in a similar manner to Example 92 except that 4-(tert-butyl)-N-[4-(4-fluorophenyl)-3-(2-hydroxyethoxy)-1-methyl-1H-pyrazol-5-yl]benzenesulfonamide (96 mg) (Preparation 62) was substituted for 4-(tert-butyl)-N-[3-(2-hydroxyethoxy)-1-methyl-4-(3-methylphenyl)-1H-pyrazol-5-yl]benzenesulfonamide (Preparation 61). The desired product was recovered as an off white solid. (41 mg)

$\delta_H$ (300 MHz, CDCl$_3$) 8.52 (2H, s), 7.00 (2H, d), 7.18 (2H, d), 6.96–6.88 (2H, m), 6.74–6.64 (2H, m), 4.70–4.66 (2H, m), 4.58–4.44 (2H, m), 3.82 (3H, m), 1.24 (9H, s). m/z (electrospray) {MH$^+$]=604; C$_{26}$H$_{28}$BrN$_5$O$_4$S requires 604.1.

Example 94

N-[3-{2-[(5-bromo-2-pyrimidinyl)oxy]ethoxy}-1-methyl-4-(4-vinylphenyl)-1H-pyrazol-5-yl]-4-(tert-butyl)benzenesulfonamide

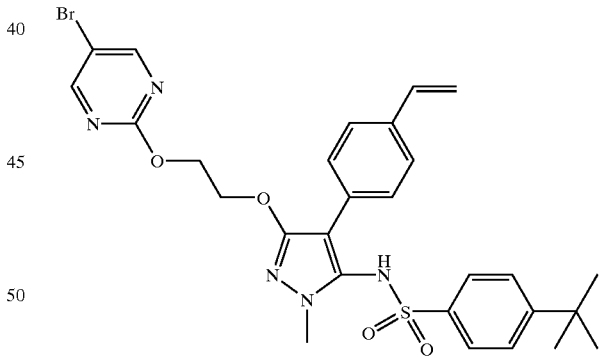

The title compound was prepared in a similar manner to Example 92 except that 4-(tert-butyl)-N-[3-(2-hydroxyethoxy)-1-methyl-4-(4-vinylphenyl)-1H-pyrazol-5-yl]benzenesulfonamide (64 mg) (Preparation 63) was substituted for 4-(tert-butyl)-N-[3-(2-hydroxyethoxy)-1-methyl-4-(3-methylphenyl)-1H-pyrazol-5-yl] benzenesulfonamide (Preparation 61) and the amount of sodium hydride, (60% dispersion in oil), used was 12 mg. The desired product was recovered as an off white solid. (12 mg).

$\delta_H$ (300 MHz, CDCl$_3$) 8.48 (2H, s), 7.38 (2H, d), 7.12 (2H, d), 7.02 (2H, d), 6.86 (2h, d), 6.72 (1H, s), 6.60–6.48 (1H, m), 5.62 (1H, d), 5.16, 1H, d), 4.72–4.64 (2H, m), 4.56–4.52 (2H, m), 3.82 (3H, s), 1.10 (9H, s). m/z (electrospray) [MH$^+$]=611.9; $C_{28}H_{31}BrN_5O_4S$ requires 612.1.

Example 95

N-(4-(4-acetylphenyl)-3-{2-[(5bromo-2-pyrimidinyl)oxy]ethoxy}-1-methyl-1H-pyrazol-5-yl)-4-(tert-butyl)benzenesulfonamide

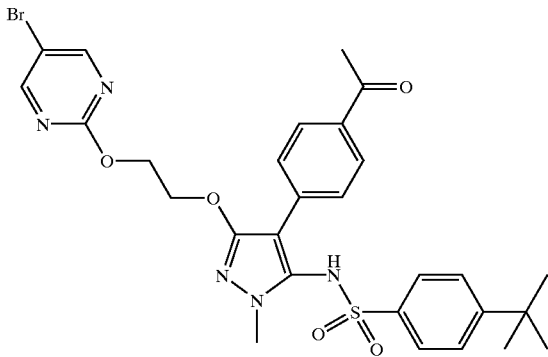

The title compound was prepared in a similar manner to Example 92 except that N-[4-(4-acetylphenyl)-3-(2-hydroxyethoxy)-1-methyl-1H-pyrazol-5-yl]-4-(tert-butyl)benzenesulfonamide (80 mg) (Preparation 64) was substituted for 4-(tert-butyl)-N-[3-(2-hydroxyethoxy)-1-methyl-4-(3-methylphenyl)-1H-pyrazol-5-yl]benzenesulfonamide (Preparation 61) and the amount of sodium hydride, (60% dispersion in oil), used was 15 mg. The desired product was recovered as an off white solid. (2 mg).

$\delta_H$ (300 MHz, CDCl$_3$) 8.50 (2H, s), 7.60 (2H, d), 7.42 (2H, d), 7.16–7.06 (4H, m), 6.58 (1H, s), 4.74–4.66 (2H, m), 4.64–4.56 (2H, m), 3.84 (3H, s), 2.52 (3H, s), 1.18 (9H, s). m/z (electrospray) [MH$^+$]=628; $C_{28}H_{31}BrN_5O_5S$ requires 628.1

Example 96

N-[3-{2-[(5-bromo-2-pyrimidinyl)oxy]ethoxy}-4-(3-chlorophenyl)-1-methyl-1H-pyrazol-5-yl]-4-(tert-butyl)benzenesulfonamide

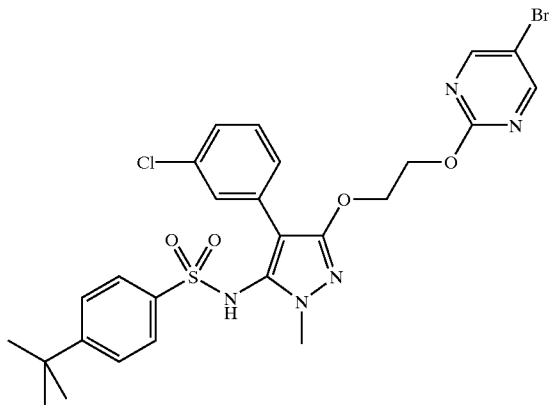

To a solution of isobutyl 2-{3-[2-(acetyloxy)ethoxy]-4-iodo-1-methyl-1H-pyrazol-5-yl}-2-{[4-(tert-butyl)phenyl]sulfonyl}acetate (Preparation 6) (600 mg, 0.96 mmol) in dioxane (5 ml) 3-chlorophenylboronic acid (143 mg, 1.05 mmol), cesium carbonate (1.25 g, 3.8 mmol) and water (1 ml) were added. The resulting solution was deoxygenated by placing it under vacuum and subsequently re-pressurising with nitrogen gas. This process was repeated a further three times. Tetrakis(triphenylphosphine)palladium(0) (20 mg) was added and the mixture was degassed following the same process as above. The reaction mixture was then heated to reflux for 3 hours. To the reaction mixture ethanol (10 ml) and aqueous sodium hydroxide (2N, 10 ml) were added; the reaction mixture was stirred at room temperature over-night. The reaction mixture was partitioned between saturated aqueous ammonium chloride (100 ml) and ethyl acetate (50 ml). The aqueous layer was extracted with ethyl acetate (2×50 ml). The organics were combined, dried on magnesium sulphate, filtered and concentrated under reduced pressure to yield the crude product.

The crude material (100 mg) was dissolved in tetrahydrofuran (2 ml) and N,N-dimethylacetamide (0.5 ml), the resulting solution was cooled to 0° C. To the solution were added sodium hydride (20 mg of a 60% dispersion in oil) followed by 5-bromo-2-chloropyrimidine (66 mg). The reaction was stirred for one hour at 0° C. and then at room temperature overnight. Water (3 ml) was then added to the reaction followed by saturated aqueous ammonium chloride (3 ml) and the mixture was extracted with ethyl acetate (3×5 mls). The combined organics were then washed with 1:1 saturated ammonium chloride and water (4×15 ml) and dried over magnesium sulfate, filtered and concentrated under reduced pressure to yield the crude material (141 mg). The crude material was purified by HPLC on a 5µ ODS Phenomenex Magellen™ column with a gradient elution of acetonitrile (5% to 95%) and 0.1M NH$_4$OAc (95% to 5%) to yield the desired product as an off white solid (3 mg).

$\delta_H$ (300 MHz, CDCl$_3$) 8.50 (2H, s), 7.44 (2H, d), 7.16 (2H, d), 6.98–6.86 (4H, m), 6.56 (1H, s), 4.74–4.68 (2H, m), 4.62–4.56 (2H, m), 3.84 (3H, s), 1.24 (9H, s). m/z (electrospray) [MH$^+$]=620; $C_{26}H_{29}BrClN_5O_4S$ requires 620.1.

Example 97

N-{3-{2-[(5-bromo-2-pyrimidinyl)oxy]ethoxy}-1-methyl-4-[4-(trifluoromethoxy)phenyl]-1H-pyrazol-5-yl}-(tert-butyl)benzenesulfonamide

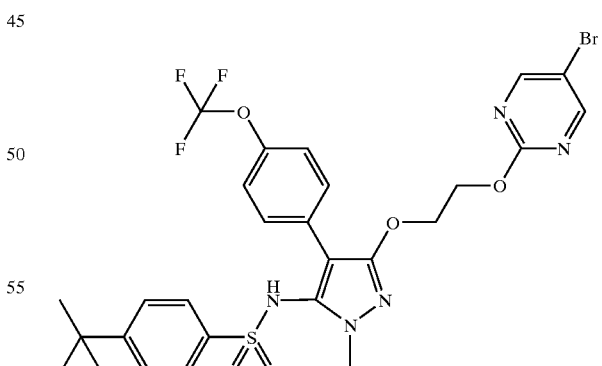

The title compound was prepared in a similar manner to Example 92 except that 4-(tert-butyl)-N-{3-(2-hydroxyethoxy)-1-methyl-4-[4-trifluoromethoxy)phenyl]-1H-pyrazol-5-yl}benzenesulfonamide (98 mg) (Preparation 65) was substituted for 4-(tert-butyl)-N-[3-(2-hydroxyethoxy)-1-methyl-4-(3-methylphenyl)-1H-pyrazol-5-yl]benzenesulfonamide (Preparation 61) and the amount of sodium hydride, (60% dispersion in oil), used was 17 mg. The desired product was recovered as an off white solid. (2 mg).

$\delta_H$ (300 MHz, CDCl$_3$) 8.50 (2H, s), 7.42 (2H, d), 7.18 (2H, d), 6.96 (2H, d), 6.86 (2H, d), 6.54 (1H, s), 4.72–4.64 (2H, m), 4.60–4.54 (2H, m), 3.82 (3H, s), 1.26 (9H, s). m/z (thermospray) [MH]$^+$=671.4; C$_{27}$H$_{28}$BrF$_3$N$_5$O$_5$S requires 671.5

Example 98

N-{3-{2-[(5-bromo-2-pyrimidinyl)oxy]ethoxy}-4-[4-(hydroxymethyl)phenyl]-1-methyl-1H-pyrazol-5-yl}-4-(tert-butyl)benzenesulfonamide

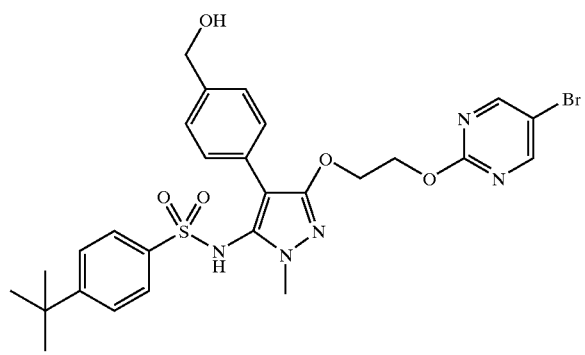

*Streptomyces rimosus* subsp. *rimosus* ATCC10970 maintained on a ¼ strength ATCC172 agar slope was inoculated as a loopful of spores into a 300 ml Erlenmeyer flask containing 50 ml of AS7-H inoculum medium. This was allowed to incubate for 2 days at 28° C., 200 rpm on an Infors Multitron™ Shaker with 1" throw. 2 mls of this inoculum medium was then transferred to each of sixteen 300 ml Erlenmeyer flask containing 50 ml of AP-5H production medium and incubated under the same conditions for a further 24 hours. At this point 20 mg of N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (Example 3) dissolved in 0.5 ml of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid, 1.4 g.

The crude extract was purified by preparative reversed phase HPLC with a Phenomenex Magellen™ 5μ C18 column (150 mm×21.2 mm) in two injections. Using a gradient mobile phase of 35% to 20% water/methanol from 1.5 to 20 minutes at a flow rate of 20 ml/min, the product was eluted at 12.3 minutes. The product fractions were concentrated under reduced pressure to yield the title compound as a colourless amorphous solid (4.0 mg).

HPLC retention time—Method A; 13.5 minutes.

$\delta_H$ (400 MHz, CDCl$_3$) 8.50 (2H, s), 7.40 (2H, d), 7.15 (2H, d), 7.00 (2H, d), 6.90 (2H, d), 4.70 (2H, m), 4.60 (2H, s), 4.55 (2H, m), 3.80 (3H, s), 1.25 (9H, s) m/z (ESI) [MH$^+$]=616.1211; C$_{27}$H$_{31}$BrN$_5$O$_5$S requires 616.1229 m/z (ESI) [MNa$^+$]=638.1050; C$_{27}$H$_{30}$BrN$_5$O$_5$SNa requires 638.1049

$v_{max}$ (NaCl, film) 3265, 2963, 1570, 1549, 1428, 1326, 1167, 1086, 1053

Example 99

4-[3-{2-[(5-bromo-2-pyrimidinyl)oxy]ethoxy}-5-({[4-(tert-butyl)phenyl]sulfonyl}amino)-1-methyl-1H-pyrazol-4-yl]benzoic acid

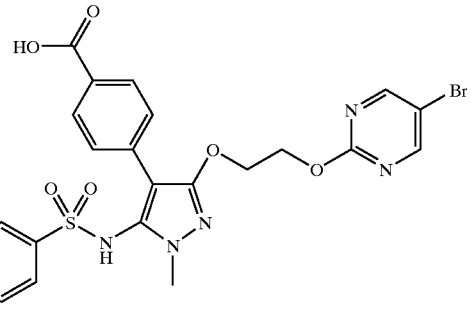

*Streptomyces lydicus* SX1298 maintained on a ¼ strength ATCC172 agar slope was inoculated as a loopful of spores into a 300 ml Erlenmeyer flask containing 50 ml of AS7-H inoculum medium. This was allowed to incubate for 2 days at 28° C., 200 rpm on an Infors Multitron™ Shaker with 1" throw. 2 mls of this inoculum medium was then transferred to each of four 300 ml Erlenmeyer flask containing 50 ml of AP-5H production medium and incubated under the same conditions for a further 24 hours. At this point 5 mg, 10 mg, 15 mg, 20 mg of N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (Example 3) dissolved in 0.5 ml of methanol was added respectively to each of the four flasks and the fermentation allowed to continue under the same conditions for a further 6 hours. Each flask was then extracted with 200 mls of ethyl acetate and the combined ethyl acetate solubles concentrated to dryness to give a gum solid, 0.05 g.

The crude extract was purified by preparative reversed phase HPLC with a Phenomenex Magellen™ 5μ C18 column (150 mm×21.2 mm) in one injection. Using a gradient mobile phase of 35% to 20% (0.1% aqueous trifluoroacetic acid)/methanol from 0 to 20 minutes at a flow rate of 20 ml/min, the product was eluted at 19.0 minutes. The product fractions were concentrated under reduced pressure to yield the title compound as a colourless amorphous solid (84.4 mg).

HPLC retention time—Method A; 13.0 minutes.

$\delta_H$ (300 MHz, CDCl$_3$) 8.60 (2H, s), 8.35 (1H, bs), 7.50 (2H, d), 7.35 (2H, d), 7.00 (2H, d), 6.95 (2H, d), 4.70 (2H, m), 4.40 (2H, m), 3.85 (3H, s), 1.20 (9H, s) m/z (ESI) [MH$^+$]=630.1016; C$_{27}$H$_{29}$BrN$_5$O$_6$S requires 630.1022 m/z (ESI) [MNa$^+$]=652.0813; C$_{27}$H$_{28}$BrN$_5$O$_6$SNa requires 652.0841

Example 100

N-{3-{2-[(5-bromo-2-pyrimidinyl)oxy]ethoxy}-4-[4-(hydroxymethyl)phenyl]-1-methyl-1H-pyrazol-5-yl}-4-(2-hydroxy-1,1-dimethylethyl)benzenesulfonamide

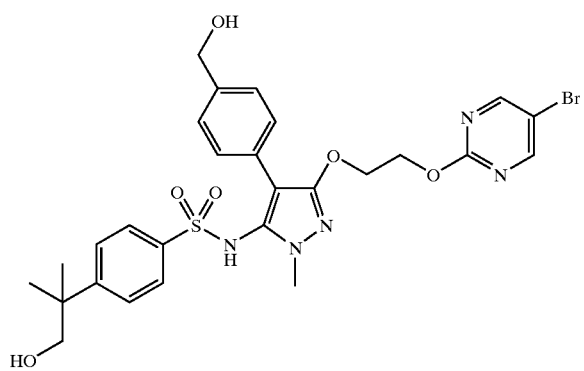

*Streptomyces rimosus* subsp. *rimosus* ATCC10970 maintained on a ¼ strength ATCC172 agar slope was inoculated as a loopful of spores into a 300 ml Erlenmeyer flask containing 50 ml of AS7-H inoculum medium. This was allowed to incubate for 2 days at 28° C., 200 rpm on an Infors Multitron Shaker with 1" throw. 2 mls of this inoculum medium was then transferred to each of sixteen 300 ml Erlenmeyer flask containing 50 ml of AP-5H production medium and incubated under the same conditions for a further 24 hours. At this point 20 mg of N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (Example 3) dissolved in 0.5 ml of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid, 1.4 g.

The crude extract was purified by preparative reversed phase HPLC with a Phenomenex Magellen™ 5μ C18 column (150 mm×21.2 mm) in three injections. Using a gradient mobile phase of 35% to 20% (0.1% aqueous trifluoroacetic acid)/methanol from 1.5 to 20 minutes at a flow rate of 20 ml/min, the product was eluted at 6.7 min. The product fractions were concentrated under reduced pressure to yield the title compound as a colourless amorphous solid (30.7 mg).

HPLC retention time—Method A; 6.2 minutes.

$\delta_H$ (300 MHz, CDCl$_3$) 8.50 (2H, s), 7.45 (3H, d), 7.15 (2H, d), 6.95 (4H, m), 4.65 (2H, m), 4.55 (2H, m), 4.50 (2H, s), 3.85 (3H, s), 3.55 (2H, s), 1.10 (6H, s) m/z (ESI) [MNa$^+$]=654.1001; C$_{27}$H$_{30}$BrN$_5$O$_6$SNa requires 654.0998

Example 101

N-[3-{2-[(5-bromo-2-pyrimidinyl)oxy]ethoxy}-1-methyl-4-(4-carboxymethylphenyl)-1H-pyrazol-5-yl]-4-(tert-butyl hydroxy)benzenesulfonamide

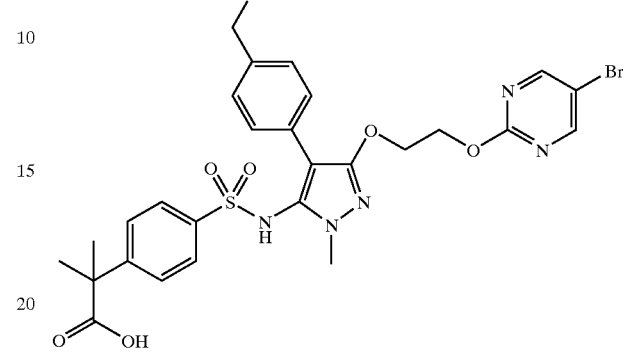

*Amycolata autotrophica* ATCC35203 maintained on a ¼ strength ATCC172 agar slope was inoculated as a loopful of spores into five 300 ml Erlenmeyer flasks each containing 50 ml of of MY inoculum medium. This was allowed to incubate for 2 days at 28° C., 200 rpm on an Infors Multitron Shaker with 1" throw. Two mls of this inoculum was then transferred to each of sixty 300 ml Erlenmeyer flask containing 50 ml of MY production medium and incubated under the same conditions for a further 24 hours. At this point 20 mg of N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (Example 3) dissolved in 0.5 ml of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid, 1.35 g.

The crude extract was purified by preparative reversed phase HPLC with a Phenomenex Magellen™ 5μ C18 column (150 mm×21.2 mm) in six injections. Using a gradient mobile phase of 35% to 20% water/methanol from 1.5 to 20 minutes at a flow rate of 20 ml/min, the product was eluted at 7.3 minutes. The product fractions were concentrated under reduced pressure to yield the title compound as a colourless amorphous solid (120.9 mg).

HPLC retention time—Method A; 6.4 minutes.

$\delta_H$ (300 MHz, d$_6$DMSO) 8.65 (2H, s), 7.40 (2H, d), 7.20 (2H, d), 7.15 (2H, d), 6.95 (2H, d), 4.60 (2H, m), 4.45 (2H, m), 4.40 (2H, s), 3.50 (3H, s), 1.40 (6H, s) m/z (ESI) [MH$^+$]=646.0940; C$_{27}$H$_{29}$BrN$_5$O$_7$S requires 646.0971 m/z (ESI) [MNa$^+$]=668.0773; C$_{27}$H$_{28}$BrN$_5$O$_7$SNa requires 668.0791

$\nu_{max}$ (KBr disc) 3290, 3056, 2970, 1727, 1576, 1557, 1457, 1420, 1321, 1165

Example 102

2-[4-({[3-{2-[(5-bromo-2-pyrimidinyl)oxy]ethoxy}-1-methyl-4-(4-methylphenyl)-1H-pyrazol-5-yl]amino}sulfonyl)phenyl]-2-methylpropyl acetate

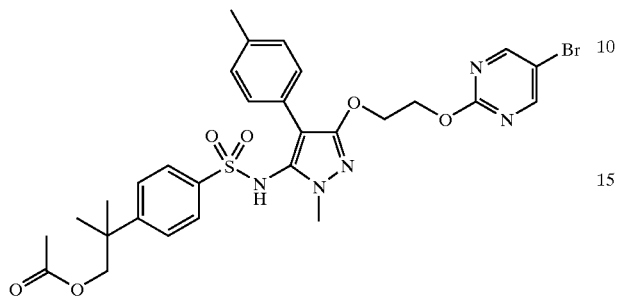

*Streptomyces rimosus* subsp. *rimosus* ATCC10970 maintained on a ¼ strength ATCC172 agar slope was inoculated as a loopful of spores into a 300 ml Erlenmeyer flask containing 50 ml of AS7-H inoculum medium. This was allowed to incubate for 2 days at 28° C., 200 rpm on an Infors Multitron Shaker™ with 1" throw. 2 mls of this inoculum medium was then transferred to each of sixteen 300 ml Erlenmeyer flask containing 50 ml of AP-5H production medium and incubated under the same conditions for a further 24 hours. At this point 20 mg of N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (Example 3) dissolved in 0.5 ml of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid, 1.4 g.

The crude extract was purified by preparative reversed phase HPLC with a Phenomenex Magellen™ 5μ C18 column (150 mm×21.2 mm) in seven injections. Using a gradient mobile phase of 35% to 20% water/methanol from 1.5 to 20 minutes at a flow rate of 20 ml/min, the product was eluted at 16.5 minutes. The product fractions were concentrated under reduced pressure to yield the title compound as a colourless amorphous solid (4.7 mg).

HPLC retention time—Method A; 16.9 minutes.

$\delta_H$ (300 MHz, CDCl$_3$) 8.50 (2H, s), 7.40 (2H, d), 7.15 (2H, d), 6.85 (2H, d), 2.75 (2H, d), 4.65 (2H, m), 4.55 (2H, m), 4.00 (2H, s), 3.80 (3H, s), 2.25 (3H, s), 2.00 (3H, s), 1.30 (6H, s) m/z (ESI) [M+H]$^+$=660.1308; C$_{29}$H$_{33}$BrN$_5$O$_6$S requires 660.1314 m/z (ESI) [M+Na]$^+$=680.1123; C$_{29}$H$_{32}$BrN$_5$O$_6$SNa requires 680.1154

$\nu_{max}$ (NaCl, film) 3270, 2966, 1738, 1570, 1427, 1326, 1244, 1168, 1085, 1044

Example 103

N-(4-(1,3-benzodioxol-5-yl)-3-{2-[(5-chloro-2-pyrimidinyl)oxy]ethoxy}-1-methyl-1H-pyrazol-5-yl)-5-isopropyl-2-pyridinesulfonamide

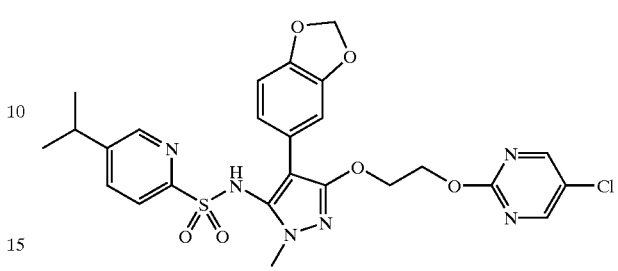

In an oven-dried flask a solution of tetrahydrofuran (50 ml) and dimethylacetamide (3 ml) was treated with sodium hydride as a 60% dispersion in oil (460 mg) under an atmosphere of nitrogen. The reaction was stirred for 5 min and then treated with N-[4-(1,3-benzodioxol-5-yl)-3-(2-hydroxyethoxy)-1-methyl-1H-pyrazol-5-yl]-5-isopropyl-2-pyridinesulfonamide (1.0 g) (Preparation 66). The reaction was stirred for 3 h and was then treated with 2-chloro-5-(methylsulfonyl)pyrimidine (460 mg). After stirring for a further 3 h the reaction mixture was concentrated and the residue was partitioned between water (100 ml) and ethyl acetate (100 ml). The aqueous was extracted with ethyl acetate (3×75 ml) and the combined organics were dried over sodium sulfate. The solvent was removed and the crude residue was purified on a silica (40 g) column eluting with 20% ether in dichloromethane rising to 45% ether in dichloromethane to yield the title compound as an off-white foam (560 mg).

$\delta_H$ (400 MHz, CDCl$_3$) 1.25 (m, 6H), 2.90 (m, 1H), 3.80 (s, 3H), 4.55 (m, 2H), 4.70 (m, 2H), 5.85 (s, 2H), 6.50 (s, 3H), 7.45 (m, 1H), 7.55 (m, 1H), 8.20 (m, 1H), 8.40 (s, 2H) m/z (thermospray) [MH$^+$]=573.5; C$_{25}$H$_{26}$ClN$_6$O$_6$S requires 573.1

Example 104

N-(4-(1,3-benzodioxol-5-yl)-3-{2-[(5-chloro-2-pyrimidinyl)oxy]ethoxy}-1-methyl-1H-pyrazol-5-yl)-5-(2-hydroxy-1-methylethyl)-2-pyridinesulfonamide

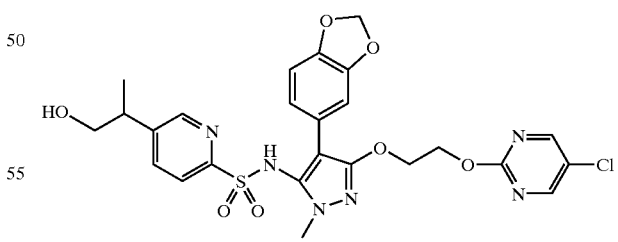

*Streptomyces rimosus* subsp. *rimosus* ATCC10970 maintained on a ¼ strength ATCC172 agar slope was inoculated as a loopful of spores into a 300 ml Erlenmeyer flask containing 50 ml of AS7-H inoculum medium. This was allowed to incubate for 2 days at 28° C., 200 rpm on an Infors Multitron Shaker™ with 1" throw. 2 mls of this inoculum medium was then transferred to each of twenty 300 ml Erlenmeyer flask containing 50 ml of AP-5H production medium and incubated under the same conditions for a further 24 hours. At this point 5 mg of N-(4-(1,3-benzodioxol-5-yl)-3-{2-[(5-chloro-2-pyrimidinyl)oxy]ethoxy}-1-methyl-1H-pyrazol-5-yl)-5-isopropyl-2-pyridinesulfonamide (Example 103) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm) in one injection. Using a gradient mobile phase of 85:15 to 15:85 water/methanol from 0 to 25 minutes at a flow rate of 20 ml/min, the product was eluted at 16.0 minutes. The fractions containing product were further purified using a Phenomenex Lichrosphere™ 5μ DIOL column (250 mm×21.2 mm) in one injection. Using an isocratic mobile phase of 40:60 isopropanol/dichloromethane, the product was eluted at 7.2 minutes. The product fractions were concentrated under reduced pressure to yield the title compound as a colourless amorphous solid (8.4 mg).

HPLC retention time—Method A; 5.5 minutes.

$\delta_H$ (400 MHz, CD$_3$OD) 8.50 (2H, s); 8.20 (1H, s); 7.55 (2H, m); 6.60 (2H, m); 6.45 (1H, d); 5.85 (2H, s); 4.70 (2H, m); 4.50 (2H, m); 3.75 (3H, s); 3.55 (2H, d); 2.85 (1H, m); 1.15 (3H, d) m/z (ESI) [MH$^+$]=589.1267; C$_{25}$H$_{26}$ClN$_6$O$_7$S requires 589.1272 m/z (ESI) [MNa$^+$]=611.1101; C$_{25}$H$_{26}$ClN$_6$O$_7$SNa requires 611.1092

$\nu_{max}$ (PE) 3239, 2949, 1580, 1427, 1326, 1232, 1176, 1041.

Example 105

2-[(4-(1,3-benzodioxol-5-yl)-5-{[(5-isopropyl-2-pyridinyl)sulfonyl]amino}-1-methyl-1H-pyrazol-3-yl)oxy]ethyl acetate

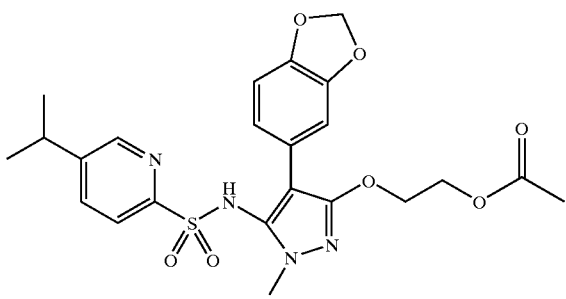

2-(4-Isopropyl)pyridinesulphonyl chloride (4.19 g) was added to a solution of 4-dimethylaminopyridine (2.39 g) in pyridine (15 ml) at 0° C. A solution of 2-{[5-amino-4-(1,3-benzodioxol-5-yl)-1-methyl-1H-pyrazol-3-yl]oxy}ethyl acetate (Preparation 33) in pyridine (20 ml) was added to the mixture. The reaction was allowed to rise to room temperature and left to stir for 16 hours. The mixture was treated with citric acid (10% aq., 500 ml) and extracted with ethyl acetate (2×250 ml). The combined organic phases were washed with brine (250 ml), dried over magnesium sulfate, filtered and evaporated under reduced pressure. The residue was purified by column chromatography on silca (300 g) eluted with a gradient of ethyl acetate:hexane (2:1 to 1:0) to yield the title compound as a yellow solid (2.28 g).

$\delta_H$ (300 MHz, CDCl$_3$) 8.20 (1H, s), 7.95 (1H, br), 7.60 (1H, d), 7.45 (1H, d), 6.50 (3H, m), 5.85 (2H, s), 4.35 (2H, t), 4.10 (2H, t), 3.80 (3H, s), 2.90 (1H, sept), 1.25 (6H, d), 2.10 (3H, s). m/z (thermospray) [MH$^+$]503.0; C$_{23}$H$_{27}$N$_4$O$_7$S requires 503.1

Example 106

N-[3-{2-[(5-chloro-2-pyrimidinyl)oxy]ethoxy}-4-(3,4-dihydroxyphenyl)-1-methyl-1H-pyrazol-5-yl]-5-(2-hydroxy-1-methylethyl)-2-pyridinesulfonamide

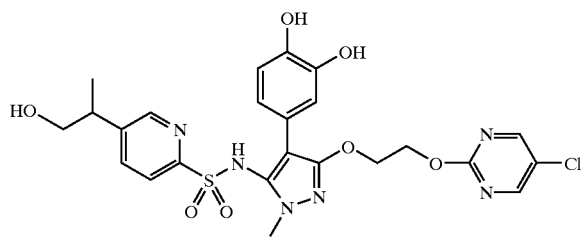

*Streptomyces rimosus* subsp. *rimosus* ATCC10970 maintained on a ¼ strength ATCC172 agar slope was inoculated as a loopful of spores into a 300 ml Erlenmeyer flask containing 50 ml of AS7-H inoculum medium. This was allowed to incubate for 2 days at 28° C., 200 rpm on an Infors Multitron Shaker™ with 1" throw. 2 mls of this inoculum medium was then transferred to each of twenty 300 ml Erlenmeyer flask containing 50 ml of AP-5H production medium and incubated under the same conditions for a further 24 hours. At this point 5 mg of N-(4-(1,3-benzodioxol-5-yl)-3-{2-[(5-chloro-2-pyrimidinyl)oxy]ethoxy}-1-methyl-1H-pyrazol-5-yl)-5-isopropyl-2-pyridinesulfonamide (Example 103) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm) in one injection. Using a gradient mobile phase of 85% to 15% water/methanol from 0 to 25 minutes at a flow rate of 20 ml/min, the product was eluted at 16.0 minutes. The fractions containing product were further purified using a Phenomenex Lichrosphere™ 5μ DIOL column (250 mm×21.2 mm) in one injection. With an isocratic mobile phase of 40% isopropanol/dichloromethane, the product was eluted at 9.8 minutes. The product fractions were concentrated under reduced pressure to yield the title compound as a colourless amorphous solid (5.2 mg).

$\delta_H$ (400 MHz, CD$_3$OD) 8.50 (2H, s), 8.15 (1H, s), 7.50 (2H, s), 6.55 (1H, m), 6.40 (1H, m), 6.35 (1H, m), 4.70 (2H, m), 4.50 (2H, m), 3.75 (3H, s), 2.90 (1H, sept), 1.25 (6H, d) m/z (ESI) [MH$^+$]=561.1307; C$_{24}$H$_{26}$ClN$_6$O$_6$S requires 561.1323 m/z (ESI) [MNa$^+$]=583.1085; C$_{24}$H$_{25}$ClN$_6$O$_6$SNa requires 583.1143

$\nu_{max}$ (PE) 3231, 2964, 1580, 1427, 1327, 1267, 1178, 937

Example 107

4-(tert-Butyl)-N-[3-methoxy-4-(2-methoxyphenoxy)-1-methyl-1H-pyrazol-5-yl]benzenesulfonamide

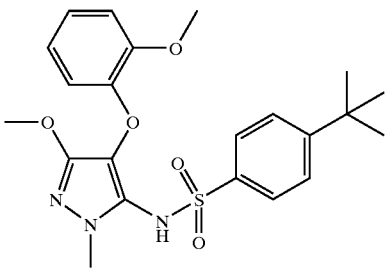

A solution of 3-methoxy-4-(2-methoxyphenoxy)-1-methyl-1H-pyrazol-5-amine (Preparation 68) (45 mg), (4-tert-butyl)benzenesulfonamide (42 mg) and 4-dimethylaminopyridine (22 mg) in dry pyridine (2 ml) was stirred at room temperature for 16 hours. A further aliquot of (4-tert-butyl)benzenesulfonamide (42 mg) was added to the reaction mixture and stirring at room temperature was continued for a further 24 hours. The reaction mixture was diluted with ethanol (2 ml) and 1.0M aqueous sodium hydroxide solution (4 ml) and was then stirred at room temperature for 4 hours. The mixture was diluted with aqueous 1.0M hydrochloric acid (20 ml) and then extracted with ethyl acetate (3×15 ml). The combined organic extracts were washed with aqueous 1.0M hydrochloric acid (20 ml), dried (magnesium sulfate) and then concentrated under vacuum. The residue was purified by chromatography on silica (5 g) using 40% ethyl acetate/pentane as eluant to give the title compound as an off-white solid (27 mg), $R_f$ 0.85 (ethyl acetate), m.p. 187.6° C.

$\delta_H$ (300 MHz, CDCl$_3$) 7.67 (2H, d), 7.29 (2H, d), 7.00–6.93 (1H, m), 6.87–6.71 (4H, m), 3.83 (6H, s), 3.77 (3H, s), 1.24 (9H, s) m/z (EI) [MH$^+$]=446.1757; C$_{22}$H$_{28}$N$_3$O$_5$S requires 446.1750

$\nu_{max}$ (polyethylene card) 3269, 2928, 2849, 1540, 1500, 1462 cm$^{-1}$

Example 108

N-[1-benzyl-3-(2-hydroxyethoxy)-4-(4-methylphenyl)-1H-pyrazol-5-yl]-4-(tert-butyl)benzenesulfonamide

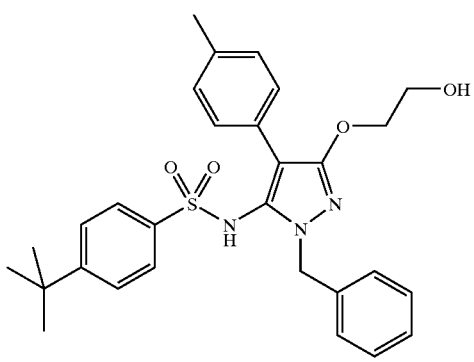

To a stirring solution of 2-{[1-benzyl-5-(bis{[4-(tert-butyl)phenyl]sulfonyl}amino)-4-(4-methylphenyl)-1H-pyrazol-3-yl]oxy}ethyl acetate (Preparation 40) (1.01 g) in ethanol (20 ml) was slowly added sodium hydroxide solution (2M, 2 ml). The reaction mixture was left stirring at room temperature overnight. The solvent was removed in-vacuo and the residue was taken up in ethyl acetate (30 ml) and washed with water (15 ml) followed by brine (1 ml). It was then dried (MgSO$_4$) and the solvent removed in-vacuo to yield the crude material as a yellow oil (ca.1 g). Purification was achieved using the Biotage™ Flash 40 system (silica, 90 g) with a gradient elution of hexane (75% to 65%) and ethyl acetate (25% to 35%) to yield the title product as a yellow solid (250 mg).

$\delta_H$ (400 MHz, CDCl$_3$) 7.40(2H, d), 7.30–7.40(3H, m), 7.25(2H, d), 7.15(2H, d), 6.80–6.95(4H, m), 6.55(1H, br), 5.40(2H, s), 4.30–4.35(2H, m), 3.80–3.90(2H, m), 3.05(1H, t), 2.25(3H, s), 1.25(9H, s). m/z (thermospray) [MH$^+$]= 520.6; C$_{29}$H$_{34}$N$_3$O$_4$S requires 519.7.

Example 109

N-[1-benzyl-3-{2-[(5-chloro-2-pyrimidinyl)oxy]ethoxy}-4-(4-methylphenyl)-1H-pyrazol-5-yl]-4-(tert-butyl benzenesulfonamide

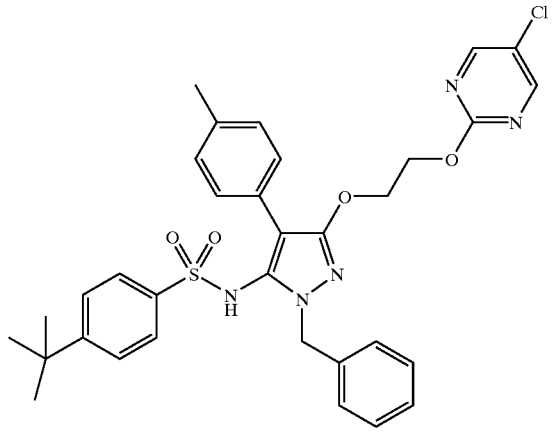

To a stiring solution of N-[1-benzyl-3-(2-hydroxyethoxy)-4-(4-methylphenyl)-1H-pyrazol-5-yl]-4-(tert-butyl)benzene sulfonamide (Example 108) (50 mg) in tetrahydrofuran (1 ml) was added sodium hydride (8 mg of a 60% dispersion in oil) and the reaction mixture stirred for 15 minutes. After which time a solution 5-chloro-2-(methylsulfonyl)pyrimidine (21 mg) in tetrahydrofuran (1 ml) and dimethylformamide (0.2 ml) was added to the reaction mixture and this was left stirring at room temperature for three days. The reaction mixture was diluted with water (50 ml) and extracted into ethyl acetate (2×50 ml). The combined organics were washed with brine (30 ml), dried (Na$_2$SO$_4$) and the solvent removed in vacuo to yield the crude material. This was purified using the Biotage™ Flash 12 system (silica, 12 g) with a gradient elution of hexane (100% to 50%) and ethyl acetate (0% to 50%) to yield the title product as a white solid (27 mg).

$\delta_H$ (400 MHz, CDCl$_3$) 8.40(2H, s), 7.40(2H, d), 7.20–7.35(5H, m), 7.15(2H, d), 6.80(4H, s), 6.35(1H, br), 5.40(2H, s), 4.70(2H, t), 4.55(2H, t), 2.20(3H, s), 1.25(9H, s). m/z (thermospray) [MH$^+$]=632.4; C$_{33}$H$_{35}$ClN$_5$O$_4$S requires 632.2.

Preparation 1

4-(tert-butyl)-N-{[4-(tert-butyl)phenyl]sulfonyl}-N-[1-methyl-4-(4-methylphenyl)-3-(2-phenoxyethoxy)-1H-pyrazol-5-yl]benzenesulfonamide

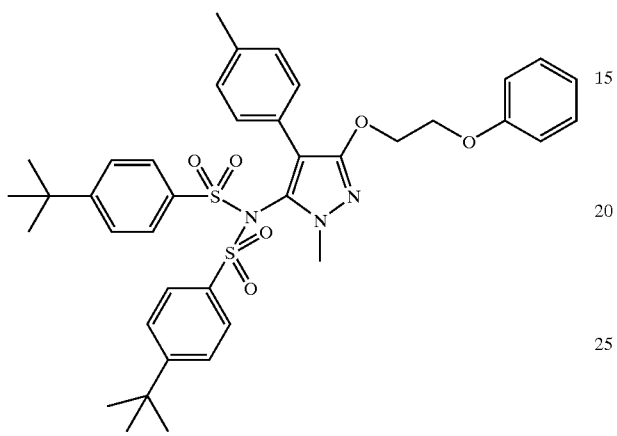

To 1-methyl-4-(4-methylphenyl)-3-(2-phenoxyethoxy)-1H-pyrazol-5-amine (Preparation 2) (105 mg) in dichloromethane (5 ml) at room temperature was added 4-tert-butylbenzenesulfonylchloride (265 mg), tetrabutylammonium hydrogen sulfate (28 mg) and potassium hydroxide (265 mg). The mixture was sonicated for 3 hrs. The reaction was diluted with water (10 ml) and extracted with ethyl acetate (10 ml). The organic fraction was dried over magnesium sulfate, filtered and concentrated under reduced pressure. The residue was purified by column chromatography silica (10 g) eluted with dichloromethane to yield the title compound as a white solid (101 mg).

$\delta_H$ (300 MHz, CDCl$_3$) 7.80 (4H, d), 7.40 (4H, d), 6.90–7.35 (9H, m), 4.60 (2H, t), 3.10 (3H, s), 2.15 (3H, s), 1.15 (18H, s). m/z (thermospray) [MH$^+$]=716.3; C$_{45}$H$_{46}$N$_3$O$_6$S$_2$ requires 716.3

Preparation 2

1-methyl-4-(4-methylphenyl)-3-(2-phenoxyethoxy)-1H-pyrazol-5-amine

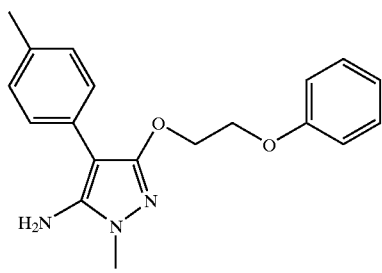

To 5-amino-1-methyl-4-(4-methylphenyl)-1H-pyrazol-3-ol (Preparation 3a) (50 mg) in dimethylformamide (2 ml) at room temperature was added sodium hydride (60% dispersion in oil, 10 mg) and β-bromophenetole (49.5 mg). The mixture was stirred for 2 hrs. The reaction was diluted with water (10 ml) and extracted with ethyl acetate (10 ml). The organic fraction was dried over magnesium sulfate, filtered and concentrated under reduced pressure. The residue was purified by column chromatography on silica (10 g) eluted with ether to yield the title compound as a white solid (20 mg).

$\delta_H$ (300 MHz, CDCl$_3$) 7.10–7.40 (4H, m), 7.15 (2H, d), 6.85–7.00 (3H, m), 4.55 (2H, t), 4.30 (2H, t), 3.65 (2H, br. s), 3.55 (3H, s), 2.35 (3H, s). m/z (thermospray) [MH$^+$]= 324.2; C$_{19}$H$_{22}$N$_3$O$_2$ requires 324.2

Preparation 3

(3a) 5-amino-1-methyl-4-(4-methylphenyl)-1H-pyrazol-3-ol (3b) 3-amino-1-methyl-4-(4-methylphenyl)-1H-pyrazol-5-ol

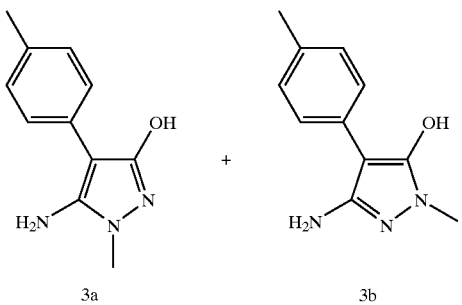

To ethyl (4-methylphenyl)cyanoacetate (*Synthesis*, 1985, 5, 506) (22.5 g) in ethanol (150 ml) at room temperature was added methylhydrazine (8.8 ml) dropwise over 30 minutes the mixture was heated to reflux temperature for 20 hrs. The reaction was evaporated to dryness. The residue was recrystalised in ethanol to yield the title compound (3a) as a white solid (8.3 g). The filtrate was taken, concentrated under reduced pressure and purified by column chromatography (silica, 500 g) eluted with dichloromethane:methanol (10:1) to yield the title compound (3b) as a white solid (855 mg).

(3a): $\delta_H$ (300 MHz, d$_6$ DMSO) 9.40 (1H, br. s), 7.40 (2H, d), 7.05 (2H, d), 5.60 (2H, br. s), 3.10 (3H, s), 2.25 (3H, s). m/z (thermospray) [MH$^+$]=204.2; C$_{11}$H$_{13}$N$_3$O+H requires 204.1

(3b): $\delta_H$ (300 MHz, d$_6$ DMSO) 9.00 (1H, br. s), 7.45 (2H, d), 7.05 (2H, d), 6.10 (2H, br. s), 3.30 (3H, s), 2.25 (3H, s). m/z (thermospray) [MH$^+$]=204.2; C$_{11}$H$_{14}$N$_3$O requires 204.1

Preparation 4

2-{[5-bis{[4-(tert-butyl)phenyl]sulfonyl}amino)-1-methyl-4-(4-methylphenyl)-1H-pyrazol-3-yl]oxy}ethyl acetate

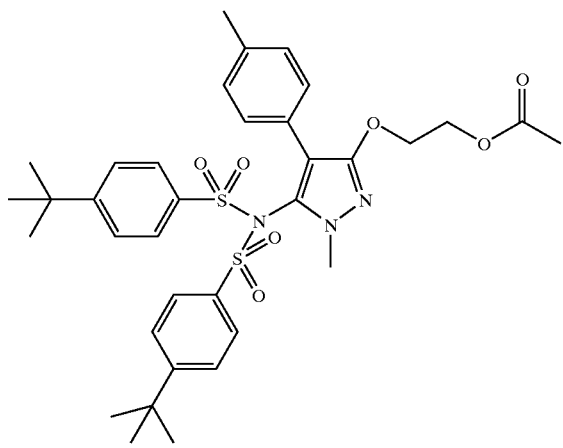

To 2-{[5-amino-1-methyl-4-(4-methylphenyl)-1H-pyrazol-3-yl]oxy}ethyl acetate (Preparation 5) (100 mg) in dichloromethane (3 ml) at room temperature was added 4-tert-butylbenzenesulfonylchloride (88 mg), tetrabutylanumonium hydrogen sulfate (14 mg) and potassium hydroxide (42 mg), the mixture was sonicated for 3 hrs. The reaction was diluted with water (10 ml) and extracted with ethyl acetate (10 ml). The organic fraction was dried over magnesium sulfate, filtered and concentrated under reduced pressure. The residue was purified by column chromatography (silica, 10 g) eluted with dichloromethane to yield the title compound as a white solid (80 mg).

$\delta_H$ (300 MHz, CDCl$_3$) 7.80 (4H, d), 7.40 (4H, d), 6.35 (2H, d), 6.85 (2H, d), 4.35–4.45 (4H, m), 3.10 (3H, s), 2.15 (3H, s), 2.05 (3H, s), 1.35 (18H, s).

Preparation 5

2-{[5-amino-1-methyl-4-(4-methylphenyl)-1H-pyrazol-3-yl]oxy}ethyl acetate

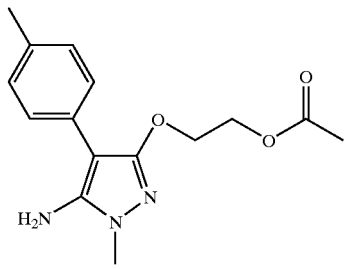

To 5-amino-1-methyl-4-(4-methylphenyl)-1H-pyrazol-3-ol (Preparation 3a) (250 mg) in dimethyl formamide (5 ml) at room temperature was added potassium carbonate (510 mg) and 2-bromoethyl acetate (205 mg), the mixture was stirred for 16 hrs. The reaction was diluted with water (60 ml) and extracted with ethyl acetate (3×30 ml). The organic fractions were combined, washed with water (2×30 ml) and brine (30 ml) and dried over magnesium sulfate, filtered concentrated under reduced pressure. The residue was purified by column chromatography (silica, 30 g) eluted with ethyl acetate:hexane (1:1) to yield the title compound as a white solid (151 mg).

$\delta_H$ (300 MHz, CDCl$_3$) 7.35 (2H, d), 7.15 (2H, t), 4.05 (4H, s), 3.60 (2H, br. s), 3.55 (3H, s), 2.35 (3H, s), 2.05 (3H, s). m/z (thermospray) [MH$^+$]=290.4; C$_{15}$H$_{20}$N$_3$O$_3$ requires 290.2

Preparation 6 isobutyl 2-{3-[2-(acetyloxy)ethoxy]-4-iodo-1-methyl-1H-pyrazol-5-yl}-2-{[4-(tert-butyl)phenyl]sulfonyl}acetate

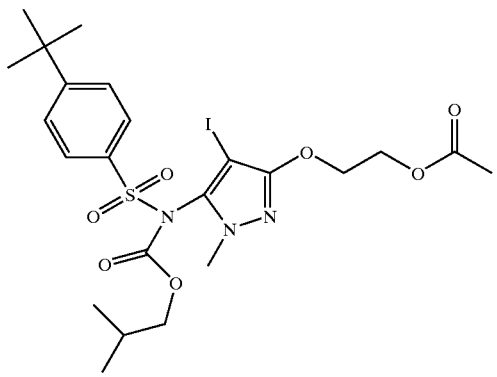

To 2-{[5-({[4-(tert-butyl)phenyl]sulfonyl}amino)-4-iodo-1-methyl-1H-pyrazol-3-yl]oxy}ethyl acetate (Preparation 7) (2 g) in solution in dichloromethane (50 ml) was added pyridine (0.51 ml) followed by isobutyl chloroformate(0.75 ml) dropwise. The reaction mixture was stirred at room temperature for 45 minutes. The solution was concentrated under reduced pressure to yield the crude product as a green sticky oil (2.6 g) which was purified by flash chromatography on silica eluted with hexane:ethyl acetate (1:5 to 3:5) to yield the desired product as a pale green solid (30 g).

$\delta_H$ (300 MHz, CDCl$_3$) 8.08 (2H, d), 7.58 (2H, d), 4.40 (4H, s), 3.99–3.85 (1H, m), 3.80 (3H, s), 1.92–1.81 (1H, m), 1.22 (9H, s), 0.82–0.76 (6H, m). m/z (thermospray) [MH$^+$]= 622.5; C$_{23}$H$_{33}$IN$_3$O$_7$S requires 622.1

Preparation 7

2-{[5-({[4-(tert-butyl)phenyl]sulfonyl}amino)-4-iodo-1-methyl-1H-pyrazol-3-yl]oxy}ethyl acetate

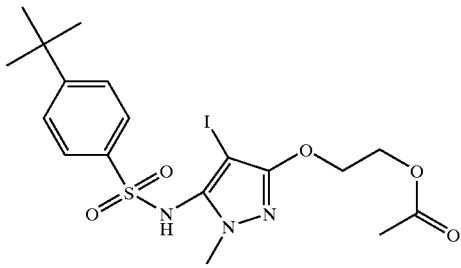

To 2-{[5-({[4-(tert-butyl)phenyl]sulfonyl}amino)-1-methyl-1H-pyrazol-3-yl)oxy}ethyl acetate (Preparation 8) (1.15 g) in solution in tetrahydrofuran (200 ml) was added portionwise N-iodosuccinimide (18 g), at room temperature. The reaction mixture was stirred at room temperature for 2 hours. The reaction was then diluted with ethyl acetate (150 ml), water (50 ml) and brine (50 ml). A 1M solution of sodium metabisulphite (100 ml) was added and the organic layer separated. The organics were washed successively with a diluted solution of sodium metabisulphite (100 ml) and then brine (50 ml). The solution was dried on magnesium sulfate, filtered and concentrated under reduced pressure to yield the desired product as an off pink solid (33.6 g)

$\delta_H$ (300 MHz, CDCl$_3$)) 7.68 (2H, d), 7.51 (2H, d), 7.23 (4H, s), 4.38 (4H, s), 3.84 (3H, s), 2.08 (3H, s), 1.34 (9H, s). m/z (thermospray) [MH$^+$]=522.0; C$_{18}$H$_{25}$IN$_3$O$_5$S$_2$ requires 522.1

Preparation 8

2-{[5-({[4-(tert-butyl)phenyl]sulfonyl}amino)-1-methyl-1H-pyrazol-3yl]oxy}ethyl acetate

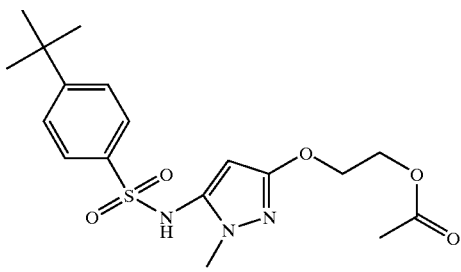

To tert-butyl 3-[2-(acetyloxy)ethoxy]-5-({[4-(tert-butyl)phenyl]sulfonyl}amino)-1-methyl-1H-pyrazole-4-carboxylate (Preparation 9) (1.48 g) in dichloromethane (20 ml) was added trifluoroacetic acid (10 ml), at room temperature. The reaction mixture was stirred at room temperature for 2.5 hours and then refluxed for 3 hours. The reaction mixture was then diluted with a saturated solution of aqueous ammonium chloride (20 ml), and the aqueous was then extracted with ethyl acetate (2×20 ml). The organics were dried with magnesium sulfate, filtered and concentrated under reduced pressure. The crude material was purified by chromatography on a suction column packed with silica eluted with ethyl acetate:hexane (3:5) to yield the desired product as an off white solid (200 mg).

$\delta_H$ (300 MHz, CDCl$_3$) 7.71 (2H, d), 7.52 (2H, d), 5.20 (1H, s), 4.38–4.30 (2H, m), 4.30–4.22 (2H, m), 3.60 (3H, s), 2.08 (3H, s), 1.38 (9H, s). m/z (thermospray) [MH$^+$]=396.1; C$_{18}$H$_{25}$N$_3$O$_5$S requires 396.2

Preparation 9 tert-butyl 3-[2-(acetyloxy)ethoxy]-5-({[4-(tert-butyl)phenyl]sulfonyl}amino)-1-methyl-1H-pyrazole-4-carboxylate

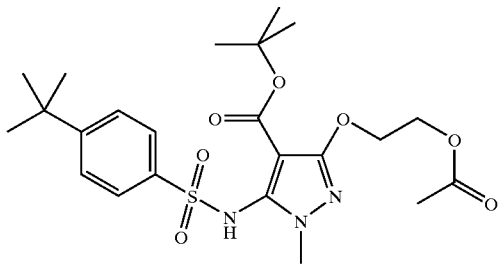

To tert-butyl 3-[2-(acetyloxy)ethoxy]-5-amino-1-methyl-1H-pyrazole-4-carboxylate (Preparation 10) (70 g) in solution in tetrahydrofuran (1 lit.) at 0° C. was added sodium hydride (20.2 g of a 60% dispersion in oil). The reaction mixture was stirred at room temperature for one hour and then 4-(tert-butyl)benzenesulfonyl chloride (58.88 g) was added dropwise. The reaction mixture was stirred at room temperature overnight and was then diluted with water (200 ml) at 0° C., followed by a saturated solution of ammonium chloride (200 ml) while allowing the mixture to warm to room temperature. The white precipitate was filtered off and disposed of. The aqueous and organic layers were separated and the aqueous extracted with ethyl acetate (100 ml). The combined organics were dried on magnesium sulfate, filtered and concentrated under reduced pressure. The crude was purified by chromatography on a suction column packed with silica eluted with ethyl acetate:hexane (1:4) to yield the desired product as white solid (16 g).

$\delta_H$ (400 MHz, CDCl$_3$) 7.60 (2H, d), 7.44 (2H, d), 4.38 (4H, s), 3.82 (3H, s), 2.05 (3H, s), 1.30 (9H, s), 1.25 (9H, s). m/z (positive ion electrospray) [MH$^+$]=496.1; C$_{23}$H$_{34}$N$_3$O$_7$S requires 496.2

Preparation 10 tert-butyl 3-[2-(acetyloxy)ethoxy]-5-amino-1-methyl-1H-pyrazole-4-carboxylate

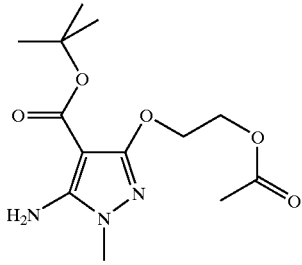

To tert-butyl 5-amino-3-(2-hydroxyethoxy)-1-methyl-1H-pyrazole-4-carboxylate (Preparation 11) (60 g) in tetrahydrofuran (500 ml), under nitrogen and at room temperature, was added triethylamine (41.7 ml), 4-dimethylaminopyridine (400 mg) followed by acetic anhydride (28.6 ml) dropwise. The reaction was stirred at room temperature overnight and was then concentrated under reduced pressure. The residue was diluted with ethyl acetate (300 ml) and washed with brine (2×100 ml). The organics were dried with magnesium sulfate, filtered and concentrated under reduced pressure to yield the desired product as white solid (71 g).

$\delta_H$ (400 MHz, CDCl$_3$) 4.40–4.28 (4H, m), 3.40 (3H, s), 2.05 (3H, s), 1.50 (9H, s). m/z (thermospray) [MH$^+$]=300.1; C$_{13}$H$_{22}$N$_3$O$_5$ requires 300.2

Preparation 11 tert-butyl 5-amino-3-(2-hydroxyethoxy)-1-methyl-1H-pyrazole-4-carboxylate

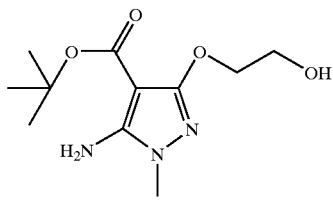

The tert-butyl 2-cyano-2-(1,3-dioxolan-2-ylidene)acetate (Synthesis, 1988, 981) (48.5 g) and methyl hydrazine (15 ml) were dissolved in methanol (400 ml) and the reaction refluxed for 3 hours. The reaction was concentrated under reduced pressure to yield the desired product as a beige gum (65 g).

$\delta_H$ (300 MHz, CDCl$_3$) 4.33–4.27 (2H, m), 3.97 (2H, bs), 4.33–4.27 (2H, m), 3.92–3.82 (2H, m), 3.42 (3H, s), 1.52 (9H, s). m/z (thermospray) [MH$^+$=257.9; C$_{11}$H$_{20}$N$_3$O$_4$ requires 258.1

Preparation 12
4-(tert-butyl)-N-{3-(2-hydroxyethoxy)-1-methyl-4-[4-(trifluoromethyl)phenyl]-1H-pyrazol-5-yl}-N-[(2-methoxyethoxy)methyl]benzenesulfonamide

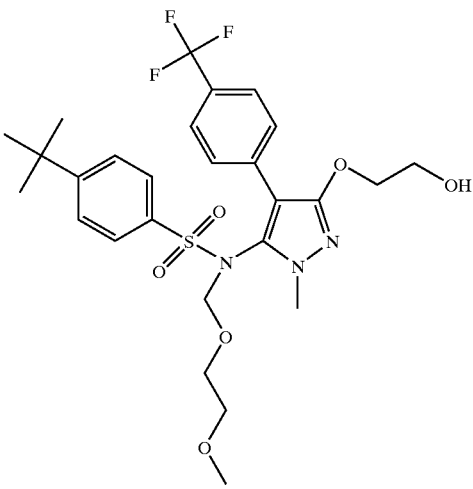

To 2-({5-{{[4-(tert-butyl)phenyl]sulfonyl}[(2-methoxyethoxy)methyl]amino}-1-methyl-4-[4-(trifluoromethyl)phenyl]-1H-pyrazol-3-yl}oxy)ethyl acetate (Preparation 13) (200 mg) in methanol (20 ml) was added a solution of potassium carbonate (90 mg) in water (5 ml), at room temperature. The reaction mixture was stirred at room temperature for 1.5 hours. The reaction mixture was stripped down and the residue partitioned between ethyl acetate (15 ml) and water (15 ml). The aqueous layer was extracted with ethyl acetate (2×15 ml). The combined organics were back-washed with brine (15 ml). The solution was dried over magnesium sulfate, filtered and concentrated under reduced pressure to yield the desired product as an off white solid (170 mg).

$\delta_H$ (300 MHz, CDCl$_3$) 7.52 (2H, d), 7.48–7.21 (4H, m), 5.27 (1H, d), 4.98 (1H, d), 4.22–4.18 (2H,m), 3.98–3.92 (3H, m), 3.80–3.70 (4H, m), 3.55–3.50 (2H, m), 3.38 (3H, s), 1.22 (9H, s).

Preparation 13
2-({5-{{[4-(tert-butyl)phenyl]sulfonyl}[(2-methoxyethoxy)methyl]amino}-1-methyl-4-[4-(trifluoromethyl)phenyl]-1H-pyrazol-3-yl}oxy)ethyl acetate

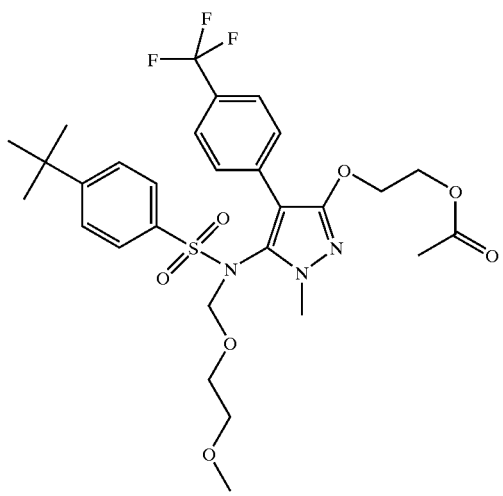

To 2-[(5-{{[4-(tert-butyl)phenyl]sulfonyl}[(2-methoxyethoxy)methyl]amino}-4-iodo-1-methyl-1H-pyrazol-3-yl)oxy]ethyl acetate (Preparation 14) (300 mg) in solution in toluene (5 ml) were successively added ethanol (1 ml), cesium carbonate (805 mg) in water (2 ml), and 4-(trifluoromethyl)phenylboronic acid (187 mg) at room temperature. The reaction mixture was degassed (vacuum followed by nitrogen atmosphere). This operation was repeated 5 times. The tetrakis(triphenylphosphine)-palladium(0) (15 mg) was then added and the reaction mixture degassed twice. The reaction mixture was refluxed for 1.5 hours and then cooled to room temperature and concentrated under reduced pressure. The residue was partitioned between ethyl acetate (20 ml) and a saturated solution of sodium carbonate (20 ml). The organic layer was separated and washed with a saturated solution of sodium carbonate (10 ml) and then brine (10 ml). The solution was dried on magnesium sulfate, the solution filtered on celite and concentrated under reduced pressure. The crude material was purified by chromatography on a suction column packed with silica eluted with ethyl acetate:hexane (1:2 to 3:1 gradually) to yield the desired product as an off white solid (200 mg).

$\delta_H$ (300 MHz, CDCl$_3$) 7.53 (2H, d), 7.33–7.25 (6H, m), 5.28 (1H, d), 4.97 (1H, d), 4.52–4.38 (4H,m), 3.98–3.89 (1H, m), 3.82–3.70 (4H, m), 3.55–3.49 (2H, m), 3.36 (3H, s), 2.18 (3H, s), 1.22 (9H, s).

Preparation 14

2-[(5-{{[4-(tert-butyl)phenyl]sulfonyl}[(2-methoxyethoxy)methyl]amino}-4-iodo-1-methyl-1H-pyrazol-3-yl)oxy]ethyl acetate

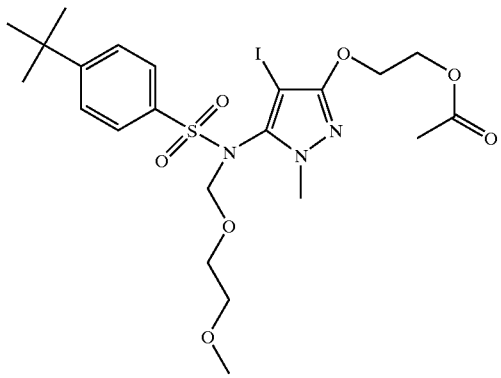

To 2-{[5-({[4-(tert-butyl)phenyl]sulfonyl}amino)-4-iodo-1-methyl-1H-pyrazol-3-yl)oxy}ethyl acetate (Preparation 7) (8 g) in solution in tetrahydrofuran (200 ml) was added sodium hydride (860 mg of a 60% dispersion in oil), at room temperature. The reaction was stirred at room temperature for 0.5 hours and 2-methoxyethoxymethyl chloride (2.7 ml) was added dropwise. The reaction was stirred for an other 0.5 hours and was then diluted with a saturated aqueous solution of ammonium chloride (50 ml) and reduced under reduced pressure. Ethyl acetate (100 ml) was added and the organic layer separated. The organics were washed with brine (20 ml), dried over magnesium sulfate, filtered and concentrated under reduced pressure. The crude material was purified by chromatography on a suction column packed with silica eluted with ethyl acetate:hexane (1:1) to yield the desired product as pale yellow oil (9.5 g).

$\delta_H$ (400 MHz, CDCl$_3$) 7.68 (2H, d), 7.50 (2H, d), 5.20 (1H, s), 4.92 (1H, d), 4.40–4.32 (4H, m), 4.08–4.00 (1H, m), 3.81 (3H, s), 3.81–3.73 (1H, m) 3.60–3.52 (2H, m), 3.36 (3H, s), 2.08 (3H, s), 1.38 (9H, s).

Preparation 15

4-(tert-butyl)-N-[3-(2-hydroxyethoxy)-1-methyl-4-phenyl-1H-pyrazol-5-yl]-N-[(2-methoxyethoxy)methyl]benzenesulfonamide

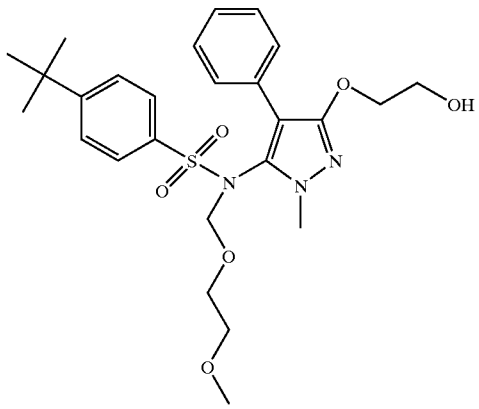

To 2-[(5-{{[4-(tert-butyl)phenyl]sulfonyl}[(2-methoxyethoxy)methyl]amino}-1-methyl-4-phenyl-1H-pyrazol-3-yl)oxy]ethyl acetate (Preparation 16) (1.112 g) in solution in methanol (100 ml) was added a solution of potassium carbonate (890 mg) in water (25 ml), at room temperature. The reaction was stirred at room temperature for 1.5 hours, and then overnight. The reaction was stripped down and the residue partitioned between dichloromethane (20 ml) and water (20 ml). The aqueous layer was extracted with dichloromethane (10 ml). The organics were combined and back-washed with brine (10 ml). The solution was dried on magnesium sulfate, filtered and concentrated under reduced pressure to yield the desired product as an off white solid (528 mg)

δ$_H$ (300 MHz, CDCl$_3$) 7.50 (2H, d), 7.22 (2H, d), 5.22 (1H, d), 4.96 (1H, d), 4.40–4.32 (2H,m), 3.95–3.90 (3H, m), 3.80–3.71 (4H, m), 3.55–3.50 (2H, m),3.38 (3H, s), 1.24 (9H, s). m/z (positive ion electrospray) [MH$^+$]=518; C$_{26}$H$_{36}$N$_3$O$_6$S requires 518.2

Preparation 16

2-[(5-{{[4-(tert-butyl)phenyl]sulfonyl}[(2-methoxyethoxy)methyl]amino}-1-methyl-4-phenyl-1H-pyrazol-3-yl)oxy]ethyl acetate

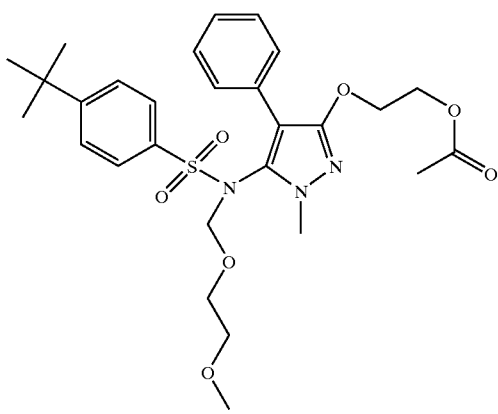

2-[(5-{{[4-(tert-Butyl)phenyl]sulfonyl}[(2-methoxyethoxy)methyl]amino}-4-iodo-1-methyl-1H-pyrazol-3-yl)oxy]ethyl acetate (Preparation 14) (1.95 g), benzeneboronic acid (0.78 g) and cesium carbonate (5.26 g) were suspended in 1,4-dioxane (50 ml) and water (5 ml). The mixture was degassed (vacuum and nitrogen atmosphere×5) and then tetrakis(triphenylphosphine) palladium(0) (50 mg) was added and the mixture degassed again. The mixture was heated at reflux for 2 hours and cooled to room temperature overnight. The reaction was quenched with saturated aqueous sodium bicarbonate solution and extracted with ethyl acetate (20 ml×3). The combined organics were washed with saturated aqueous sodium bicarbonate solution, dried with magnesium sulfate, filtered and concentrated under reduced pressure. Chromatography on silica eluting with a gradient elution of ethyl acetate:hexane (1:2 to 2:1) yielded the desired product as an off white solid (1.112 g).

δ$_H$ (300 MHz, CDCl$_3$)) 7.50 (2H, d), 7.22 (2H, d), 7.00 (4H, s), 5.28 (1H, d), 4.97 (1H, d), 4.52–4.38 (4H,m), 4.00–3.89 (1H, m), 3.80–3.70 (4H, m), 3.55–3.49 (2H, m),3.38 (3H,s), 2.16(3H, s), 1.26 (9H, s). m/z (thermospray) [MH$^+$]=560.5; C$_{28}$H$_{38}$N$_3$O$_7$S requires 560.2

Preparation 17

N-[4-(1,3-benzodioxol-5-yl)-3-(2-hydroxyethoxy)-1-methyl-1H-pyrazol-5-yl]-4-(tert-butyl)-N-[(2-methoxyethoxy)methyl]benzenesulfonamide

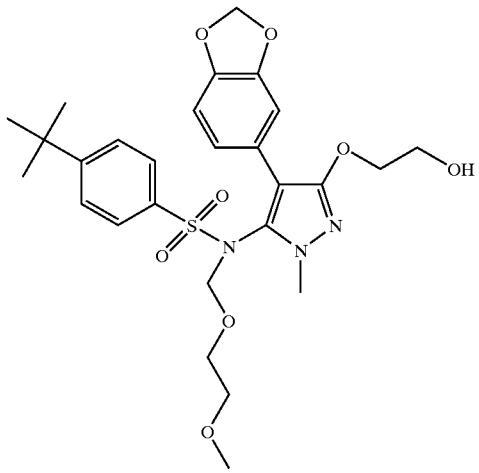

The title compound was made according to the procedure of Preparation 15 except that 2-[(4-(1,3-benzodioxol-5-yl)-5-{{[4-(tert-butyl)phenyl]sulfonyl}[(2-methoxyethoxy)methyl]amino}-1-methyl-1H-pyrazol-3-yl)oxy]ethyl acetate (Preparation 18) (928 mg) was used in place of 2-[(5-{{[4-(tert-butyl)phenyl]sulfonyl}[(2-methoxyethoxy)methyl]amino}-1-methyl-4-phenyl-1H-pyrazol-3-yl)oxy]ethyl acetate (Preparation 16) (1.112 g). The desired product was obtained as an off white solid (380 mg).

δ$_H$ (300 MHz, CDCl$_3$) 7.55 (2H, d), 7.29 (2H, d), 6.58 (1H, s), 6.43 (2H, s), 5.22 (1H, d), 4.96 (1H, d), 4.42–4.32 (2H,m), 3.99–3.91 (3H, m), 3.80–3.71 (4H, m), 3.59–3.50 (2H, m),3.38 (3H, s), 1.24 (9H, s). m/z (positive ion electrospray) [MH$^+$]=562; C$_{27}$H$_{36}$N$_3$O$_8$S requires 562.2

Preparation 18

2-[(4-(1,3-benzodioxol-5-yl)-5-{{[4-(tert-butyl)phenyl]sulfonyl}[(2-methoxyethoxy)methyl]amino}-1-methyl-1H-pyrazol-3-yl)oxy]ethyl acetate

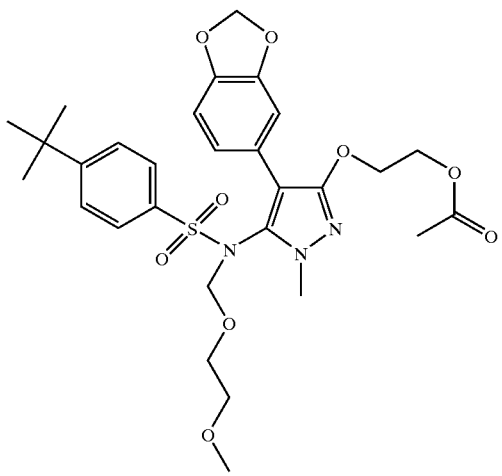

The title compound was made according to the procedure of Preparation 16 except that 1,3-benzodioxol-5-ylboronic acid (1.06 g) was used in place of benzeneboronic acid (0.78 g). The desired product was obtained as an off white solid (928 mg).

δ$_H$ (300 MHz, CDCl$_3$) 7.52 (2H, d), 7.28 (2H, d), 6.60 (1H, s), 6.48–6.38 (2H, m), 5.80 (2H, s), 5.22 (1H, d), 4.92 (1H, d), 4.42–4.35 (4H,m), 3.96–3.89 (1H, m), 3.78–3.68 (4H, m), 3.55–3.47 (2H, m), 3.32 (3H, s), 2.00 (3H, s), 1.26 (9H, s).

Preparation 19

4-(tert-butyl)-N-[4-(4-chlorophenyl)-3-(2-hydroxyethoxy)-1-methyl-1H-pyrazol-5-yl]-N-[(2-methoxyethoxy)methyl]benzenesulfonamide

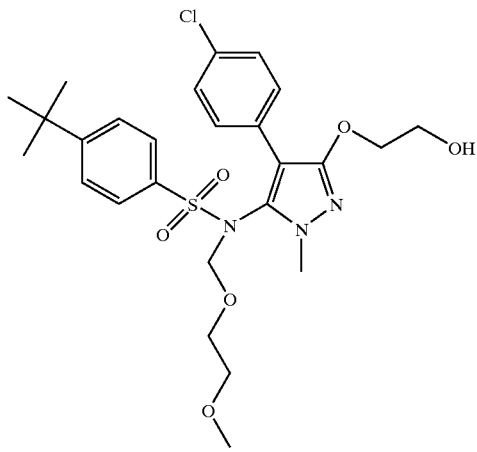

The title compound was made according to the procedure of Preparation 15 except that 2-{(5-{{[4-(tert-butyl)phenyl]sulfonyl}[(2-methoxyethoxy)methyl]amino}-4-(4-chlorophenyl)-1-methyl-1H-pyrazol-3-yl]oxy}ethyl acetate (Preparation 20) (1.37 g) was used in place of 2-[(5-{{[4-(tert-butyl)phenyl]sulfonyl}[(2-methoxyethoxy)methyl]amino}-1-methyl-4-phenyl-1H-pyrazol-3-yl)oxy]ethyl acetate (Preparation 16) (1.112 g). The desired product was obtained as an off white solid (610 mg).

δ$_H$ (300 MHz, CDCl$_3$) 7.20 (2H, m), 7.00 (4H, s), 6.78 (2H, d), 5.22 (1H, d), 4.98 (1H, d) 4.42–4.35 (2H,m), 3.99–3.91 (3H, m), 3.81–3.72 (4H, m), 3.60–3.51 (2H, m), 3.38 (3H, s), 1.24 (9H, s). m/z (positive ion electrospray) [MH$^+$]=552; C$_{26}$H$_{35}$ClN$_3$O$_6$S requires 552.2; [MNa$^+$]574; C$_{26}$H$_{34}$ClN$_3$NaO$_6$S requires 574.2.

Preparation 20

2-{[5-{{[4-(tert-butyl)phenyl]sulfonyl}[(2-methoxyethoxy)methyl]amino}4-(4-1-methyl-1H-pyrazol-3-yl]oxy}ethyl acetate

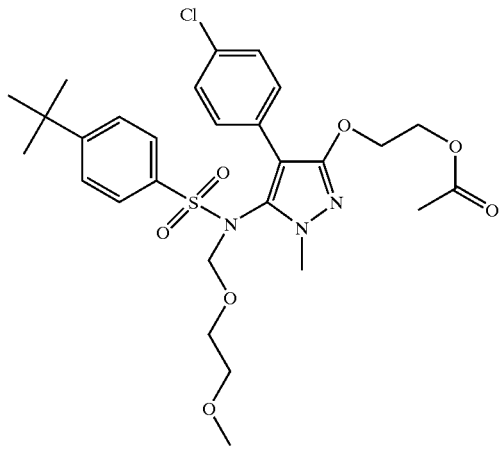

The title compound was made according to the procedure of Preparation 16 except that 4-chlorophenylboronic acid (1.0 g) was used in place of benzeneboronic acid (0.78 g). The desired product was obtained as an off white solid (1.37 g).

δ$_H$ (300 MHz, CDCl$_3$) 7.50 (2H, d), 7.25 (2H, d), 7.08–6.90 (4H, m), 5.22 (1H, d), 5.00 (1H, d), 4.56–4.37 (4H,m), 4.00–3.92 (1H, m), 3.82–3.75 (4H, m), 3.58–3.52 (2H, m), 3.38 (3H, s), 2.08 (3H, s), 1.30 (9H, s). m/z (thermospray) [MH$^+$]=594.4; C$_{28}$H$_{37}$ClN$_3$O$_7$S requires 594.2

Preparation 21

4-(tert-butyl)-N-[3-(2-hydroxyethoxy)-4-(4-methoxyphenyl)-1-methyl-1H-pyrazol-5-yl]-N-[-methoxyethoxy)methyl]benzenesulfonamide

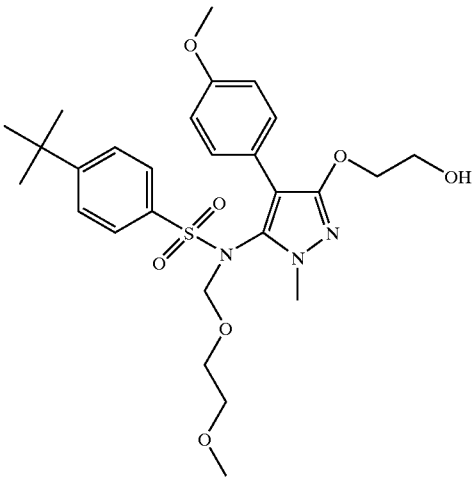

The title compound was made according to the procedure of Preparation 15 except that 2-{[5-{{[4-(tert-butyl)phenyl]sulfonyl}[(2-methoxyethoxy)methyl]amino}-4-(4-methoxyphenyl)-1-methyl-1H-pyrazol-3-yl]oxy}ethyl acetate (Preparation 22) (1.15 g) was used in place of 2-[(5-{{[4-(tert-butyl)phenyl]sulfonyl}[(2-methoxyethoxy)methyl]amino}-1-methyl-4-phenyl-1H-pyrazol-3-yl)oxy]ethyl acetate (Preparation 16) (1.112 g). The desired product was obtained as an off white solid (507 mg).

$\delta_H$ (300MHz, CDCl$_3$) 7.43 (2H, d), 7.28 (2H, d), 6.92 (2H, d), 6.59 (2H, d), 5.22 (1H, d), 4.92 (1H, d), 4.40–4.32 (2H,m), 3.98–3.89 (3H, m), 3.80–3.70 (7H, m), 3.55–3.49 (2H, m), 3.36 (3H, s), 1.30 (9H, s). m/z (positive ion electrospray) [M$^+$]=548; C$_{27}$H$_{37}$ClN$_3$O$_7$S+H requires 548.2; [M+Na$^+$]570; C$_{27}$H$_{37}$ClN$_3$NaO$_7$S requires 570.2

Preparation 22

2-{[5-{{[4-(tert-butyl)phenyl]sulfonyl}[(2-methoxyethoxy)methyl]amino}-4-(4-methoxyphenyl)-1-methyl-1H-pyrazol-3-yl]oxy}ethyl acetate

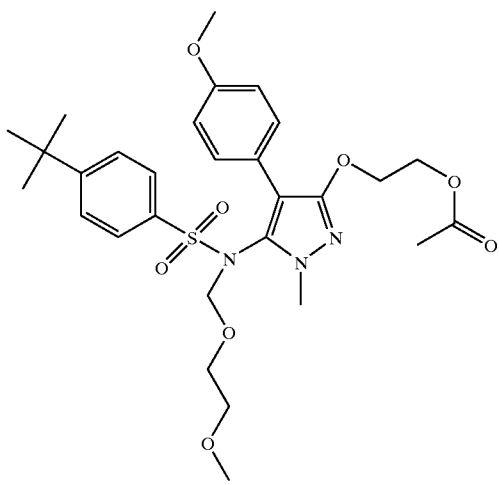

The title compound was made according to the procedure of Preparation 16 except that 4-methoxyphenylboronic acid (0.97 g) was used in place of benzeneboronic acid (0.78 g). The desired product was obtained as an off white solid (1.15 g).

$\delta_H$ (300 MHz, CDCl$_3$) 7.51 (2H, d), 7.28 (2H, d), 6.93 (2H, d), 6.55 (2H, d), 5.24 (1H, d), 4.90 (1H, d), 4.50–4.37 (4H,m), 4.00–3.90 (2H, m), 3.78 (3H, s), 3.72 (3H, m), 3.56–3.52 (2H, m), 3.38 (3H, s), 2.08 (3H, s), 1.27 (9H, s). m/z (thermospray) [MH$^+$]=590.5; C$_{29}$H$_{40}$N$_3$O$_8$S requires 590.3

Preparation 23

2-{[3-(bis{[4-(tert-butyl)phenyl]sulfonyl}amino)-1-methyl-4-(4-methylphenyl)-1H-pyrazol-5-yl]oxy}ethyl acetate

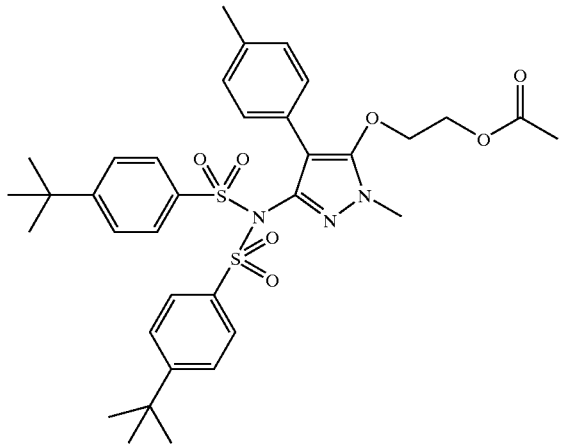

To 2-{[3-amino-1-methyl-4-(4-methylphenyl)-1H-pyrazol-5-yl]oxy}ethyl acetate (Preparation 24) (155 mg) in dichloromethane (20 ml) at room temperature was added 4-tert-butylbenzenesulfonyl chloride (374 mg), tetrabutylammonium hydrogen sulfate (45 mg) and potassium hydroxide (374 mg) and then the mixture was sonicated for 5.25 hrs. The reaction was diluted with dichloromethane (100 ml) and washed with water (3×100 ml) and brine (100 ml). The organic fractions were combined, dried over magnesium sulfate, filtered and concentrated under reduced pressure. The residue was purified by column chromatography (silica, 10 g) eluted with dichloromethane:hexane (4:1) to yield the title compound as a white solid (38 mg).

$\delta_H$ (300 MHz, CDCl$_3$) 7.80 (4H, d), 7.40 (4H, d), 7.35 (2H, d), 6.95 (2H, d), 4.20 (2H, t), 4.00 (2H, t), 3.75 (3H, s), 2.30 (3H, s), 2.05 (3H, s), 1.30 (18H, s). m/z (thermospray) [MH$^+$]=682.4; C$_{35}$H$_{44}$N$_3$O$_7$S$_2$ requires 682.3

Preparation 24

2-{[3-amino-1-methyl-4-(4-methylphenyl)-1H-pyrazol-5yl]oxy}ethyl acetate

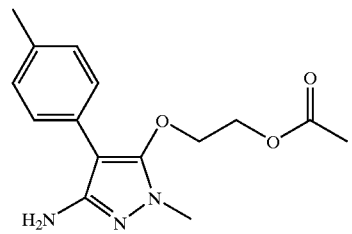

To 3-amino-1-methyl-4-(4-methylphenyl)-1H-pyrazol-5-ol (Preparation 3b) (855 mg) in dimethylformamide (10 ml) at room temperature was added cesium carbonate (4.11 g) and 2-bromoethyl acetate (703 mg), the mixture was stirred for 45 minutes. The reaction was diluted with 2M hydrochloric acid (10 ml) and extracted with ether (2×100 ml). The organic fractions were combined, washed with water (2×100 ml) and brine (100 ml), dried over magnesium sulfate, filtered and concentrated under reduced pressure. The residue was purified by column chromatography (silica, 30 g) eluted with ethyl acetate:hexane (5:1) to yield the title compound as a white solid (155 mg).

$\delta_H$ (300 MHz, CDCl$_3$) 7.35 (2H, d), 7.20 (2H, d), 4.20 (2H, t), 4.00 (2H, t), 3.70 (2H, br. s), 3.55 (3H, s), 2.35 (3H, s), 2.05 (3H, s).

Preparation 25

4-(tert-butyl)-N-{[4-(tert-butyl)phenyl]sulfonyl}-N-[3-[2-(4-fluorophenoxy)ethoxy]-1-methyl-4-(4-methylphenyl)-1H-pyrazol-5-yl]benzenesulfonamide

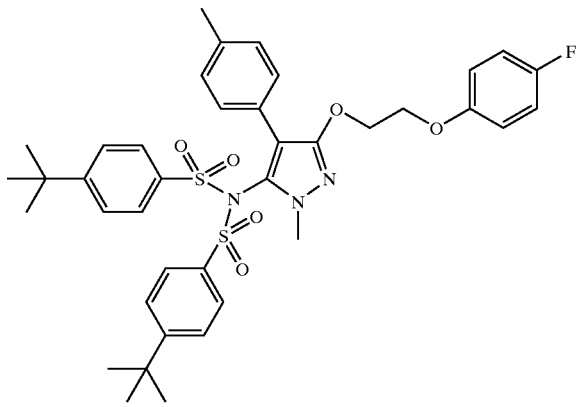

To 3-[2-(4-fluorophenoxy)ethoxy]-1-methyl-4-(4-methylphenyl)-1H-pyrazol-5-ylamine (Preparation 26) (105mg) in dichloromethane (20ml) at room temperature was added 4-tert-butylbenzenesulfonyl chloride (2 g), tetrabutylammonium hydrogen sulfate (75 mg) and potassium hydroxide (690 mg), the mixture was sonicated for 3 hrs. The reaction was partitioned between 2N aqueous hydrochloric acid and ethyl acetate. The organic layer was separated, washed with water, then brine, dried over magnesium sulfate, filtered and concentrated under reduced pressure. The residue was purified by column chromatography using silica gel, eluting with a solvent gradient of pentane:ethyl acetate (39:1 to 4:1), to yield the title compound as a glass (180 mg).

$\delta_H$ (300 MHz, CDCl$_3$) 7.80 (4H, d), 7.40 (6H, m), 6.80–7.00 (6H, m), 4.55 (2H, t), 4.30 (2H, t), 3.10 (3H, s), 2.15 (3H, s), 1.30 (18H, s). m/z (positive ion electrospray) [MH$^+$]=734.1; C$_{39}$H$_{45}$FN$_3$O$_6$S$_2$ requires 734.3

Preparation 26

3-[2-(4fluorophenoxy)ethoxy]-1-methyl-4-(4-methylphenyl)-1H-pyrazol-5ylamine

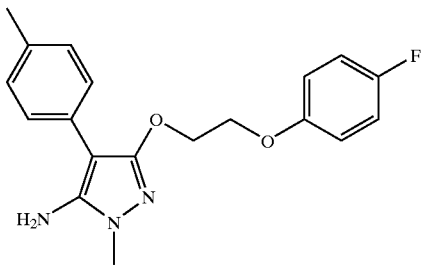

To 5-amino-1-methyl-4-(4-methylphenyl)-1H-pyrazol-3-ol (Preparation 3a) (5 g) in dimethylformamide (30 ml) at room temperature was added potassium carbonate (24.8 g) and 4-fluorophenoxyethylbromide (5.6 g), the mixture was stirred for 16 hrs. The reaction was partitioned between water (100 ml) and diethyl ether (100 ml). The aqueous layer was separated and extracted with further diethyl ether (4×100 ml). The organic fractions were combined, washed with water, then brine, dried over magnesium sulfate, filtered, and concentrated under reduced pressure azeotroping with xylene. The residue was purified by column chromatography on silica gel eluting with a solvent gradient, pentane:ethylacetate (7:3 to 0:1, by volume) to yield the title compound as a white solid (4.95 g).

$\delta_H$ (300M, CDCl$_3$) 7.35 (2H, d), 7.15 (2H, d), 6.80–7.00 (4H, m), 4.55 (2H, t), 4.25 (2H, t), 3.65 (2H, s), 3.55 (3H, s), 2.35 (3H, s). m/z (positive ion electrospray) [MH$^+$]= 342.1; C$_{19}$H$_{38}$FN$_3$O$_2$ requires 342.2

Preparation 27

4-(tert-butyl)-N-[1-(2-{[tert-butyl(dimethyl)silyl]oxy}ethyl)-3-(2-[{5-chloro-2-pyrimidinyl}oxy]ethoxy)-4-(4-methylphenyl)-1H-pyrazol-5-yl]benzenesulfonamide

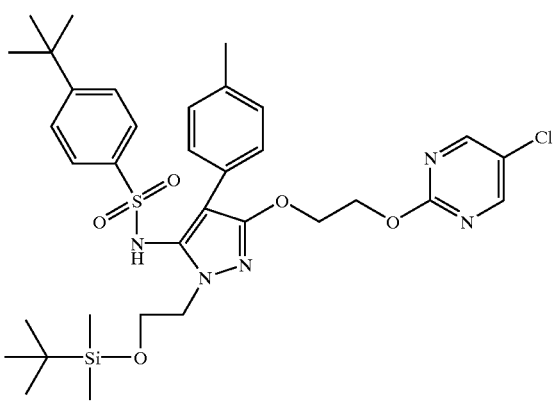

Sodium hydride (16 mg, 60% suspension in mineral oil) was added to a stirred solution of 4-(tert-butyl)-N-[1-(2-{[tert-butyl(dimethyl)silyl]oxy}ethyl)-3-(2-hydroxyethoxy)-4-(4-methylphenyl)-1H-pyrazol-5-yl]benzenesulfonamide (105 mg) (Preparation 28) in anhydrous THF (5 ml) at room temperature under a nitrogen atmosphere and the resulting mixture was stirred for 10 minutes at room temperature. DMF (2 ml) was added to the reaction mixture, followed by 5-chloro-2-(methylsulphonyl)pyrimidine (39 mg) and the resulting mixture was stirred at room temperature overnight. The reaction mixture was poured into an aqueous solution of 1.0M citric acid (50 ml) and ether (50 ml) and the aqueous phase was separated. The organic phase was washed with water (30 ml) and then dried over magnesium sulfate, filtered and concentrated under pressure. The orange/brown residue was purified by chromatography on a Biotage Flash 12i cartridge at 10 psi using 20% ethyl acetate/hexane as eluent to give the title compound as a pale yellow oil (90 mg).

$\delta_H$ (300 MHz, CDCl$_3$) 8.41 (2H, s), 7.45 (2H, d), 7.27 (1H, broad s), 7.19 (2H, d), 7.08 (2H, d), 6.84 (2H, d), 4.71 (2H, t), 4.56 (2H, t), 4.13 (2H, t), 3.87 (3H, t), 2.24 (3H, s), 1.27 (9H, s), 0.90 (9H, s), 0.04 (6H, s). m/z (thermospray) [MH$^+$]=700.9; C$_{34}$H$_{37}$ClN$_5$O$_5$SSi requires 700.3

Preparation 28

4-(tert-butyl)-N-[1-(2-{[tert-butyl(dimethyl)silyl]oxy}ethyl)-3-(2-hydroxyethoxy)-4-(4-methylphenyl)-1H-pyrazol-5-yl]benzenesulfonamide

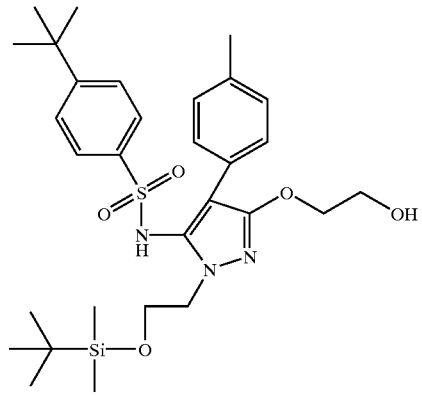

A mixture of 2-{[5-(bis{[4-(tert-butyl)phenyl]sulfonyl}amino}-1-(2-{[tert-butyl(dimethyl)silyl]oxy}ethyl}-4-{4-methylphenyl}-1H-pyrazol-3-yl]oxy}ethyl acetate (300 mg) (Preparation 29) and 1.0M sodium hydroxide solution (2 ml) in ethanol (20 ml) was stirred at room temperature overnight. The reaction mixture was evaporated in vacuo and the residue was then diluted with 1.0M citric acid (50 ml) and extracted with ethyl acetate (2×50 ml). The combined organic extracts were dried over magnesium sulfate, filtered and concentrated under reduced pressure. The residue was purified by chromatography on a Biotage Flash™ 12i column at 10 psi using 25% ethyl acetate/hexane as eluent to give the title compound as a colourless oil (105 mg).

$\delta_H$ (300 MHz, CDCl$_3$) 7.47 (2H, d), 7.30 (1H, broad s), 7.20 (2H, d), 7.12 (2H, d), 6.92 (2H, d), 4.37–4.32(2H, m), 4.13 (2H, t), 3.93–3.86 (4H, m), 3.14 (1H, t), 2.27 (3H, s), 1.29 (9H, s), 0.89 (9H, s), 0.03 (6H, s). m/z (thermospray) [MH$^+$]=588.7; C$_{30}$H$_{46}$N$_3$O$_5$SSi requires 588.3

Preparation 29

2-{[5-(bis{[4-(tert-butyl)phenyl]sulfonyl}amino}-1-{2-{[tert-butyl(dimethyl)silyl]oxy}ethyl}-4-{4-methylphenyl}-1H-pyrazol-3-yl]oxy}ethyl acetate

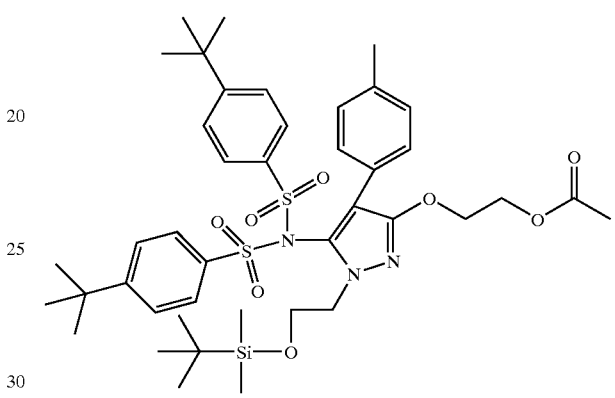

A solution of 2-{[5-amino-1-(2-{[tert-butyl(dimethyl)silyl]oxy}ethyl)-4-(4-methylphenyl)-1H-pyrazol-3-yl]oxy}ethyl acetate (0.35 g) (Preparation 30), 4-(tert-butyl)phenylsulfonyl chloride (0.25 g) and 4-(N,N-dimethyl)aminopyridine (98 mg) in pyridine (4 ml) was stirred at room temperature overnight. Tlc (30:70 ethyl acetate/hexane) indicated a new less polar product had formed, but the reaction appeared to have proceeded only 50% to completion. A further aliquot of the sulfonyl chloride (0.25 g) was added to the reaction mixture and stifling at room temperature was continued for a further 4 days. Tlc analysis then indicated complete disappearance of the starting materials and a single new product was observed. The reaction mixture was poured into saturated copper (II) sulfate solution (100 ml) and the aqueous mixture was extracted with ether (2×5 ml). The combined ether extracts were washed with saturated copper (II) sulfate solution (30 ml). The organic extract was dried over magnesium sulfate, filtered and concentrated under reduced pressure to leave a yellow/brown gum. The gum was recrystallised from methanol/water to give the title compound as yellow crystals (325 mg).

$\delta_H$ (300 MHz, CDCl$_3$) 7.83 (4H, d), 7.39 (4H, d), 7.37 (2H, d), 6.89 (2H, d), 4.42 (4H, m), 4.02 (2H, t), 3.50 (2H, t), 2.26 (3H, s), 2.09 (3H, s), 1.35 (18H, s), 0.86 (9H, s), 0.02 (6H, s). m/z (thermospray) [MH$^+$]=826.0; C$_{42}$H$_{60}$N$_3$O$_8$S$_2$Si requires 826.4

Preparation 30

2-{[5-amino-1-(2-{[tert-butyl(dimethyl)silyl]oxy}ethyl)-4-(4-methylphenyl)-1H-pyrazol-3-yl]oxy}ethyl acetate

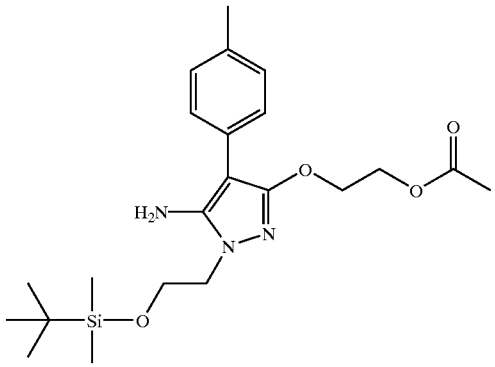

2-Bromoethyl acetate (0.29 g) was added dropwise over 1 minute to a stirred suspension of 5-amino-1-{2-[(tert-butyl)dimethylsilyl]oxyethyl}-4-(4-methylphenyl)-1-H-pyrazol-3-ol (0.60 mg) (Preparation 31) and caesium carbonate (1.69 g) in anhydrous dimethylformamide (10 ml), under a nitrogen atmosphere, at room temperature. The resulting mixture was stirred overnight. The reaction was quenched by adding 1.0M citric acid (40 ml) and the resulting aqueous mixture was extracted with ethyl acetate (2×50 ml). The combined organic extracts were washed with water (40 ml), brine (40 ml), dried over magnesium sulfate, filtered and concentrated under reduced pressure. The residue was purified by chromatography using a Biotage Flash™ 40 column at 10 psi, with a step gradient of ethyl acetate/hexane (1:3 to 1:2) to give the title compound as a yellow oil (0.35 g).

$\delta_H$ (300 MHz, CDCl$_3$) 7.33 (2H, d), 7.18 (2H, d), 4.39 (4H, s), 4.18 (2H, broad s), 4.04 (2H, t), 3.92 (2H, t), 2.35 (3H, s), 2.07 (3H, s), 0.85 (9H, s), 0.01 (6H, s). m/z (thermospray) [MH$^+$]=434.6; C$_{22}$H$_{36}$N$_3$O$_4$Si requires 434.3

Preparation 31

5amino-1-{2-[(tert-butyl)dimethylsilyl]oxyethyl}-4-(4-methylphenyl)-1-H-pyrazol-3-ol

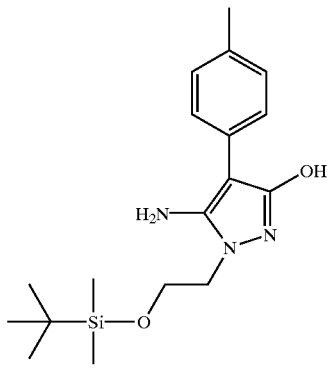

Sodium hydride (0.35 g, 60% suspension in mineral oil) was added in one portion to a stirred solution of 5-amino-1-(2-hydroxyethyl)-4-(4-methylphenyl)-1-H-pyrazol-3-ol (1.0 g) (Preparation 32) in anhydrous N,N-dimethylacetamide (20 ml) under a nitrogen atmosphere at room temperature. The initial effervescence observed subsided after 2–3 minutes and an orange/brown mixture resulted. After a further 7 minutes, tert-butyldimethylsilyl chloride (0.65 g) was added to the mixture in one portion and the reaction mixture was stirred at room temperature for 2 hours. Saturated aqueous ammonium chloride (50 ml) was added to the reaction mixture and the resulting aqueous medium was extracted with ethyl acetate (2×50 ml). The combined organic extracts were washed with water (40 ml), brine (40 ml) then dried over magnesium sulfate, filtered and concentrated under reduced pressure. The residue was recrystallised from dichloromethane/hexane to give the title compound as a white solid (0.66 g). m.p. 193.5–195° C.

$\delta_H$ (300 MHz, CDCl$_3$) 7.37 (2H, d), 7.20 (2H, d), 4.38 (2H, broad s), 3.99 (2H, t), 3.99 (2H, t), 3.89 (2H, t), 2.36 (3H, s), 0.86 (9H, s), 0.01 (6H, s); m/z (thermospray) [M$^+$]=347.4; C$_{18}$H$_{30}$N$_3$O$_2$Si requires 347.2.

Preparation 32

5-amino-1-(2-hydroxyethyl)-4-(4-methylphenyl)-1l-H-pyrazol-3-ol

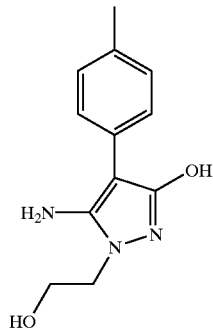

2-Hydroxyethylhydrazine (5.87 g) was added dropwise over 5 minutes to a stirred solution of ethyl cyano-(4-methylphenyl)acetate (*Synthesis*, 1985, 5, 506) (10.14 g) in absolute ethanol (200 ml) and the resulting mixture was then heated under reflux overnight. The reaction mixture was cooled to room temperature and the ethanol was evaporated under reduced pressure. The resulting yellow/orange oil was triturated with methanol and the solid was isolated by filtration to give the title compound as a white solid (3.1 g).

$\delta_H$ (300 MHz, D$_6$-DMSO) 7.48 (2H, d), 7.08 (2H, d), 6.06 (2H, broad s), 3.56 (2H, t), 3.46 (2H, t), 3.28 (2H, broad s), 2.25 (3H, s). m/z (thermospray) [MH$^+$]=234.1; C$_{12}$H$_{16}$N$_3$O$_2$ requires 234.1

Preparation 33

2-{[5-amino-4-(1,3-benzodioxol-5-yl)-1-methyl-1H-pyrazol-3-yl]oxy}ethyl acetate

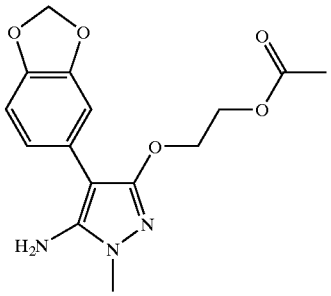

5-Amino-4-(1,3-benzodioxol-5-yl)-1-methyl-1H-pyrazol-3-ol (Preparation 34) (11.39 g) was dissolved in dimethylformamide (40 ml), cesium carbonate (15.9 g) was added followed by 2-bromoethylacetate (8.16 g). The mixture was stirred at room temperature for 16 hours. The mixture was treated with water (750 ml) and extracted with ethyl acetate (2×250 ml). The organic fractions were combined washed with water (3×350 ml), brine (250 ml), dried over magnesium sulfate, filtered and evaporated. The crude product was purified on silica (300 g) eluting with ethyl acetate:hexane (3:1) to yield the title compound as a white solid (5.57 g).

$\delta_H$ (300 MHz, CDCl$_3$) 6.95 (1H, s), 6.90 (2H, s), 5.95 (2H, s), 4.40 (4H, s), 3.60 (2H, s), 3.50 (3H, s), 2.05 (3H, s).

Preparation 34

5-amino-4-(1,3-benzodioxol-5yl)-1-methyl-1H-pyrazol-3-ol

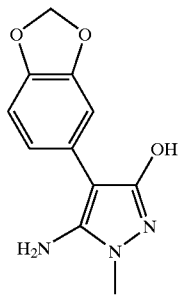

Methylhydrazine (6 ml) was added dropwise to a solution of ethyl 2-(1,3-benzodioxol-5-yl)-2-cyanoacetate (20.0 g) in ethanol (100 ml) and the mixture was refluxed overnight. The solution was subsequently allowed to cool to room temperature. Concentration to dryness afforded a residue, which was triturated with hot ethanol. The residue was washed with cold ethanol and dried to afford the title compound as a white solid (15.0 g).

$\delta_H$ (400 MHz, CDCl$_3$) 9.45 (1H, br. s), 7.05 (1H, s), 6.90 (1H, d), 6.80 (1H, d), 5.90 (2H, s), 5.65 (2H, br), 3.15 (3H, s). m/z (positive ion thermospray) [MH$^+$]=234.1; C$_{11}$H$_{12}$N$_3$O$_3$ requires 234.1

Preparation 35

N-[3-(2-acetoxyethoxy)-1-methyl-4-(4-methylphenyl)-1H-pyrazol-5-yl]-pyridine-2-sulfonamide

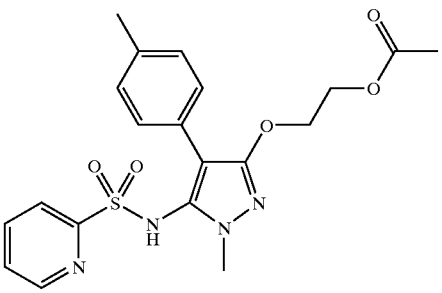

To 2-{[5-amino-1-methyl-4-(4-methylphenyl)-1H-pyrazol-3-yl]oxy}ethyl acetate (Preparation 5) (750 mg) in dry pyridine (5 ml) at room temperature was added pyridine-2-sulphonyl chloride (748 mg), the mixture was stirred for 72 hours. The reaction was concentrated under reduced pressure and the residue re-evaporated from toluene. The residue was then partitioned between ethyl acetate (20 ml) and water (20 ml), dried over magnesium sulfate, filtered and concentrated under reduced pressure to yield the title compound as a yellow solid.

$\delta_H$ (400 MHz, CDCl$_3$) 8.20 (1H, m), 7.50–7.60 (2H, m), 7.15 (1H, m), 7.10 (1H, bs), 6.85 (4H, m), 3.85 (3H, s), 2.30 (3H, s), 2.00 (3H, s). m/z (positive ion thermospray) [MH$^+$]= 431.3; C$_{20}$H$_{23}$N$_4$O$_5$S requires 431.5

Preparation 36

4-(tert-butyl)-N-{[4-(tert-butyl)phenyl]sulfonyl}-N-[3-(2-methoxyethoxy)-1-methyl-4-(4-methylphenyl)-1H-pyrazol-5-yl]benzenesulfonamide

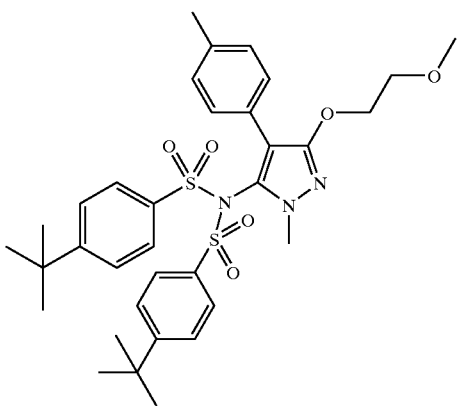

3-(2-Methoxyethoxy)-1-methyl-4-(4-methylphenyl)-1H-pyrazol-5-ylamine (Preparation 37) (183 mg) was dissolved in dichloromethane (5 ml) and tert-butylbenzenesulfonyl chloride (652 mg), potassium hydroxide (550 mg) and tetra-n-butylammonium hydrogen sulfate (61 mg) were added sequentially. The reaction was sonicated for 3 hours. The solvent was removed under reduced pressure. The residue was dissolved in ethyl acetate (50 ml), washed with water (50 ml), dried over magnesium sulfate, filtered and evaporated. The residue was purified by column chromatography over silica (20 g) eluted with a gradient of pentane:ethyl acetate (1:0 to 1:1) to yield the title compound as a white solid (278 mg).

$\delta_H$ (400 MHz, CDCl$_3$) 7.80 (4H, d), 7.40 (6H, m), 6.90 (2H, d), 4.40 (2H, m), 4.40 (2H, m), 3.70 (2H, m), 3.40 (3H, s), 3.20 (3H, s), 2.25 (3H, s), 1.35 (18H, s). m/z (positive ion thermospray) [MH$^+$]=654.0; C$_{34}$H$_{44}$N$_3$O$_6$S$_2$ requires 654.1

Preparation 37

3-(2-methoxyethoxy)-1-methyl-4-(4-methylphenyl)-1H-pyrazol-5-ylamine

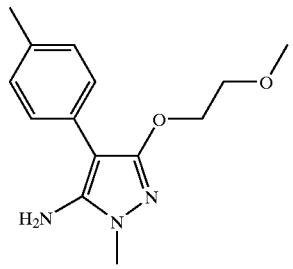

5-Amino-1-methyl-4-(4-methylphenyl)-1H-pyrazol-3-ol (Preparation 3a) (305 mg) was dissolved in dimethylformamide (2 ml), potassium carbonate (622 mg) and 2-bromoethyl methyl ether (208 mg) were added. The reaction was stirred at room temperature for 1.5 hours and then at 50° C. for 12 hours. The solvent was removed under reduced pressure. The crude product was purified on silica (10 g) eluted with a solvent gradient of pentane:ethyl acetate (1:0 to 0:1) to yield the title compound as a white solid (201 mg).

$\delta_H$ (400 MHz, CDCl$_3$) 7.35 (2H, d), 7.20 (2H, d), 4.35 (2H, m), 3.70 (2H, m), 3.65 (2H, s), 3.60 (3H, s), 3.40 (3H, s), 2.35 (3H, s). m/z (positive ion thermospray) [MH$^+$]=262.0; C$_{14}$H$_{20}$N$_3$O$_2$ requires 262.1

Preparation 38

4-(tert-butyl)-N-{[(4-(tert-butyl)phenyl]sulfonyl}-N-[3-(2-ethoxyethoxy)-1-methyl-4-(4-methylphenyl)-1H-pyrazol-5-yl]benzenesulfonamide

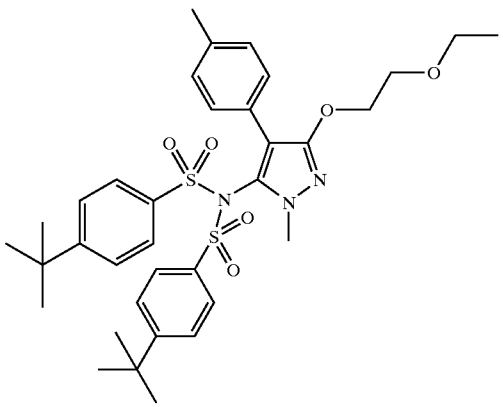

The method used in Preparation 36 was used to prepare the title compound from 3-(2-ethoxyethoxy)-1-methyl-4-(4-methylphenyl)-1H-pyrazol-5-ylamine (Preparation 39).

$\delta_H$ (400 MHz, CDCl$_3$) 7.80 (4H, d), 7.40 (6H, m), 6.85 (2H, d), 4.40 (2H, m), 3.75 (2H, m), 3.40 (2H, q), 3.15 (3H, s), 2.25 (3H, s), 1.35 (18H, s), 1.25 (3H, t). m/z (positive ion thermospray) [MH$^+$]=668.0; C$_{35}$H$_{46}$N$_3$O$_6$S$_2$ requires 668.1

Preparation 39

3-(2-ethoxyethoxy)-1-methyl-4-(4-methylphenyl)-1H-pyrazol-5-ylamine

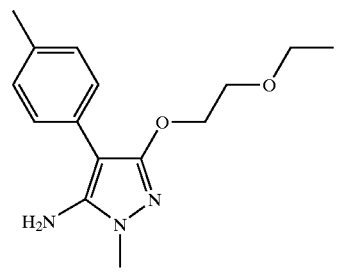

The method of Preparation 37 was used to prepare the title compound from 5-amino-1-methyl-4-(4-methylphenyl)-1H-pyrazol-3-ol (Preparation 3a) and 2-bromoethyl ethyl ether.

$\delta_H$ (400 MHz, CDCl$_3$) 7.35 (2H, d), 7.20 (2H, d), 4.35 (2H, m), 3.70 (2H, m), 3.65 (5H, m), 2.35 (3H, s), 1.20 (3H, t). m/z (positive ion thermospray) [MH$^+$]=276.0; C$_{15}$H$_{22}$N$_3$O$_2$ requires 276.1

Preparation 40

2-{[1-benzyl-5-(bis{[4-(tert-butyl)phenyl]sulfonyl}amino)-4-(4-methylphenyl)-1H-pyrazol-3-yl]oxy}ethyl acetate

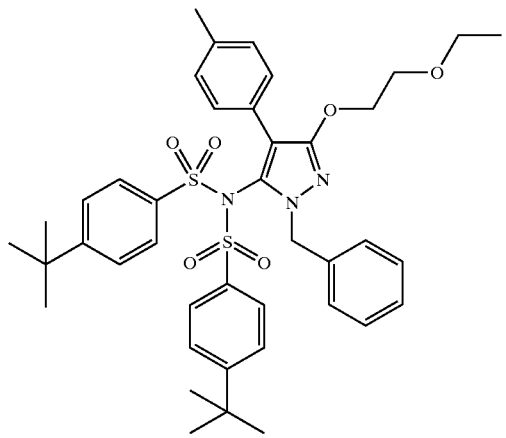

To a stirring solution of 2-{[5-amino-1-benzyl-4-(4-methylphenyl)-1H-pyrazol-3-yl]oxy}ethyl acetate (Preparation 41) (1.747 g) in dimethylacetamide (20 ml) under nitrogen at room temperature was added sodium hydride (0.38 g of a 60% dispersion in oil). This was then cooled to 0° C. and 4-tert-butylsulphonyl chloride (2.22 g) was added. The reaction mixture was allowed to warm up to room temperature and left stirring over night. The reaction mixture was carefully quenched with water (15 ml) and extracted into ethyl acetate (3×20 ml). The organics were combined and washed with brine (30 ml), dried (MgSO₄) and the solvent removed in vacuo to yield the crude material as a dark brown oil (ca. 4 g). This was purified using the Biotage™ Flash 40 system (silica, 90 g) with a gradient elution of hexane (95% to 80%) and ethyl acetate (5% to 20%) to yield the title product as a white solid (1.01 g, 28%).

$\delta_H$ (300 MHz, CDCl$_3$) 7.75(4H, d), 7.30–7.40(5H, m), 7.20(4H, d), 7.10(2H, d), 6.85(2H, d), 4.80(2H, s), 4.35–4.40(4H, m), 2.25(3H, s), 1.30(18H, s). m/z (thermospray) [MH$^+$]=757.8; C$_{41}$H$_{48}$N$_3$O$_7$S$_2$ requires 757.9.

Preparation 41

2-{[5-amino-1-benzyl-4-(4-methylphenyl)-1H-pyrazol-3-yl]oxy}ethyl acetate

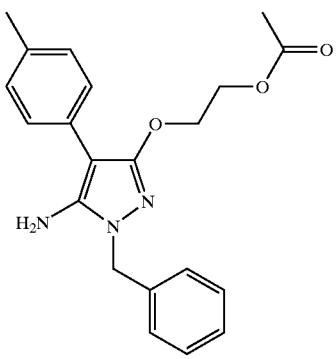

To a stirring suspension of 5-amino-1-benzyl-4-(4-methylphenyl)-1H-pyrazol-3-ol (Preparation 42) (2.4 g) and cesium carbonate (8.4 g) in dimethylformamide (30 ml) under nitrogen at room temperature was added 2-bromoethyl acetate (1.44 g) and the reaction mixture stirred overnight. The reaction was quenched with 2M hydrochloric acid (100 ml) and extracted into ethyl acetate (2×100 ml). The two combined organic extracts were further washed with water (2×100 ml), then dried (MgSO₄) and the solvent removed under reduced pressure to give the crude material. This was purified using the Biotage™ Flash 40 system (90 g Silica) with a gradient elution of hexane (75% to 30%) and ethyl acetate (25% to 70%) to yield the title product as a brown oil.(1.75 g, ca. 60%)

$\delta_H$ (400 MHz, CDCl$_3$) 7.35–7.40(4H, m), 7.30(1H, d), 7.15–7.20(4H,m), 5.10(2H, s), 4.40–4.45(4H, m), 3.55(2H, br), 2.35(3H, s), 2.10(3H, s). m/z (thermospray) [MH$^+$]=365.8; C$_{21}$H$_{24}$N$_3$O$_3$ requires 365.4.

Preparation 42

5-amino-1-benzyl-4-(4-methylphenyl)-1H-pyrazol-3-ol

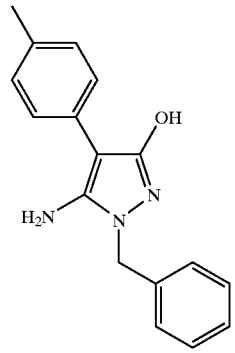

To a stirring suspension of ethyl-2-cyano-2-phenylacetate (10.34 g) and benzylhydrazine dihydrochloride (14.87 g) in ethanol (200 ml) at room temperature was added triethylamine (21.27 ml). The reaction mixture was heated to reflux for 24 hours. The solvent was removed under reduced pressure to yield the crude material as a brown oil. This was re-dissolved in ethyl acetate (100 ml) and washed with water (2×75 ml), then dried (MgSO₄) and the solvent removed in vacuo to yield a pale brown oil. This was recrystallised from methanol to yield the title product as pale yellow crystals (2.5 g, ca. 20%)

$\delta_H$ (400 MHz, d$_6$ DMSO) 9.55(1H, br), 7.40(2H, d), 7.30–7.35(2H, m), 7.20–7.25(3H, m), 7.10(2H, d), 5.60(2H, br), 4.90(2H, s), 2.25(3H, s). m/z (thermospray) [MH$^+$]= 280.2; C$_{17}$H$_{18}$N$_3$O requires 279.3

Example 43

4-(1,3-benzodioxol-5-yl)-3-methoxy-1-methyl-1H-pyrazol-5-amine

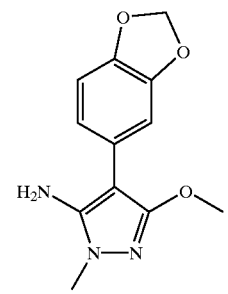

To a solution of 5-amino-4-(1,3-benzodioxol-5-yl)-1-methyl-1H-pyrazol-3-(50.0 g) (Preparation 46) in dimethylformamide (250 ml) was added potassium carbonate (88.7 g). The reaction was purged with nitrogen, treated with methyl iodide (13.3 ml) and left to stir for 48 h. The reaction mixture was poured into water (1500 ml) and extracted with ethyl acetate (5×300 ml). The organics were washed once with brine (250 ml), dried over magnesium sulfate and concentrated under reduced pressure. The residue was puri fied by silica (700 g) column chromatography eluting with a gradient of 5% methanol in dichloromethane to 10% methanol in dichloromethane to afford the title compound as a white solid (5.2 g).

$\delta_H$ (300 MHz, $d_6$ DMSO) 3.45 (3H, s), 3.75 (3H, s), 5.20 (2H, br, s), 5.95 (2H, s), 6.80–6.85 (2H, m), 6.95 (1H, s) m/z (thermospray) [MH$^+$]=248.5 $C_{12}H_{14}N_3O_3$ requires 248.1

Preparation 44

(E)-N-[4-(1,3benzodioxol-5-yl)-3-(2-hydroxyethoxy)-1-methyl-1H-pyrazol-5-yl]-2-phenylethenesulfonamide

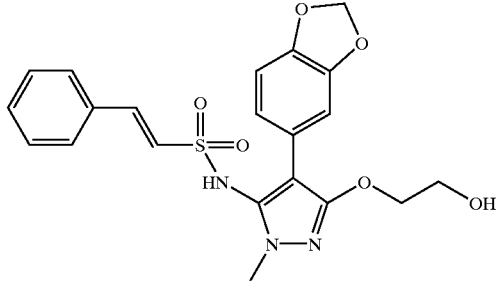

(E)-2-phenylethensulfonyl chloride (381 mg) and dimethylaminopyridine (77 mg) were added at room temperature under an atmosphere of nitrogen to a solution of 2-{[5-amino-4-(1,3-benzodioxol-5-yl)-1-methyl-1H-pyrazol-3-yl]oxy}-1-ethanol (200 mg) (Preparation 45) in anhydrous pyridine (6 ml). After 24 h, the mixture was concentrated under reduced pressure. To the yellow solid was added water (30 ml), an aqueous solution of HCl (1N) to acidify the solution and the mixture was extracted with dichloromethane (3×30 ml). The organic fractions were combined, dried on sodium sulfate and concentrated under reduced pressure. The residue was dissolved in ethanol (6 ml) and dichloromethane (1 ml) and an excess of an aqueous solution of sodium hydroxyde (2N) was added. The reaction was stirred overnight. The reaction mixture was then diluted with dichloromethane (100 ml), acidified with an aqueous solution of HCl (1N). The phases were separated and the aqueous phase was extracted with dichloromethane (2×50 ml). The combined organic fractions were dried on sodium sulfate and concentrated under reduced pressure. The residue was purified by column chromatography (silica, 20 g) eluted with dichloromethane:methanol (95:5) to yield the title compound as colourless solid (257 mg).

$\delta_H$ (300 MHz, CDCl$_3$) 3.8 (3H, s), 3.9 (2H, m), 4.35 (2H, m), 5.7 (2H, s), 6.6 (1H, d), 6.75 (2H, m), 7.05 (2H, d), 7.15 (1H, d), 7.2–7.4 (4H, m). m/z (electrospray) [MH$^+$] 444.1227; $C_{21}H_{22}N_3O_6S$ requires 444.1229

Preparation 45

2-{[5-amino-4-(1,3-benzodioxol-5-yl)-1-methyl-1H-pyrazol-3-yl]oxy}-1-ethanol

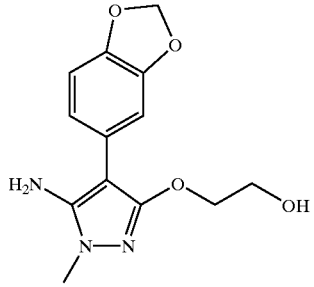

To a solution of 2-{[5-amino-4-(1,3-benzodioxol-5-yl)-1-methyl-1H-pyrazol-3-yl]oxy}ethyl acetate (100 mg) (Preparation 33) in ethanol (6 ml) at room temperature, was added sodium hydroxyde (10 mg). After one hour, the reaction was diluted with water (5 ml) and an aqueous saturated solution of ammonium chloride (10 ml). The mixture was extracted with ethyl acetate (3×6 ml). The organic fraction was dried over sodium sulfate and concentrated under reduced pressure to yield the title compound as a white solid (85 mg).

$\delta_H$ (300 MHz, CDCl$_3$) 3.5 (3H, s), 3.8 (2H, m), 4.2 (2H, m), 5.9 (2H, s), 6.8 (1H, d), 6.9 (1H, d), 7.0 (1H, s). m/z (electrospray) [MH$^+$]278 $C_{13}H_{16}N_3O_4$ requires 278.

Preparation 46

5-amino-4-(1,3-benzodioxol-5-yl)-1-methyl-1H-pyrazol-3-ol

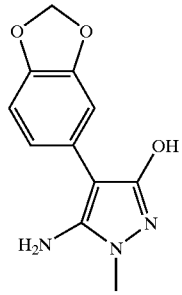

Methylhydrazine (6 ml) was added dropwise to a solution of ethyl 2-(1,3-benzodioxol-5-yl)-2-cyanoacetate (20.0 g) in ethanol (100 ml) and the mixture was refluxed overnight. The solution was subsequently allowed to cool to room temperature. Concentration to dryness afforded a residue, which was triturated with hot ethanol. The residue was washed with cold ethanol and dried to afford the title compound as a white solid (15.0 g).

$\delta_H$ (400 MHz, CDCl$_3$) 9.45 (1H, br. s), 7.05 (1H, s), 6.90 (1H, d), 6.80 (1H, d), 5.90 (2H, s), 5.65 (2H, br), 3.15 (3H, s). m/z (positive ion thermospray) [MH$^+$]=234.1; $C_{11}H_{12}N_3O_3$ requires 234.1

Preparation 47

N-4-(1,3-benzodioxol-5-yl)-3-{2-[(5-chloro-2-pyrimidinyl)oxy]ethoxy}-1-methyl-1H-pyrazol-5-yl)-N-(phenylsulfonyl)benzenesulfonamide

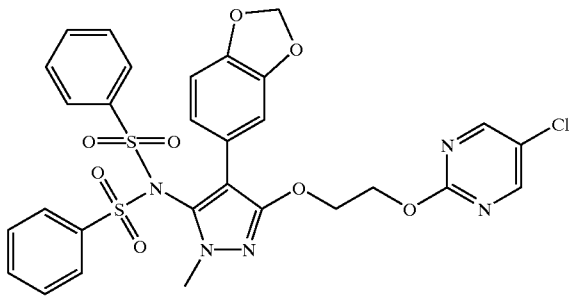

Benzenesulfonyl chloride (32 μl) was carefully added at room temperature under an atmosphere of nitrogen to a solution of 4-(1,3-benzodioxol-5-yl)-3-{2-[(5-chloro-2-pyrimidinyl)oxy]ethoxy}-1-methyl-1H-pyrazol-5-ylamine (Preparation 48) (50 mg) and dimethylamino pyridine (16 mg) in anhydrous pyridine (2.4 ml). After 12 h, some more benzenesulfonylchloride (16 μl) was added and the reaction was stirred overnight. The mixture was concentrated under reduced pressure, then a saturated solution of ammonium chloride (6 ml), ethyl acetate (6 ml), and brine (6 ml) were sequentially added to the residue. The aqueous phase was extracted with ethyl acetate (2×8 ml) and the combined organic fractions were washed with brine (10 ml), dried over sodium sulfate and concentrated under reduced pressure. The black residue was purified by preparative TLC (silica) eluted with dichloromethane : methanol (95 : 5) yielding the title compound as a pale yellow oil (71 mg).

$\delta_H$ (300 MHz, CDCl$_3$) 3.2 (s, 3H), 4.6 (2H, m), 4.75 (2H, m), 5.85 (2H, s), 6.45 (1H, d), 6.8 (1H, s), 6.95 (1H, d), 7.4 (4H, t), 7.45 (2H, d), 7.6 (2H, t), 7.95 (4H, d), 8.4 (2H, s). m/z (electrospray) [MH$^+$]670 C$_{29}$H$_{25}$ClN$_5$O$_7$S$_2$ requires 670.

Preparation 48

4-(1,3-benzodioxol-5-yl)-3-{2-(5-chloro-2-pyrimidinyl)oxy]ethoxy}-1-methyl-1H-pyrazol-5-ylamine

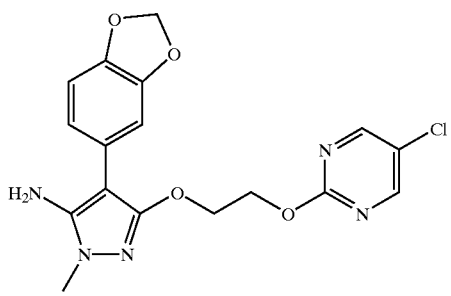

To a −78° C. cooled solution of 2-{[5-amino-4-(1,3-benzodioxol-5-yl)-1-methyl-1H-pyrazol-3yl]oxy}-1-ethanol (710 mg) (Preparation 45) in anhydrous tetrahydrofurane (25 ml) under an atmosphere of nitrogen, was added sodium hydride (60% dispersion in oil, 113 mg) and the mixture was stirred for 10 minutes at this temperature before 5chloro-2-(methylsulfonyl)pyrimidine (543 mg) was added in one portion and the mixture was stirred overnight at room temperature. The TLC indicated an incomplete reaction so the mixture was cooled to −78° C. and another portion of sodium hydride (60% dispersion in oil, 100 mg) was added. The mixture was stirred for 12 h at room temperature. Again, the TLC indicated an incomplete reaction. The mixture was cooled again to −78° C. and sodium hydride (60% dispersion in oil, 100 mg) was added. After 10 minutes at this temperature, 5-chloro-2-(methylsulfonyl)pyrimidine (200 mg) was added in one portion. The reaction was stirred overnight at room temperature. An aqueous saturated solution of ammonium chloride (1 ml) was carefully added before the reaction mixture was concentrated under reduced pressure. The residue was dissolved in a mixture of water (20 ml) and dichloromethane (20 ml). The phases were separated and the aqueous phase was extracted with dichloromethane (2×20 ml). The combined organic fractions were dried over sodium sulfate and concentrated under reduced pressure. The residue was purified by column chromatography (silica, 30 g) eluted with dichloromethane:methanol (95: 5) yielding the title compound as a colourless oil (910 mg).

$\delta_H$ (300MHz, CDCl$_3$) 3.55 (3H, s), 3.65 (2H, br.s), 4.55 (2H, m), 4.75 (2H, m), 5.95 (2H, s), 6.8 (2H, m), 6.9 (1H, s), 8.4 (2H, s). m/z (electrospray) [MH$^+$]390.0955 C$_{17}$H$_{17}$ClN$_5$O$_4$ requires 390.0964.

Preparation 49

N-(4-(1,3-benzodioxol-5-yl)-3-{2-[(5-chloro-2-pyrimidinyl)oxy]ethoxy}-1-methyl-1H-pyrazol-5-yl)-N-(methylsulfonyl)methanesulfonamide

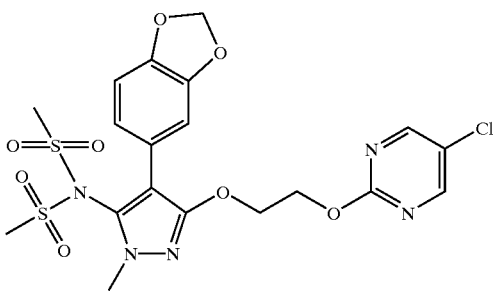

Methanesulfonyl chloride (20 ul) was added at room temperature under an atmosphere of nitrogen to a mixture of 4-(1,3-benzodioxol-5-yl)-3-{2-[(5-chloro-2-pyrimidinyl)oxy]ethoxy}-1-1H-pyrazol-5-ylamine (50 mg) (Preparation 48), dimethylaminopyridine (16 mg) in anhydrous pyridine (2.4 ml) and the reaction was stirred for 24 h. The mixture was concentrated under reduced pressure, then a saturated solution of ammonium chloride (6 ml), ethyl acetate (6 ml), and brine (6 ml) were sequentially added to the residue. The aqueous phase was extracted with ethyl acetate (2×8 ml) and the combined organic fractions were washed with brine (10 ml), dried over sodium sulfate and concentrated under reduced pressure. The oil was purified by preparative TLC (silica) eluted with dichloromethane:methanol (95:5) to yield the title compound as a pale yellow oil (71 mg).

$\delta_H$ (300 MHz, CDCl$_3$) 3.2 (6H, s), 3.75 (3H, s), 4.6 (2H, m), 4.75 (2H, m), 5.95 (2H, m), 6.8 (1H, d), 7.0–7.1 (3H, m), 7.0 (1H, s), 8.4 (2H, s). m/z (electrospray) [MH$^+$]546.0528 C$_{19}$H$_{21}$ClN$_5$O$_8$S$_2$ requires 546.0501.

Preparation 50

4-(1,3-benzodioxol-5-yl)-3-(cyclopropylmethoxy)-1-methyl-1H-pyrazol-5-ylamine

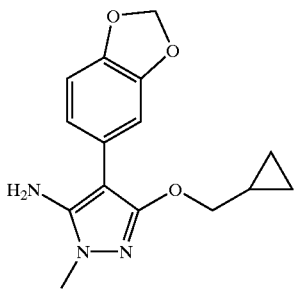

To 5-amino-4-(1,3-benzodioxol-5-yl)-1-methyl-1H-pyrazol-3-ol (500 mg) (Preparation 46) in anhydrous dimethylformamide (21 ml) under an atmosphere of nitrogen at room temperature was added solid potassium carbonate (980 mg) and bromomethylcyclopropane (230 µl). The mixture was stirred overnight then quenched by the addition of water (100 ml) and a saturated aqueous solution of ammonium chloride (50 ml). The solution was extracted with ethyl acetate (3×40 ml). The organic fraction was dried over sodium sulfate and concentrated under reduced pressure. The residue was purified by column chromatography (silica, 30 g) eluted with hexane:ethyl acetate (1:2) to yield the title compound as a colourless oil (365 mg).

$\delta_H$ (300 MHz, CDCl$_3$) 0.3 (2H, m), 0.6 (2H, m), 1.25 (1H, m), 3.55 (3H, s), 3.65 (2H, s, br.), 4.0 (2H, d), 5.95 (2H, s), 6.8–6.9 (2H, m), 7.0 (1H, s). m/z (electrospray) [MH$^+$] 288.1338 C$_{15}$H$_{19}$N$_3$O$_3$ requires 288.1348.

Preparation 51 ethyl 2-{4-[([3-{2-(acetyloxy)ethoxy]-4-(1,3-benzodioxol-5yl)-1-methyl-1H-pyrazol-5-yl]{[4-(2-ethoxy-1,1-dimethyl-2-oxoethyl)phenyl]sulfonyl}amino)sulfonyl]phenyl}-2-methylpropanoate

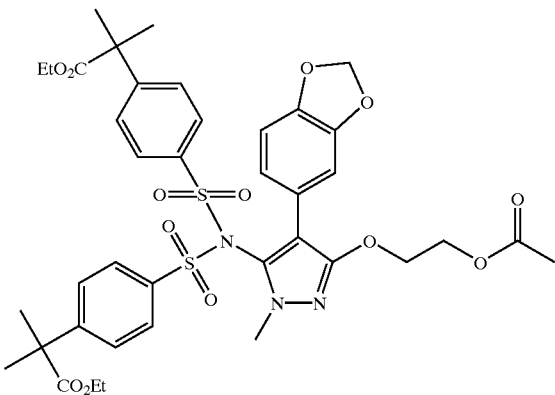

2-{[5-Amino-4-(1,3-benzodioxol-5-yl)-1-methyl-1H-pyrazol-3-yl]oxy}ethyl acetate (1 g) (Preparation 33) was added at room temperature under an atmosphere of nitrogen to a solution of ethyl 2-[4-(chlorosulfonyl)phenyl]-2-methylpropanoate (365 mg) and dimethylaminopyridine (154 mg) in anhydrous pyridine (11.5 ml). The reaction was left overnight then dimethylaminopyridine (76 mg) and ethyl 2-[4-(chlorosulfonyl)phenyl]-2-methylpropanoate (71 mg) was added. The reaction mixture was stirred overnight, concentrated under reduced pressure. An aqueous solution of HCl (0.001N, 100 ml) was added to the yellow residue and the mixture was extracted with dichloromethane (3×50 ml). The organic fraction was dried over sodium sulfate, concentrated under reduced pressure, and the residue was purified by column chromatography (silica, 20 g) eluted with hexane ethyl acetate (21). The oily residue was then dissolved in methanol and soon a white solid precipitated and was collected (3.9 mg).

$\delta_H$ (300 MHz, CDCl$_3$) 1.2 (6H, t), 1.6 (12H, s), 2.1 (3H, s), 3.15 (3H, s), 4.15 (4H, q), 4.4 (4H, m), 5.9 (2H, s), 6.4 (1H, d), 6.95 (1H, d), 7.05 (1H, s), 7.65 (8H, 2 AB syst). m/z (electrospray) [MH$^+$]828.2459 C$_{39}$H$_{46}$N$_3$O$_{13}$S$_2$ requires 828.2472.

Preparation 52

2-{[4-(1,3-benzodioxol-5-yl)-1-benzyl-5-(bis{[4-(tert-butyl)phenyl]sulfonyl}amino)-1H-pyrazol-3-yl]oxy}ethyl acetate

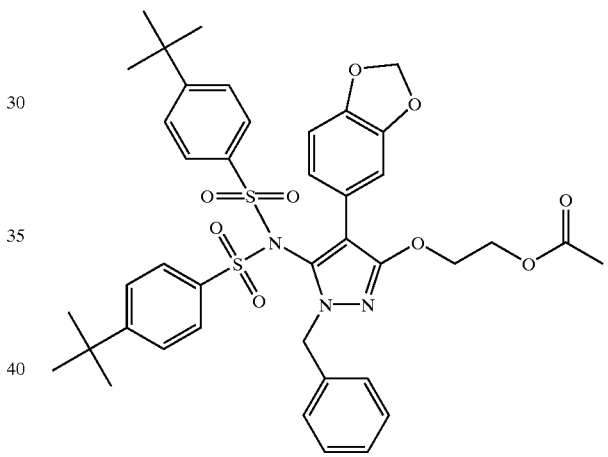

4-(tert-Butyl)benzenesulfonyl chloride (27.2 g) was added in two portions, at room temperature and under an atmosphere of nitrogen, to a mixture of 2-{[5-amino-4-(1,3-benzodioxol-5-yl)-1-benzyl-1H-pyrazol-3-yl]oxy}ethyl acetate (21 g) (Preparation 53) and dimethylaminopyridine (6.5 g) in anhydrous pyridine (500 ml). After 24 h, another portion of 4-(tert-butyl)benzenesulfonyl chloride (6.5 g) was added and the mixture stirred overnight. The reaction mixture was then concentrated under vacuum. Water (500 ml) was added to the oily yellow residue and the mixture was extracted with ethyl acetate (3×400 ml). The combined organic fractions were washed with brine (400 ml) and concentrated under reduced pressure. The residue was purified by column chromatography (silica, 700 g) eluted with hexane ethyl acetate (4:1) yielding the title compound as a white solid (24.5 g).

$\delta_H$ (300 MHz, CDCl$_3$) 1.3 (9H, s), 2.05 (3H, s), 4.4 (4H, m), 4.8 (2H, s), 5.9 (2H, s), 6.45 (1H, d), 7.0–7.2 (4H, m), 7.35 (3H, m), 7.5 (8H, AB syst). m/z (electrospray) [MH$^+$] 788.3 C$_{41}$H$_{46}$N$_3$O$_9$S$_2$ requires 788.3.

Preparation 53

2-{[5-amino-4-(1,3-benzodioxol-5-yl)-1-benzyl-1H-pyrazol-3-yl]oxy}ethyl acetate

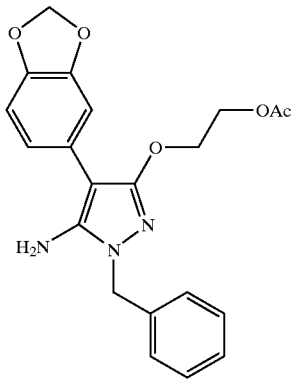

To a stirred mixture of 5-amino-4-(1,3-benzodioxol-5-yl)-1-benzyl-1H-pyrazol-3-ol (30 g) (Preparation 59) and cesium carbonate (94.8 g) in anhydrous dimethylformamide (340 ml), under an atmosphere of nitrogen, 2-bromoethyl acetate (16.2 g) was added drop-wise over 10 minutes and the reaction was stirred overnight. The reaction was quenched by the addition of an aqueous solution of HCl (2N, 260 ml) then ethyl acetate (600 ml) and water (100 ml) were added. The aqueous phase was extracted with ethyl acetate (3×500 ml) and the combined organic fractions were washed with brine (500 ml) and dried over $Na_2SO_4$. The dark oil was purified by flash chromatography (heptane/EtOAc; 1/1) (silica, 1000 g) yielding of the title compound as a dark oil (22.5 g).

$\delta_H$ (300 MHz, $d_6$ DMSO) 2.00 (3H, s), 4.25 (4H, m), 5.05 (2H, s), 5.40 (2H, br. s), 6.80–6.95 (2H, m), 7.00 (1H, s), 7.05–7.35 (5H, m). m/z (electrospray) [MH$^+$]396.1560 $C_{21}H_{22}N_3O_5$ requires 396.1559

Preparation 54

2-{4-(1,3-benzodioxol-5-yl)-5-methoxy-3-[(methoxymethyl)(phenethylsulfonyl)amino]-1H-pyrazol-1-yl}ethyl acetate

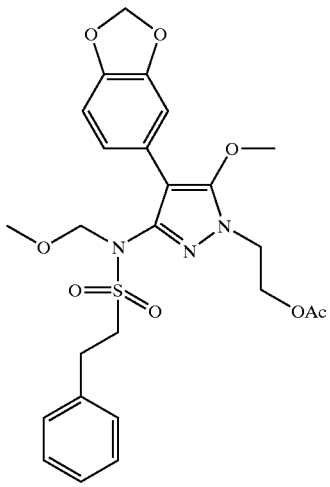

Sodium hydride (60% dispersion in oil, 162 mg) was added at room temperature under an atmosphere of nitrogen to a solution of N-[4-(1,3-benzodioxol-5-yl)-3-methoxy-1H-pyrazol-5-yl]-N-(methoxymethyl)-2-phenyl-1-ethanesulfonamide (Preparation 55) in anhydrous tetrahydrofurane. After 10 minutes, 2-bromoethyl acetate (446 μl) was added and the reaction mixture was refluxed overnight. At room temperature, some more 2-bromoethylacetate (446 μl) was added and the reaction was refluxed for 24 h. Then at room temperature, some more sodium hydride (50 mg) was added and the reaction was refluxed for 24 h. At room temperature, the reaction was quenched by the addition of an aqueous saturated solution of ammonium chloride (5 ml), water (10 ml) and the mixture was extracted with ethyl acetate (3×10 ml). The combined organic fractions were washed with brine (20 ml), dried on sodium sulfate and concentrated under reduced pressure to yield a dark oil which was purified by column chromatography (silica, 10 g), eluted with hexane:ethyl acetate (4:1) then (2:1) yielding the title compound as a colourless oil (92 mg).

$\delta_H$ (300 MHz, CDCl$_3$) 2.00 (3H, s), 3.20 (3H, s), 3.20 (2H, m), 3.70 (3H, s), 3.70 (2H, m), 4.20 (2H, t), 4.40 (2H, t), 4.75 (2H, s), 6.00 (2H, s), 6.80 (1H, d), 7.00 (2H, m), 7.20–7.40 (5H, m). m/z (thermospray) [MH$^+$]532.1743 $C_{25}H_{30}N_3O_8S$ requires 532.1753

Preparation 55

N-[4-(1,3-benzodioxol-5-yl)-3-methoxy-1H-pyrazol-5-yl]-N-(methoxymethyl)-2-phenyl-1-ethanesulfonamide

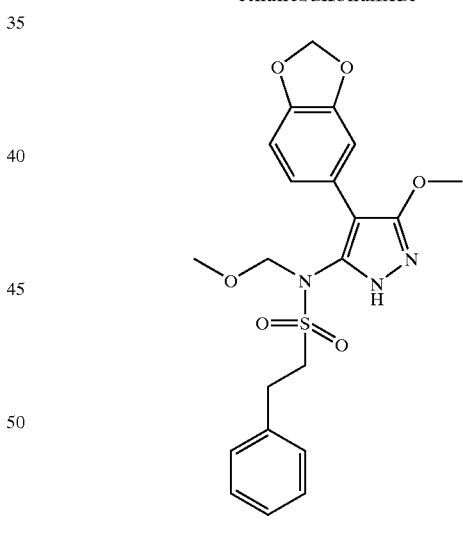

Sodium hydride (60% dispersion in oil, 5 mg) was added at room temperature under an atmosphere of nitrogen to a solution of N-[4-(1,3-benzodioxol-5-yl)-3-methoxy-1H-pyrazol-5-yl]-2-phenyl-1-ethanesulfonamide (Preparation 56) in anhydrous tetrahydrofuran (2.5 ml). After 10 minutes, bromomethyl methyl ether (12 μl) was added and the reaction was stirred overnight. An aqueous saturated solution of ammonium chloride (4 ml) was added and the mixture was extracted with ethyl acetate (3×6 ml). The combined organic fractions were washed with brine (6 ml),

Preparation 56

N-[4-(1,3-benzodioxol-5-yl)-3-methoxy-1H-pyrazol-5-yl]-2-phenyl-1-ethanesulfonamide

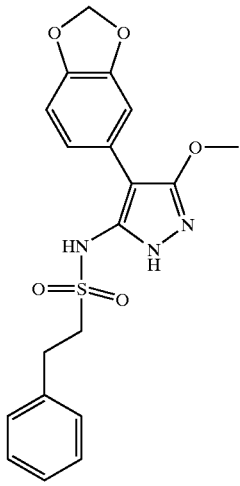

(E)-N-[4-(13,-benzodioxol-5-yl)-1-benzyl-3-methoxy-1H-pyrazol-5-yl]-2-phenyl-1-ethanesulfonamide (1.2 g) (Preparation 57) was dissolved in acetic acid (50 ml). Under an atmosphere of nitrogen, Pearlmann's catalyst (JM type 91, 200 mg) was added and the reaction was stirred for 24 h under 2 bars of hydrogen at 50° C. The reaction mixture was filtered on a short pad of Celite® and concentrated under reduced pressure. To the oily residue was added water (dichloromethane (200 ml). The phases were separated, the organic phase washed with a 10% aqueous solution of sodium bicarbonate (2×100 ml). The aqueous phase was then extracted with dichloromethane (2×10 ml), the combined organic fractions were dried over sodium sulfate and concentrated under reduced pressure to yield the title compound as a colourless oil (0.96 g).

$\delta_H$ (300 MHz, CD$_3$OD) 2.85 (2H, m), 3.05 (2H, m), 3.95 (3H, s), 5.85 (2H, s), 6.80 (1H, d), 6.90 (2H, m), 7.00 (2H, m), 7.20 (3H, m). m/z (electrospray) [MH$^+$]402.1126 C$_{19}$H$_{20}$N$_3$O$_5$S requires 402.1123

Preparation 57

(E)-N-[4-(1,3-benzodioxol-5-yl)-1-benzyl-3-methoxy-1H-pyrazol-5-yl]-2-phenyl-1-ethenesulfonamide

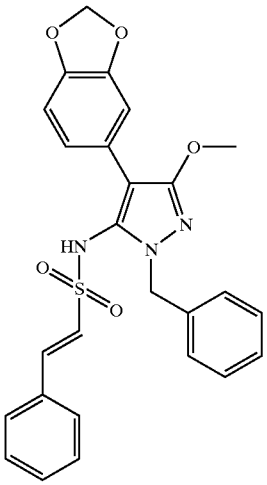

(E)-2-phenylethensulfonyl chloride (138 mg) and dimethylaminopyridine (40 mg) were added at room temperature under an atmosphere of nitrogen to a solution of 4-(1,3-benzodioxol-5-yl)-1-benzyl-3-methoxy-1H-pyrazol-5-amine (Preparation 58) (100 mg) in anhydrous pyridine (3 ml). After 24 h, another portion of (E)-2-phenylethensulfonyl chloride (32 mg) was added and the reaction was stirred for 48 h before the mixture was concentrated under reduced pressure. To the beige solid was added an aqueous solution of HCl (1N, 10 ml) and the mixture was extracted with dichloromethane (3×10 ml). The organic fractions were combined, dried on sodium sulfate and concentrated under reduced pressure. The residue was dissolved in ethanol (5 ml) and an aqueous solution of sodium hydroxyde (2N, 2.25 ml) was added. The reaction was stirred overnight. The reaction mixture was then diluted with water (20 ml), acidified with an aqueous solution of HCl (2N) and the solution was extracted with ethyl acetate (3×15 ml). The combined organic fractions were washed with brine (15 ml), dried on sodium sulfate and concentrated under reduced pressure. The residue was purified by column chromatography (silica, 10 g) eluted with hexane:ethyl acetate (2:1) to yield the title compound as colourless oil (109 mg) which crystallises in a mixture of ether and ethyl acetate.

$\delta_H$ (300 MHz, CDCl$_3$) 3.95 (3H, s), 5.40 (2H, s), 5.7 (2H, s), 6.25 (1H, s), 6.30 (1H, s), 6.65 (1H, m), 6.75 (2H, m), 7.05 (2H, d), 7.20 (1H, d), 7.25–7.40 (9H, m). m/z (electrospray) [MH$^+$]490.1443 C$_{26}$H$_{24}$N$_3$O$_5$S requires 490.1437

Preparation 58

4-(1,3-benzodioxol-5-yl)-benzyl-3-methoxy-1H-pyrazol-5-amine

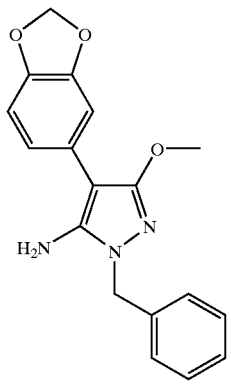

Cesium carbonate (1.05 g) and methyl iodide (0.46 g) were sequentially added at room temperature under an atmosphere of nitrogen to a solution of 5-amino-4-(1,3-benzodioxol-5-yl)-1-benzyl-1H-pyrazol-3-ol (1.0 g) (Preparation 59) in anhydrous dimethylformamide (10 ml). After 10 h, the reaction mixture was diluted water (100 ml) and the mixture was extracted with ether (3×100 ml). The organic fractions were washed with brine (100 ml), dried over magnesium sulfate, and concentrated under reduced pressure. The oily residue was purified by column chromatography (silica, 50 g) eluted with hexane:ethyl acetate (1:1) yielding the title compound as a white solid (260 mg).

δhd H(300 MHz, CDCl$_3$) 3.55 (2H, br. s), 3.95 (3H, s), 5.10 (2H, s), 5.95 (2H, s), 6.80 (2H, m), 7.00 (1H, s), 7.20 (2H, d), 7.25–7.40 (5H, m). m/z (electrospray) [MH$^+$] 324.1335 C$_{18}$H$_{18}$N$_3$O$_3$ requires 324.1348

Preparation 59

5-amino-4-(1,3-benzodioxol-5-yl)-1)-benzyl-1H-pyrazol-3-ol

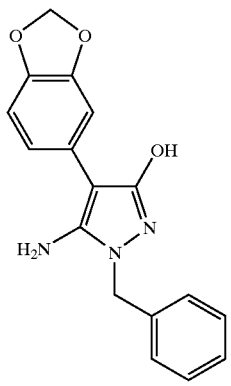

To a stirred suspension of ethyl 2-(1,3-benzodioxol-5-yl)-2-cyanoacetate (76 g) and benzylhydrazine hydrochloride (99 g) in ethanol (1300 ml), triethylamine (152 ml) was slowly added at room temperature. The solution was refluxed for two days, then concentrated under reduced pressure. To the dark residue, ethyl acetate (800 ml) and water (1000 ml) were added. The white precipitate was collected by filtration washed with water and ethyl acetate, then dried under reduced pressure to give the title compound as a white solid (41 g).

δ$_H$ (300 MHz, d$_6$ DMSO) 4.85 (2H, s), 5.65 (2H, br. s), 5.95 (2H, s), 6.80 (1H, d), 6.95 (1H, d), 7.05 (1H, s), 7.10–7.35 (5H, m), 9.6 (1H, s, br.). m/z (electrospray) [MH$^+$]310.1195 C$_{17}$H$_{16}$N$_3$O$_3$ requires requires 310.1192

Example 60

4-(tert-butyl)-N-[4-(4-cyanophenyl)-3-(2-hydroxyethoxy)-1-methyl-1H-pyrazol-5-yl]benzenesulfonamide

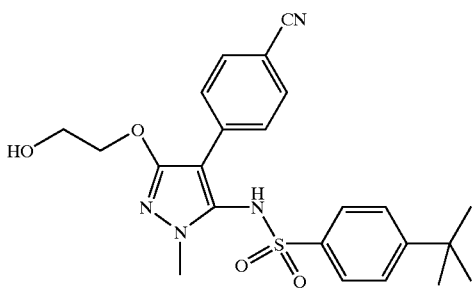

The title compound was made in a similar manner to Preparation 61 except that 4-cyanophenylboronic acid (147 mg) was used in place of 3-methylphenylboronic acid. The desired product was recovered as an off-white solid (50 mg).

δ$_H$ (300 MHz, CDCl$_3$) 7.45 (2H, d), 7.15 (2H, d), 7.10–7.00 (4H, m), 6.90 (1H, s, br.) 4.40 (2H, t), 3.95 (2H, t), 3.80 (3H, s), 1.25 (9H, s).

Preparation 61

4-(tert-butyl)-N-[3-(2-hydroxyethoxy)-1-methyl-4-(3-methylphenyl)-1H-pyrazol-5-yl]benzenesulfonamide

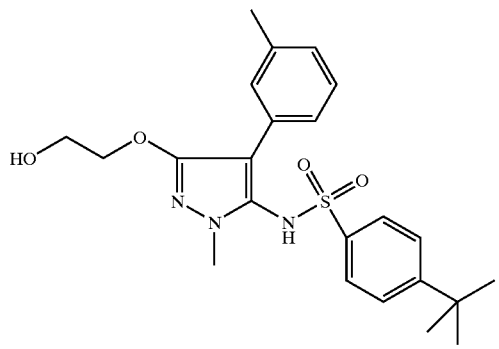

To a solution of isobutyl 2-{3-[2-(acetyloxy)ethoxy]-4-iodo-1-methyl-1H-pyrazol-5-yl}-2-{[-(tert-butyl)phenyl]sulfonyl}acetate (Preparation 6) (600 mg, 0.96mmol) in dioxane (5 ml) 4-methylphenylboronic acid (143 mg, 1.05 mmol), cesium carbonate (1.25 g, 3.8 mmol) and water (1 ml) were added. The resulting solution was de-oxygenated by placing it under vacuum and subsequently re-pressurising with nitrogen gas. This process was repeated a further three times. Tetrakis(triphenylphosphine)palladium (0) (20 mg) was added and the mixture was degassed following the same process as above. The reaction mixture was then heated to reflux for 3 hours. To the reaction mixture ethanol 10 ml) and aqueous sodium hydroxide (2N, 10 ml) were added; the reaction mixture was stirred at room temperature overnight. The reaction mixture was partitioned between saturated aqueous ammonium chloride (100 ml) and ethyl acetate (50 ml). The aqueous layer was extracted with ethyl acetate (2×50 ml). The organics were combined, dried on magnesium sulphate, filtered and concentrated under reduced pressure to yield the crude product. The crude material was purified by HPLC on a 5□ ODS Phenomenex Magellen column with a gradient elution of acetonitrile (5% to 95%) and 0.1M NH$_4$OAc (95% to 5%) to yield the desired product as an off white solid (101 mg).

$\delta_H$ (300 MHz, CDCl$_3$) 7.4 (2H, d), 7.12 (2H, d), 6.98–6.78 (4H, m), 4.36–4.28 (2H, m), 3.94–3.86 (2H, m), 3.98 (3H, s), 2.16 (3H, s), 1.12 (9H, s). m/z (negative ion electrospray) [M−H$^-$]=442; C$_{23}$H$_{30}$N$_3$O$_4$S requires 442.2

Example 62

4-(tert-butyl)-N-[4-(4-fluorophenyl)-3-(2-hydroxyethoxy)-1-methyl-1H-pyrazol-5-yl]benzenesulfonamide

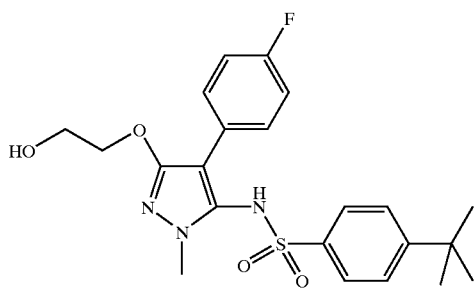

The title compound was made in a similar manner to Preparation 61 except that 4-fluorophenylboronic acid (147 mg) was used in place of 3-methylphenylboronic acid. The desired product was recovered as an off-white solid (98 mg).

$\delta_H$ (300 MHz, CDCl$_3$) 7.40 (2H, d), 7.16 (2H, d), 7.00–6.92 (2H, m), 6.76–6.66 (2H, m), 4.36–4.28 (2H, m), 4.94–4.86 (2H, m), 3.78 (3H, s), 1.24 (9H, s). m/z (negative ion electrospray) [M−H$^-$]=446; C$_{22}$H$_{27}$FN$_3$O$_4$S requires 447.2.

Example 63

4-(tert-butyl)-N-[3-(2-hydroxyethoxy)-1-methyl-4-(4-vinylphenyl)-1H-pyrazol-5-yl]benzenesulfonamide

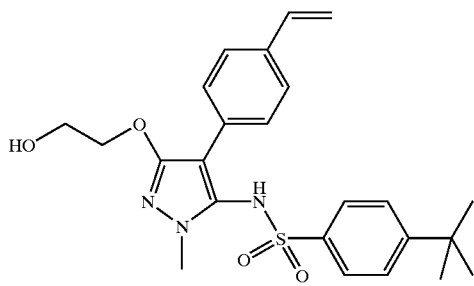

The title compound was made in a similar manner to Preparation 61 except that 4-vinylphenylboronic acid (155 mg) was used in place of 3-methylphenylboronic acid. The desired product was recovered as an off-white solid (64 mg).

$\delta_H$ (300 MHz, CDCl$_3$) 7.40 (2H, d), 7.14–7.04 (4H, m), 6.62–6.48 (1H, m), 5.62 (1H, d), 5.18 (1H, d), 4.36–4.28 (2H, m), 3.92–3.84 (2H, m), 3.78 (3H, s), 1.20 (9H, s). m/z (negative ion electrospray) [MH$^-$]=454; C$_{24}$H$_{38}$N$_3$O$_4$S requires 454.18

Example 64

N-[4-(4-acetylphenyl)-3-(2-hydroxyethoxy)-1-methyl-1H-pyrazol-5-yl]-4-(tert-butyl)benzenesulfonamide

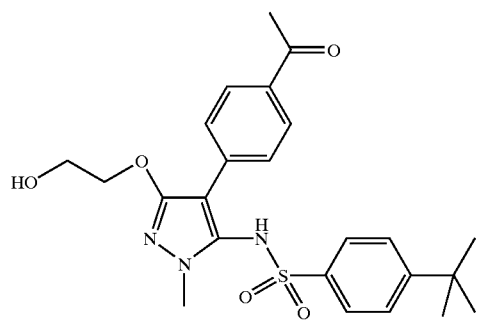

The title compound was made in a similar manner to Preparation 61 except that 4-acetylphenylboronic acid (327 mg) was used in place of 3-methylphenylboronic acid. The desired product was recovered as an off-white solid (80 mg)

$\delta_H$ (300 MHz, CD$_3$OD) 7.65 (2H, d), 7.44–7.36 (4H, m), 7.18 (2H, d), 4.30–4.24 (2H, m), 3.88–3.82 (2H, m), 3.72 (3H, s), 2.52 (3H, s), 1.16 (9H, s). m/z (thermospray) [MH$^+$]=472.3; C$_{24}$H$_{30}$N$_3$O$_5$S requires 472.2.

Preparation 65

4-(tert-butyl)-N-{3-(2-hydroxyethoxy)-1-methyl-4-[4-(trifluoromethoxy)phenyl]-1H-pyrazol-5-yl}benzenesulfonamide

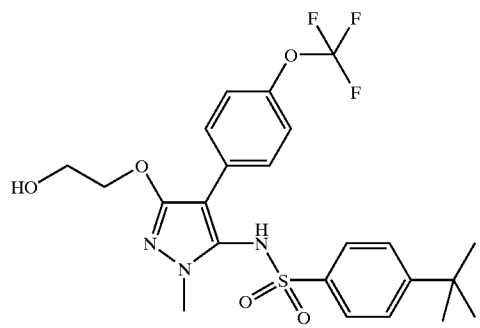

The title compound was made in a similar manner to Preparation 61 except that 4-(trifluoromethoxy)phenylboronic acid (216 mg) was used in place of 3-methylphenylboronic acid. The desired product was recovered as an off-white solid (71 mg).

$\delta_H$ (300 MHz, CDCl$_3$) 7.40 (2H, d), 7.20 (2H, d), 7.00 (2H, d), 6.92 (2H, d), 4.38–4.32 (2H, m), 3.94–3.86 (2H, m), 3.82 (3H, s), 1.24 (9H, s). m/z (negative ion electrospray) [M−H$^-$]=512; C$_{22}$H$_{27}$F$_3$N$_3$O$_5$S requires 512.2.

Preparation 66

N-[4-(1,3-benzodioxol-5-yl)-3-(2-hydroxyethoxy)-1-methyl-1H-pyrazol-5-yl]-5-isopropyl-2-pyridinesulfonamide

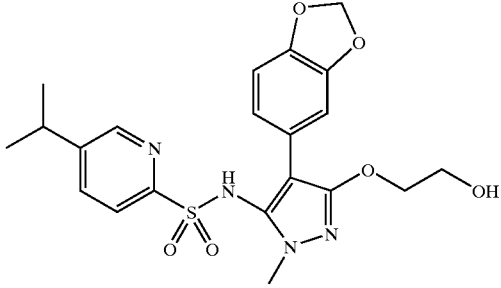

To a solution of 2-[(4-(1,3-benzodioxol-5-yl)-5-{bis[(5-isopropyl-2-pyridinyl)sulfonyl]amino}-1-methyl-1H-pyrazol-3-yl)oxy]ethyl acetate (Preparation 67) (9.0 g) in ethanol (200 ml) was added 2.0M aqueous sodium hydroxide (25 ml). The reaction was stirred for 30 min and concentrated under reduced pressure and the residue was poured onto 0.5M aqueous citric acid (300 ml). This was extracted with ethyl acetate (3×80 ml) and dried over magnesium sulfate. The solvent was removed under reduced pressure and the crude residue was purified by silica (230 g) chromatography eluting with a gradient of 50% ethyl acetate in hexane to 70% ethyl acetate in hexane to afford the title product as a white solid (5.0 g)

$\delta_H$ (400 MHz, CDCl$_3$) 1.25 (6H, s), 2.90 (m, 1H), 3.80 (3H, s), 3.90 (2H, m), 4.30 (2H, m), 5.85 (2H, s), 6.55–6.60 (3H, m), 7.45 (1H, m), 7.60 (1H, m), 8.20 (1H, s) m/z (electrospray) [MH$^+$]=461 C$_{21}$H$_{25}$N$_4$O$_6$S requires 461.1

Preparation 67

2-[-(4-(1,3-benzodioxol-5-yl)-5-{bis[(5-isopropyl-2-pyridinyl)sulfonyl]amino}-1-methyl-1H-pyrazol-3-yl)oxy]ethyl acetate

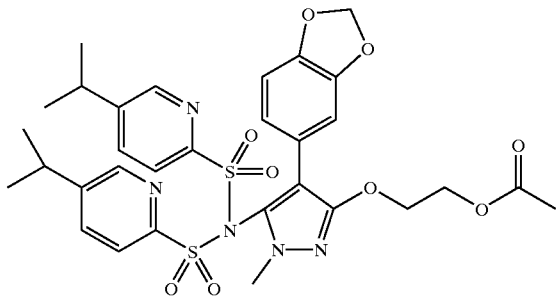

To a solution of DMAP (6.17 g) in anhydrous pyridine (100 ml) under an atmosphere of nitrogen and at 0° C. was added 5-isopropyl-2-pyrindinylsulfonyl chloride (11.1 g). The reaction was then treated dropwise at 0° C. with a solution of 2-{[5-amino-4-(1,3-benzodioxol-5-yl)-1-methyl-1H-pyrazol-3-yl]oxy}ethyl acetate (Preparation 33) (10.8 g) in anhydrous pyridine (20 ml). The reaction was allowed to warm to room temperature and then stirred for 12 h. The reaction mixture was poured into 1.0M aqueous citric acid (500 ml) and extracted with ethyl acetate (3×200 ml). The combined organics were washed with brine (150 ml) and dried over magnesium sulfate. The solvent was removed under reduced pressure and the residue was purified on a silica (700 g) column using an eluent gradient of 30% ethyl acetate in hexane to 50% ethyl acetate in hexane to afford the title product as a white solid (9.5 g).

$\delta_H$ (400 MHz, CDCl$_3$) 1.30 (12H, s), 2.05 (3H, s), 3.05 (m, 2H), 3.95 (3H, s), 4.35–4.40 (4H, m), 5.85 (2H, s), 6.55 (1H, d), 6.95 (1H, d), 7.05 (1H, s), 7.65 (2H, d), 8.05 (2H, d), 8.40 (2H, s) m/z Accurate mass spec [MH$^+$]=686.195 C$_{31}$H$_{36}$N$_5$O$_9$S$_2$ requires 686.195

Preparation 68

3-methoxy-4-(2-methoxyphenoxy)-1-methyl-1H-pyrazol-5-amine

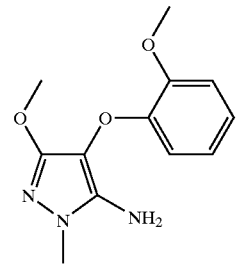

A mixture of 5-amino-4-(2-methoxyphenoxy)-1-methyl-1,2dihydro-3H-pyrazol-3-one (Preparation 69) (300 mg), caesium carbonate (1.25 g) and iodomethane (200 mg) in dry dimethylformamide (5 ml) was stirred under a nitrogen atmosphere for 24 hours at room temperature. The reaction mixture was partitioned between ethyl acetate (7×25 ml) and water (40 ml) and the combined organic extracts were dried (magnesium sulfate) and concentrated under vacuum. The residue was purified by chromatography on a Biotage Flash™ 40s silica cartridge (40 g silica) using neat ethyl acetate and then 1% methanol/dichloromethane as eluants to give the title compound as a brown solid (90 mg), R$_f$ 0.57 (10% methanol/dichloromethane).

$\delta_H$ (300 MHz, CDCl$_3$) 7.02–6.80 (4H, m), 3.92 (3H, s), 3.87 (3H, s), 3.54 (3H, s), 3.40 (2H, broad s) m/z (APCI) [MH$^+$]=250.3; C$_{12}$H$_{16}$N$_3$O$_3$ requires 250.3

Preparation 69

5-amino-4-(2-methoxyphenoxy)-1-methyl-1,2-dihydro-3H-pyrazol-3-one

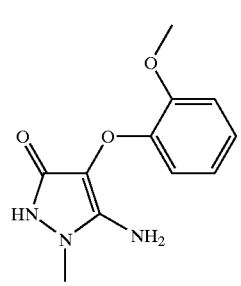

A solution of ethyl 2-cyano2-(2-methoxyphenoxy)acetate (Preparation 70) (2.0 g) and methylhydrazine (0.39 g) in ethanol (10 ml) was heated under reflux for 16 hours. The reaction mixture was concentrated under vacuum and the residue was then dissolved in methanol and evaporated onto silica (20 g). The compound-impregnated silica was loaded onto a 40 g Biotage Flash™ 40 Biotage silica cartridge and the cartridge was eluted with 1–10% methanol in dichloromethane to give the title compound as a brown solid (320 mg), $R_f$ 0.44 (10% methanol/dichloromethane).

$\delta_H$ (300 MHz, $d_6$ DMSO) 9.23 (1H, broad s), 6.95 (1H, dd), 6.88 (1H, td), 6.78 (1H, td), 6.72 (1H, 5.62 (2H, broad s), 3.79 (3H, s), 3.09 (3H, s) m/z (EI) [MH$^+$]=236.1025; $C_{11}H_{14}N_3O_3$ requires 236.1030

$v_{max}$ (polyethylene card) 3377, 3130, 2927, 2915, 1644, 1586, 1496 cm$^{-1}$ Preparation 70

Ethyl 2-cyano-2-(2-methoxyphenoxy)acetate

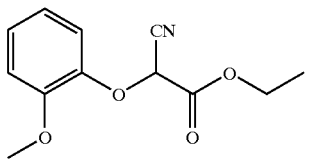

A solution of tetrabutylammonium cyanide (8.4 g) in dichloromethane (200 ml) was stirred over 4A molecular sieves for 2 hours and was then cooled to 0° C. Ethyl 2-bromo-2-(2-methoxyphenoxy)acetate (Preparation 71) (9.8 g) in dichloromethane (100 ml) was added dropwise over 10 minutes to the reaction mixture and after the addition was complete, the reaction mixture was warmed to room temperature. The reaction mixture was stirred overnight at room temperature. Further tetrabutylammonium cyanide (1.0 g) was added to the reaction mixture and stirring at room temperature was continued for a further 2 hours. The reaction mixture was filtered through a pad of silica (200 g) under vacuum and the silica pad was then washed with dichloromethane (2×300 ml). The combined filtrates were concentrated under vacuum to give the product as a pale yellow liquid, 5.0 g, $R_f$ 0.53 (dichloromethane).

$\delta_H$(300 MHz, CDCl$_3$) 7.22–7.14 (2H, m), 7.01–6.93 (2H, m), 5.76 (1H, s), 4.40 (2H, q), 3.88 (3H, s), 1.39 (3H, t)

$v_{max}$ (polyethylene card) 3071, 2984, 2944, 2846, 1766, 1600, 1504 cm$^{-1}$ m/z (electrospray) [MH$^+$=236.0, requires 236.1

Preparation 71

Ethyl 2-bromo2-(2-methoxyphenoxy)acetate

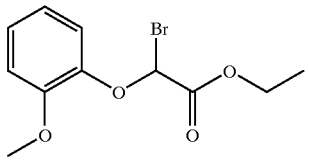

A solution of N-bromosuccinimide (13.35 g), azoisobutyronitrile (200 mg) and ethyl 2-(2-methoxyphenoxy)acetate (15.1 g) in anhydrous carbon tetrachloride (ex. calcium hydride) (100 ml) was irradiated with a 120 W sunlamp under reflux and a nitrogen atmosphere for 7 hours. The resulting suspension was allowed to stand at room temperature for 72 hours and was then filtered to remove the suspended solids, which were washed with toluene (40 ml). The combined filtrates were evaporated under vacuum leaving a brown liquid (22 g) $R_f$ 0.75 (dichloromethane).

$\delta_H$ (300 MHz, CDCl$_3$) 7.23–7.13 (2H, m), 6.99–6.89 (2H, m), 6.62 (1H, s), 4.40 (2H, q), 3.87 (3H, s), 1.40 (3H, t)

What is claimed is:

1. A compound of formula (IA) or (IB):

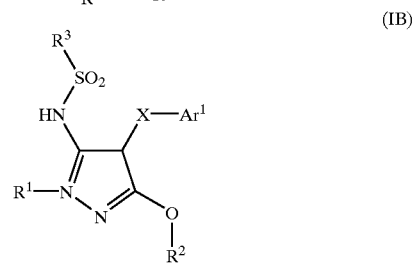

wherein $R_1$ is H, $C_{1-6}$ alkyl optionally substituted by one or more halo, OR$^4$ or NR$^4$R$^5$ groups; $C_{2-6}$ alkenyl optionally substituted by one or more halo groups; $C_{2-6}$ alkynyl optionally substituted by one or more halo groups; C(O)R$^4$; CO$_2$R$^4$; CH$_2$aryl$^4$; CONR$^4$R$^5$; aryl$^4$ or het$^3$, $R^2$ is $C_{1-6}$ alkyl, cyclopropylmethyl, or CH$_2$CH$_2$OG where G is H $C_{1-6}$ alkyl optionally substituted by a $C_{3-6}$ cycloalkyl group, C(O)R$^4$, CONHAr$^2$ or Ar$^2$, $R^4$ and $R^5$ are each independently H or $C_{1-6}$ alkyl optionally substituted by one or more halo groups, X is a direct link, O, S, SO, SO$_2$, CO or CH$_2$, $R^3$ is a) a $C_{6-14}$ aromatic hydrocarbon group; or b) an optionally benzo-fused 5- or 6-membered heterocyclic group with one to three hetero-atoms in the heterocyclic ring, which hetero-atoms are independently selected from N, O and S; or c) CH$_2$CH$_2$Ph, or CH:CHPh; or d) $C_{1-6}$ alkyl, optionally substituted by 1–4 substituents selected from: halo, $C_{1-6}$ alkoxy, CO$_2$R$^4$, OC(O)R$^4$ and NR$^4$R$^5$; each of which groups (a), (b) and (c) is optionally substituted by up to four substituents independently selected from i) $C_{1-6}$ alkyl, optionally substituted by 1–4 substituents selected from: halo, OR$^4$, CO$_2$R$^4$, OC(O)R$^4$ and NR$^4$R$^5$; ii) $C_{1-6}$ alkoxy; iii) CO$_2$R$^4$ or OC(O)R$^4$; iv) Halo; v) NO$_2$; vi) CN; vii) NR$^4$R$^5$; viii) $C_{1-3}$ alkylenedioxy; ix) OH; and x) Alkoxy carbonyl;

Ar$^1$ and Ar$^2$ are each independently aryl$^5$ or het$^1$

"aryl$^4$" is a phenyl or naphthyl group optionally substituted by up to three substituents independently selected from $C_{1-3}$ alkyl, CF$_3$, halogen, $C_{1-3}$ alkoxy, CF$_3$O, OH, NO$_2$, CN, NR$^4$R$^5$, COR$^4$, CO$_2$R$^4$, CONR$^4$R$^5$, S(O)$_p$($C_{1-3}$ alkyl), CH$_2$NR$^4$R$^5$, NR$^4$COR$^5$, COCF$_3$, CH$_2$OH, S(O)$_p$CF$_3$, and C(=NH)NH$_2$, "aryl$^5$" is a phenyl, 1,3-benzodioxyl or naphthyl group optionally substituted by up to three substituents independently selected from $C_{1-3}$ alkyl, CF$_3$, halogen, $C_{1-3}$ alkoxy, OCF$_3$, OH, NO$_2$, CN, NR$^4$R$^5$, C(O)R$^4$, CO$_2$R$^4$, CONR$^4$R$^5$, S(O)$_p$($C_{1-3}$ alkyl), $CH_2NR^4R^5$, $NR^4COR^5$, $COCF_3$, $CH_2OH$, $S(O)_p$ $CF_3$, $C(=NH)NH_2$, $C_{2-3}$ alkynyl, $C_{2-3}$ alkenyl, phenyl and het², "het¹" is a 5- to 7-membered heterocyclic group with one to three hetero-atoms in the heterocyclic ring, which hetero-atoms are independently selected from N, O and S, which heterocyclic ring is optionally benzo-fused, which group may be fully saturated or partially or fully unsaturated, and which is optionally substituted by up to three substituents independently selected from $C_{1-3}$ alkyl, $CF_3$, halogen, $C_{1-3}$ alkoxy, $CF_3O$, OH, $NO_2$, CN, $NR^4R^5$, $COR^4$, $CO_2R^4$, $CONR^4R^5$, $S(O)_p(C_{1-3}$ alkyl), $CH_2NR^4R^5$, $NR^4COR^5$, $COCF_3$, $CH_2OH$, $S(O)_pCF_3$, $C(=NH)NH_2$, $C_{2-3}$ alkynyl, $C_{2-3}$ alkenyl, phenyl and het², and, when present in the "G" moiety, is linked to the O atom to which it is joined to the remainder of the compound of formula (IA) or (IB) via a carbon atom in said "het1" group, "het²" is a 5- to 7-membered heterocyclic group with one to three hetero-atoms in the heterocyclic ring, which hetero-atoms are independently selected from N, O and S, which group may be fully saturated or partially or fully unsaturated, and p is 0, 1 or 2, and pharmaceutically acceptable salts thereof.

2. A compound as claimed in claim 1 wherein:

$R^1$ is H, $CH_3$, $CH_2Ph$, or $CH_2CH_2OH$;

$R^2$ is $CH_3$, cyclopropylmethyl, or $CH_2CH_2OG$, wherein G is H, Ph, $C(O)CH_3$, $C_{1-2}$ alkyl, N-(2-pyridyl) aminocarbonyl, 4-fluorophenyl or pyrimidin-2-yl, said pyrimidin-2-yl optionally substituted at the 5 position by F, Cl, Br, $CH_3$, $CH_2OH$, C(O)H, $NO_2$, $NH_2$, $SCH_3$, $S(O)CH_3$, $SO_2CH_3$, furan-2-yl or thien-2-yl;

$R^3$ is a) Phenyl, optionally substituted at the 4 position by: $CH(CH_3)_2$, $C(CH_3)_3$, $C(CH_3)_2CO_2Et$, $C(CH_3)_2CO_2H$, $C(CH_3)_2CH_2OH$, $C(CH_3)_2CH_2OC(O)CH_3$, Cl, Br, I, $CH_3O$, $CF_3$, or $C(CH_3)_2CH_2CH_3$; b) Pyrid-2-yl, optionally substituted at the 5 position by $CH(CH_3)_2$, $CH_3$ or $CH(CH_3)CH_2OH$; or c) $CH_2CH_2Ph$, or CH:CHPh, said Ph groups optionally substituted by H, halo or $C_{1-3}$ alkyl;

X is a direct link or O; and $Ar^1$ is a) Phenyl, optionally substituted at the 4 position by: $CF_3$, CN, vinyl, $C(O)CH_3$, $OCF_3$, COOH, F, Cl, $OCH_3$, $CH_2OH$, or $CH_3$; or b) 3,4-dihydroxyphenyl, 3,4-dimethoxyphenyl, 3-methylphenyl, 3-methoxyphenyl, 3-chlorophenyl, benzo[b]thien-2-yl, or 1,3-benzodiox-5-yl.

3. A compound as claimed in claim 1 wherein:

$R^2$ is H, or $CH_3$;

$R^2$ is $CH_2CH_2OG$, wherein G is Et or pyrimidin-2-yl, said pyrimidin-2-yl optionally substituted at the 5 position by Cl, Br, $CH_2OH$, $SO_2CH_3$, $SCH_3$, $S(O)CH_3$ or thien-2-yl;

$R^3$ is a) Phenyl, optionally substituted at the 4-position by: $C(CH_3)_3$, $C(CH_3)_2CO_2H$, $C(CH_3)_2CH_2OH$, $C(CH_3)_2CH_2OC(O)CH_3$, or $C(CH_3)_2CH_2CH_3$; b) Pyrid-2-yl, substituted at the 5 position by $CH(CH_3)CH_2OH$; or c) $CH_2CH_2Ph$, CH:CHPh, said Ph groups optionally substituted by H, Cl or $C_{1-2}$ alkyl;

X is a direct link; and $Ar^1$ is a) Phenyl, optionally substituted at the 4 position by; F, Cl, $OCH_3$, $CH_2OH$, or $CH_3$; or b) 3,4-dimethoxyphenyl, 3-methylphenyl, 3-methoxyphenyl, or 1,3-benzodiox-5-yl.

4. A compound as claimed in claim 1 wherein:

$R^1$ is $CH_3$;

$R^2$ is $CH_2CH_2OG$, wherein G is pyrimidin-2-yl, said pyrimidin-2-yl optionally substituted at the 5 position by Cl, or Br;

$R^3$ is a) Phenyl, substituted at the 4 position by: $C(CH_3)_3$, $C(CH_3)_2CO_2H$, $C(CH_3)_2CH_2OH$, or $C(CH_3)_2CH_2OC(O)CH_3$; b) Pyrid-2-yl, substituted at the 5 position by $CH(CH_3)CH_2OH$; or c) $CH_2CH_2Ph$, or CH:CHPh;

X is a direct link; and $Ar^1$ is a) Phenyl, substituted at the 4 position by $CH_2OH$ or $CH_3$; or b) 1,3-benzodiox-5-yl.

5. A compound as claimed in claim 1 wherein:

$R^1$ is H; $C_{1-6}$ alkyl optionally substituted by one or more halo, $OR^4$ or $NR^4R^5$ groups; $C_{2-6}$ alkenyl optionally substituted by one or more halo groups; $C_{2-6}$ alkynyl optionally substituted by one or more halo groups; CO—$C_{1-6}$ alkyl optionally substituted by one or more halo groups; $CO_2$—$C_{1-6}$ alkyl optionally substituted by one or more halo groups; $CONR^4R^5$; aryl⁴ or het¹, $R^2$ is $CH_2CH_2OG$ where G is H or $Ar^2$, and $R^3$ is a phenyl group or an optionally benzo-fused 5- or 6-membered heterocyclic group with one to three hetero-atoms in the heterocyclic ring, which heteroatoms are independently selected from N, O and S, each of which groups is optionally substituted by up to three substituents independently selected from halogen; $C_{1-6}$ alkyl optionally substituted by OH, halo, $NR^4R^5$ or $CO_2R^4$; CN; $OC_{1-6}$ alkyl optionally substituted by one or more halogen; and $CO_2R^4$.

6. A compound as claimed in claim 1 selected from the group consisting of:

N-(4-(1,3-benzodioxol-5-yl)-3-{2-[(5-bromo-2-pyrimidinyl)oxy]ethoxy}-1-methyl-1H-pyrazol-5-yl)-4-(tert-butyl)benzenesulfonamide, N-(4-(1,3-benzodioxol-5-yl)-3-{2-[5-chloro-2-pyrimidinyl)oxy]ethoxy)}-1-methyl-1H-pyrazol-5-yl)-4-(tert-butyl)benzenesulphonamide, N-(4-(1,3-benzodioxol-5-yl)-1-methyl-3-(2-{[5-(methylsulfonyl)-2-pyrimidinyl]oxy}ethoxy)-1H pyrazol-5-yl]-4-(tert-butyl)benzenesulfonamide, N(4-(1,3-benzodioxol-5-yl)-3-{2-[(5-chloro-2-pyrimidinyl)oxy]ethoxy}-1-methyl-1H-pyrazol-5-yl)-1-methyl-1H imidazole-4-sulfonamide, N-(4-(1,3-benzodioxol-5-yl)-3-{2-[(5-chloro-2-pyrimidinyl)oxy]ethoxy}-1-methyl-1H-pyrazol-5-yl)-4-(2-hydroxy-1,1-dimethylethyl)benzenesulfonamide, N-(4-(1,3-benzodioxol-5-yl)-3-{2-[(5-chloro-2-pyrimidinyl)oxy]ethoxy}-1-methyl-1H-pyrazol-5-yl) benzenesulfonamide, N-(4-(1,3-benzodioxol-5-yl)-3-{2-[(5-chloro-2-pyrimidinyl)oxy]ethoxy}-1-methyl-1H-pyrazol-5-yl)-1-methyl-1H-imidazole-4-sulfonamide, N-[4-(1,3-benzodioxol-5-yl)-3-(2-{[5-(methylsulfonyl)-2-pyrimidinyl]oxy}ethoxy)-1H-pyrazol-5-yl]-4-(tert-butyl)benzenesulfonamide, N-[3-{2-[(5-bromo-2-pyrimidinyl)oxy]ethoxy}-1-methyl-4-(4-methylphenyl)-1H-pyrazol-5-yl]-4-(tert-pentyl)benzenesulfonamide, 2-[4-({[3-{2-[(5-bromo-2-pyrimidinyl)oxy]ethoxy}-1-methyl-4-(4-methylphenyl)-1H-pyrazol-5-yl]amino}sulfonyl)phenyl]-2-methylpropanoic acid, N-[3-{2-[(5-bromo-2-pyrimidinyl)oxy]ethoxy}-1-methyl-4-(4-methylphenyl)-1H-pyrazol-5-yl]-4-(2-hydroxy-1,1-dimethylethyl)benzenesulfonamide, N-[3-(2-ethoxyethoxy)-1-methyl-4-(4-methylphenyl)-1H-pyrazol-5-yl]-4-(2-hydroxy-1,1-dimethylethyl)benzenesulfonamide, N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide, 4-(tert-butyl)-N-[3-{2-[(5-chloro-2-pyrimidinyl)oxy]ethoxy}-1-methyl-4-(4-methylphenyl)-1H-pyrazol-5-yl]benzenesulfonamide, 4-(tert-butyl)-N-[3-{2-[(5-methylthio-2-pyrimidinyl)oxy]ethoxy}-1-methyl-4-(4-methylphenyl)-1H-pyrazol-5-yl]benzenesulfonamide, 4-(tert-butyl)-N-[1-methyl-4-(4-methylphenyl)-3-{2-[(5-methylsulfinyl-2-pyrimidinyl)oxy]ethoxy}-1H pyrazol-5-yl]benzenesulfonamide, 4-(tert-butyl)-N-[1-methyl-4-(4-methylphenyl)-3-{2-[(5-methylsulfonyl-2-pyrimidinyl)oxy]ethoxy}-1H-pyrazol-5-yl]benzenesulfonamide, 4-tert-butyl-N-[3-(2-{[2-(hydroxymethyl)-5-pyrimidinyl]oxy}ethoxy)-1-methyl-4-(4-methylphenyl)-1H-pyrazol-5-yl]benzenesulfonamide, N-[3-{2-[(5-bromo-2-pyrimidinyl)oxy]ethoxyl}-4-(4-chlorophenyl)-1-methyl-1H-pyrazol-5-yl]-4-(tert-butyl)benzenesulfonamide, N-[3-{2-[(5-bromo-2-pyrimidinyl)oxy]ethoxy}-4-(4-methoxyphenyl)-1-methyl-1H-pyrazol-5-yl]-4-(tert-butyl)benzenesulfonamide, 4-(tert-butyl)-N-[3-{2-[(5-bromo-2-pyrimidinyl)oxy}eethoxy}4-(3-methoxyphenyl)-1-methyl-1H-pyrazol-5-yl-benzenesulphonamide, 4-(tert-butyl)-N-[3-{2-[(5-bromo-2-pyrimidinyl)oxy]ethoxy}-4-(3,4-dimethoxyphenyl)-1-methyl-1H-pyrazol-5-yl]-4-benzenesulphonamide, N-[3-{2-[(5-bromo-2-pyrimidinyl)oxy]ethoxy}-4-(4-fluorophenyl)-1-methyl-1H-pyrazol-5-yl]-4-(tert-butyl)benzenesulfonamide, N-{3-{2-[(5-bromo-2-pyrimidinyl)oxy]ethoxy}-4-[4-(hydroxymethyl)phenyl]-1-methyl-1H-pyrazol-5-yl}-4-(tert-butyl)benzenesulfonamide, N-{3-{2-[(5-bromo-2-pyrimidinyl)oxy]ethoxy}-4-[4-(hydroxymethyl)phenyl]-1-methyl-1H-pyrazol-5-yl}-4-(2-hydroxy-1,1-dimethylethyl)benzenesulfonamide, N-[3-{2-[(5bromo-2-pyrimidinyl)oxy]ethoxy}-1-methyl-4-(4-carboxymethylphenyl)-1H-pyrazol-5-yl]-4-(tert-butyl hydroxy)benzenesulfonamide, 2-[4-({[3-{2-[(5-bromo-2-pyrimidinyl)oxy]ethoxy}-1-methyl-4-(4-methylphenyl)-1H-pyrazol-5-yl]amino}sulfonyl)phenyl]-2-methylpropyl acetate, N-[3-{2-[(5-bromo-2-pyrimidinyl)oxy]ethoxy}-1-methyl-4-(4-methylphenyl)-1H-pyrazol-5-yl]-5-isopropyl-2-pyridinesulfonamide, 5-isopropyl-N-[1-methyl-4-(4-methylphenyl)-3-(2-{[5-(methylsulfonyl)-2-pyrimidinyl]oxy}ethoxy)-1H-pyrazol-5-yl]-2-pyridinesulfonamide, N-[3-(2-{[5-(hydroxymethyl)-2-pyrimidinyl]oxy}ethoxy)-1-methyl-4-(4-methylphenyl)-1H-pyrazol-5-yl]-5-isopropyl-2-pyridinesulfonamide, N-(4-(1,3-benzodioxol-5-yl)-3-{2-[(5-chloro-2-pyrimidinyl)oxy]ethoxy}-1-methyl-1H-pyrazol-5-yl)-5-isopropyl-2-pyridinesulfonamide, N-(4-(1,3-benzodioxol-5-yl)-3-{2-[(5-chloro-2-pyrimidinyl)oxy]ethoxy}-1-methyl-1H-pyrazol-5-yl)-5-(2-hydroxy-1-methylethyl)-2-pyridinesulfonamide, N-(4-(1,3-benzodioxol-5-yl)-3-{2-[(5-bromo-2-pyrimidinyl)oxy]ethoxy}-1-methyl-1H-pyrazol-5-yl)-5-isopropyl-2-pyridinesulfonamide, N-[4-(1,3-benzodioxol-5-yl)-1-methyl-3-(2-{[5-(methylsulfonyl)-2-pyrimidinyl]oxy}ethoxy)-1H-pyrazol-5-yl]-5-isopropyl-2-pyridinesulfonamide, N-[4-1,3-benzodioxol-5-yl)-3-{2-[(5-brompyrimidin-2-yl)oxy]ethoxy}-1-methyl-1H-pyrazol-5-yl]-2-pyridine sulphonamide, and N-[4-1,3-benzodioxol-5-yl)-3-{2-[(5-chloropyrimidin-2-yl)-oxy]ethoxy}-1-methyl-1H-pyrazol-5-yl]-2-pyridine sulphonamide.

7. A compound as claimed in claim 6 selected from the group consisting of:

N-[4-(1,3-benzodioxol-5-yl)-1-methyl-3-(2-{[5-(methylsulfonyl)-2-pyrimidinyl]oxy}ethoxy)-1H-pyrazol-5-yl]-5-isopropyl-2-pyridinesulfonamide, N-(4-(1,3-benzodioxol-5-yl)-3-{2-[(5-chloro-2-pyrimidinyl)oxy]ethoxy}-1-methyl-1H-pyrazol-5-yl)-5-(2-hydroxy-1-methylethyl)-2-pyridinesulfonamide, N-(4-(1,3-benzodioxol-5-yl)-3-{2-[(5-bromo-2-pyrimidinyl)oxy]ethoxy}-methyl-1H-pyrazol-5-yl)-4-(tert-butyl)benzenesulfonamide, N-(4-(1,3-benzodioxol-5-yl)-3-{2-[(5-chloro-2-pyrimidinyl)oxy]ethoxy}-1-methyl-1H-pyrazol-5-yl)-4-(2-hydroxy-1,1-dimethylethyl)benzenesulfonamide, N-[4-(1,3-benzodioxol-5-yl)-3-(2-{[5-(methylsulfonyl)-2-pyrimidinyl]oxy}ethoxy)-1H-pyrazol-5-yl]-4-(tert-butyl)benzenesulfonamide, 2-[4-({[3-{2-[(5-bromo-2-pyrimidinyl)oxy]ethoxy}-1-methyl-4-(4-methylphenyl)-1H pyrazol-5-yl]amino}sulfonyl)phenyl]-2-methylpropanoic acid, N-[3-{2-[(5-bromo-2-pyrimidinyl)oxy]ethoxy}-1-methyl-4-(4-methylphenyl)-1H-pyrazol-5-yl]-4-(2-hydroxy-1,1-dimethylethyl)benzenesulfonamide, N-[3-(2-ethoxyethoxy)-1-methyl-4-(4-methylphenyl)-1H-pyrazol-5-yl]-4-(2-hydroxy-1,1-dimethylethyl)benzenesulfonamide, 4-(tert-butyl)-N-[3-{2-[(S-chloro-2-pyrimidinyl)oxy]ethoxy}-1-methyl-4-(4-methylphenyl)-1H-pyrazol-5-yl]benzenesulfonamide, 4-(tert-butyl)-N-[1-methyl-4-(4-methylphenyl)-3-{2-[(5-methylsulfonyl-2-pyrimidinyl)oxy]ethoxy}-1H-pyrazol-5-yl]benzenesulfonamide, N-{3-{2-[(5-bromo-2-pyrimidinyl)oxy]ethoxy}-4-[4-(hydroxymethyl)phenyl]-1-methyl-1H-pyrazol-5-yl}-4-(tent-butyl)benzenesulfonamide, and N-{3-{2-[(5-bromo-2-pyrimidinyl)oxy]ethoxy}-4-[4-(hydroxymethyl)phenyl]-1-methyl-1H-pyrazol-5-yl}-4-(2-hydroxy-1,1-dimethylethyl)benzenesulfonamide.

8. A method of treating restenosis, acute/chronic renal failure, pulmonary hypertension, systemic hypertension; benign prostatic hyperplasia, male erectile dysfunction, prostate cancer, metastatic bone cancer, congestive heart failure, stroke, subarachnoid haemorrhage, angina, atherosclerosis, cerebral and cardiac ischaemia, prevention of ischaemia/reperfusion injury, cyclosporin induced nephrotoxicity, glaucoma, radiocontrast nephropathy, diabetic neuropathy, allergy, restoration of organ perfusion in haemorrhagic shock, lipoprotein lipase related disorders, chronic obstructive pulmonary disease and hyaline membrane disease in newborn; which comprises administering a therapeutically effective amount of a compound or salt as claimed in claim 1 to a patient in need of such treatment.

* * * * *